United States Patent
Sun et al.

(10) Patent No.: US 11,788,078 B2
(45) Date of Patent: Oct. 17, 2023

(54) PROCESSES FOR PRODUCING ETHANOL

(71) Applicant: Novozymes A/S, Bagsvaerd (DK)

(72) Inventors: Tianqi Sun, Aurora (CA); Ming Li, Beijing (CN); Junxin Duan, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/509,504

(22) Filed: Oct. 25, 2021

(65) Prior Publication Data

US 2022/0042003 A1    Feb. 10, 2022

Related U.S. Application Data

(63) Continuation of application No. 16/814,079, filed on Mar. 10, 2020, now Pat. No. 11,180,746, which is a continuation of application No. 16/002,596, filed on Jun. 7, 2018, now Pat. No. 10,626,384, which is a continuation of application No. 14/345,364, filed as application No. PCT/CN2012/081160 on Sep. 7, 2012, now Pat. No. 9,994,834.

(60) Provisional application No. 61/539,111, filed on Sep. 26, 2011.

(30) Foreign Application Priority Data

Sep. 9, 2011 (WO) ................ PCT/CN2011/079526

(51) Int. Cl.
    *C12N 9/30* (2006.01)
    *C12N 9/26* (2006.01)
    *C12P 19/02* (2006.01)
    *C12P 19/14* (2006.01)

(52) U.S. Cl.
CPC ............ *C12N 9/242* (2013.01); *C12N 9/2411* (2013.01); *C12P 19/02* (2013.01); *C12P 19/14* (2013.01); *C12Y 302/01001* (2013.01)

(58) Field of Classification Search
None
See application file for complete search history.

(56) References Cited

U.S. PATENT DOCUMENTS

| | | |
|---|---|---|
| 8,512,986 B2 | 8/2013 | Fukuyama |
| 8,945,889 B2 | 2/2015 | Ge |
| 10,626,384 B2 | 4/2020 | Sun et al. |

FOREIGN PATENT DOCUMENTS

| | | |
|---|---|---|
| WO | 2003/12071 A2 | 2/2003 |
| WO | 2003/016535 A2 | 2/2003 |
| WO | 2006/069290 A2 | 6/2006 |
| WO | 2009/108941 A2 | 9/2009 |
| WO | 2010/091221 A1 | 8/2010 |

OTHER PUBLICATIONS

Su et al. (Int'l J. of Hydrogen Energy, vol. 34, 2009, pp. 1780-1786).*
Geneseq ABB90178—WO 2003/12071 Fumigatis (2003).
Geneseq Access No. AXR39756—WO 2009/108941 Plant biomass degrading enzyme (2009).
XP 001397301 Alpha-amylase [*Aspergillus niger* CBS 513.88] (2011).
Cuomo et al., 2011, GenBank EGE86564 Alpha-amylase [*Ajellomyces dermatitidis* ATCC 18188] (2011).
Amlacher et al, 2011, GenBank EGS22522 Alpha-amylase [*Chaetomium thermophilum* var. *thermophilum* DSM 1495] (2011).
Eric et al., 2010, NCBI XP_001908940 hypothetical protein [*Podospora anserina* S mat+] (2010).
Fedorova et al., 2008, NCBI XP_002150655 alpha-amylase, putative [*Penicillium marneffei* ATCC 18224] (2008).
Birren et al., 2008, NCBI XP-001228699 hypothetical protein CHGG_02183 [*Chaetomium globosum* CBS 148.51].
Bunni et al., 1989, Enzy Microbiol Technol 11(6), 370-375.
Bunni et al, 1992, Biotechnol Lett 14(12), 1109-1114.
Sivaramakrishnan et al, 2006, Food Technol Biotechnol 44 (2), 173-184.
GenBank Access No. ADW25837—WO 2005/003311 (2005).
NCBI Reference Sequence XP_002717495.1—WO 2006/069290 (2006).
NCBI Reference Sequence XP_002717496.1—WO 2006/069290 (2006).
NCBI Reference Sequence XP_002717497.1—(2008).
Birren et al., NCBI XP-001228699 hypothetical protein CHGG_02183 [*Chaetomium globosum* CBS 148.51] (2008).
Geneseq Access No. XP_002717497 (2008).

* cited by examiner

*Primary Examiner* — Hope A Robinson
(74) *Attorney, Agent, or Firm* — David Fazzolare

(57) ABSTRACT

The present invention relates to isolated polypeptides having alpha-amylase activity, catalytic domains, carbohydrate binding domains and polynucleotides encoding the polypeptides, catalytic domains or carbohydrate binding domains. The invention also relates to nucleic acid constructs, vectors, and host cells comprising the polynucleotides as well as methods of producing and using the polypeptides, catalytic domains or carbohydrate binding domains.

11 Claims, 5 Drawing Sheets

Specification includes a Sequence Listing.

PROCESSES FOR PRODUCING ETHANOL

CROSS-REFERENCE TO RELATED APPLICATIONS

This application is a continuation of U.S. application Ser. No. 16/814,079 filed Mar. 10, 2020, now U.S. Pat. No. 11,180,746, which is a continuation of U.S. application Ser. No. 16/002,596 filed Jun. 7, 2018 now U.S. Pat. No. 10,626,384, which is a continuation of U.S. application Ser. No. 14/345,364 filed Oct. 30, 2014, now U.S. Pat. No. 9,994,834, which is a 35 U.S.C. 371 national application of PCT/CN2012/081160 filed Sep. 7, 2012, which claims priority or the benefit under 35 U.S.C. 119 of International application no. PCT/CN11/079526 filed Sep. 9, 2011 and U.S. provisional application No. 61/539,111 filed Sep. 26, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having alpha-amylase activity, catalytic domains, and carbohydrate binding domains, and polynucleotides encoding the polypeptides, catalytic domains, and carbohydrate binding domains. The invention also relates to nucleic acid constructs, vectors, and host cells comprising the polynucleotides as well as methods of producing and using the polypeptides, catalytic domains, and carbohydrate binding domains.

Description of the Related Art

Alpha-amylases (alpha-1,4-glucan-4-glucanohydrolases, EC. 3.2.1.1) constitute a group of enzymes which catalyze hydrolysis of starch and other linear and branched 1,4-glucosidic oligo- and polysaccharides.

For a number of years alpha-amylase enzymes have been used for a variety of different purposes, the most important of which are starch liquefaction, textile desizing, textile washing, starch modification in the paper and pulp industry, and for brewing, ethanol production and baking.

The object of the present invention is to provide alpha-amylases for conversion of starch into maltodextrins, mono- and disaccharides and/or useful in processes involving starch liquefaction, textile washing, textile desizing, starch modification in the paper and pulp industry, and for brewing, ethanol production and baking.

A polypeptide from *Aspergillus fumigatus* having alpha-amylase activity is disclosed in WO 2003/012071 (GeneseqP:ABB80178). A polypeptide from *Aspergillus terreus* having alpha-mylase activity is disclosed in WO 2010/091221. A polypeptide having alpha-amylase activity is disclosed in GENESEQP:AXR39756. A polypeptide having alpha-amylase activity from *Aspergillus niger* is disclosed in WO2003/016535-A2. A polypeptide is disclosed in WO2009/108941. A polypeptide having alpha-amylase activity from *Thermoascus aurantiacus* is disclosed in WO2006069290.

SUMMARY OF THE INVENTION

The present invention relates to isolated polypeptides having alpha-amylase activity selected from the group consisting of:

(a) a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 10; a polypeptide having at least 93%, e.g., at least 94%, at least 95%, at least 96%, at least 97%, at least 98%, at least 99%, or 100% sequence identity to the mature polypeptide of SEQ ID NO: 20; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6; a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 8; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 12; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14; a polypeptide having at least 88%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 16; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 18; a polypeptide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 22; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 24; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 28; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 30; or a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 32;

(b) a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 9, (ii) genomic DNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 19, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 3, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 5, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 7, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 11, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 13, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 15, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 17, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 23, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 25, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 27, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 29, (ii) the cDNA sequence thereof, or (iii) the full-length complement of (i) or (ii); or a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 31, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 21, (ii) the genomic DNA sequence thereof, or (iii) the full-length complement of (i) or (ii);

(c) a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the genomic DNA sequence thereof; a polypeptide encoded by a polynucleotide having at least 93%, e.g., at least 94%, at least 95%, at least 96%, at least 97%, at least 98%, at least 99%, or 100% sequence identity to the mature polypeptide coding sequence of SEQ ID NO: 19 or the cDNA sequence sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof; a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 7 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 11 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13 or the cDNA sequence thereof; a polypeptide encoded by a polynucleotide having at least 88%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17 or the cDNA sequence thereof; a polypeptide encoded by a polynucleotide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 21 or the genomic DNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25 or the cDNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 27 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29 or the cDNA sequence thereof; or a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 31 or the cDNA sequence thereof;

(d) a variant of the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more positions; and (e) a fragment of the polypeptide of (a), (b), (c), or (d) that has alpha-amylase activity.

The present invention also relates to isolated polypeptides comprising a catalytic domain selected from the group consisting of:

(a) a catalytic domain having at least 85% sequence identity to amino acids 23 to 501 of SEQ ID NO: 10, at least 93% sequence identity to amino acids 17 to 494 of SEQ ID NO: 20, at least 70% sequence identity to amino acids 21 to 495 of SEQ ID NO: 2, at least 70% sequence identity to amino acids 29 to 512 of SEQ ID NO: 4, at least 70% sequence identity to amino acids 22 to 512 of SEQ ID NO: 6, at least 90% sequence identity to amino acids 21 to 496 of SEQ ID NO: 8, at least 85% sequence identity to amino acids 20 to 497 of SEQ ID NO: 12, at least 70% sequence identity to amino acids 23 to 514 of SEQ ID NO: 14, at least 88% sequence identity to amino acids 29 to 533 of SEQ ID NO: 16, at least 70% sequence identity to amino acids 22 to 493 of SEQ ID NO: 18, at least 80% sequence identity to amino acids 23 to 500 of SEQ ID NO: 22, at least 75% sequence identity to amino acids 24 to 499 of SEQ ID NO: 24, at least 70% sequence identity to amino acids 21 to 497 of SEQ ID NO: 26, at least 75% sequence identity to amino acids 22 to 498 of SEQ ID NO: 28, at least 85% sequence identity to amino acids 25 to 498 of SEQ ID NO: 30, or at least 90% sequence identity to amino acids 23 to 500 of SEQ ID NO: 32;

(b) a catalytic domain encoded by a polynucleotide that hybridizes under low, medium, medium-high, high, or very high stringency conditions with (i) nucleotides 67 to 1503 of SEQ ID NO: 9, (ii) the genomic DNA thereof, or (iii) the full-length complement of (i) or (ii); a polynucleotide that hybridizes under low, medium, medium-high, high, or very high stringency conditions with (i) nucleotides 61 to 1699 of SEQ ID NO: 1, (ii) the cDNA sequence thereof, or (iii) the full-length complement of (i) or (ii); a polynucleotide that hybridizes under low, medium, medium-high, high, or very high stringency conditions with (i) nucleotides 85 to 1602 of SEQ ID NO: 3, (ii) the cDNA sequence thereof, or (iii) the full-length complement of (i) or (ii); a polynucleotide that hybridizes under low, medium, medium-high, high, or very high stringency conditions with (i) nucleotides 64 to 2137 of SEQ ID NO: 5, (ii) the cDNA sequence thereof, or (iii) the full-length complement of (i) or (ii); a polynucleotide that hybridizes under low, medium, medium-high, high, or very high stringency conditions with (i) nucleotides 64 to 1545 of SEQ ID NO: 7, (ii) the cDNA sequence thereof, or (iii) the full-length complement of (i) or (ii); a polynucleotide that hybridizes under low, medium, medium-high, high, or very high stringency conditions with (i) nucleotides 58 to 1964 of SEQ ID NO: 11, (ii) the cDNA sequence thereof, or (iii) the full-length complement of (i) or (ii); a polynucleotide that hybridizes under low, medium, medium-high, high, or very high stringency conditions with (i) nucleotides 67 to 2173 of SEQ ID NO: 13, (ii) the cDNA sequence thereof, or (iii) the full-length complement of (i) or (ii); a polynucleotide that hybridizes under low, medium, medium-high, high, or very high stringency conditions with (i) nucleotides 85 to 2309 of SEQ ID NO: 15, (ii) the cDNA sequence thereof, or (iii) the full-length complement of (i) or (ii); a polynucleotide that hybridizes under low, medium, medium-high, high, or very high stringency conditions with (i) nucleotides 64 to 1706 of SEQ ID NO: 17, (ii) the cDNA sequence thereof, or (iii) the full-length complement of (i) or (ii); a polynucleotide that hybridizes under low, medium, medium-high, high, or very high stringency conditions with (i) nucleotides 49 to 2007 of SEQ ID NO: 19, (ii) the cDNA sequence thereof, or (iii) the full-length complement of (i) or (ii); a polynucleotide that hybridizes under low, medium, medium-high, high, or very high stringency conditions with nucleotides 70 to 2309 of SEQ ID NO: 23, (ii) the cDNA sequence thereof, or (iii) the full-length complement of (i) or (ii); a polynucleotide that hybridizes under low, medium, medium-high, high, or very high stringency conditions with (i) nucleotides 61 to 2154 of SEQ ID NO: 25, (ii) the cDNA sequence thereof, or (iii) the full-length complement of (i) or (ii); a polynucleotide that hybridizes under low, medium, medium-high, high, or very high stringency conditions with (i) nucleotides 64 to 1622 of SEQ ID NO: 27, (ii) the cDNA sequence thereof, or (iii) the full-length complement of (i) or (ii); a polynucleotide that hybridizes under low, medium, medium-high, high, or very high stringency conditions with (i) nucleotides 73 to 2355 of SEQ ID NO: 29, (ii) the cDNA sequence thereof, or (iii) the full-length complement of (i) or (ii); a polynucleotide that hybridizes under low, medium, medium-high, high, or very high stringency conditions with (i) nucleotides 67 to 1650 of SEQ ID NO: 31, (ii) the cDNA sequence thereof, or (iii) the full-length complement of (i) or (ii); (ii a or a polynucleotide that hybridizes under low, medium, medium-high, high, or very high stringency conditions with (i) nucleotides 67 to 1500 of SEQ ID NO: 21, (ii) the genomic DNA thereof, or (iii) the full-length complement of (i) or (ii);

(c) a catalytic domain encoded by a polynucleotide having at least 85% sequence identity to nucleotides 67 to 1503 of SEQ ID NO: 9, at least 93% sequence identity to nucleotides 49 to 2007 of SEQ ID NO: 19, at least 70% sequence identity to nucleotides 61 to 1699 of SEQ ID NO: 1, at least 70% sequence identity to nucleotides 85 to 1602 of SEQ ID NO: 3, at least 70% sequence identity to nucleotides 64 to 2137 of SEQ ID NO: 5, at least 90% sequence identity to nucleotides 64 to 1545 of SEQ ID NO: 7, at least 85% sequence identity to nucleotides 58 to 1964 of SEQ ID NO: 11, at least 70% sequence identity to nucleotides 67 to 2173 of SEQ ID NO: 13, at least 88% sequence identity to nucleotides 85 to 2309 of SEQ ID NO: 15, at least 70% sequence identity to nucleotides 64 to 1706 of SEQ ID NO: 17, at least 80% sequence identity to nucleotides 67 to 1500 of SEQ ID NO: 21, at least 75% sequence identity to nucleotides 70 to 2309 of SEQ ID NO: 23, at least 70% sequence identity to nucleotides 61 to 2154 of SEQ ID NO: 25, at least 75% sequence identity to nucleotides 64 to 1622 of SEQ ID NO: 27, at least 85% sequence identity to nucleotides 73 to 2355 of SEQ ID NO: 29, or at least 90% sequence identity to nucleotides 67 to 1650 of SEQ ID NO: 31;

(d) a variant of amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18, amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32 comprising a substitution, deletion, and/or insertion at one or more positions; and (e) a fragment of the catalytic domain of (a), (b), (c), or (d) that has alpha-amylase activity.

The present invention also relates to isolated polypeptides comprising a carbohydrate binding domain selected from the group consisting of:

(a) a carbohydrate binding domain having at least 93% sequence identity to amino acids 520 to 627 of SEQ ID NO: 20, at least 75% sequence identity to amino acids 528 to 630 of SEQ ID NO: 24, at least 70% sequence identity to amino acids 529 to 631 of SEQ ID NO: 26, at least 85% sequence identity to amino acids 524 to 627 of SEQ ID NO: 30;

(b) a carbohydrate binding domain encoded by a polynucleotide that hybridizes under low, medium, medium-high, high, or very high stringency conditions with (i) nucleotides 2083 to 2406 of SEQ ID NO: 19, (ii) the cDNA sequence thereof, or (iii) the full-length complement of (i) or (ii); a polynucleotide that hybridizes under low, medium, medium-high, high, or very high stringency conditions with (i) nucleotides 2456 to 2858 of SEQ ID NO: 23, (ii) the cDNA sequence thereof, or (iii) the full-length complement of (i) or (ii); a polynucleotide that hybridizes under low, medium, medium-high, high, or very high stringency conditions with (i) nucleotides 2307 to 2673 of SEQ ID NO: 25, (ii) the cDNA sequence thereof, or (iii) the full-length complement of (i) or (ii); or a polynucleotide that hybridizes under low, medium, medium-high, high, or very high stringency conditions with (i) nucleotides 2502 to 2917 of SEQ ID NO: 29, (ii) the cDNA sequence thereof, or (iii) the full-length complement of (i) or (ii);

(c) a carbohydrate binding domain encoded by a polynucleotide having at least 93% sequence identity to nucleotides 2083 to 2406 of SEQ ID NO: 19, at least 75% sequence identity to nucleotides 2456 to 2858 of SEQ ID NO: 23, at least 70% sequence identity to nucleotides 2307 to 2673 of SEQ ID NO: 25, or at least 85% sequence identity to nucleotides 2502 to 2917 of SEQ ID NO: 29 or the cDNA sequence thereof;

(d) a variant of amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30 comprising a substitution, deletion, and/or insertion at one or more positions; and (e) a fragment of the carbohydrate binding domain of (a), (b), (c), or (d) that has binding activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to use of the present alpha-amylase for starch modification in the food industry, starch modification in the paper and pulp industry, starch liquefaction, textile washing, textile desizing, brewing, ethanol production and/or baking.

The present invention also relates to use of the present alpha-amylase for production of ethanol, especially in a process comprising hydrolyzing an ungelatinized starch.

The present invention also relates to a polynucleotide encoding a signal peptide comprising or consisting of amino acids 1 to 18 of SEQ ID NO: 2, amino acids 1 to 28 of SEQ ID NO: 4, amino acids 1 to 19 of SEQ ID NO: 6, amino acids 1 to 20 of SEQ ID NO: 8, amino acids 1 to 22 of SEQ ID NO: 10, amino acids 1 to 19 of SEQ ID NO: 12, amino acids 1 to 20 of SEQ ID NO: 14, amino acids 1 to 25 of SEQ ID NO: 16, amino acids 1 to 21 of SEQ ID NO: 18, amino acids 1 to 16 of SEQ ID NO: 20, amino acids 1 to 25 of SEQ ID NO: 22, amino acids 1 to 19 of SEQ ID NO: 24, amino acids 1 to 20 of SEQ ID NO: 26, amino acids 1 to 21 of SEQ ID NO: 28, amino acids 1 to 24 of SEQ ID NO: 30, or amino acids 1 to 20 of SEQ ID NO: 32, each of which is operably linked to a gene encoding a protein; nucleic acid constructs, expression vectors, and recombinant host cells comprising the polynucleotides; and methods of producing a protein.

Figure 1:
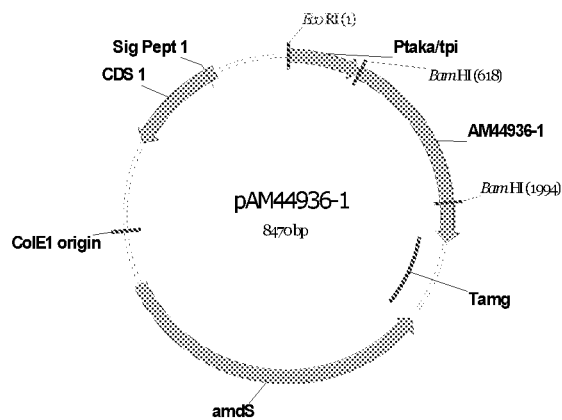
FIG. 1 shows the plasmid of pAM44936-1.
Figure 2:
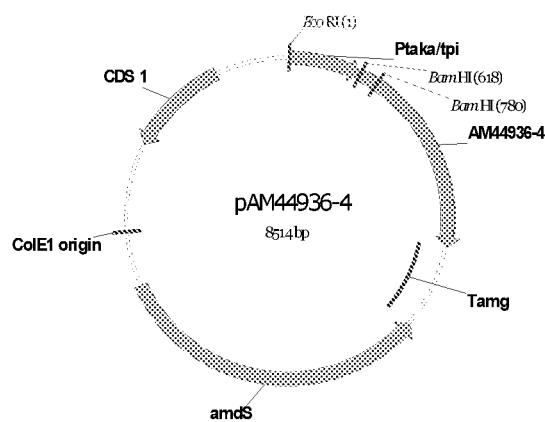
FIG. 2 shows the plasmid of pAM44936-4.
Figure 3:
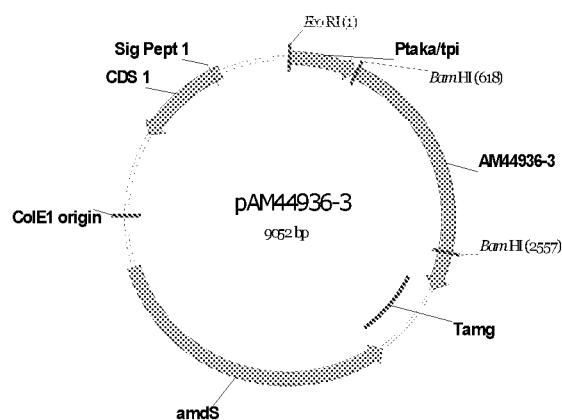
FIG. 3 shows the plasmid of pAM44936-3.
Figure 4:
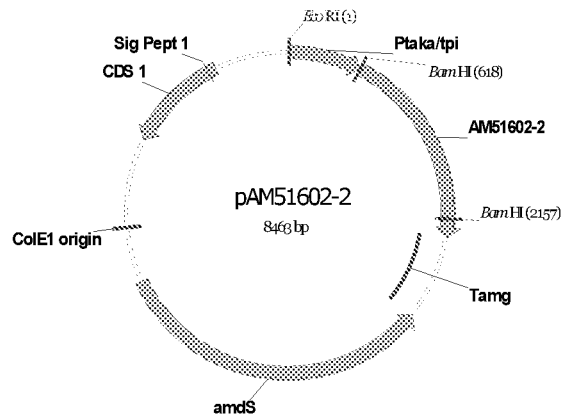
FIG. 4 shows the plasmid of pAM51602-2.
Figure 5:
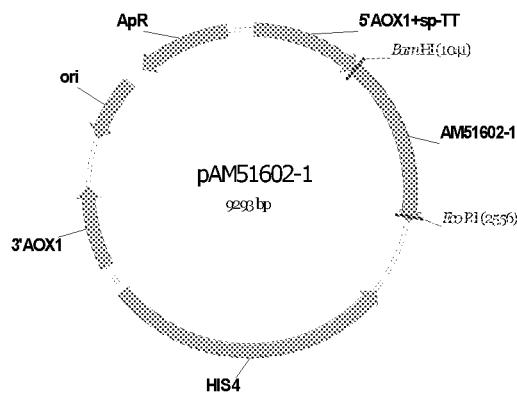
FIG. 5 shows the plasmid of pAM51602-1.
Figure 6:
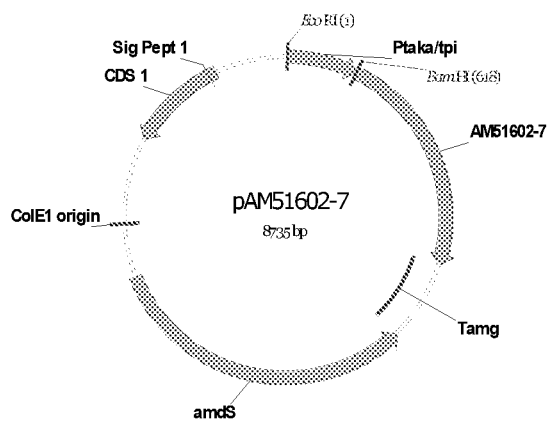
FIG. 6 shows the plasmid of pAM51602-7.
Figure 7:
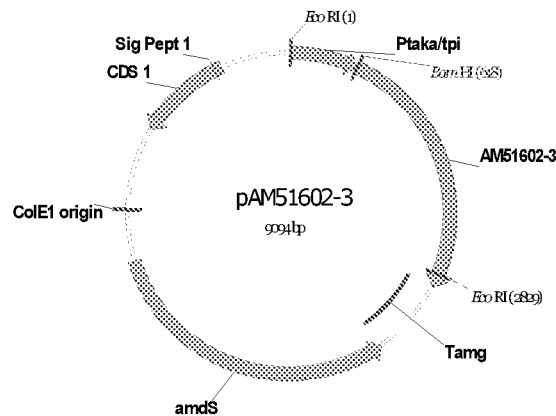
FIG. 7 shows the plasmid of pAM51602-3.
Figure 8:
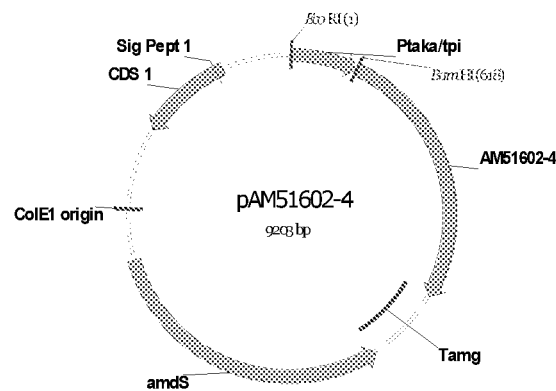
FIG. 8 shows the plasmid of pAM51602-4.
Figure 9:
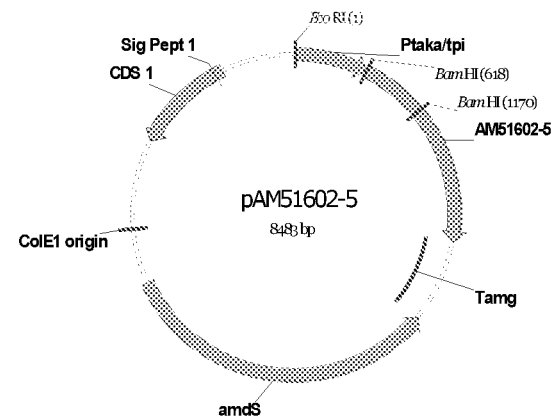
FIG. 9 shows the plasmid of pAM51602-5.
Figure 10:
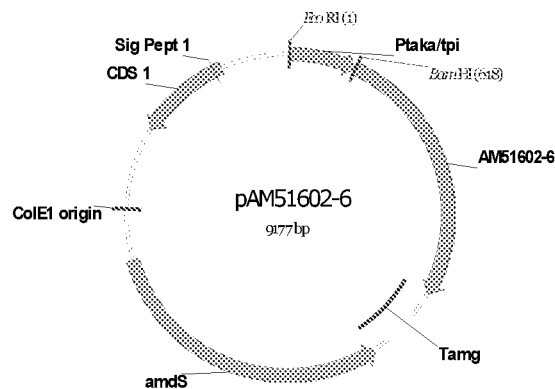
FIG. 10 shows the plasmid of pAM51602-6.
Figure 11:
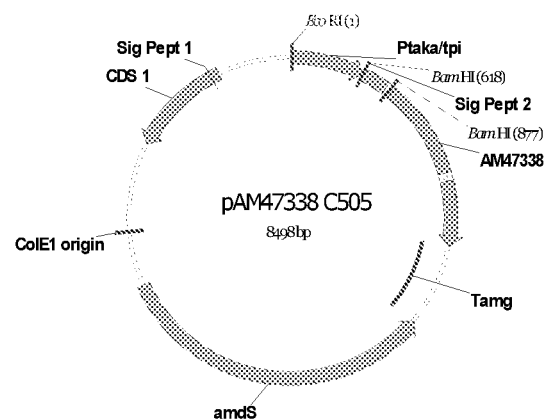
FIG. 11 shows the plasmid of pAM47338 C505.
Figure 12:
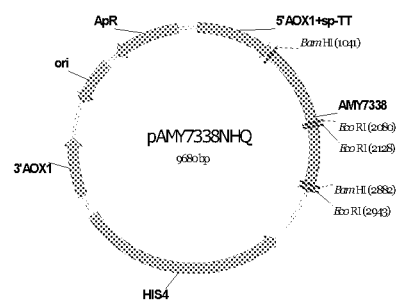
FIG. 12 shows the plasmid of pAMY7338NHQ.
Figure 13:
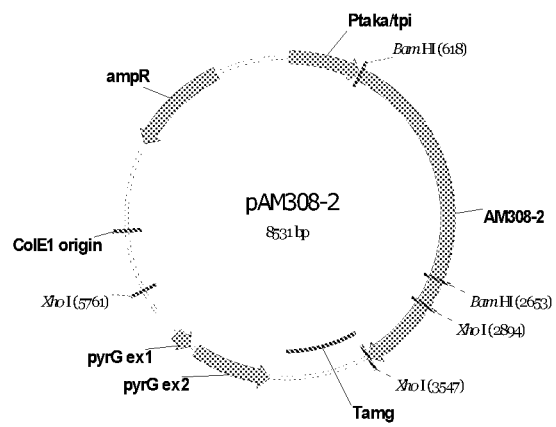
FIG. 13 shows the plasmid of pAM308-2.
Figure 14:
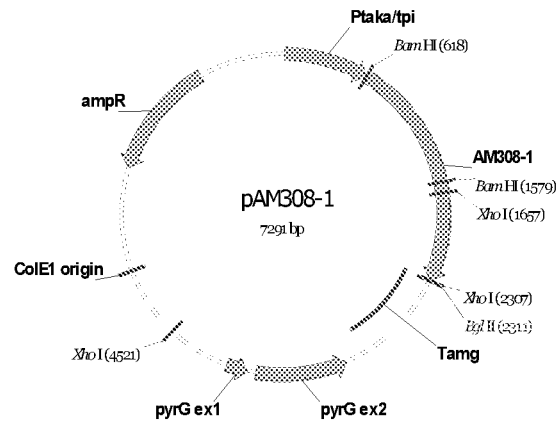
FIG. 14 shows the plasmid of pAM308-1.

DEFINITIONS alpha-amylase: The term "alpha-amylase" means an alpha-amylase activity (E.C. 3.2.1.1) that catalyzes the endohydrolysis of (1→4)-alpha-D-glucosidic linkages in polysaccharides containing three or more (1→4)-alpha-linked D-glucose units. The term "alpha-amylase activity" corresponds to the enzymes grouped in E.C. 3.2.1.1. For purposes of the present invention, alpha-amylase activity is determined according to the procedure described in the Examples. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 10. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 20. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 2. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 4. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 6. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 8. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 12. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 14. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 16. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 18 In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 22. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 24. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 26. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 28. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 30. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 32.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Carbohydrate binding domain: The term "carbohydrate binding domain" or "CBD" is defined herein as an amino acid sequence comprising a CBD of family 20, also known as a starch binding domain. In SEQ ID NO: 20, amino acids 520 to 627 are the CBD; in SEQ ID NO: 24, amino acids 528 to 630 are the CBD; in SEQ ID NO: 26, amino acids 529 to 631 are the CBD; in SEQ ID NO: 30, amino acids 524 to 627 are the CBD.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding domain having one or more (e.g., several) amino acids absent from the amino and/or carboxyl terminus of a mature polypeptide or domain; wherein the fragment has alpha-amylase or carbohydrate binding activity. In one aspect, a fragment contains at least 407 amino acid residues, preferably at least 430 amino acid residues, more preferably 453 amino acid residues of SEQ ID NO: 2. In one aspect, a fragment contains at least 449 amino acid residues, preferably at least 476 amino acid residues, more preferably 503 amino acid residues of SEQ ID NO: 4. In one aspect, a fragment contains at least 460 amino acid residues, preferably at least 487 amino acid residues, more preferably 514 amino acid residues of SEQ ID NO: 6. In one aspect, a fragment contains at least 446 amino acid residues, preferably at least 472 amino acid residues, more preferably 498 amino acid residues of SEQ ID NO: 8. In one aspect, a fragment contains at least 406 amino acid residues, preferably at least 431 amino acid residues, more preferably 455 amino acid residues of SEQ ID NO: 10. In one aspect, a fragment contains at least 399 amino acid residues, preferably at least 423 amino acid residues, more preferably 447 amino acid residues of SEQ ID NO: 12. In one aspect, a fragment contains at least 462 amino acid residues, preferably at least 489 amino acid residues, more preferably 516 amino acid residues of SEQ ID NO: 14. In one aspect, a fragment contains at least 468 amino acid residues, preferably at least 495 amino acid residues, more preferably 522 amino acid residues of SEQ ID NO: 16. In one aspect, a fragment contains at least 401 amino acid residues, preferably at least 425 amino acid residues, more preferably 449 amino acid residues of SEQ ID NO: 18. In one aspect, a fragment contains at least 517 amino acid residues, preferably at least 548 amino acid residues, more preferably 579 amino acid residues of SEQ ID NO: 20. In one aspect, a fragment contains at least 406 amino acid residues, preferably at least 429 amino acid residues, more preferably 453 amino acid residues of SEQ ID NO: 22. In one aspect, a fragment contains at least 518 amino acid residues, preferably at least 549 amino acid residues, more preferably 580 amino acid residues of SEQ ID NO: 24. In one aspect, a fragment contains at least 517 amino acid residues, preferably at least 548 amino acid residues, more preferably 579 amino acid residues of SEQ ID NO: 26. In one aspect, a fragment contains at least 433 amino acid residues, preferably at least 459 amino acid residues, more preferably 485 amino acid residues of SEQ ID NO: 28. In one aspect, a fragment contains at least 512 amino acid residues, preferably at least 542 amino acid residues, more preferably 572 amino acid residues of SEQ ID NO: 30. In one aspect, a fragment contains at least 416 amino acid residues, preferably at least 440 amino acid residues, more preferably 464 amino acid residues of SEQ ID NO: 32. In one specific embodiment a fragment comprises amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18, amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32.

In one specific embodiment a fragment comprises a carbohydrate binding domain having at least 93% sequence identity to amino acids 520 to 627 of SEQ ID NO: 20, at least 75% sequence identity to amino acids 528 to 630 of SEQ ID NO: 24, at least 70% sequence identity to amino acids 529 to 631 of SEQ ID NO: 26, or at least 85% sequence identity to amino acids 524 to 627 of SEQ ID NO: 30.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 23 to 502 of SEQ ID NO: 10, amino acids 17 to 627 of SEQ ID NO: 20, amino acids 19 to 495 of SEQ ID NO: 2, amino acids 29 to 559 of SEQ ID NO: 4, amino acids 20 to 561 of SEQ ID NO: 6, amino acids 21 to 545 of SEQ ID NO: 8, amino acids 20 to 497 of SEQ ID NO: 12, amino acids 21 to 564 of SEQ ID NO: 14, amino acids 26 to 574 of SEQ ID NO: 16, amino acids 22 to 495 of SEQ ID NO: 18, amino acids 26 to 504 of SEQ ID NO: 22, amino acids 20 to 631 of SEQ ID NO: 24, amino acids 21 to 631 of SEQ ID NO: 26, amino acids 22 to 533 of SEQ ID NO: 28, amino acids 25 to 627 of SEQ ID NO: 30, or amino acids 21 to 509 of SEQ ID NO: 32 based on the programs (e.g., SignalP (Nielsen et al., 1997, Protein Engineering 10: 1-6)) that predicts amino acids 1 to 18 of SEQ ID NO: 2, amino acids 1 to 28 of SEQ ID NO: 4, amino acids 1 to 19 of SEQ ID NO: 6, amino acids 1 to 20 of SEQ ID NO: 8, amino acids 1 to 22 of SEQ ID NO: 10, amino acids 1 to 19 of SEQ ID NO: 12, amino acids 1 to 20 of SEQ ID NO: 14, amino acids 1 to 25 of SEQ ID NO: 16, amino acids 1 to 21 of SEQ ID NO: 18, amino acids 1 to 16 of SEQ ID NO: 20, amino acids 1 to 25 of SEQ ID NO: 22, amino acids 1 to 19 of SEQ ID NO: 24, amino acids 1 to 20 of SEQ ID NO: 26, amino acids 1 to 21 of SEQ ID NO: 28, amino acids 1 to 24 of SEQ ID NO: 30, or amino acids 1 to 20 of SEQ ID NO: 32 are signal peptides. It is known in the art that a host cell may produce a mixture of two of more different mature polypeptides with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-amylase activity. In one aspect, the mature polypeptide coding sequence is nucleotides 55 to 1699 of SEQ ID NO: 1, nucleotides 85 to 1743 of SEQ ID NO: 3, nucleotides 58 to 2284 of SEQ ID NO: 5, nucleotides 61 to 1692 of SEQ ID NO: 7, nucleotides 58 to 1964 of SEQ ID NO: 11, nucleotides 61 to 2323 of SEQ ID NO: 13, nucleotides 76 to 2432 of SEQ ID NO: 15, nucleotides 64 to 1712 of SEQ ID NO: 17, nucleotides 49 to 2406 of SEQ ID NO: 19, nucleotides 58 to 2858 of SEQ ID NO: 23, nucleotides 61 to 2673 of SEQ ID NO: 25, nucleotides 64 to 1727 of SEQ ID NO: 27, nucleotides 73 to 2917 of SEQ ID NO: 29, or nucleotides 61 to 1677 of SEQ ID NO: 31, or the cDNA sequence thereof, or nucleotides 67 to 1503 of SEQ ID NO: 9, or nucleotides 67 to 1500 of SEQ ID NO: 21, or the genomic DNA sequence thereof; based on the program e.g., SignalP (Nielsen et al., 1997, supra) that predicts nucleotides 1 to 54 of SEQ ID NO: 1, nucleotides 1 to 84 of SEQ ID NO: 3, nucleotides 1 to 57 of SEQ ID NO: 5, nucleotides 1 to 60 of SEQ ID NO: 7, nucleotides 1 to 66 of SEQ ID NO: 9, nucleotides 1 to 57 of SEQ ID NO: 11, nucleotides 1 to 62 of SEQ ID NO: 13, nucleotides 1 to 75 of SEQ ID NO: 15, nucleotides 1 to 63 of SEQ ID NO: 17, nucleotides 1 to 48 of SEQ ID NO: 19, nucleotides 1 to 75 of SEQ ID NO: 21, nucleotides 1 to 57 of SEQ ID NO: 23, nucleotides 1 to 60 of SEQ ID NO: 25, nucleotides 1 to 63 of SEQ ID NO: 27, nucleotides 1 to 72 of SEQ ID NO: 29, or nucleotides 1 to 60 of SEQ ID NO: 31 encode a signal peptide.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Sequence identity between the mature polypeptides of the alpha-amylase sequences of the present invention

| | SEQ ID NO: 2 | SEQ ID NO: 4 | SEQ ID NO: 6 | SEQ ID NO: 8 | SEQ ID NO: 10 | SEQ ID NO: 12 | SEQ ID NO: 14 | SEQ ID NO: 16 | SEQ ID NO: 18 | SEQ ID NO: 20 | SEQ ID NO: 22 | SEQ ID NO: 24 | SEQ ID NO: 26 | SEQ ID NO: 28 | SEQ ID NO: 30 | SEQ ID NO: 32 |
|---|---|---|---|---|---|---|---|---|---|---|---|---|---|---|---|---|
| SEQ ID NO: 2 | 100.0 | 54.03 | 50.94 | 51.49 | 51.90 | 60.17 | 50.95 | 51.47 | 68.99 | 58.28 | 47.76 | 53.57 | 50.63 | 46.38 | 52.00 | 48.31 |
| SEQ ID NO: 4 | 54.03 | 100.0 | 45.08 | 50.49 | 66.46 | 50.53 | 46.94 | 46.61 | 54.14 | 50.59 | 49.26 | 44.32 | 46.97 | 45.04 | 44.98 | 50.83 |
| SEQ ID NO: 6 | 50.94 | 45.08 | 100.0 | 42.75 | 45.76 | 50.85 | 66.73 | 66.54 | 52.23 | 47.28 | 45.61 | 47.07 | 47.50 | 41.67 | 48.33 | 47.07 |
| SEQ ID NO: 8 | 51.49 | 50.49 | 42.75 | 100.0 | 47.26 | 49.89 | 44.16 | 45.82 | 48.08 | 49.90 | 46.30 | 44.16 | 44.08 | 44.05 | 44.18 | 47.30 |
| SEQ ID NO: 10 | 51.90 | 66.46 | 45.76 | 47.26 | 100.0 | 48.19 | 44.07 | 43.64 | 50.21 | 47.79 | 47.26 | 44.94 | 43.88 | 44.33 | 44.07 | 48.43 |
| SEQ ID NO: 12 | 60.17 | 50.53 | 50.85 | 49.89 | 48.19 | 100.0 | 49.79 | 52.87 | 61.19 | 71.82 | 44.18 | 54.78 | 52.34 | 45.49 | 55.11 | 47.32 |
| SEQ ID NO: 14 | 50.95 | 46.94 | 66.73 | 44.16 | 44.07 | 49.79 | 100.0 | 66.22 | 52.54 | 47.67 | 42.80 | 44.66 | 44.64 | 40.48 | 46.93 | 44.84 |
| SEQ ID NO: 16 | 51.47 | 46.61 | 66.54 | 45.82 | 43.64 | 52.87 | 66.22 | 100.0 | 51.37 | 46.98 | 44.69 | 44.16 | 45.12 | 41.05 | 48.71 | 43.75 |
| SEQ ID NO: 18 | 68.99 | 54.14 | 52.23 | 48.08 | 50.21 | 61.19 | 52.54 | 51.37 | 100.0 | 59.49 | 46.06 | 52.85 | 49.26 | 44.66 | 50.42 | 47.55 |
| SEQ ID NO: 20 | 58.28 | 50.59 | 47.28 | 49.90 | 47.79 | 71.82 | 47.67 | 46.98 | 59.49 | 100.0 | 44.30 | 55.39 | 52.58 | 42.29 | 51.99 | 46.06 |
| SEQ ID NO: 22 | 47.76 | 49.26 | 45.61 | 46.30 | 47.26 | 44.18 | 42.80 | 44.69 | 46.06 | 44.30 | 100.0 | 44.40 | 46.52 | 71.55 | 43.56 | 72.44 |
| SEQ ID NO: 24 | 53.57 | 44.32 | 47.07 | 44.16 | 44.94 | 54.78 | 44.66 | 44.16 | 52.85 | 55.39 | 44.40 | 100.0 | 66.34 | 42.26 | 66.55 | 43.48 |
| SEQ ID NO: 26 | 50.63 | 46.97 | 47.50 | 44.08 | 43.88 | 52.34 | 44.64 | 45.12 | 49.26 | 52.58 | 46.52 | 66.34 | 100.0 | 44.69 | 65.33 | 44.73 |
| SEQ ID NO: 28 | 46.38 | 45.04 | 41.67 | 44.05 | 44.33 | 45.49 | 40.48 | 41.05 | 44.66 | 42.29 | 71.55 | 42.26 | 44.69 | 100.0 | 40.92 | 69.75 |
| SEQ ID NO: 30 | 52.00 | 44.98 | 48.33 | 44.18 | 44.07 | 55.11 | 46.93 | 48.71 | 50.42 | 51.99 | 43.56 | 66.55 | 65.33 | 40.92 | 100.0 | 43.97 |
| SEQ ID NO: 32 | 48.31 | 50.83 | 47.07 | 47.30 | 47.43 | 47.32 | 44.84 | 13.75 | 47.55 | 46.06 | 72.44 | 43.48 | 44.73 | 69.75 | 43.97 | 100.0 |

Subsequence: The term "subsequence" means a polynucleotide having one or more (e.g., several) nucleotides absent from the 5' and/or 3' end of a mature polypeptide coding sequence; wherein the subsequence encodes a fragment having alpha-amylase activity. In one aspect, a subsequence contains at least 1221 nucleotides, preferably at least 1290 nucleotides, more preferably at least 1359 nucleotides of SEQ ID NO: 1. In one aspect, a subsequence contains at least 1347 nucleotides, preferably at least 1428 nucleotides, more preferably at least 1503 nucleotides of SEQ ID NO: 3. In one aspect, a subsequence contains at least 1380 nucleotides, preferably at least 1461 nucleotides, more preferably at least 1542 nucleotides of SEQ ID NO: 5. In one aspect, a subsequence contains at least 1338 nucleotides, preferably at least 1416 nucleotides, more preferably at least 1494 nucleotides of SEQ ID NO: 7. In one aspect, a subsequence contains at least 1218 nucleotides, preferably at least 1293 nucleotides, more preferably at least 1341 nucleotides of SEQ ID NO: 9. In one aspect, a subsequence contains at least 1197 nucleotides, preferably at least 1269 nucleotides, more preferably at least 1341 nucleotides of SEQ ID NO: 11. In one aspect, a subsequence contains at least 1386 nucleotides, preferably at least 1467 nucleotides, more preferably at least 1548 nucleotides of SEQ ID NO: 13. In one aspect, a subsequence contains at least 1404 nucleotides, preferably at least 1485 nucleotides, more preferably at least 1566 nucleotides of SEQ ID NO: 15. In one aspect, a subsequence contains at least 1203 nucleotides, preferably at least 1275 nucleotides, more preferably at least 1347 nucleotides of SEQ ID NO: 17. In one aspect, a subsequence contains at least 1551 nucleotides, preferably at least 1644 nucleotides, more preferably at least 1737 nucleotides of SEQ ID NO: 19. In one aspect, a subsequence contains at least 1218 nucleotides, preferably at least 1287 nucleotides, more preferably at least 1359 nucleotides of SEQ ID NO: 21. In one aspect, a subsequence contains at least 1554 nucleotides, preferably at least 1647 nucleotides, more preferably at least 1740 nucleotides of SEQ ID NO: 23. In one aspect, a subsequence contains at least 1551 nucleotides, preferably at least 1644 nucleotides, more preferably at least 1737 nucleotides of SEQ ID NO: 25. In one aspect, a subsequence contains at least 1299 nucleotides, preferably at least 1377 nucleotides, more preferably at least 1455 nucleotides of SEQ ID NO: 27. In one aspect, a subsequence contains at least 1536 nucleotides, preferably at least 1626 nucleotides, more preferably at least 1716 nucleotides of SEQ ID NO: 29. In one aspect, a subsequence contains at least 1248 nucleotides, preferably at least 1320 nucleotides, more preferably at least 1392 nucleotides of SEQ ID NO: 31.

In one aspect, the subsequence contains a catalytic domain encoded by a polynucleotide having at least 85% sequence identity to nucleotides 67 to 1503 of SEQ ID NO: 9, at least 93% sequence identity to nucleotides 49 to 2007 of SEQ ID NO: 19, at least 70% sequence identity to nucleotides 61 to 1699 of SEQ ID NO: 1, at least 70% sequence identity to nucleotides 85 to 1602 of SEQ ID NO: 3, at least 70% sequence identity to nucleotides 64 to 2137 of SEQ ID NO: 5, at least 90% sequence identity to nucleotides 64 to 1545 of SEQ ID NO: 7, at least 85% sequence identity to nucleotides 58 to 1964 of SEQ ID NO: 11, at least 70% sequence identity to nucleotides 67 to 2173 of SEQ ID NO: 13, at least 88% sequence identity to nucleotides 85 to 2309 of SEQ ID NO: 15, at least 70% sequence identity to nucleotides 64 to 1706 of SEQ ID NO: 17, at least 80% sequence identity to nucleotides 67 to 1500 of SEQ ID NO: 21, at least 75% sequence identity to nucleotides 70 to 2309 of SEQ ID NO: 23, at least 70% sequence identity to nucleotides 61 to 2154 of SEQ ID NO: 25, at least 75% sequence identity to nucleotides 64 to 1622 of SEQ ID NO: 27, at least 85% sequence identity to nucleotides 73 to 2355 of SEQ ID NO: 29, or at least 90% sequence identity to nucleotides 67 to 1650 of SEQ ID NO: 31.

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides Having Alpha-Amylase Activity

In an embodiment, the present invention relates to isolated polypeptides having a sequence identity to the mature polypeptide of SEQ ID NO: 10 of at least 85%, e.g., at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 20 of at least 93%, e.g., at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 2 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 4 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 6 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 8 of at least 90%, e.g., at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 12 of at least 85%, e.g., at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 14 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 16 of at least 88%, e.g., at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 18 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 22 of at least 80%, e.g., at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 24 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 26 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 28 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 30 of at least 85%, e.g., at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 32 of at least 90%, e.g., at least 91%, at least 92%, at least 93%, at least 94%, at least 95%, at least 96%, at least 97%, at least 98%, at least 99%, or 100%, which have alpha-amylase activity.

In one aspect, the polypeptides differ by no more than 10 amino acids, e.g., 1, 2, 3, 4, 5, 6, 7, 8, 9 or 10, from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32.

A polypeptide of the present invention preferably comprises or consists of the amino acid sequence of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 or an allelic variant thereof; or is a fragment thereof having alpha-amylase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32. In another aspect, the polypeptide comprises or consists of amino acids 23 to 502 of SEQ ID NO: 10, amino acids 17 to 627 of SEQ ID NO: 20, amino acids 19 to 495 of SEQ ID NO: 2, amino acids 29 to 559 of SEQ ID NO: 4, amino acids 20 to 561 of SEQ ID NO: 6, amino acids 21 to 545 of SEQ ID NO: 8, amino acids 20 to 497 of SEQ ID NO: 12, amino acids 21 to 564 of SEQ ID NO: 14, amino acids 26 to 574 of SEQ ID NO: 16, amino acids 22 to 495 of SEQ ID NO: 18, amino acids 26 to 504 of SEQ ID NO: 22, amino acids 20 to 631 of SEQ ID NO: 24, amino acids 21 to 631 of SEQ ID NO: 26, amino acids 22 to 533 of SEQ ID NO: 28, amino acids 25 to 627 of SEQ ID NO: 30, or amino acids 21 to 509 of SEQ ID NO: 32.

In another embodiment, the present invention relates to an isolated polypeptide having alpha-amylase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 9, (ii) genomic DNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 19, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 3, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 5, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 7, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 11, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 13, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 15, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 17, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 23, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 25, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 27, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 29, (ii) the cDNA sequence thereof, or (iii) the full-length complement of (i) or (ii); or a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 31, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 21, (ii) the genomic DNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 9, SEQ ID NO: 19, SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 21, SEQ ID NO: 23, SEQ ID NO: 25, SEQ ID NO: 27, SEQ ID NO: 29, or SEQ ID NO: 31 or a subsequence thereof, as well as the polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 or a fragment thereof, may be used to design nucleic acid probes to identify and clone DNA encoding polypeptides having alpha-amylase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having alpha-amylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 9, SEQ ID NO: 19, SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 21, SEQ ID NO: 23, SEQ ID NO: 25, SEQ ID NO: 27, SEQ ID NO: 29, or SEQ ID NO: 31 or a subsequence thereof, the carrier material is used in a Southern blot.

For purposes of the present invention, hybridization indicates that the polynucleotide hybridizes to a labeled nucleic acid probe corresponding to (i) SEQ ID NO: 9, SEQ ID NO: 19, SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 21, SEQ ID NO: 23, SEQ ID NO: 25, SEQ ID NO: 27, SEQ ID NO: 29, or SEQ ID NO: 31; (ii) the mature polypeptide coding sequence of SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or the cDNA sequence thereof; (iii) the mature polypeptide coding sequence of SEQ ID NO: 9 or SEQ ID NO: 21, or genomic DNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 67 to 1503 of SEQ ID NO: 9, nucleotides 49 to 2406 of SEQ ID NO: 19, nucleotides 55 to 1699 of SEQ ID NO: 1, nucleotides 85 to 1743 of SEQ ID NO: 3, nucleotides 58 to 2284 of SEQ ID NO: 5, nucleotides 61 to 1692 of SEQ ID NO: 7, nucleotides 58 to 1964 of SEQ ID NO: 11, nucleotides 61 to 2323 of SEQ ID NO: 13, nucleotides 76 to 2432 of SEQ ID NO: 15, nucleotides 64 to 1712 of SEQ ID NO: 17, nucleotides 67 to 1500 of SEQ ID NO: 21, nucleotides 58 to 2858 of SEQ ID NO: 23, nucleotides 61 to 2673 of SEQ ID NO: 25, nucleotides 64 to 1727 of SEQ ID NO: 27, nucleotides 73 to 2917 of SEQ ID NO: 29, or nucleotides 61 to 1677 of SEQ ID NO: 31. In another aspect, the nucleic acid probe is a polynucleotide that encodes the polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or the cDNA sequence thereof; or SEQ ID NO: 9 or SEQ ID NO: 21.

In another embodiment, the present invention relates to an isolated polypeptide having alpha-amylase activity encoded by a polynucleotide having a sequence identity to the mature polypeptide coding sequence of SEQ ID NO: 9 of at least 85%, e.g., at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 19 or the cDNA sequence sequence thereof of at least 93%, e.g., at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 1 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 3 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 5 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 7 or the cDNA sequence thereof of at least 90%, e.g., at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 11 or the cDNA sequence thereof of at least 85%, e.g., at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 13 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 15 or the cDNA sequence thereof of at least 88%, e.g., at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 17 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 21 of at least 80%, e.g., at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 23 or the cDNA sequence thereof of at least 75%, e.g., at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 25 or the cDNA sequence thereof of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 27 or the cDNA sequence thereof of at least 75%, e.g., at least 80%, at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 29 or the cDNA sequence thereof of at least 85%, e.g., at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 31 or the cDNA sequence thereof of at least 90%, e.g., at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more (e.g., several) positions. In an embodiment, the number of amino acid substitutions, deletions and/or insertions introduced into the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 is at most 10, e.g., 1, 2, 3, 4, 5, 6, 7, 8, 9 or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, Function, and Genetics 6: 240-248; and Stevens, 2003, *Drug Discovery World* 4: 35-48.

Sources of Polypeptides Having Alpha-amylase Activity

A polypeptide having alpha-amylase activity of the present invention may be a *Chaetomium, HumicolaMyceliophthora, Talaromyces,* or *Thermoascus,* polypeptide.

In another aspect, the polypeptide is a *Thermoascus* polypeptide, e.g., a polypeptide obtained from *Thermoascus aurantiacus*. In another aspect, the polypeptide is a *Talaromyces* polypeptide, e.g., a polypeptide obtained from *Talaromyces emersonii*. In another aspect, the polypeptide is a *Chaetomium* polypeptide, e.g., a polypeptide obtained from *Chaetomium thermophilum*. In another aspect, the polypeptide is a *Humicola* polypeptide, e.g., a polypeptide obtained from *Humicola insolens*. In another aspect, the polypeptide is a *Myceliophthora* polypeptide, e.g., a polypeptide obtained from *Myceliophthora fergusii*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 23 to 501 of SEQ ID NO: 10 of at least 85%, e.g., at least 90%, at least 95%, at least 96%, at least 97%, at least 98%, at least 99%, or 100%; having a sequence identity to amino acids 17 to 494 of SEQ ID NO: 20 of at least 93%, e.g., at least 94%, at least 95%, at least 96%, at least 97%, at least 98%, at least 99%, or 100%; having a sequence identity to amino acids 21 to 495 of SEQ ID NO: 2 of at least 70%, e.g., at least 75%, at least 80%, at least 85%, at least 90%, at least 95%, at least 96%, at least 97%, at least 98%, at least 99%, or 100%; having a sequence identity to amino acids 29 to 512 of SEQ ID NO: 4 of at least 70%, e.g., at least 75%, at least 80%, at least 85%, at least 90%, at least 95%, at least 96%, at least 97%, at least 98%, at least 99%, or 100%; having a sequence identity to amino acids 22 to 512 of SEQ ID NO: 6 of at least 70%, e.g., at least 75%, at least 80%, at least 85%, at least 90%, at least 95%, at least 96%, at least 97%, at least 98%, at least 99%, or 100%; having a sequence identity to amino acids 21 to 496 of SEQ ID NO: 8 of at least 90%, e.g., at least 91%, at least 92%, at least 93%, at least 94%, at least 95%, at least 96%, at least 97%, at least 98%, at least 99%, or 100%; having a sequence identity to amino acids 20 to 497 of SEQ ID NO: 12 of at least 85%, e.g., at least 90%, at least 95%, at least 96%, at least 97%, at least 98%, at least 99%, or 100%; having a sequence identity to amino acids 23 to 514 of SEQ ID NO: 14 of at least 70%, e.g., at least 75%, at least 80%, at least 85%, at least 90%, at least 95%, at least 96%, at least 97%, at least 98%, at least 99%, or 100%; having a sequence identity to amino acids 29 to 533 of SEQ ID NO: 16 of at least 88%, e.g., at least 90%, at least 95%, at least 96%, at least 97%, at least 98%, at least 99%, or 100%; having a sequence identity to amino acids 22 to 493 of SEQ ID NO: 18 of at least 70%, e.g., at least 75%, at least 80%, at least 85%, at least 90%, at least 95%, at least 96%, at least 97%, at least 98%, at least 99%, or 100%; having a sequence identity to amino acids 23 to 500 of SEQ ID NO: 22 of at least 80%, e.g., at least 85%, at least 90%, at least 95%, at least 96%, at least 97%, at least 98%, at least 99%, or 100%; having a sequence identity to amino acids 24 to 499 of SEQ ID NO: 24 of at least 75%, e.g., at least 80%, at least 85%, at least 90%, at least 95%, at least 96%, at least 97%, at least 98%, at least 99%, or 100%; having a sequence identity to amino acids 21 to 497 of SEQ ID NO: 26 of at least 70%, e.g., at least 75%, at least 80%, at least 85%, at least 90%, at least 95%, at least 96%, at least 97%, at least 98%, at least 99%, or 100%; having a sequence identity to amino acids 22 to 498 of SEQ ID NO: 28 of at least 75%, e.g., at least 80%, at least 85%, at least 90%, at least 95%, at least 96%, at least 97%, at least 98%, at least 99%, or 100%; having a sequence identity to amino acids 25 to 498 of SEQ ID NO: 30 of at least 85%, e.g., at least 90%, at least 95%, at least 96%, at least 97%, at least 98%, at least 99%, or 100%; or having a sequence identity to amino acids 23 to 500 of SEQ ID NO: 32 of at least 90%, e.g., at least 91%, at least 92%, at least 93%, at least 94%, at least 95%, at least 96%, at least 97%, at least 98%, at least 99%, or 100%.

In one aspect, the catalytic domains comprise amino acid sequences that differ by no more than 10 amino acids, e.g., 1, 2, 3, 4, 5, 6, 7, 8, 9, or 10, from amino acids 23 to 501 of SEQ ID NO: 10. In one aspect, the catalytic domains comprise amino acid sequences that differ by no more than 10 amino acids, e.g., 1, 2, 3, 4, 5, 6, 7, 8, 9, or 10, from amino acids 17 to 494 of SEQ ID NO: 20. In one aspect, the catalytic domains comprise amino acid sequences that differ by no more than 10 amino acids, e.g., 1, 2, 3, 4, 5, 6, 7, 8, 9, or 10, from amino acids 21 to 495 of SEQ ID NO: 2. In one aspect, the catalytic domains comprise amino acid sequences that differ by no more than 10 amino acids, e.g., 1, 2, 3, 4, 5, 6, 7, 8, 9, or 10, from amino acids 29 to 512 of SEQ ID NO: 4. In one aspect, the catalytic domains comprise amino acid sequences that differ by no more than 10 amino acids, e.g., 1, 2, 3, 4, 5, 6, 7, 8, 9, or 10, from amino acids 22 to 512 of SEQ ID NO: 6. In one aspect, the catalytic domains comprise amino acid sequences that differ by no more than 10 amino acids, e.g., 1, 2, 3, 4, 5, 6, 7, 8, 9, or 10, from amino acids 21 to 496 of SEQ ID NO: 8. In one aspect, the catalytic domains comprise amino acid sequences that differ by no more than 10 amino acids, e.g., 1, 2, 3, 4, 5, 6, 7, 8, 9, or 10, from amino acids 20 to 497 of SEQ ID NO: 12. In one aspect, the catalytic domains comprise amino acid sequences that differ by no more than 10 amino acids, e.g., 1, 2, 3, 4, 5, 6, 7, 8, 9, or 10, from amino acids 23 to 514 of SEQ ID NO: 14. In one aspect, the catalytic domains comprise amino acid sequences that differ by no more than 10 amino acids, e.g., 1, 2, 3, 4, 5, 6, 7, 8, 9, or 10, from amino acids 29 to 533 of SEQ ID NO: 16. In one aspect, the catalytic domains comprise amino acid sequences that differ by no more than 10 amino acids, e.g., 1, 2, 3, 4, 5, 6, 7, 8, 9, or 10, from amino acids 22 to 493 of SEQ ID NO: 18. In one aspect, the catalytic domains comprise amino acid sequences that differ by no more than 10 amino acids, e.g., 1, 2, 3, 4, 5, 6, 7, 8, 9, or 10, from amino acids 23 to 500 of SEQ ID NO: 22. In one aspect, the catalytic domains comprise amino acid sequences that differ by no more than 10 amino acids, e.g., 1, 2, 3, 4, 5, 6, 7, 8, 9, or 10, from amino acids 24 to 499 of SEQ ID NO: 24. In one aspect, the catalytic domains comprise amino acid sequences that differ by no more than 10 amino acids, e.g., 1, 2, 3, 4, 5, 6, 7, 8, 9, or 10, from amino acids 21 to 497 of SEQ ID NO: 26. In one aspect, the catalytic domains comprise amino acid sequences that differ by no more than 10 amino acids, e.g., 1, 2, 3, 4, 5, 6, 7, 8, 9, or 10, from amino acids 22 to 498 of SEQ ID NO: 28. In one aspect, the catalytic domains comprise amino acid sequences that differ by no more than 10 amino acids, e.g., 1, 2, 3, 4, 5, 6, 7, 8, 9, or 10, from amino acids 25 to 498 of SEQ ID NO: 30. In one aspect, the catalytic domains comprise amino acid sequences that differ by no more than 10 amino acids, e.g., 1, 2, 3, 4, 5, 6, 7, 8, 9, or 10, from amino acids 23 to 500 of SEQ ID NO: 32.

The catalytic domain preferably comprises or consists of amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18 amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32 or an allelic variant thereof; or is a fragment thereof having alpha-amylase activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 61 to 1699 of SEQ ID NO: 1 (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 85 to 1602 of SEQ ID NO: 3, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 64 to 2137 of SEQ ID NO: 5, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 64 to 1545 of SEQ ID NO: 7, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 58 to 1964 of SEQ ID NO: 11, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 67 to 2173 of SEQ ID NO: 13, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 85 to 2309 of SEQ ID NO: 15, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 64 to 1706 of SEQ ID NO: 17, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 49 to 2007 of SEQ ID NO: 19, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 67 to 1500 of SEQ ID NO: 21, (ii) the genomic DNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 70 to 2309 of SEQ ID NO: 23, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 61 to 2154 of SEQ ID NO: 25, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 64 to 1622 of SEQ ID NO: 27, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 73 to 2355 of SEQ ID NO: 29, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 67 to 1650 of SEQ ID NO: 31, (ii) the cDNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 67 to 1503 of SEQ ID NO: 9, (ii) genomic DNA sequence thereof, or (iii) the full-length complement of (i) or (ii). In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with nucleotides 67 to 1500 of SEQ ID NO: 21, (ii) genomic DNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 67 to 1503 of SEQ ID NO: 9 of at least 85%, e.g., at least 90%, at least 95%, at least 96%, at least 97%, at least 98%, at least 99%, or 100%. In another embodiment, the present invention also relates to catalytic domains encoded by polynucleotides having a sequence identity to nucleotides 49 to 2007 of SEQ ID NO: 19 of at least 93%, e.g., at least 94%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 61 to 1699 of SEQ ID NO: 1 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 85 to 1602 of SEQ ID NO: 3 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 64 to 2137 of SEQ ID NO: 5 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 64 to 1545 of SEQ ID NO: 7 of at least 90%, e.g., at least 91%, at least 92%, at least 93%, at least 94%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 58 to 1964 of SEQ ID NO: 11 of at least 85%, e.g., at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 67 to 2173 of SEQ ID NO: 13 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 85 to 2309 of SEQ ID NO: 15 of at least 88%, e.g., at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 64 to 1706 of SEQ ID NO: 17 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 67 to 1500 of SEQ ID NO: 21 of at least 80%, e.g., at least 85%, at least 90%, at least 95%, at least 96%, at least 97%, at least 98%, at least 99%, or 100%. In another embodiment, the present invention also relates to catalytic domains encoded by polynucleotides having a sequence identity to nucleotides 70 to 2309 of SEQ ID NO: 23 of at least 75%, e.g., at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 61 to 2154 of SEQ ID NO: 25 of at least 70%, e.g., at least 75%, at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 64 to 1622 of SEQ ID NO: 27 of at least 75%, e.g., at least 80%, at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 73 to 2355 of SEQ ID NO: 29 of at least 85%, e.g., at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 67 to 1650 of SEQ ID NO: 31 of at least 90%, e.g., at least 91%, at least 92%, at least 93%, at least 94%, at least 95%, at least 96%, at least 97%, at least 98%, at least 99%, or 100%, or the cDNA sequence thereof.

The polynucleotide encoding the catalytic domain preferably comprises or consists of nucleotides 67 to 1503 of SEQ ID NO: 9, nucleotides 49 to 2007 of SEQ ID NO: 19, nucleotides 61 to 1699 of SEQ ID NO: 1, nucleotides 85 to 1602 of SEQ ID NO: 3, nucleotides 64 to 2137 of SEQ ID NO: 5, nucleotides 64 to 1545 of SEQ ID NO: 7, nucleotides 58 to 1964 of SEQ ID NO: 11, nucleotides 67 to 2173 of SEQ ID NO: 13, nucleotides 85 to 2309 of SEQ ID NO: 15, nucleotides 64 to 1706 of SEQ ID NO: 17, nucleotides 67 to 1500 of SEQ ID NO: 21, nucleotides 70 to 2309 of SEQ ID NO: 23, nucleotides 61 to 2154 of SEQ ID NO: 25, nucleotides 64 to 1622 of SEQ ID NO: 27, nucleotides 73 to 2355 of SEQ ID NO: 29, nucleotides 67 to 1650 of SEQ ID NO: 31.

In another embodiment, the present invention also relates to catalytic domain variants of amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18, amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32 comprising a substitution, deletion, and/or insertion at one or more (e.g., several) positions. In one aspect, the number of amino acid substitutions, deletions and/or insertions introduced into the sequence of amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18, amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32 is 10, e.g., 1, 2, 3, 4, 5, 6, 8, or 9.

Binding Domains

In one embodiment, the present invention also relates to carbohydrate binding domains having a sequence identity to amino acids 520 to 627 of SEQ ID NO: 20 of at least 93%, e.g., at least 94%, at least 95%, at least 96%, at least 97%, at least 98%, at least 99%, or 100%; having a sequence identity to amino acids 528 to 630 of SEQ ID NO: 24 of at least 75%, e.g., at least 80%, at least 85%, at least 90%, at least 91%, at least 92%, at least 93%, at least 94%, at least 95%, at least 96%, at least 97%, at least 98%, at least 99%, or 100%; having a sequence identity to amino acids 529 to 631 of SEQ ID NO: 26 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%; having a sequence identity to amino acids 524 to 627 of SEQ ID NO: 30 of at least 85% e.g., at least 90%, at least 91%, at least 92%, at least 93%, at least 94%, at least 95%, at least 96%, at least 97%, at least 98%, at least 99%, or 100%. In one aspect, the carbohydrate binding domains comprise amino acid sequences that differ by no more than 10 amino acids, e.g., 1, 2, 3, 4, 5, 6, 7, 8, or 9, from amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30.

The carbohydrate binding domain preferably comprises or consists of amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30 or an allelic variant thereof; or is a fragment thereof having carbohydrate binding activity.

In another embodiment, the present invention also relates to carbohydrate binding domains encoded by polynucleotides that hybridize under very low stringency conditions, low stringency conditions, medium stringency conditions, medium-high stringency conditions, high stringency conditions, or very high stringency conditions (as defined above) with (i) the nucleotides 2083 to 2406 of SEQ ID NO: 19, nucleotides 2456 to 2858 of SEQ ID NO: 23, nucleotides 2307 to 2673 of SEQ ID NO: 25, or nucleotides 2502 to 2917 of SEQ ID NO: 29 (ii) the cDNA sequence thereof, or (iii) the full-length complement of (i) or (ii) (Sambrook et al., 1989, supra).

In another embodiment, the present invention also relates to carbohydrate binding domains encoded by polynucleotides having a sequence identity to nucleotides 2083 to 2406 of SEQ ID NO: 19 of at least 93%, e.g., at least 94%, at least 95%, at least 96%, at least 97%, at least 98%, at least 99%, or 100%. In another embodiment, the present invention also relates to carbohydrate binding domains encoded by polynucleotides having a sequence identity to nucleotides 2456 to 2858 of SEQ ID NO: 23 of at least 75%, e.g., at least 80%, at least 85%, at least 90%, at least 91%, at least 92%, at least 93%, at least 94%, at least 95%, at least 96%, at least 97%, at least 98%, at least 99%, or 100%. In another embodiment, the present invention also relates to carbohydrate binding domains encoded by polynucleotides having a sequence identity to nucleotides nucleotides 2307 to 2673 of SEQ ID NO: 25 of at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100%. In another embodiment, the present invention also relates to carbohydrate binding domains encoded by polynucleotides having a sequence identity to nucleotides 2502 to 2917 of SEQ ID NO: 29 of at least 85%, e.g., at least 90%, at least 91%, at least 92%, at least 93%, at least 94%, at least 95%, at least 96%, at least 97%, at least 98%, at least 99%, or 100%.

The polynucleotide encoding the carbohydrate binding domain preferably comprises or consists of nucleotides 2083 to 2406 of SEQ ID NO: 19, nucleotides 2456 to 2858 of SEQ ID NO: 23, nucleotides 2307 to 2673 of SEQ ID NO: 25, or nucleotides 2502 to 2917 of SEQ ID NO: 29.

In another embodiment, the present invention also relates to carbohydrate binding domain variants of amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30 comprising a substitution, deletion, and/or insertion at one or more (e.g., several) positions. In one aspect, the number of amino acid substitutions, deletions and/or insertions introduced into the sequence of amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30 is 10, e.g., 1, 2, 3, 4, 5, 6, 8, or 9.

A catalytic domain operably linked to the carbohydrate binding domain may be from an amylase, preferably an alpha-amylase, more preferably an acid alpha-amylase. The polynucleotide encoding the catalytic domain may be obtained from any prokaryotic, eukaryotic, or other source.

Polynucleotides

The present invention also relates to isolated polynucleotides encoding a polypeptide, a catalytic domain, or carbohydrate binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Thermoascus, Talaromyces, Chaetomium, Humicola* or *Myceliophthora* polypeptide, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or the cDNA sequence thereof, or SEQ ID NO: 9, or SEQ ID NO: 21, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the production of the polypeptide in an expression host.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No.* 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Thermoascus, Talaromyces, Chaetomium, Humicola,* or *Myceliophthora* cell. In a more preferred aspect, the cell is *Thermoascus aurantiacus, Talaromyces emersonii, Chaetomium thermophilum,* or *Myceliophthora fergusii* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium,* temperate grass, such as *Agrostis,* and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention.

The composition may further comprise an enzyme selected from the group comprising of; an additional fungal alpha-amylase (EC 3.2.1.1), a beta-amylase (E.C. 3.2.1.2), a glucoamylase (E.C.3.2.1.3), a pullulanases (E.C. 3.2.1.41), a phytase (E.C.3.1.2.28) and a protease (E.C. 3.4.). The glucoamylase may preferably be derived from a strain of *Aspergillus* sp., such as *Aspergillus niger*, or from a strain of *Talaromyces* sp. and in particular derived from *Talaromyces leycettanus* such as the glucoamylase disclosed in U.S. patent no. Re. 32, 153, *Talaromyces duponti* and/or *Talaromyces* thermopiles such as the glucoamylases disclosed in U.S. Pat. No. 4,587,215 and more preferably derived from *Talaromyces emersonii*. Most preferably the glucoamylase is derived from *Talaromyces emersonii* strain CBS 793.97 and/or having the sequence disclosed as SEQ ID NO: 7 in WO 99/28448. Further preferred is a glucoamylase which has an amino acid sequence having at least 50%, at least 60%, at least 70%, at least 80%, at least 90%, at least 95%, at least 96%, at least 97%, at least 98%, or even at least 99% identity to the aforementioned amino acid sequence. A commercial *Talaromyces* glucoamylase preparation is supplied by Novozymes A/S as SPIRIZYME FUEL.

Also preferred for a composition comprising the polypeptide of the present invention and a glucoamylase are polypeptides having glucoamylase activity which are derived from a strain of the genus *Trametes*, preferably *Trametes cingulate*. Further preferred is polypeptide having glucoamylase activity and having at least 50%, at least 60%, at least 70%, at least 80%, at least 90% or even at least 95% identity with amino acids for mature polypeptide of SEQ ID NO: 2 in WO 2006/069289.

Also preferred for a composition comprising the polypeptide of the present invention and a glucoamylase are polypeptides having glucoamylase activity which are derived from a strain of the genus *Pachykytospora*, preferably *Pachykytospora papyracea* or the *E. coli* strain deposited at DSMZ and given the no. DSM 17105. Further preferred are polypeptides having glucoamylase activity and having at least 50%, at least 60%, at least 70%, at least 80%, at least 90% or even at least 95% identity with amino acids for mature polypeptide of SEQ ID NO: 5 in WO 2006/069289.

The composition described above may preferably comprise acid alpha-amylase present in an amount of 0.01 to 10 AFAU/g DS, preferably 0.1 to 5 AFAU/g DS, more preferably 0.5 to 3 AFAU/AGU, and most preferably 0.3 to 2 AFAU/g DS. The dosage of the polypeptide composition of the invention and other conditions under which the composition is used may be determined on the basis of methods known in the art.

The polypeptide compositions may be prepared in accordance with methods known in the art and may be in the form of a liquid or a dry composition. For instance, the polypeptide composition may be in the form of granulate or a microgranulate. The polypeptide to be included in the composition may be stabilized in accordance with methods known in the art.

The compositions may be a fermentation broth formulation or a cell composition, as described herein. Consequently, the present invention also relates to fermentation broth formulations and cell compositions comprising a polypeptide having cellulolytic enhancing activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

Uses

The present invention is also directed to methods for using the polypeptides having alpha-amylase activity, or compositions thereof.

The polypeptide or the composition of the present invention may be used in starch conversion, starch to sugar conversion and ethanol production etc, e.g., in liquefying and/or saccharifying a gelatinized starch or a granular starch, as well as a partly gelatinized starch. A partly gelatinized starch is a starch which to some extent is gelatinized, i.e., wherein part of the starch has irreversibly swelled and gelatinized and part of the starch is still present in a granular state. It can be used in a process for liquefying starch, wherein a gelatinized or granular starch substrate is treated in aqueous medium with the enzyme. The polypeptide or the composition of the present invention may also be used in a process for saccharification of a liquefied starch substrate. A preferred use is in a fermentation process wherein a starch substrate is liquefied and/or saccharified in the presence of the polypeptide or the composition of the present invention to produce glucose and/or maltose suitable for conversion into a fermentation product by a fermenting organism, preferably a yeast. Such fermentation processes include a process for producing ethanol for fuel or drinking ethanol (portable alcohol), a process for producing a beverage, a process for producing desired organic compounds, such as citric acid, itaconic acid, lactic acid, gluconic acid, sodium gluconate, calcium gluconate, potassium gluconate, glucono delta lactone, or sodium erythorbate; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

Furthermore, due to the superior hydrolysis activity of the polypeptide of the first aspect the amount of glucoamylase during the saccharification step can be reduced. The glucoamylase may preferably be derived from a strain within *Aspergillus* sp., *Artomyces* sp., *Gloeophyllum* sp., *Pachykytospora* sp., *Pycnoporus* sp., *Nigrofomes* sp., or *Talaromyces* sp., *Trametes* sp., more preferably from *Aspergillus niger*, *Talaromyces emersonii*, *Trametes cingulata* or *Pachykytospora papyracea*.

In a preferred embodiment, the polypeptide of the present invention is used in a process comprising fermentation to produce a fermentation product, e.g., ethanol, from a gelatinized starch. Such a process for producing ethanol from gelatinized starch by fermentation comprises: (i) liquefying the gelatinized starch with a polypeptide with alpha-amylase activity of the present invention; (ii) saccharifying the liquefied mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In another preferred embodiment, the polypeptide of the present invention is used in a process comprising fermentation to produce a fermentation product, e.g., ethanol, from an ungelatinized ("raw") starch. Such a process for producing ethanol from ungelatinized starch-containing material by fermentation comprises: (i) contacting the ungelatinized starch with a polypeptide with alpha-amylase activity of the present invention to degrade the ungelatinized starch; (ii) saccharifying the mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In further embodiments, the polypeptide of the present invention may also be useful in textile, fabric or garment desizing or washing, in baking, detergent and pulp and paper production.

Signal Peptide

The present invention also relates to an isolated polynucleotide encoding a signal peptide comprising or consisting of 1 to 18 of SEQ ID NO: 2, amino acids 1 to 28 of SEQ ID NO: 4, amino acids 1 to 19 of SEQ ID NO: 6, amino acids 1 to 20 of SEQ ID NO: 8, amino acids 1 to 22 of SEQ ID NO: 10, amino acids 1 to 19 of SEQ ID NO: 12, amino acids 1 to 20 of SEQ ID NO: 14, amino acids 1 to 25 of SEQ ID NO: 16, amino acids 1 to 21 of SEQ ID NO: 18, amino acids 1 to 16 of SEQ ID NO: 20, amino acids 1 to 25 of SEQ ID NO: 22, amino acids 1 to 19 of SEQ ID NO: 24, amino acids 1 to 20 of SEQ ID NO: 26, amino acids 1 to 21 of SEQ ID NO: 28, amino acids 1 to 24 of SEQ ID NO: 30, or amino acids 1 to 20 of SEQ ID NO: 32. The present invention also relates to an isolated polynucleotide encoding a signal peptide comprising or consisting of 1 to 18 of SEQ ID NO: 2, amino acids 1 to 28 of SEQ ID NO: 4, amino acids 1 to 19 of SEQ ID NO: 6, amino acids 1 to 20 of SEQ ID NO: 8, amino acids 1 to 22 of SEQ ID NO: 10, amino acids 1 to 19 of SEQ ID NO: 12, amino acids 1 to 20 of SEQ ID NO: 14, amino acids 1 to 25 of SEQ ID NO: 16, amino acids 1 to 21 of SEQ ID NO: 18, amino acids 1 to 16 of SEQ ID NO: 20, amino acids 1 to 25 of SEQ ID NO: 22, amino acids 1 to 19 of SEQ ID NO: 24, amino acids 1 to 20 of SEQ ID NO: 26, amino acids 1 to 21 of SEQ ID NO: 28, amino acids 1 to 24 of SEQ ID NO: 30, or amino acids 1 to 20 of SEQ ID NO: 32. The polynucleotides may further comprise a gene encoding a protein, which is operably linked to the signal peptide. The protein is preferably foreign to the signal peptide. In one aspect, the polynucleotide encoding the signal peptide is nucleotides 1 to 54 of SEQ ID NO: 1, nucleotides 1 to 84 of SEQ ID NO: 3, nucleotides 1 to 57 of SEQ ID NO: 5, nucleotides 1 to 60 of SEQ ID NO: 7, nucleotides 1 to 66 of SEQ ID NO: 9, nucleotides 1 to 57 of SEQ ID NO: 11, nucleotides 1 to 62 of SEQ ID NO: 13, nucleotides 1 to 75 of SEQ ID NO: 15, nucleotides 1 to 63 of SEQ ID NO: 17, nucleotides 1 to 48 of SEQ ID NO: 19, nucleotides 1 to 75 of SEQ ID NO: 21, nucleotides 1 to 57 of SEQ ID NO: 23, nucleotides 1 to 60 of SEQ ID NO: 25, nucleotides 1 to 63 of SEQ ID NO: 27, nucleotides 1 to 72 of SEQ ID NO: 29, or nucleotides 1 to 60 of SEQ ID NO: 31. The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Thermoascus aurantiacus* (NN044936) was used as the source of polypeptides having amylase activity. NN044936 was isolated from a soil sample collected from China by the dilution plate method with PDA medium at 45° C. It was then purified by transferring a single conidium onto a YG agar plate. The strain NN044936 was identified as *Thermoascus aurantiacus*, based on both morphological characteristics and ITS rDNA sequence.

*Talaromyces emersonii* (NN051602) was used as the source of polypeptides having amylase activity. NN051602 was isolated from a compost sample from China. It was isolated using a single spore isolation technique on PDA plate under 45° C. The strain NN051602 was identified as *Talaromyces emersonii* (alternative name: *Penicillium emersonii*), based on both morphological characteristics and ITS rDNA sequence.

*Humicola insolens* (NN047338) was used as the source of polypeptides having amylase activity. NN047338 was isolated from a soil sample collected from China by the dilution plate method with PDA medium at 45° C. It was then purified by transferring a single conidium onto a YG agar plate. The strain NN047338 was identified as *Humicola insolens*, based on both morphological characteristics and ITS rDNA sequence.

*Myceliophthora fergusii* (NN000308) was used as the source of polypeptides having amylase activity. NN000308 was purchased from Centraalbureau voor Schimmelcultures named as CBS174.70. The strain NN000308 was identified as *Corynascus thermophilus* (previously identified as

*Thielavia thermophila*, —syn. *Myceliophthora fergusii*), based on both morphological characteristics and ITS rDNA sequence.

Media and Solutions

YG agar plates were composed of 5.0 g of yeast extract, 10.0 g of glucose, 20.0 g of agar, and deionized water to 1 liter.

YMD medium was composed of 0.3% yeast extract, 0.5% peptone, of 0.3% malt extract and 5% maltodextrin.

PDA agar plates were composed of potato infusion (potato infusion was made by boiling 300 g of sliced (washed but unpeeled) potatoes in water for 30 minutes and then decanting or straining the broth through cheesecloth). Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

YPG medium contained 0.4% of yeast extract, 0.1% of $KH_2PO_4$, 0.05% of $MgSO_4.7H_2O$, 1.5% glucose in deionized water.

COVE-N-gly slants were composed of 218 g sorbitol, 10 g glycerol, 2.02 g KNOB, 50 ml COVE salt solution, 25 g agar powder and deionized water to 1 liter.

COVE plates for protoplast regeneration were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, were added.

COVE top agarose were composed of 342.3 g sucrose, 20 ml COVE salt solution, 6 g GTG agarose (SeaKem, Cat #50070) and deionized water to 1 liter. The medium was sterilized by autoclaving at 15 psi for 15 minutes (Bacteriological Analytical Manual, 8th Edition, Revision A, 1998). The medium was cooled to 60° C., and 10 mM acetamide and 15 mM CsCl were added.

COVE-2 plate for isolation were composed of 30 g sucrose, 20 ml COVE salt solution, 30 g agar powder and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide was added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionized water to 1 liter.

MD medium was composed of 1.34% YNB (Yeast Nitrogen Base), $4\times10^{-5}$% biotin and 2% dextrose. For plates, 7.5 g agar was added to 200 ml of water autoclave, cooled to 60° C. and then 25 ml of 10×YNB, 25 ml of 10× D-glucose and 400 μl of 500× biotin were added.

BMSY was composed of 1% yeast extract, 2% peptone (Bacto), 100 mM potassium phosphate buffer, pH 6.0, 1.34% YNB, $4\times10^{-5}$% biotin and 1.82% Sorbitol.

10 g of yeast extract, 20 g peptone (Bacto) and 18.2 g Sorbitol were dissolved in 800 ml water and autoclaved for 20 minutes on liquid cycle. When the autoclaved medium was cooled to room temperature, 100 ml of 1 M potassium phosphate buffer (pH 6.0) and 100 ml of 10×YNB and 2 ml of 500× biotin were added.

Determination of Alpha-Amylase Activity

The activity of any acid alpha-amylase may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, i.e., acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

Reaction condition: 10 microliters standard or enzyme sample, 70 microliters $H_2O$, and 80 microliters starch working solution (The final concentration was starch 0.35 g/L, Acetate buffer 50 mM pH 5.0, NaCl 0.1 M, $CaCl_2$ 3 mM) mixed and react for 2 minutes with shaking at 37° C. Add 40 microliters Iodine working solution (the final iodine concentration was 0.04 g/L) and react at 37° C. for 1 minute. Reading $OD_{590}$ (Before reading, shaking 10 seconds).

FUNGAMYL™ (available from Novozymes A/S) is used as standard.

Example 1: *Thermoascus aurantiacus* Genomic DNA Extraction

*Thermoascus aurantiacus* strain NN044936 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 2: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, geneID (Parra et al., 2000, Genome Research 10(4):511-515) was used for gene prediction. BlastalI version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH13 amylase enzyme candidates were identified directly by analysis of the Blast results. Agene (Munch and Krogh, 2006, BMC Bioinformatics 7:263) and SignalP (Nielsen et al., 1997, Protein Engineering 10: 1-6) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

Three annotated alpha-amylase genes (shown in table 1) were selected for expression cloning.

TABLE 1

| Alpha-amylase genes from *Thermoascus aurantiacus* | | |
| --- | --- | --- |
| PE number | Gene name | DNA sequence |
| PE04100002473 | AM44936-1 | SEQ ID NO: 1 |
| PE04100002262 | AM44936-4 | SEQ ID NO: 3 |
| PE04100002588 | AM44936-3 | SEQ ID NO: 5 |

Example 3: Cloning of 3 Alpha-Amylase Genes from the *Thermoascus aurantiacus* Genomic DNA Based on the DNA information obtained from genome sequencing, oligonucleotide primers, shown below in table 2, were designed to amplify the 3 alpha-amylase genes (SEQ ID NO: 1, 3, 5) from the genomic DNA of *Thermoascus aurantiacus* NN044936. Primers were synthesized by Invitrogen (Invitrogen, Beijing, China).

TABLE 2

| Primers to amplify full-length amylase genes from *Thermoascus aurantiacus* genomic DNA | | |
| --- | --- | --- |
| Related SEQ ID | Primer name | Sequence (5'-3') |
| Ta 1_forward (SEQ ID NO: 33) | AM44936-1_C505_bam | acacaactggggatccacc ATGAAGTTTTCCGTACTCTTTA CAAGTGC |
| Ta 1_reverse (SEQ ID NO: 34) | AM44936-1_C505_xho | ccctctagatctcgag AATTTCAACGACCACATATACC CG |
| Ta 2 _forward (SEQ ID NO: 35) | AM44936-4_P355_BamH | acacaactggggatcc acc ATGGTCAAGATGTTTGGGTCAC G |
| Ta 2_reverse (SEQ ID NO: 36) | AM44936-4_P355_BglII | gtcaccctctagatctcgag CCCAGTGATCCTCCCGATCCTA TA |
| Ta 3 _forward (SEQ ID NO: 37) | AM44936-3_C505_BamHI | acacaactggggatcc acc ATGGAAGTGTGGAAGATAGTGC T |
| Ta 3_reverse (SEQ ID NO: 38) | AM44936-3_C505_XhoI | ccctctagatctcgag TGCTTTCCCCGTCAGAACA |

Upper characters represent the 5'- and 3'-regions of the genes to be amplified, while lower cases were homologous to the vector sequences at insertion sites of pCaHj505 vector. The expression vector pCaHj505 contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amdS+ *Aspergillus* transformant. pCaHj505 was described in WO 98/11203.

For each gene, 20 pmol of primer pair (each of the forward and reverse) were used in a PCR reaction composed of 2 µl of *Thermoascus aurantiacus* NN044936 genomic DNA, 10 µl of 5× GC Buffer, 1.5 µl of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR products were isolated by 0.7% agarose gel electrophoresis using 90 mM Tris-borate and 1 mM EDTA (TBE) buffer where product bands at expected size of each PCR reaction were visualized under UV light. The PCR products were then purified from solution by using a GFX PCR DNA and Gel Band Purification Kit (GE Healthcare, Buckinghamshire, UK) according to the manufacturer's instructions.

TABLE 3

| Size of PCR products in Example 3 | |
| --- | --- |
| Gene name | Size of PCR product |
| AM44936-1 | 1.8 kb |
| AM44936-4 | 1.8 kb |
| AM44936-3 | 2.4 kb |

Plasmid pCaHj505 was digested with BamHI and XhoI, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

An IN-FUSION™ CF Dry-down Cloning Kit (Clontech Laboratories, Inc., Mountain View, Calif., USA) was used to clone the fragment directly into the expression vector pCaHj505.

The PCR products and the digested vector were ligated together using an IN-FUSION™ CF Dry-down Cloning Kit (Clontech Laboratories, Inc., Mountain View, Calif., USA) resulting in plasmids in table 4 respectively, in which transcription of *Thermoascus aurantiacus* alpha-amylase genes was under the control of a TAKA-amylase promoter from *Aspergillus oryzae*. The cloning operation was according to the manufacturer's instruction. In brief, for each ligation reaction 30 ng of with BamHI and XhoI digested pCaHj505 and 60 ng of purified PCR products were added to the reaction vial and resuspended with the powder in a final volume of 10 µl with addition of deionized water. The reactions were incubated at 37° C. for 15 minutes and then 50° C. for 15 minutes. Three microliters of the reaction products were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAM44936-1_C505, pAM44936-4_C505 and pAM44936-3_C505 for expression in *A. niger* were extracted from correct *E. coli* transformants, by using a QIAprep Spin Miniprep Kit (QIAGEN Inc., Valencia, Calif., USA).

TABLE 4

Plasmid (expression constructs)

| Gene name | Plasmid |
| --- | --- |
| AM44936-1 | pAM44936-1_C505 |
| AM44936-4 | pAM44936-4_C505 |
| AM44936-3 | pAM44936-3_C505 |

Example 4: *Talaromyces emersonii* Genomic DNA Extraction

*Talaromyces emersonii* strain NN051602 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 5: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, geneID (Parra et al., 2000, Genome Research 10(4):511-515) was used for gene prediction. BlastalI version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH13 amylase enzyme candidates were identified directly by analysis of the Blast results. Agene (Munch and Krogh, 2006, BMC Bioinformatics 7:263) and SignalP (Nielsen et al., 1997, Protein Engineering 10: 1-6) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

Seven annotated alpha-amylase genes (shown in table 5) were selected for expression cloning.

TABLE 5

Alpha-amylase genes from *Talaromyces emersonii*

| PE number | Gene name | DNA sequence |
| --- | --- | --- |
| PE04230001317 | AM51602-2 | SEQ ID NO: 7 |
| PE04230004150 | AM51602-1 | SEQ ID NO: 9 |
| PE04230000784 | AM51602-7 | SEQ ID NO: 11 |
| PE04230003498 | AM51602-3 | SEQ ID NO: 13 |
| PE04230005951 | AM51602-4 | SEQ ID NO: 15 |
| PE04230002553 | AM51602-5 | SEQ ID NO: 17 |
| PE04230002139 | AM51602-6 | SEQ ID NO: 19 |

Example 6: Cloning of 6 Alpha-Amylase Genes from the *Talaromyces emersonii* Genomic DNA Based on the DNA information obtained from genome sequencing, oligonucleotide primers, shown below in table 6, were designed to amplify the 6 alpha-amylase genes (SEQ ID NOs: 7, 11, 13, 15, 17 and 19) from the genomic DNA of *Talaromyces emersonii* NN051602. Primers were synthesized by Invitrogen (Invitrogen, Beijing, China).

TABLE 6

Primers to amplify full-length six amylase genes from *Talaromyces emersonii* genomic DNA

| Related SEQ ID | Primer name | Sequence (5'-3') |
| --- | --- | --- |
| Te 1_forward (SEQ ID NO: 39) | AM51602-2_C505_bam | acacaactggggatcc acc ATGAAATTCCCAACGTCCATCG |
| Te 1_reverse (SEQ ID NO: 40) | AM51602-2_C505_xho | ccctctagatctcgag ATTTACAGCACAATCACGGCAG ATATG |
| Te 3_forward (SEQ ID NO: 41) | AM51602-7_P355_bam | acacaactggggatcc acc ATGCTGTCGTTTATCCTTGCAG TTTTC |
| Te 3_reverse (SEQ ID NO: 42) | AM51602-7_C505_bam | acacaactggggatcc acc ATGCTGTCGTTTATCCTTGCAG TTT |
| Te 4_forward (SEQ ID NO: 43) | AM51602-7_C505_xho | ccctctagatctcgag TTACGACTGACACAGCTTGCCC |
| Te 4_reverse (SEQ ID NO: 44) | AM51602-3_C505_xho | ccctctagatctcgag ACCTTTTAGAAGGGAAAGCCCA TG |
| Te 5_forward (SEQ ID NO: 45) | AM51602-4_C505_bam | acacaactggggatcc acc ATGGCGCCCCCTTGGA |
| Te 5_reverse (SEQ ID NO: 46) | AM51602-4_C505_xho | ccctctagatctcgag ACCATCACAACAGAGTCATCTC CATC |
| Te 6_forward (SEQ ID NO: 47) | AM51602-5_C505_bam | acacaactggggatcc acc ATGAAGTTGCCCCTGTTTATTG CAAG |
| Te 6_reverse (SEQ ID NO: 48) | AM 51602-5_C505_xho | ccctctagatctcgag ACTGTTACAGATCACACAACCC TGAGC |
| Te 7_forward (SEQ ID NO: 49) | AM51602-6_C505_bam | acacaactggggatcc acc ATGACGCCTTTCGTCCTGCT |
| Te 7_reverse (SEQ ID NO: 50) | AM 51602-6_C505_xho | ccctctagatctcgag ACTATCTCCATGTGTCGACAAT CGTCT |

Upper characters represent the 5'- and 3'-regions of the genes to be amplified, while lower cases were homologous to the vector sequences at insertion sites of pCaHj505 vector. The expression vector pCaHj505 contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amds+*Aspergillus* transformant.

For each gene, 20 pmol of primer pair (each of the forward and reverse) were used in a PCR reaction composed of 2 μl of *Talaromyces emersonii* NN051602 genomic DNA, 10 μl of 5× GC Buffer, 1.5 μl of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 μl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR products were isolated by 0.7% agarose gel electrophoresis using 90 mM Tris-borate and 1 mM EDTA (TBE) buffer where product bands at expected size of each PCR reaction were visualized under UV light. The PCR products were then purified from solution by using a GFX PCR DNA and Gel Band Purification Kit (GE Healthcare, Buckinghamshire, UK) according to the manufacturer's instructions.

Size of PCR Products

| Gene name | SEQ ID NO. of the gene | Size of PCR product |
|---|---|---|
| AM51602-2 | SEQ ID NO: 7 | 1.7 kb |
| AM51602-7 | SEQ ID NO: 11 | 2.0 kb |
| AM51602-3 | SEQ ID NO: 13 | 2.4 kb |
| AM51602-4 | SEQ ID NO: 15 | 2.4 kb |
| AM51602-5 | SEQ ID NO: 17 | 1.7 kb |
| AM51602-6 | SEQ ID NO: 19 | 2.4 kb |

Plasmid pCaHj505 was digested with BamHI and XhoI, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

An an IN-FUSION™ CF Dry-down Cloning Kit (Clontech Laboratories, Inc., Mountain View, Calif., USA) was used to clone the fragment directly into the expression vector pCaHj505.

The PCR products and the digested vector were ligated together using an IN-FUSION™ CF Dry-down Cloning Kit (Clontech Laboratories, Inc., Mountain View, Calif., USA) resulting in plasmids in table 7 respectively, in which transcription of *Talaromyces emersonii* alpha-amylase genes was under the control of a TAKA-amylase promoter from *Aspergillus oryzae*. The cloning operation was according to the manufacturer's instruction. In brief, for each ligation reaction 30 ng of with BamHI and XhoI digested pCaHj505 and 60 ng of purified PCR products were added to the reaction vial and resuspended with the powder in a final volume of 10 μl with addition of deionized water. The reactions were incubated at 37° C. for 15 minutes and then 50° C. for 15 minutes. Three microliters of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAM51602-2_C505, pAM51602-7_C505, pAM51602-3_C505, pAM51602-4_C505, pAM51602-5_C505 and pAM51602-6_C505 for expression in *A. niger* were extracted from correct *E. coli* transformants, by using a QIAprep Spin Miniprep Kit (QIAGEN Inc., Valencia, Calif., USA).

TABLE 7

| Plasmid (expression constructs) | |
|---|---|
| Gene name | Plasmid |
| AM51602-2 | pAM51602-2_C505 |
| AM51602-7 | pAM51602-7_C505 |
| AM51602-3 | pAM51602-3_C505 |
| AM51602-4 | pAM51602-4_C505 |
| AM51602-5 | pAM51602-5_C505 |
| AM51602-6 | pAM51602-6_C505 |

Example 7: Expression of *Talaromyces emersonii* Alpha-Amylase Genes in *Aspergillus niger*

An agar slant (COVE-N-gly) was inoculated with spores of *Aspergillus niger* HowB112, and grown at 32° C. until it was completely sporulated. The spores were resuspended in 5-10 ml of sterile 0.05% tween20 water. About $10^8$ spores were transferred to a 500 ml baffled shake flask containing 100 ml YPG medium with 10 mM $NaNO_3$, and incubated at 32° C. for 16 hours at 99 rpm in Innova shaker. Then the mycelia were harvested for protoplasts preparation. *Aspergillus niger* HowB112 protoplasts preparation and transformation were done according to the method described in patent WO 2004/111218 or EP 238023. Ten micrograms of pAM51602-2_0505, pAM51602-7_0505, pAM51602-3_0505, pAM51602-4_0505, pAM51602-5_0505 and pAM51602-6_0505 each were used to transform *Aspergillus niger* HowB112 separately.

The *Aspergillus niger* HowB112 transformants with pAM51602-2_C505, pAM51602-7_C505, pAM51602-3_C505, pAM51602-4_C505, pAM51602-5_C505 or pAM51602-6_C505 were selected on the COVE plates for protoplast regeneration (described in the Media and Solution part). About 15 transformants were observed on the selective plates for each transformation. Six transformants from each transformation were isolated on COVE-2 plate for 3-4 days at 32° C.

After isolation those six transformants for each transformation were inoculated separately into 3 ml of YMD medium in 24-well plate and incubated at 30° C., 220 rpm. After 3 days incubation, 20 μl of supernatant from each culture were analyzed on NuPAGE Novex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). SDS-PAGE profiles of the cultures showed that they had the excepted protein bands of expression products of pAM51602-2, pAM51602-7, pAM51602-3, pAM51602-4, pAM51602-5 and pAM51602-6. The expression product numbers and expression strain numbers of those six genes were shown in table 8.

TABLE 8

| Expression strains | | | |
|---|---|---|---|
| Expression construct | Expression product | Expression strain | protein |
| pAM51602-2_C505 | P2459F | O5MXA | SEQ ID NO: 8 |
| pAM51602-7_C505 | P2454N | | |
| pAM51602-3_C505 | P245A1 | O5MX9 | SEQ ID NO: 14 |
| pAM51602-4_C505 | P245A2 | O5MX8 | SEQ ID NO: 16 |
| pAM51602-5_C505 | P245A3 | | |
| pAM51602-6_C505 | P245A4 | O5MX7 | SEQ ID NO: 20 |

Example 8: Fermentation of *A. niger* Expression Strains

A slant of each expression strain in table 8 was washed with 10 ml of YMD and inoculated into a 2 liter flask containing 400 ml of YMD medium to generate broth for characterization of the enzyme. The culture was incubated at 30° C. on shaker at 150 rpm. The culture was harvested on day 3 and filtered using a 0.45 µm DURAPORE Membrane (Millipore, Bedford, Mass., USA). The filtered culture broth was used for enzyme characterization.

Example 9: Characterization of the Alph-Amylase Expressed by O5MXA

The culture supernatant was firstly precipitated by ammonium sulfate, then dialysized to 20 mM NaAc at pH5.5. Dialysized sample was loaded into 30 ml SEPHAROSE Fast Flow (GE Healthcare), equilibrated with 20 mM NaAc at pH5.5. Then the protein was eluted with a linear sodium chloride (0-1000 mM). Fractions from the column were analyzed for amylase activity.

The fractions with amylase activity were pooled and dialysized again to 20 mM NaAc at pH5.5 and loaded into MonoQ column (GE Healthcare), equilibrated with 20 mM NaAc at pH5.5. Then the protein was eluted with a linear sodium chloride (0-1000 mM). Fractions from the column were analyzed for amylase activity Fractions with amylase activity were checked by SDS-PAGE and the pure fractions were pooled. The SDS-PAGE showed the molecular weight of the alph-amylase expressed by O5MXA (corresponding to the molecular weight of the mature polypeptide of SEQ ID NO: 8) was about 60 kDa.

The alpha-amylase as purified was characterized according to the following methods.

AZCL-HE-Amylose Assay

Two microliters of alpha-amylase samples (0.5 mg/ml) and 100 µl 0.2% AZCL-HE-amylose (Megazyme International Ireland Ltd.) at pH4.3 were mixed separately in a Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. Optical density at 595 nm ($OD_{595}$) was read as a measure of amylase activity. Each reaction was done with triplicate and a buffer blind was included in the assay (instead of alpha-amylase).

pH Profile

Two microliter alpha-amylase samples and 40 µl 1% AZCL-HE-amylose in 100 µl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, and 10.0 with HCl or NaOH were mixed in an Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. $OD_{595}$ was read as a measure of amylase activity. Each reaction was done with triplicate and a buffer blind was included in the assay (instead of alpha-amylase).

As shown in table 9, the optimal pH for this amylase is pH5.0, but this amylase shows high activity at pH4.0. The highest activity at pH5.0 was set as 100%.

TABLE 9

| pH profile of the alpha-amylase | | | | | | | | | |
|---|---|---|---|---|---|---|---|---|---|
| pH | 2 | 3 | 4 | 5 | 6 | 7 | 8 | 9 | 10 |
| alph-amylase expressed by O5MXA (relative activity) | 13.9 | 13.1 | 85 | 100 | 70.2 | 46.5 | 18.4 | 13.9 | 11.1 | pH Stability

Two microliters of alpha-amylase sample was added into 100 µl buffer (100 mM Na-acetate) at pH4.0, incubated at 40° C. for 0, 10, 30, 60 and 120 mins. The alpha-amylase sample was added into 40 µl of 1% AZCL-HE-amylose in water at 40° C. for 20 min, 60 µl taken for $OD_{595}$. As shown in table 10, this amylase is not very stable at pH4.0 after 30 min incubation, but it might work well at the application condition. The activity at 0 min set as 100%, and others show the residual activity.

TABLE 10

| pH stability of the alpha-amylase | | | | | |
|---|---|---|---|---|---|
| Time (mins) | 0 | 10 | 30 | 60 | 120 |
| alpha-amylase expressed by O5MXA (relative activity) | 100 | 84.5 | 21.4 | 11.5 | 13 |

Temperature Profile

Two microliters of alpha-amylase sample was added into 100 µl buffer (50 mM NaAc) at pH 4.3 containing 0.2% AZCL-HE-amylose, incubating for 20 mins at different temperature and 60 µl supernatant was taken for $OD_{595}$.

As shown in table 11, alph-amylase expressed by O5MXA works well at low temperature. The highest activity at 40° C. was set as 100%.

TABLE 11

| Temperature profile of the alpha-amylase | | | | | | | | |
|---|---|---|---|---|---|---|---|---|
| Temperature (° C.) | 20 | 30 | 40 | 50 | 60 | 70 | 80 | 90 |
| alph-amylase expressed by | 56.7 | 91.2 | 100 | 84.7 | 39 | 17.7 | 14.1 | 11.6 |

TABLE 11-continued

Temperature profile of the alpha-amylase

| Temperature (° C.) | 20 | 30 | 40 | 50 | 60 | 70 | 80 | 90 |
|---|---|---|---|---|---|---|---|---|
| O5MXA (relative activity) | | | | | | | | |

Temperature Stability

Two microliter alpha-amylase sample was added into 100 µl 50 mM NaAc at pH4.3 and incubated at 50° C. for 0, 10, 30, 60 and 120 mins, then they were put on ice at each time point. 40 µl 1% AZCL-HE-amylose in water was added at 37° C. for 20 mins, 60 µl taken for $OD_{595}$.

This amylase shows relative thermostability at 50° C. as table shown 12. At beginning the activity was set as 100%, and residual activities were shown at other time points.

TABLE 12

Temperature stability of the alpha-amylase

| Time (mins) | 0 | 10 | 30 | 60 | 120 |
|---|---|---|---|---|---|
| alpha-amylase expressed by O5MXA (relative activity) | 100 | 95.5 | 71.5 | 17.9 | 10.3 |

Example 10: Characterization of the Alph-Amylase Expressed by O5MX9

The culture supernatant was firstly precipitated by ammonium sulfate, then dialysized to 20 mM NaAc at pH5.0. Dialysized sample was loaded into 30 ml Q SEPHAROSE Fast Flow (GE Healthcare), equilibrated with 20 mM NaAc at pH5.0. Then the protein was eluted with a linear sodium chloride (0-1000 mM). Fractions from the column were analyzed for amylase activity.

The fractions with amylase activity were pooled and dialysized again to 20 mM NaAc at pH5.0 and loaded into MONOQ column (GE Healthcare), equilibrated with 20 mM NaAc at pH5.0. Then the protein was eluted with a linear sodium chloride (0-1000 mM). Fractions from the column were analyzed for amylase activity.

Fractions with amylase activity were checked by SDS-PAGE and the pure fractions were pooled. The SDS-PAGE showed the molecular weight of alph-amylase expressed by O5MX9 (corresponding to the molecular weight of the mature polypeptide of SEQ ID NO: 14) was about 62 kDa.

The alpha-amylase as purified was characterized according to the following methods.

AZCL-HE-amylose Assay

Two microliter alpha-amylase samples (0.5 mg/ml) and 100 µl 0.2% AZCL-HE-amylose (Megazyme International Ireland Ltd.) at pH4.3 were mixed separately in a Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. $OD_{595}$ was read as a measure of amylase activity. Each reaction was done with triplicate and a buffer blind was included in the assay (instead of alpha-amylase).

pH Profile

Two microliter alpha-amylase samples and 40 µl 1% AZCL-HE-amylose in 100 µl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, and 10.0 with HCl or NaOH were mixed in an Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. $OD_{595}$ was read as a measure of amylase activity. Each reaction was done with triplicate and a buffer blind was included in the assay (instead of alpha-amylase).

As shown in table 13, the optimal pH for this amylase is pH5.0, but this amylase has high activity at pH4.0.

TABLE 13 pH Profile of the alpha-amylase

| pH | 2 | 3 | 4 | 5 | 6 | 7 | 8 | 9 | 10 |
|---|---|---|---|---|---|---|---|---|---|
| alph-amylase expressed by O5MXA9 (relative activity) | 12.4 | 11.6 | 88.9 | 100 | 74.2 | 52.7 | 20.4 | 13.6 | 10.4 | pH Stability

Two microliter alpha-amylase sample was added into 100 µl buffer (100 mM Na-acetate) at pH4.0, incubated at 40° C. for 0, 10, 30, 60 and 120 mins. The alpha-amylase sample was added into 40 µl 1% AZCL-HE-amylose in water at 40° C. for 20 min, 60 µl taken for $OD_{595}$. As shown in table 14, this amylase is not very stable at pH4.0 after 30 min incubation, but it might work well at the real application condition.

TABLE 14 pH stability of the alpha-amylase

| Time (mins) | 0 | 10 | 30 | 60 | 120 |
|---|---|---|---|---|---|
| alpha-amylase expressed by O5MX9 (relative) | 100 | 92.4 | 25 | 10.7 | 9.7 |

Temperature Profile

Two microliter alpha-amylase sample was added into 100 µl buffer (50 mM NaAc) at pH 4.3 containing 0.2% AZCL-HE-amylose, incubating for 20 mins at different temperatures and 60 µl supernatant was taken for $OD_{595}$.

As shown in table 15, alph-amylase expressed by the alph-amylase expressed by O5MX9 works well at low temperature as table shown, and its optimal temperature is 50° C.

TABLE 15

Temperature profile of the alpha-amylase

| Temperature (° C.) | 20 | 30 | 40 | 50 | 60 | 70 | 80 | 90 |
|---|---|---|---|---|---|---|---|---|
| alph-amylase expressed by O5MX9 (relative activity) | 39.3 | 75.7 | 82.8 | 100 | 44.2 | 8.9 | 14.3 | 11.4 |

Temperature Stability

Two microliter alpha-amylase sample was added into 100 µl 50 mM NaAc at pH4.3 and incubated at 50° C. for 0, 10, 30, 60 and 120 mins, then they were put on ice at each time point. 40 μl % AZCL-HE-amylose in water was added at 37° C. for 20 mins, 60 μl taken for $OD_{595}$.

This amylase shows relative thermostability at 50° C. as shown table 16.

TABLE 16

Temperature stability of the alpha-amylase

| Time (mins) | 0 | 10 | 30 | 60 | 120 |
|---|---|---|---|---|---|
| alpha-amylase expressed by O5MX9 (relative acitivity) | 100 | 90.3 | 64.9 | 16.1 | 12.5 |

Example 11: Characterization of the Alph-Amylase Expressed by O5MX7

The culture supernatant was firstly precipitated by ammonium sulfate, then dialysized to 20 mM NaAc at pH4.5. Dialysized sample was loaded into 30 ml beta-cyclodextrin linked SEPHAROSE (GE Healthcare), equilibrated with 20 mM NaAc at pH4.5 Then the protein was eluted with a linear beta-cyclodextrin (0-2 mM). Fractions from the column were analyzed for amylase activity.

Fractions with amylase activity were checked by SDS-PAGE and the pure fractions were pooled. The SDS-PAGE showed the molecular weight of the alph-amylase expressed by O5MX7 (corresponding to the molecular weight of the mature polypeptide of SEQ ID NO: 20) was about 80 kDa.

The alpha-amylase as purified was characterized according to the following methods.

AZCL-HE-Amylose Assay

Two microliter alpha-amylase samples (0.5 mg/ml) and 100 μl 0.2% AZCL-HE-amylose (Megazyme International Ireland Ltd.) at pH4.3 were mixed separately in a Microtiter plate and placed on ice before reaction. The assay was initiated by transferring the Microtiter plate to an EPPENDORF thermomixer, which was set to the assay temperature 40° C. Then 60 μl supernatant was transferred to a new microtiter plate. $OD_{595}$ was read as a measure of amylase activity. Each reaction was done with triplicate and a buffer blind was included in the assay (instead of alpha-amylase).

pH Profile

Two microliters of alpha-amylase samples and 40 μl 1% AZCL-HE-amylose in 150 μl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, 10.0, and 11.0 with HCl or NaOH were mixed in an Microtiter plate and placed on ice before reaction. The assay was initiated by transferring the Microtiter plate to an EPPENDORF thermomixer, which was set to the assay temperature 40° C. Then 60 μl supernatant was transferred to a new microtiter plate. $OD_{595}$ was read as a measure of amylase activity. Each reaction was done with triplicate and a buffer blind was included in the assay (instead of alpha-amylase).

As shown in table 17, the optimal pH for this amylase is pH5.0, but this amylase has high activity at pH3.0 and 4.0, showing it is an acidic amylase.

TABLE 17 pH profile of the alpha-amylase

| pH | 2 | 3 | 4 | 5 | 6 | 7 | 8 | 9 | 10 | 11 |
|---|---|---|---|---|---|---|---|---|---|---|
| alpha-amylase expressed by O5MX7 (relative activity) | 13.2 | 81 | 93 | 100 | 79.5 | 61 | 39 | 24.4 | 16.8 | 14.5 | pH Stability

Two microliter alpha-amylase sample was added into 100 μl buffer (100 mM Na-acetate) at pH3.5, incubated at 40° C. for 0, 10, 30, 60 and 120 mins. The alpha-amylase was added into 40 μl 1% AZCL-HE-amylose in water at 40° C. for 20 min, 60 μl taken for $OD_{595}$.

This amylase is very stable at pH3.5, and even with higher activity at acidic condition as shown in table 18.

TABLE 18 pH stability of the alpha-amylase

| Time (mins) | 0 | 10 | 30 | 60 | 120 |
|---|---|---|---|---|---|
| alpha-amylase expressed by O5MX7 (relative activity) | 100 | 107.6 | 123.4 | 172.4 | 160.8 |

Temperature Profile

Two microliter alpha-amylase sample was added into 100 μl buffer (50 mM NaAc) at pH 4.3 containing 0.2% AZCL-HE-amylose, incubating for 20 mins at different temperature and 60 μl supernatant was taken for $OD_{595}$.

As shown in table 19, alph-amylase expressed by O5MX7 works well at high temperature, and its optimal temperature is 70° C.

TABLE 19

Temperature profile of the alpha-amylase

| Temperature (° C.) | 20 | 30 | 40 | 50 | 60 | 70 | 80 | 90 |
|---|---|---|---|---|---|---|---|---|
| alph-amylase expressed by O5MX7 (relative activity) | 42.6 | 60.2 | 68.6 | 67.4 | 81.4 | 100 | 43.7 | 18.3 |

Temperature Stability

Two micorliter alpha-amylase sample was added into 100 μl 50 mM NaAc at pH4.3 and incubated at 60° C. for 0, 10, 30, 60 and 120 mins, then they were put on ice at each time point. 40 μl 1% AZCL-HE-amylose in water was added at 40° C. for 20 mins, 60 μl taken for $OD_{595}$.

This amylase shows very stable at high temperature (60° C.), more than 80% activity was remain after 120 mins at 60° C. as shown in table 20.

TABLE 20

Temperature stability of the alpha-amylase

| Time (mins) | 0 | 10 | 30 | 60 | 120 |
|---|---|---|---|---|---|
| alpha-amylase expressed by O5MX7 (relative activity) | 100 | 87.6 | 79.3 | 83.9 | 80.9 |

Example 12: Preparation of *Talaromyces emersonii* Strain Total RNA and cDNA Total RNA was prepared from the powdered mycelia by using RNeasy plant mini kit (QIAGEN, Cat. No. 74904). The cDNA was synthesized by following the instruction of 3' Rapid Amplification of cDNA End System (Invitrogen Corp., Carlsbad, Calif., USA).

Example 13: Cloning of AM51602-1 (SEQ ID NO: 9) from the *Talaromyces emersonii* cDNA Based on the DNA information obtained from genome sequencing, oligonucleotide primers, shown below in table 21, were designed to amplify AM51602-1 (SEQ ID NO: 9), without transmembrane domain, from cDNA of *Talaromyces emersonii*. Primers were synthesized by Invitrogen (Invitrogen, Beijing, China).

TABLE 21

Primers to amplify AM51602-1 (SEQ ID NO: 9) from *Talaromyces emersonii* cDNA

| Related SEQ ID | Primer name | Sequence (5'-3') |
|---|---|---|
| Te 2_forward (SEQ ID NO: 51) | AM51602-1_ pLIZG9_Bam | attattcgaaggatcc aaa ATGAAGGGGCCGCG |
| Te 2_reverse (SEQ ID NO: 52) | AM51602- 1_pLIZG8_EcoRI | ggtgctgatggaattc agc TACACCGCAGAGGCCGCTT |

Upper characters represent the 5'- and 3'-regions of the genes to be amplified, while lower cases were homologous to the vector sequences at insertion sites of pLIZG8HQ vector. The expression vector pLIZG8HQ contained the α-factor secretion signal derived from *S. cerevisiae*, the 5'AOX1 promoter derived from *Pichia pastoris* and the 3'AOX1 alcohol oxidase1 terminator elements. Furthermore pLIZG8HQ had pBR322 derived sequences for selection and propagation in *E. coli*, and a His4 gene, which encoded an histidinol dehydrogenase derived from *Pichia pastoris* for selection of a transformant of a His mutant *Pichia* strain.

For each gene, 20 μmol of primer pair (each of the forward and reverse) were used in a PCR reaction composed of 2 μl of *Talaromyces emersonii* cDNA, 10 μl of 5× GC Buffer, 1.5 ul of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 μl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR product was isolated by 0.7% agarose gel electrophoresis using 90 mM Tris-borate and 1 mM EDTA (TBE) buffer where product bands at expected size of each PCR reaction were visualized under UV light. The 1.7 kb PCR product was purified from solution by using a GFX PCR DNA and Gel Band Purification Kit (GE Healthcare, Buckinghamshire, UK) according to the manufacturer's instructions.

Plasmid pLIZG8HQ was digested with BamHI and EcoRI, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

The PCR product and the digested vector pLIZG8HQ were ligated together using an IN-FUSION™ CF Dry-down Cloning Kit (Clontech Laboratories, Inc., Mountain View, Calif., USA) resulting in plasmid pAM51602-1_LIZG8. The cloning operation was according to the manufacturer's instruction. In brief, for each ligation reaction 30 ng of with BamHI and EcoRI digested pLIZG8HQ and 60 ng of purified PCR products were added to the reaction vial and resuspended with the powder in a final volume of 10 μl with addition of deionized water. The reactions were incubated at 37° C. for 15 minutes and then 50° C. for 15 minutes. Three microliters of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing under selection on the LB ampicillin plates. *E. coli* transformants containing expression constructs were detected by colony PCR and confirmed by DNA sequencing with vector primers (by SinoGenoMax Company Limited, Beijing, China). Plasmid DNA pAM51602-1_LIZG8 for expression in *Pichia. pastoris* was extracted from correct *E. coli* transformant, using a QIAprep Spin Miniprep Kit (QIAGEN Inc., Valencia, Calif., USA).

Example 14: Expression of AM51602-1 (SEQ ID NO: 9) in *Pichia pastoris*

*Pichia pastoris* Competent Cell Preparation

The $OD_{595}$ of the overnight culture of *Pichia pastoris* in YPD in shaking flask was 1.0. Cells were pelleted by centrifugation at 2000 rpm, 5 mins, 4° C. Cell pellet was then suspended in YPD plus 4-(2-hydroxyethyl)-1-piperazineethanesulfonic acid (HEPES) and Dithiothreitol (DTT) and stand at 30° C. for 15 mins. Cells were pelleted and washed with cold water and 1M sorbitol subsequently. Finally cells were suspended in small amount of 1M sorbitol and stored in 40 μl aliquots at −70° C.

Transformation of *Pichia pastoris* with pAM51602-1 LIZG8

Plasmid DNA pAM51602-1_LIZG8 was linearized with PmeI leading to insertion of the plasmid at the chromosomal 5'AOX1 locus. Linearized plasmid DNA (500 ng) was mixed with 40 μl of competent cells and stored on ice for 5 min. Cells were transferred to an ice-cold 0.2 cm electroporation cuvette. Transformation was performed using a Bio-Rad GenePulser II. Parameters used were 1500 V, 50 μF and 200Ω. Immediately after pulsing, cells were suspended in 1 ml of ice cold 1 M sorbitol. The mixtures were plated on MD plates. Plates were incubated at 28° C. for 3-4 days.

Screening Clones for Expression in Small Scale

Four candidate clones from each transformation were cultured in a 3 ml scale using 24-deep well plates (Whatman, UK). Cells were grown in BMSY media at 28° C. with vigorous shaking. After 2.5 days 0.5% methanol was added to the culture to induce heterologous gene expression. Culture was continuously grown for 4 days with a daily addition of 0.5% methanol under the same growth condition. Samples of culture were taken daily during induction and stored at −20° C. for SDS-PAGE analysis and amylase activity assay.

The culture broth showed amylase activity by testing against AZCL-amylose. 20 µl of culture supernatant was analyzed on NuPAGE Novex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). On SDS-PAGE culture showed a band of 65 kDa, corresponding to the theoretical molecular weight of expression product P241QD. This P241QD expressing *Pichia pastoris* strain was designated as O4S2F.

Example 15: Fermentation of *Pichia pastoris* Expression Strain O4S2F

Single colony of O4S2F was inoculated into a 2 liter flask containing 400 ml BMSY media to generate broth for characterization of the enzyme. The culture was incubated at 28° C. with vigorous shaking. After 2.5 days 0.5% methanol was added to the culture to induce heterologous gene expression. Culture was continuously grown for 4 days with a daily addition of 0.5% methanol under the same growth condition. The culture was harvested by centrifugation and filtered using a 0.45 µm DURAPORE Membrane (Millipore, Bedford, Mass., USA). The filtered culture broth was used for enzyme characterization.

Example 16: Characterization of the Alpha-Amylase Expressed by O4S2F

The pH of culture supernatant was adjusted to 7.0 with NaOH, and then filtered through a 0.45 µm filter. The solution was applied to a 40 ml Ni-SEPHAROSE High Performance column (GE Healthcare) equilibrated with 20 mM PBS containing 0.3 M NaCl at pH7.0. The protein was eluted with a linear imidazole gradient (0-500 mM). Fractions from the column were analyzed for amylase activity.

Fractions with amylase activity were checked by SDS-PAGE and the pure fractions were pooled. The SDS-PAGE showed the molecular weight of the alpha-amylase expressed by O4S2F (corresponding to the molecular weight of the mature polypeptide of SEQ ID NO: 10) was about 55 kDa.

The alpha-amylase as purified was characterized according to the following methods.

AZCL-HE-amylose Assay

Eight microliters of alpha-amylase samples (0.5 mg/ml) and 100 µl 0.2% AZCL-HE-amylose (Megazyme International Ireland Ltd.) at pH4.3 were mixed separately in a Microtiter plate and placed on ice before reaction. The assay was initiated by transferring the Microtiter plate to an EPPENDORF thermomixer, which was set to the assay temperature 40° C. Then 60 µl supernatant was transferred to a new microtiter plate. $OD_{595}$ was read as a measure of amylase activity. Each reaction was done with triplicate and a buffer blind was included in the assay (instead of enzyme).

pH Profile

Eight microliter alpha-amylase samples and 40 µl 1% AZCL-HE-amylose in 150 µl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, and 10.0 with HCl or NaOH were mixed in an Microtiter plate and placed on ice before reaction. The assay was initiated by transferring the Microtiter plate to an EPPENDORF thermomixer, which was set to the assay temperature 50° C. Then 60 µl supernatant was transferred to a new microtiter plate. $OD_{595}$ was read as a measure of amylase activity. Each reaction was done with triplicate and a buffer blind was included in the assay (instead of enzyme).

As shown in table 22, the optimal pH for this amylase is pH4.0, but this amylase also has high activity at pH3.0, showing it is a real acidic amylase.

TABLE 22 the activity of the alpha-amylase in different pH

| pH | 2 | 3 | 4 | 5 | 6 | 7 | 8 | 9 | 10 |
|---|---|---|---|---|---|---|---|---|---|
| alpha-amylase expressed by O4S2F (Relative activity) | 40 | 75.3 | 100 | 58.5 | 38.8 | 39.4 | 35.8 | 35.6 | 36.4 | pH Stability

Eight microliter alpha-amylase sample was added into 100 µl buffer (100 mM Na-acetate) at pH 3.5, incubated at 50° C. for 0, 10, 30, 60 and 120 mins. The alpha-amylase was added into 40 µl 1% AZCL-HE-amylose in water at 50° C. for 20 min, and 60 µl was taken for $OD_{595}$.

This amylase is very stable at pH3.5 and at high temperature, shown in table 23.

TABLE 23 pH stability of the alpha-amylase

| Time (mins) | 0 | 10 | 30 | 60 | 120 |
|---|---|---|---|---|---|
| alpha-amylase expressed by O4S2F (relative activity) | 100 | 101.5 | 112.8 | 101.9 | 55.9 |

The activity was set at beginning as 100%, and residual activities were shown at other time points.

Temperature Profile

Eight microliter alpha-amylase sample was added into 100 µl buffer (50 mM NaAc) at pH 4.3 containing 0.2% AZCL-HE-amylose, incubating for 20 mins at different temperature and 60 µl supernatant was taken for $OD_{595}$.

The alpha-amylase expressed by O4S2F works well at high temperature as shown in table 24, and its optimal temperature is 70° C.

TABLE 24

Temperature profile of the alpha-amylase

| Temperature (° C.) | 30 | 40 | 50 | 60 | 70 | 80 | 90 |
|---|---|---|---|---|---|---|---|
| alpha-amylase expressed by O4S2F (relative activity) | 20 | 40.8 | 85.6 | 78.3 | 100 | 24.4 | 24.1 |

Temperature Stability

Eight microliter alpha-amylase sample was added into 100 µl 50 mM NaAc at pH4.3 and incubated at 60° C. or 70° C. for 0, 10, 30, 60 and 120 mins, then they were put on ice at each time point. Forty microliters of 1% AZCL-HE-amylose in water was added at 50° C. for 20 mins, 60 µl taken for $OD_{595}$.

This amylase shows very stable at high temperature (60° C.) and it still works on even higher temperature (70° C.) as shown in table 25.

TABLE 25

| Temperature stability of the alpha-amylase | | | | | |
|---|---|---|---|---|---|
| Time (mins) | 0 | 10 | 30 | 60 | 120 |
| alpha-amylase expressed by O4S2F (70° C. relative activity) | 100 | 43.2 | 16.2 | 18.8 | 17.2 |
| alpha-amylase expressed by O4S2F (60° C. relative activity) | 100 | 85 | 68.6 | 47 | 40 |

Example 17: *Humicola insolens* Genomic DNA Extraction

*Humicola insolens* strain NN047338 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 18: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, geneID (Parra et al., 2000, Genome Research 10(4):511-515) was used for gene prediction. BlastalI version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH13 amylase enzyme candidates were identified directly by analysis of the Blast results. Agene (Munch and Krogh, 2006, BMC Bioinformatics 7:263) and SignalP (Nielsen et al., 1997, Protein Engineering 10: 1-6) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

Two annotated alpha-amylase genes (shown in table 26) were selected for expression cloning.

TABLE 26

| alpha-amylase genes from *Humicola insolens* | | |
|---|---|---|
| PE number | Gene name | DNA sequence |
| PE04230001317 | AMY7338 | SEQ ID NO: 25 |
| PE04230004150 | AM47338 | SEQ ID NO: 27 |

Example 19: Cloning of AM47338 Gene from the *Humicola insolens* Genomic DNA

Based on the DNA information obtained from genome sequencing, oligonucleotide primers, shown below in table 27, were designed to amplify AM47338 gene (SEQ ID NO: 27) from the genomic DNA of *Humicola insolens* NN047338. Primers were synthesized by Invitrogen (Invitrogen, Beijing, China).

TABLE 27

| Primers to amplify full-length amylase genes from *Humicola insolens* genomic DNA | | |
|---|---|---|
| Related SEQ ID | Primer name | Sequence (5'-3') |
| Hi_2_forward SEQ ID NO: 53 | AM47338_C505_bam | acacaactggggatcC acc ATGCTTGCCACAATCTCGAAGATC |
| Hi_2_reverse SEQ ID NO: 54 | AM47338_C505_xho | ccctctagatctcgag CTACATCGCAACGAAGACAGCTG |

Upper characters represent the 5'- and 3'-regions of the genes to be amplified, while lower cases were homologous to the vector sequences at insertion sites of pCaHj505 vector. The expression vector pCaHj505 contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amdS+*Aspergillus* transformant.

Twenty pmol of primer pair (each of the forward and reverse) were used in a PCR reaction composed of 2 μl of *Humicola insolens* NN047338 genomic DNA, 10 μl of 5× GC Buffer, 1.5 μl of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 μl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR product was isolated by 0.7% agarose gel electrophoresis using 90 mM Tris-borate and 1 mM EDTA (TBE) buffer where product bands at expected size of each PCR reaction were visualized under UV light. The 1.9 kb PCR products were then purified from solution by using a GFX PCR DNA and Gel Band Purification Kit (GE Healthcare, Buckinghamshire, UK) according to the manufacturer's instructions.

Plasmid pCaHj505 was digested with BamHI and XhoI, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

An IN-FUSION™ CF Dry-down Cloning Kit (Clontech Laboratories, Inc., Mountain View, Calif., USA) was used to clone the fragment directly into the expression vector pCaHj505.

The PCR product and the digested vector were ligated together using an IN-FUSION™ CF Dry-down Cloning Kit (Clontech Laboratories, Inc., Mountain View, Calif., USA) resulting in plasmid pAM47338_C505, in which transcription of gene AM47338 was under the control of a TAKA-amylase promoter from *Aspergillus oryzae*. The cloning operation was according to the manufacturer's instruction.

In brief, for each ligation reaction 30 ng of with BamHI and XhoI digested pCaHj505 and 60 ng of purified PCR products were added to the reaction vial and resuspended with the powder in a final volume of 10 µl with addition of deionized water. The reactions were incubated at 37° C. for 15 minutes and then 50° C. for 15 minutes. Three microliters of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAM47338-_C505 for expression in *A. niger* were extracted from correct *E. coli* transformants, by using a QIAprep Spin Miniprep Kit (QIAGEN Inc., Valencia, Calif., USA).

Example 20: Preparation of *Humicola insolens* Strain Total RNA and cDNA

Total RNA was prepared from the powdered mycelia by using RNeasy plant mini kit (QIAGEN, Cat. No. 74904). The cDNA was synthesized by following the instruction of 3' Rapid Amplification of cDNA End System (Invitrogen Corp., Carlsbad, Calif., USA).

Example 21: Cloning of AMY7338 (SEQ ID NO: 25) from the *Humicola insolens* cDNA Based on the DNA information obtained from genome sequencing, oligonucleotide primers, shown below in table 28, were designed to amplify AMY7338 (SEQ ID NO: 25) from cDNA of *Humicola insolens*. Primers were synthesized by Invitrogen (Invitrogen, Beijing, China).

TABLE 28

Primers to amplify AMY7338 (SEQ ID NO: 25) from *Humicola insolens* cDNA

| Related SEQ ID | Primer name | Sequence (5'-3') |
|---|---|---|
| Hi 1_forward SEQ ID NO: 55 | Amy7338IFHQ_ N-Bam | Attattcgaaggatcc acc ATGAGAAACCTTCGACATAT CCT |
| Hi 1_reverse SEQ ID NO: 56 | Amy7338IFHQ_ C-Eco | ggtgctgatggaattc TCTCCACGTATGGCTGATTG |

Upper characters represent the 5'- and 3'-regions of the genes to be amplified, while lower cases were homologous to the vector sequences at insertion sites of pLIZG8HQ vector. The expression vector pLIZG8HQ contained the α-factor secretion signal derived from *S. cerevisiae*, the 5'AOX1 promoter derived from *Pichia pastoris* and the 3'AOX1 alcohol oxidase1 terminator elements. Furthermore pLIZG8HQ had pBR322 derived sequences for selection and propagation in *E. coli*, and a His4 gene, which encoded an histidinol dehydrogenase derived from *Pichia pastoris* for selection of a transformant of a His mutant *Pichia* strain.

Twenty picomoles of primer pair (each of the forward and reverse) were used in a PCR reaction composed of 2 µl of *Humicola insolens* cDNA, 10 µl of 5× GC Buffer, 1.5 ul of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 µl.

The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR product was isolated by 0.7% agarose gel electrophoresis using 90 mM Tris-borate and 1 mM EDTA (TBE) buffer where product bands at expected size of each PCR reaction were visualized under UV light. The 2.1 kb PCR product was purified from solution by using a GFX PCR DNA and Gel Band Purification Kit (GE Healthcare, Buckinghamshire, UK) according to the manufacturer's instructions.

Plasmid pLIZG8HQ was digested with BamHI and EcoRI, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

The PCR product and the digested vector pLIZG8HQ were ligated together using an IN-FUSION™ CF Dry-down Cloning Kit (Clontech Laboratories, Inc., Mountain View, Calif., USA) resulting in plasmid pAmy7338NHQ. The cloning operation was according to the manufacturer's instruction. In brief, for each ligation reaction 30 ng of with BamHI and EcoRI digested pLIZG8HQ and 60 ng of purified PCR products were added to the reaction vial and resuspended with the powder in a final volume of 10 µl with addition of deionized water. The reactions were incubated at 37° C. for 15 minutes and then 50° C. for 15 minutes. 3 µl of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing under selection on the LB ampicillin plates. *E. coli* transformants containing expression constructs were detected by colony PCR and confirmed by DNA sequencing with vector primers (by SinoGenoMax Company Limited, Beijing, China). Plasmid DNA pAmy7338NHQ for expression in *Pichia. pastoris* was extracted from correct *E. coli* transformant, using a QIAprep Spin Miniprep Kit (QIAGEN Inc., Valencia, Calif., USA).

Example 22: Expression of AMY7338 (SEQ ID NO: 25) in *Pichia pastoris*

*Pichia pastoris* Competent Cell Preparation

The $OD_{595}$ of the overnight culture of *Pichia pastoris* in YPD in shaking flask was 1.0. Cells were pelleted by centrifugation at 2000 rpm, 5 mins, 4° C. Cell pellet was then suspended in YPD plus HEPES and DTT and stand at 30° C. for 15 mins. Cells were pelleted and washed with cold water and 1M sorbitol subsequently. Finally cells were suspended in small amount of 1M sorbitol and stored in 40 µl aliquots at −70° C.

Transformation of *Pichia pastoris* with pAMY7338NHQ

Plasmid DNA pAmy7338N HQ was linearized with PmeI leading to insertion of the plasmid at the chromosomal 5'AOX1 locus. Linearized plasmid DNA (500 ng) was mixed with 40 µl of competent cells and stored on ice for 5 min. Cells were transferred to an ice-cold 0.2 cm electroporation cuvette. Transformation was performed using a Bio-Rad GenePulser II. Parameters used were 1500 V, 50 µF and 200Ω. Immediately after pulsing, cells were suspended in 1 ml of ice cold 1 M sorbitol. The mixtures were plated on MD plates. Plates were incubated at 28° C. for 3-4 days.

Screening Clones for Expression in Small Scale

Four candidate clones from each transformation were cultured in a 3 ml scale using 24-deep well plates (Whatman, UK). Cells were grown in BMSY media at 28° C. with vigorous shaking. After 2.5 days 0.5% methanol was added to the culture to induce heterologous gene expression. Culture was continuously grown for 4 days with a daily addition of 0.5% methanol under the same growth condition. Samples of culture were taken daily during induction and stored at −20° C. for SDS-PAGE analysis and amylase activity assay.

The culture broth showed amylase activity by testing against AZCL-amylose. 20 µl of culture supernatant was analyzed on NuPAGE Novex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). On SDS-PAGE culture showed a band of 65 kDa, corresponding to the theoretical molecular weight of expression product P5AH. This P5AH expressing *Pichia pastoris* strain was designated as EXP02836 (O6NCD).

Example 23: Fermentation of *Pichia pastoris* Expression Strain EXP02836

Single colony of EXP02836 was inoculated into a 2 liter flask containing 400 ml BMSY media to generate broth for characterization of the alpha-amylase. The culture was incubated at 28° C. with vigorous shaking. After 2.5 days 0.5% methanol was added to the culture to induce heterologous gene expression. Culture was continuously grown for 4 days with a daily addition of 0.5% methanol under the same growth condition. The culture was harvested by centrifugation and filtered using a 0.45 µm DURAPORE Membrane (Millipore, Bedford, Mass., USA). The filtered culture broth was used for alpha-amylase characterization.

Example 24: Characterization of AMY7338

The pH of culture supernatant was adjusted to 7.0 with NaOH, then filtered through a 0.45 urn filter. The solution was applied to a 30 ml Ni-SEPHAROSE High Performance column (GE Healthcare) equilibrated with 20 mM PBS containing 0.3M NaCl at pH7.0. The protein was eluted with a linear imidazole gradient (0-500 mM). Fractions from the column were analyzed for amylase activity.

Fractions with amylase activity were checked by SDS-PAGE and the pure fractions were pooled. The SDS-PAGE showed the molecular weight of AMY7338 (corresponding to the molecular weight of the mature polypeptide of SEQ ID NO: 26) was about 70 kDa.

The alpha-amylase of AMY7338 as purified in the example was characterized according to the following methods.

AZCL-HE-Amylose Assay

Twenty-five microliters of alpha-amylase sample and 120 µl 0.1% AZCL-HE-amylose (Megazyme International Ireland Ltd.) at pH 7.0 were mixed in a Microtiter plate and placed on ice before reaction. The assay was initiated by transferring the Microtiter plate to an EPPENDORF thermomixer, which was set to the assay temperature 40° C. Then 60 µl supernatant was transferred to a new microtiter plate. $OD_{595}$ was read as a measure of amylase activity. Each reaction was done with duplicate and a buffer blind was included in the assay (instead of alpha-amylase).

pH Profile

25 µl alpha-amylase sample and 40 µl 1% AZCL-HE-amylose in 150 µl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, and 10.0 with HCl or NaOH were mixed in an Microtiter plate and placed on ice before reaction. The assay was initiated by transferring the Microtiter plate to an EPPENDORF thermomixer, which was set to the assay temperature 40° C. Then 100 µl supernatant was transferred to a new microtiter plate. $OD_{595}$ was read as a measure of amylase activity. Each reaction was done with duplicate and a buffer blind was included in the assay (instead of alpha-amylase).

As shown in table 29, AMY7338 has activity from pH 5 to pH 8, and its optimal pH is 5.0.

TABLE 29 pH Profile of the alpha-amylase

| pH | 2 | 3 | 4 | 5 | 6 | 7 | 8 | 9 | 10 |
|---|---|---|---|---|---|---|---|---|---|
| Relative activity | 26.068 | 22.198 | 19.491 | 100 | 97.133 | 93.463 | 93.042 | 55.364 | 36.816 | pH Stability

Thirty microliter alpha-amylase sample was added into 150 µl buffer (100 mM Na-acetate) at pH4.0, incubated at 40° C. for 0, 5, 10, 30, 60 and 120 mins, 30 µl taken for reaction at each time point. The alpha-amylase sample was added into 170 µl buffer at pH4.0 containing 0.2% AZCL-HE-amylose at 40° C. for 60 min, 100 µl taken for $OD_{595}$.

As shown in table 30, the alpha-amylase of AMY7338 appears to be unstable at acidic condition.

TABLE 30 pH stability of the alpha-amylase

| Time (min) | 0 | 5 | 10 | 30 |
|---|---|---|---|---|
| Relative activity | 100 | 24.685 | 28.159 | 28.86 |

Temperature Profile

Two hundred microliter buffer (100 mM Tris-HCl) at pH 7 containing 0.1% AZCL-HE-amylose was incubated for 5 mins at 20, 30, 40, 50, 60, 70, 80, and 90° C. Then 10 ul alpha-amylase sample was added into the mixture and incubated for 30 mins. 100 ul supernatant was taken for $OD_{595}$.

As shown by the results, the alpha-amylase AMY7338 is active in a wide range of temperatures from 40 to 60° C. and its optimum temperature around 50° C.

Temperature Stability

Four hundred microliter alpha-amylase sample AMY7338 was firstly incubated at 70° C. for 0, 5, 10, 30, 60 and 120 mins, then 30 µl alpha-amylase was added into 150 µl B&R buffer at pH5.0 and 20 µl 2% AZCL-HE-amylose. This mixture was incubated at 40° C. for 10 mins and 100 µl was taken for $OD_{595}$.

As shown in table 31, AMY7338 is relative thermostable since it could work at 70° C. for 30 mins.

TABLE 31

| Temperature stability of the alpha-amylase | | | | | | |
|---|---|---|---|---|---|---|
| Time (min) | 0 | 5 | 10 | 30 | 60 | 120 |
| Relative activity | 100 | 50.96 | 45.34 | 50.332 | 43.211 | 45.724 |

Example 24: *Myceliophthora* Fergusii Genomic DNA Extraction

*Myceliophthora* fergusii strain NN000308 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 25: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, geneID (Parra et al., 2000, Genome Research 10(4):511-515) was used for gene prediction. BlastalI version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. alpha-amylase candidates were identified directly by analysis of the Blast results. Agene (Munch and Krogh, 2006, BMC Bioinformatics 7:263) and SignalP (Nielsen et al., 1997, Protein Engineering 10: 1-6) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

Two annotated alpha-amylase genes (shown in table 32) were selected for expression cloning.

TABLE 32

| alpha-amylase genes from *Myceliophthora fergusii* | | |
|---|---|---|
| PE number | Gene name | DNA sequence |
| PE05720006129 | AM308-2 | SEQ ID NO: 29 |
| PE05720000758 | AM308-1 | SEQ ID NO: 31 |

Example 26: Cloning of 2 Alpha-Amylase Genes from the *Myceliophthora fergusii* Genomic DNA Based on the DNA information obtained from genome sequencing, oligonucleotide primers, shown below in table 33, were designed to amplify the 2 alpha-amylase genes (SEQ ID: 29 and 31) from the genomic DNA of *Myceliophthora fergusii* NN000308. Primers were synthesized by Invitrogen (Invitrogen, Beijing, China).

TABLE 33

| Primers to amplify full-length amylase genes from *Myceliophthora fergusii* genomic DNA | | |
|---|---|---|
| Related SEQ ID | Primer name | Sequence (5'-3') |
| Mf 1_forward SEQ ID NO: 57 | AM308-2_ C505-BamHI | acacaactggggatcc acc ATGTTTCGCCTCGGACATGC |
| Mf 1_reverse SEQ ID NO: 58 | AM308-2_ C505_XhoI | gtcaccctctagatctcgag AAAGCCACCCCGTCACCTC |
| Mf 2_forward SEQ ID NO: 59 | AM308-1_ C505_BamHI | acacaactggggatcc acc ATGAGGACCTCCATCATCAGG |
| Mf 2_reverse SEQ ID NO: 60 | AM308-1_ C505_XhoI | gtcaccctctagatctcgag tca CGCGCTGCTATCCGGTTTAT |

Upper characters represent the 5'- and 3'-regions of the genes to be amplified, while lower cases were homologous to the vector sequences at insertion sites of pPFJo355 vector which has been described in US2010306879.

For each gene, 20 µmol of primer pair (each of the forward and reverse) were used in a PCR reaction composed of 2 µl of *Myceliophthora fergusii* NN000308 genomic DNA, 10 µl of 5× GC Buffer, 1.5 µl of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR products were isolated by 0.7% agarose gel electrophoresis using 90 mM Tris-borate and 1 mM EDTA (TBE) buffer where product bands at expected size of each PCR reaction were visualized under UV light. The PCR products were then purified from solution by using a GFX PCR DNA and Gel Band Purification Kit (GE Healthcare, Buckinghamshire, UK) according to the manufacturer's instructions.

TABLE 34

Size of PCR products in Example 26

| Gene name | Size of PCR product |
|---|---|
| AM308-2 | 3.2 kb |
| AM308-1 | 2 kb |

Plasmid pPFJo355 was digested with BamHI and BgIII, isolated by 0.7% agarose gel electrophoresis using TBE buffer, and purified using a GFX PCR DNA and Gel Band Purification Kit (GE Healthcare, Buckinghamshire, UK) according to the manufacturer's instructions.

An IN-FUSION™ CF Dry-down Cloning Kit (Clontech Laboratories, Inc., Mountain View, Calif., USA) was used to clone the fragment directly into the expression vector pPFJo355.

The PCR products and the digested vector were ligated together using an IN-FUSION™ CF Dry-down Cloning Kit resulting in plasmids in table 35 respectively, in which transcription of *Myceliophthora fergusii* alpha-amylase genes was under the control of a TAKA-amylase promoter from *Aspergillus oryzae*. The cloning operation was according to the manufacturer's instruction. In brief, for each ligation reaction 30 ng of with BamHI and BgIII digested pPFJo355 and 60 ng of purified PCR products were added to the reaction vial and resuspended with the powder in a final volume of 10 μl with addition of deionized water. The reactions were incubated at 37° C. for 15 minutes and then 50° C. for 15 minutes. Three microliter of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAM308-2_P355 and pAM308-1_P355 for expression in *A. oryzae* were extracted from correct *E. coli* transformants, by using a QIAprep Spin Miniprep Kit (QIAGEN Inc., Valencia, Calif., USA).

TABLE 35

Plasmid (Expression constructs) in Example 26

| Gene name | Plasmid |
|---|---|
| AM308-2 | pAM308-2_P355 |
| AM308-1 | pAM308-1_P355 |

Example 27: Expression of *Myceliophthora Fergusii* Alpha-Amylase Genes in *Aspergillus oryzae*

An agar slant (COVE-N-gly with 20 mM uridine) was inoculated with spores of *Aspergillus oryzae* JaL250, and grown at 37° C. until it was completely sporulated. The spores were resuspended in 5-10 ml of sterile 0.05% tween20 water. About $10^8$ spores were transferred to a 500 ml baffled shake flask containing 100 ml YPG medium with 20 mM uridine and 10 mM NaNO₃ and incubated at 32° C. for 16 hours at 99 rpm in Innova shaker. Then the mycelia were harvested for protoplasts preparation. *Aspergillus oryzae* JaL250 protoplasts preparation and transformation were done according to the method described in patent WO 2004/111218 or EP 238023. Five micrograms of pAM308-2_P355 and pAM308-1_P355 each were used to transform *Aspergillus oryzae* JaL250 separately.

The *Aspergillus oryzae* JaL250 transformants with pAM308-2_P355 or pAM308-1_P355 were selected on the COVE plates for protoplast regeneration (described in the Media and Solution part). About 30 transformants were observed on the selective plates for each transformation. Four transformants from each transformation were isolated on COVE-2 plate for 3-4 days at 37° C.

After isolation those 4 transformants for each transformation were inoculated separately into 3 ml of YPM medium in 24-well plate and incubated at 30° C., 150 rpm. After 3 days incubation, 20 μl of supernatant from each culture were analyzed on NuPAGE Novex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). SDS-PAGE profiles of the cultures showed that they had the excepted protein bands of expression products of pAM308-2_P355 and pAM308-1_P355. The expression product numbers and expression strain numbers of those 2 genes were shown in table 36.

TABLE 36

Expression strains

| Expression construct | Expression product | Expression strain |
|---|---|---|
| pAM308-2_P355 | P24AWG | |
| pAM308-1_P355 | P24EPY | O6RHU |

Example 28: Fermentation of *A. oryzae* Expression Strains

A slant of each expression strain in table 36 was washed with 10 ml of YPM and inoculated into a 2 liter flask containing 400 ml of YPM medium to generate broth for characterization of the alpha-amylase. The culture was incubated at 30° C. on shaker at 80 rpm. The culture was harvested on day 3 and filtered using a 0.45 μm DURAPORE Membrane (Millipore, Bedford, Mass., USA). The filtered culture broth was used for alpha-amylase characterization.

Example 29: Characterization of the Alpha-Amylase Expressed by O6RHU

The culture supernatant was firstly precipitated by ammonium sulfate, then dialysized to 20 mM NaAc at pH5.0. Dialysized sample was loaded into 30 ml Q SEPHAROSE Fast Flow (GE Healthcare), equilibrated with 20 mM NaAc at pH5.0. Then the protein was eluted with a linear sodium chloride (0-1000 mM). Fractions from the column were analyzed for amylase activity.

Fractions with amylase activity were checked by SDS-PAGE and the pure fractions were pooled. The SDS-PAGE showed the molecular weight of alpha-amylase expressed by O6RHU (corresponding to the molecular weight of the mature polypeptide of SEQ ID NO: 32) was about 55 kDa.

The alpha-amylase as purified was characterized according to the following methods.

AZCL-HE-amylose Assay

Twenty microliters of alpha-amylase samples (10 mg/ml) and 100 µl 0.2% AZCL-HE-amylose (Megazyme International Ireland Ltd.) at pH4.3 were mixed separately in a Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. $OD_{595}$ was read as a measure of amylase activity. Each reaction was done with triplicate and a buffer blind was included in the assay (instead of alpha-amylase).

pH Profile

Twenty liter alpha-amylase samples and 40 µl 1% AZCL-HE-amylose in 100 µl B&R buffer (Britton-Robinson buffer: 0.1 M boric acid, 0.1 M acetic acid, and 0.1 M phosphoric acid) adjusted to pH-values 2.0, 3.0, 4.0, 5.0, 6.0, 7.0, 8.0, 9.0, and 10.0 with HCl or NaOH were mixed in an Microtiter plate and placed on ice before reaction. The assay was initiated by transferring the Microtiter plate to an EPPENDORF thermomixer, which was set to the assay temperature 37° C. Then 60 µl supernatant was transferred to a new microtiter plate. $OD_{595}$ was read as a measure of amylase activity. Each reaction was done with triplicate and a buffer blind was included in the assay (instead of alpha-amylase).

As shown in table 37, the optimal pH for this amylase is pH5.0, but this amylase shows high activity at pH4.0, and it works well at a broad pH.

TABLE 37 pH profile of the alpha-amylase

| pH | 2 | 3 | 4 | 5 | 6 | 7 | 8 | 9 | 10 |
|---|---|---|---|---|---|---|---|---|---|
| alpha-amylase expressed by O6RHU (relative activity) | 17 | 27.3 | 98.3 | 100 | 80.7 | 61.1 | 36.1 | 32.1 | 24.2 | pH Stability

20 µl alpha-amylase added into 100 µl buffer (100 mM Na-acetate) at pH4.0, incubated at 40° C. for 0, 10, 30, 60 and 120 mins. The alpha-amylase was added into 40 µl 1% AZCL-HE-amylose in water at 40° C. for 20 min, 60 µl taken for $OD_{595}$.

As shown in table 38, this amylase is not very stable at pH4.0 after 30 min incubation, but it might work well at the application condition.

TABLE 38 pH stability of the alpha-amylase

| Time (mins) | 0 | 10 | 30 | 60 | 120 |
|---|---|---|---|---|---|
| alpha-amylase expressed by O6RHU (relative activity) | 100 | 66.3 | 30 | 22 | 22.6 |

Temperature Profile

20 µl alpha-amylase was added into 100 µl buffer (50 mM NaAc) at pH 4.3 containing 0.2% AZCL-HE-amylose, incubating for 20 mins at different temperature and 60 µl supernatant was taken for $OD_{595}$.

As shown in table 39, alpha-amylase expressed by O6RHU works well at low temperature as table shown, and its optimal temperature is 50° C.

TABLE 39

Temperature profile of the alpha-amylase

| Temperature (° C.) | 20 | 30 | 40 | 50 | 60 | 70 | 80 | 90 |
|---|---|---|---|---|---|---|---|---|
| alpha-amylase expressed by O6RHU (relative) | 57.4 | 78.1 | 96.8 | 100 | 31.8 | 31.6 | 25.1 | 26.9 |

Temperature Stability

Twenty microliter alpha-amylase sample was added into 100 µl 50 mM NaAc at pH4.3 and incubated at 50° C. for 0, 10, 30, 60 and 120 mins, then they were put on ice at each time point. 40 µl 1% AZCL-HE-amylose in water was added at 37° C. for 20 mins, 60 µl taken for $OD_{595}$.

As shown in table 40, this amylase shows relative thermostability at 50° C.

TABLE 40

Temperature stability of the alpha-amylase

| Time (mins) | 0 | 10 | 30 | 60 | 120 |
|---|---|---|---|---|---|
| alpha-amylase expressed by O6RHU (relative activity) | 100 | 56.8 | 30 | 19.4 | 19.2 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention is further defined in the following paragraphs:

1. An isolated polypeptide having alpha-amylase activity, selected from the group consisting of:
    (a) a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 10; a polypeptide having at least 93%, e.g., at least 94%, at least 95%, at least 96%, at least 97%, at least 98%, at least 99%, or 100% sequence identity to the mature polypeptide of SEQ ID NO: 20; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6; a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 8; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 12; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14; a polypeptide having at least 88%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 16; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 18; a polypeptide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 22; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 24; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 28; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 30; or a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 32;

(b) a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 9, (ii) genomic DNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 19, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 3, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 5, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 7, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 11, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 13, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 15, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 17, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 23, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 25, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 27, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 29, (ii) the cDNA sequence thereof, or (iii) the full-length complement of (i) or (ii); or a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 31, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 21, (ii) the genomic DNA sequence thereof, or (iii) the full-length complement of (i) or (ii);

(c) a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the genomic DNA sequence thereof; a polypeptide encoded by a polynucleotide having at least 93%, e.g., at least 94%, at least 95%, at least 96%, at least 97%, at least 98%, at least 99%, or 100% sequence identity to the mature polypeptide coding sequence of SEQ ID NO: 19 or the cDNA sequence sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof; a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 7 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 11 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13 or the cDNA sequence thereof; a polypeptide encoded by a polynucleotide having at least 88%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17 or the cDNA sequence thereof; a polypeptide encoded by a polynucleotide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 21 or the genomic DNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25 or the cDNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 27 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29 or the cDNA sequence thereof; or a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 31 or the cDNA sequence thereof;

(d) a variant of the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more positions; and (e) a fragment of the polypeptide of (a), (b), (c), or (d) that has alpha-amylase activity.

2. The polypeptide of paragraph 1, which is a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 10; a polypeptide having at least 93%, e.g., at least 94%, at least 95%, at least 96%, at least 97%, at least 98%, at least 99%, or 100% sequence identity to the mature polypeptide of SEQ ID NO: 20; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6; a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 8; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 12; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14; a polypeptide having at least 88%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 16; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 18; a polypeptide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 22; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 24; a polypeptide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26; a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 28; a polypeptide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 30; or a polypeptide having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 32.

3. The polypeptide of paragraph 1 or 2, which is a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 9, (ii) genomic DNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 19, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 3, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 5, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 7, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 11, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 13, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 15, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 17, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 23, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 25, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 27, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 29, (ii) the cDNA sequence thereof, or (iii) the full-length complement of (i) or (ii); or a polypeptide encoded by a polynucleotide that hybridizes under low stringency conditions, medium stringency conditions, medium-high stringency conditions, high stringency conditions, or very high stringency conditions with the mature polypeptide coding sequence of SEQ ID NO: 31, (ii) the cDNA sequence thereof, or (iii) the full-length complement of (i) or (ii); a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 21, (ii) the genomic DNA sequence thereof, or (iii) the full-length complement of (i) or (ii).

4. The polypeptide of any of paragraphs 1-3, which is a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the genomic DNA sequence thereof; a polypeptide encoded by a polynucleotide having at least 93%, e.g., at least 94%, at least 95%, at least 96%, at least 97%, at least 98%, at least 99%, or 100% sequence identity to the mature polypeptide coding sequence of SEQ ID NO: 19 or the cDNA sequence sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof; a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 7 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 11 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13 or the cDNA sequence thereof; a polypeptide encoded by a polynucleotide having at least 88%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17 or the cDNA sequence thereof; a polypeptide encoded by a polynucleotide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 21 or the genomic DNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23 or the cDNA sequence thereof; a polypeptide encoded by a polynucleotide having at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25 or the cDNA sequence thereof; a polypeptide encoded by a polynucleotide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 27 or the cDNA sequence thereof; a polypeptide encoded by a polynucleotide having at least 85%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29 or the cDNA sequence thereof; or a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 31 or the cDNA sequence thereof.

5. The polypeptide of any of paragraphs 1-4, comprising or consisting of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32, or the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32.

6. The polypeptide of paragraph 5, wherein the mature polypeptide is amino acids 23 to 502 of SEQ ID NO: 10, amino acids 17 to 627 of SEQ ID NO: 20, amino acids 19 to 495 of SEQ ID NO: 2, amino acids 29 to 559 of SEQ ID NO: 4, amino acids 20 to 561 of SEQ ID NO: 6, amino acids 21 to 545 of SEQ ID NO: 8, amino acids 20 to 497 of SEQ ID NO: 12, amino acids 21 to 564 of SEQ ID NO: 14, amino acids 26 to 574 of SEQ ID NO: 16, amino acids 22 to 495 of SEQ ID NO: 18, amino acids 26 to 504 of SEQ ID NO: 22, amino acids 20 to 631 of SEQ ID NO: 24, amino acids 21 to 631 of SEQ ID NO: 26, amino acids 22 to 533 of SEQ ID NO: 28, amino acids 25 to 627 of SEQ ID NO: 30, or amino acids 21 to 509 of SEQ ID NO: 32.

7. The polypeptide of any of paragraphs 1-4, which is a variant of the mature polypeptide of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more positions.

8. The polypeptide of paragraph 1, which is a fragment of SEQ ID NO: 10, SEQ ID NO: 20, SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, SEQ ID NO: 30, or SEQ ID NO: 32, wherein the fragment has alpha-amylase activity.

9. An isolated polypeptide comprising a catalytic domain selected from the group consisting of:
(a) a catalytic domain having at least 85% sequence identity to amino acids 23 to 501 of SEQ ID NO: 10, at least 93% sequence identity to amino acids 17 to 494 of SEQ ID NO: 20, at least 70% sequence identity to amino acids 21 to 495 of SEQ ID NO: 2, at least 70% sequence identity to amino acids 29 to 512 of SEQ ID NO: 4, at least 70% sequence identity to amino acids 22 to 512 of SEQ ID NO: 6, at least 90% sequence identity to amino acids 21 to 496 of SEQ ID NO: 8, at least 85% sequence identity to amino acids 20 to 497 of SEQ ID NO: 12, at least 70% sequence identity to amino acids 23 to 514 of SEQ ID NO: 14, at least 88% sequence identity to amino acids 29 to 533 of SEQ ID NO: 16, at least 70% sequence identity to amino acids 22 to 493 of SEQ ID NO: 18, at least 80% sequence identity to amino acids 23 to 500 of SEQ ID NO: 22, at least 75% sequence identity to amino acids 24 to 499 of SEQ ID NO: 24, at least 70% sequence identity to amino acids 21 to 497 of SEQ ID NO: 26, at least 75% sequence identity to amino acids 22 to 498 of SEQ ID NO: 28, at least 85% sequence identity to amino acids 25 to 498 of SEQ ID NO: 30, or at least 90% sequence identity to amino acids 23 to 500 of SEQ ID NO: 32;
(b) a catalytic domain encoded by a polynucleotide that hybridizes under low, medium, medium-high, high, or very high stringency conditions with (i) nucleotides 67 to 1503 of SEQ ID NO: 9, (ii) the genomic DNA thereof, or (iii) the full-length complement of (i) or (ii); a polynucleotide that hybridizes under low, medium, medium-high, high, or very high stringency conditions with (i) nucleotides 49 to 2007 of SEQ ID NO: 19, (ii) the cDNA sequence thereof, or (iii) the full-length complement of (i) or (ii); a polynucleotide that hybridizes under low, medium, medium-high, high, or very high stringency conditions with (i) nucleotides 61 to 1699 of SEQ ID NO: 1, (ii) the cDNA sequence thereof, or (iii) the full-length complement of (i) or (ii); a polynucleotide that hybridizes under low, medium, medium-high, high, or very high stringency conditions with (i) nucleotides 85 to 1602 of SEQ ID NO: 3, (ii) the cDNA sequence thereof, or (iii) the full-length complement of (i) or (ii); a polynucleotide that hybridizes under low, medium, medium-high, high, or very high stringency conditions with (i) nucleotides 64 to 2137 of SEQ ID NO: 5, (ii) the cDNA sequence thereof, or (iii) the full-length complement of (i) or (ii); a polynucleotide that hybridizes under low, medium, medium-high, high, or very high stringency conditions with (i) nucleotides 64 to 1545 of SEQ ID NO: 7, (ii) the cDNA sequence thereof, or (iii) the full-length complement of (i) or (ii); a polynucleotide that hybridizes under low, medium, medium-high, high, or very high stringency conditions with (i) nucleotides 58 to 1964 of SEQ ID NO: 11, (ii) the cDNA sequence thereof, or (iii) the full-length complement of (i) or (ii); a polynucleotide that hybridizes under low, medium, medium-high, high, or very high stringency conditions with (i) nucleotides 67 to 2173 of SEQ ID NO: 13, (ii) the cDNA sequence thereof, or (iii) the full-length complement of (i) or (ii); a polynucleotide that hybridizes under low, medium, medium-high, high, or very high stringency conditions with (i) nucleotides 85 to 2309 of SEQ ID NO: 15, (ii) the cDNA sequence thereof, or (iii) the full-length complement of (i) or (ii); a polynucleotide that hybridizes under low, medium, medium-high, high, or very high stringency conditions with (i) nucleotides 64 to 1706 of SEQ ID NO: 17, (ii) the cDNA sequence thereof, or (iii) the full-length complement of (i) or (ii); a polynucleotide that hybridizes under low, medium, medium-high, high, or very high stringency conditions with nucleotides 70 to 2309 of SEQ ID NO: 23, (ii) the cDNA sequence thereof, or (iii) the full-length complement of (i) or (ii); a polynucleotide that hybridizes under low, medium, medium-high, high, or very high stringency conditions with (i) nucleotides 61 to 2154 of SEQ ID NO: 25, (ii) the cDNA sequence thereof, or (iii) the full-length complement of (i) or (ii); a polynucleotide that hybridizes under low, medium, medium-high, high, or very high stringency conditions with (i) nucleotides 64 to 1622 of SEQ ID NO: 27, (ii) the cDNA sequence thereof, or (iii) the full-length complement of (i) or (ii); a polynucleotide that hybridizes under low, medium, medium-high, high, or very high stringency conditions with (i) nucleotides 73 to 2355 of SEQ ID NO: 29, (ii) the cDNA sequence thereof, or (iii) the full-length complement of (i) or (ii); a polynucleotide that hybridizes under low, medium, medium-high, high, or very high stringency conditions with (i) nucleotides 67 to 1650 of SEQ ID NO: 31, (ii) the cDNA sequence thereof, or (iii) the full-length complement of (i) or (ii); (ii or a polynucleotide that hybridizes under low, medium, medium-high, high, or very high stringency conditions with (i) nucleotides 67 to 1500 of SEQ ID NO: 21, (ii) the genomic DNA thereof, or (iii) the full-length complement of (i) or (ii);

(c) a catalytic domain encoded by a polynucleotide having at least 85% sequence identity to nucleotides 67 to 1503 of SEQ ID NO: 9, at least 93% sequence identity to nucleotides 49 to 2007 of SEQ ID NO: 19, at least 70% sequence identity to nucleotides 61 to 1699 of SEQ ID NO: 1, at least 70% sequence identity to nucleotides 85 to 1602 of SEQ ID NO: 3, at least 70% sequence identity to nucleotides 64 to 2137 of SEQ ID NO: 5, at least 90% sequence identity to nucleotides 64 to 1545 of SEQ ID NO: 7, at least 85% sequence identity to nucleotides 58 to 1964 of SEQ ID NO: 11, at least 70% sequence identity to nucleotides 67 to 2173 of SEQ ID NO: 13, at least 88% sequence identity to nucleotides 85 to 2309 of SEQ ID NO: 15, at least 70% sequence identity to nucleotides 64 to 1706 of SEQ ID NO: 17, at least 80% sequence identity to nucleotides 67 to 1500 of SEQ ID NO: 21, at least 75% sequence identity to nucleotides 70 to 2309 of SEQ ID NO: 23, at least 70% sequence identity to nucleotides 61 to 2154 of SEQ ID NO: 25, at least 75% sequence identity to nucleotides 64 to 1622 of SEQ ID NO: 27, at least 85% sequence identity to nucleotides 73 to 2355 of SEQ ID NO: 29, or at least 90% sequence identity to nucleotides 67 to 1650 of SEQ ID NO: 31;

(d) a variant of amino acids 23 to 501 of SEQ ID NO: 10, amino acids 17 to 494 of SEQ ID NO: 20, amino acids 21 to 495 of SEQ ID NO: 2, amino acids 29 to 512 of SEQ ID NO: 4, amino acids 22 to 512 of SEQ ID NO: 6, amino acids 21 to 496 of SEQ ID NO: 8, amino acids 20 to 497 of SEQ ID NO: 12, amino acids 23 to 514 of SEQ ID NO: 14, amino acids 29 to 533 of SEQ ID NO: 16, amino acids 22 to 493 of SEQ ID NO: 18, amino acids 23 to 500 of SEQ ID NO: 22, amino acids 24 to 499 of SEQ ID NO: 24, amino acids 21 to 497 of SEQ ID NO: 26, amino acids 22 to 498 of SEQ ID NO: 28, amino acids 25 to 498 of SEQ ID NO: 30, or amino acids 23 to 500 of SEQ ID NO: 32 comprising a substitution, deletion, and/or insertion at one or more positions; and (e) a fragment of the catalytic domain of (a), (b), (c), or (d) that has alpha-amylase activity.

10. The polypeptide of paragraph 9, further comprising a carbohydrate binding domain.

11. An isolated polypeptide comprising a carbohydrate binding domain operably linked to a catalytic domain, wherein the carbohydrate binding domain is selected from the group consisting of:

(a) a carbohydrate binding domain having at least 93% sequence identity to amino acids 520 to 627 of SEQ ID NO: 20, at least 75% sequence identity to amino acids 528 to 630 of SEQ ID NO: 24, at least 70% sequence identity to amino acids 529 to 631 of SEQ ID NO: 26, at least 85% sequence identity to amino acids 524 to 627 of SEQ ID NO: 30;

(b) a carbohydrate binding domain encoded by a polynucleotide that hybridizes under low, medium, medium-high, high, or very high stringency conditions with (i) nucleotides 2083 to 2406 of SEQ ID NO: 19, (ii) the cDNA sequence thereof, or (iii) the full-length complement of (i) or (ii); a polynucleotide that hybridizes under low, medium, medium-high, high, or very high stringency conditions with (i) nucleotides 2456 to 2858 of SEQ ID NO: 23, (ii) the cDNA sequence thereof, or (iii) the full-length complement of (i) or (ii); a polynucleotide that hybridizes under low, medium, medium-high, high, or very high stringency conditions with (i) nucleotides 2307 to 2673 of SEQ ID NO: 25, (ii) the cDNA sequence thereof, or (iii) the full-length complement of (i) or (ii); or a polynucleotide that hybridizes under low, medium, medium-high, high, or very high stringency conditions with (i) nucleotides 2502 to 2917 of SEQ ID NO: 29, (ii) the cDNA sequence thereof, or (iii) the full-length complement of (i) or (ii);
(c) a carbohydrate binding domain encoded by a polynucleotide having at least 93% sequence identity to nucleotides 2083 to 2406 of SEQ ID NO: 19, at least 75% sequence identity to nucleotides 2456 to 2858 of SEQ ID NO: 23, at least 70% sequence identity to nucleotides 2307 to 2673 of SEQ ID NO: 25, or at least 85% sequence identity to nucleotides 2502 to 2917 of SEQ ID NO: 29 or the cDNA sequence thereof;
(d) a variant of amino acids 520 to 627 of SEQ ID NO: 20, amino acids 528 to 630 of SEQ ID NO: 24, amino acids 529 to 631 of SEQ ID NO: 26, or amino acids 524 to 627 of SEQ ID NO: 30 comprising a substitution, deletion, and/or insertion at one or more positions; and
(e) a fragment of (a), (b), (c), (d) or (e) that has carbohydrate binding activity.
12. The polypeptide of paragraph 11, wherein the catalytic domain is obtained from amylase, preferably alpha-amylase, more preferably acid alpha-amylase.
13. A composition comprising the polypeptide of any of paragraphs 1-12 and an enzyme selected from the group consisting of: a fungal alpha-amylase (EC 3.2.1.1), a beta-amylase (E.C. 3.2.1.2), a glucoamylase (E.C.3.2.1.3), a pullulanases (E.C. 3.2.1.41), a phytase (E.C.3.1.2.28) and a protease (E.C. 3.4.).
14. Use of the polypeptide of any of paragraphs 1-12 or the composition of paragraph 13 for starch modification in the food industry, starch modification in the paper and pulp industry, starch liquefaction, textile washing, textile desizing, brewing, ethanol production and/or baking.
15. The use according to paragraph 14, for production of ethanol in a process comprising hydrolyzing an ungelatinized starch.
16. An isolated polynucleotide encoding the polypeptide of any of paragraphs 1-12.
17. A nucleic acid construct or expression vector comprising the polynucleotide of paragraph 16 operably linked to one or more control sequences that direct the production of the polypeptide in an expression host.
18. A recombinant host cell comprising the polynucleotide of paragraph 16 operably linked to one or more control sequences that direct the production of the polypeptide.
19. A method of producing the polypeptide of any of paragraphs 1-12, comprising:

(a) cultivating a cell, which in its wild-type form produces the polypeptide, under conditions conducive for production of the polypeptide; and
(b) recovering the polypeptide.
20. A method of producing a polypeptide having alpha-amylase activity, comprising:
(a) cultivating the host cell of paragraph 18 under conditions conducive for production of the polypeptide; and
(b) recovering the polypeptide.
21. A transgenic plant, plant part or plant cell comprising a polynucleotide encoding the polypeptide of any of paragraphs 1-12.
22. A method of producing a polypeptide having alpha-amylase activity, comprising:
(a) cultivating the transgenic plant or plant cell of paragraph 21 under conditions conducive for production of the polypeptide; and
(b) recovering the polypeptide.
23. An isolated polynucleotide encoding a signal peptide comprising or consisting of amino acids 1 to 18 of SEQ ID NO: 2, amino acids 1 to 28 of SEQ ID NO: 4, amino acids 1 to 19 of SEQ ID NO: 6, amino acids 1 to 20 of SEQ ID NO: 8, amino acids 1 to 22 of SEQ ID NO: 10, amino acids 1 to 19 of SEQ ID NO: 12, amino acids 1 to 20 of SEQ ID NO: 14, amino acids 1 to 25 of SEQ ID NO: 16, amino acids 1 to 21 of SEQ ID NO: 18, amino acids 1 to 16 of SEQ ID NO: 20, amino acids 1 to 25 of SEQ ID NO: 22, amino acids 1 to 19 of SEQ ID NO: 24, amino acids 1 to 20 of SEQ ID NO: 26, amino acids 1 to 21 of SEQ ID NO: 28, amino acids 1 to 24 of SEQ ID NO: 30, or amino acids 1 to 20 of SEQ ID NO: 32.
24. A nucleic acid construct or expression vector comprising a gene encoding a protein operably linked to the polynucleotide of paragraph 23, wherein the gene is foreign to the polynucleotide encoding the signal peptide.
25. A recombinant host cell comprising a gene encoding a protein operably linked to the polynucleotide of paragraph 23, wherein the gene is foreign to the polynucleotide encoding the signal peptide.
26. A method of producing a protein, comprising:
(a) cultivating a recombinant host cell comprising a gene encoding a protein operably linked to the polynucleotide of paragraph 23, wherein the gene is foreign to the polynucleotide encoding the signal peptide, under conditions conducive for production of the protein; and
(b) recovering the protein.
27. A whole broth formulation or cell culture composition comprising the polypeptide of any of paragraphs 1-12.

What is claimed is:

1. A process for producing ethanol from a gelatinized starch, the process comprising:
   (i) liquefying a gelatinized starch using a polypeptide having alpha-amylase activity to obtain a liquefied mash;
   (ii) saccharifying the liquefied mash using a glucoamylase; and
   (iii) fermenting the material obtained in step (ii) in the presence of a yeast fermenting organism to produce ethanol, wherein the polypeptide having alpha-amylase activity is selected from the group consisting of:
   (a) a polypeptide having at least 90% sequence identity to the mature polypeptide of SEQ ID NO: 2;
   (b) a polypeptide having at least 90% sequence identity to the mature polypeptide of SEQ ID NO: 4;
   (c) a polypeptide having at least 90% sequence identity to the mature polypeptide of SEQ ID NO: 6;
   (d) a polypeptide having at least 90% sequence identity to the mature polypeptide of SEQ ID NO: 10;
   (e) a polypeptide having at least 90% sequence identity to the mature polypeptide of SEQ ID NO: 12;
   (f) a polypeptide having at least 90% sequence identity to the mature polypeptide of SEQ ID NO: 14;
   (g) a polypeptide having at least 90% sequence identity to the mature polypeptide of SEQ ID NO: 16;
   (h) a polypeptide having at least 90% sequence identity to the mature polypeptide of SEQ ID NO: 18;
   (i) a polypeptide having at least 90% sequence identity to the mature polypeptide of SEQ ID NO: 22;
   (j) a polypeptide having at least 90% sequence identity to the mature polypeptide of SEQ ID NO: 24;
   (k) a polypeptide having at least 90% sequence identity to the mature polypeptide of SEQ ID NO: 26;
   (l) a polypeptide having at least 90% sequence identity to the mature polypeptide of SEQ ID NO: 28; and
   (m) a polypeptide having at least 90% sequence identity to the mature polypeptide of SEQ ID NO: 30.

2. The process of claim 1, wherein the polypeptide having alpha-amylase activity is selected from the group consisting of:

(a) a polypeptide having at least 95% sequence identity to the mature polypeptide of SEQ ID NO: 2;
(b) a polypeptide having at least 95% sequence identity to the mature polypeptide of SEQ ID NO: 4;
(c) a polypeptide having at least 95% sequence identity to the mature polypeptide of SEQ ID NO: 6;
(d) a polypeptide having at least 95% sequence identity to the mature polypeptide of SEQ ID NO: 10;
(e) a polypeptide having at least 95% sequence identity to the mature polypeptide of SEQ ID NO: 12;
(f) a polypeptide having at least 95% sequence identity to the mature polypeptide of SEQ ID NO: 14;
(g) a polypeptide having at least 95% sequence identity to the mature polypeptide of SEQ ID NO: 16;
(h) a polypeptide having at least 95% sequence identity to the mature polypeptide of SEQ ID NO: 18;
(i) a polypeptide having at least 95% sequence identity to the mature polypeptide of SEQ ID NO: 22;
(j) a polypeptide having at least 95% sequence identity to the mature polypeptide of SEQ ID NO: 24;
(k) a polypeptide having at least 95% sequence identity to the mature polypeptide of SEQ ID NO: 26;
(l) a polypeptide having at least 95% sequence identity to the mature polypeptide of SEQ ID NO: 28; and
(m) a polypeptide having at least 95% sequence identity to the mature polypeptide of SEQ ID NO: 30.

3. The process of claim 1, wherein the polypeptide comprises or consists of SEQ ID NO: 2, SEQ ID NO: 4, SEQ ID NO: 6, SEQ ID NO: 10, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, and SEQ ID NO: 30, or the mature polypeptide of SEQ ID NO: 10, SEQ ID NO: 2, SEQ ID NO: 4, SEQ ID NO: 6, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, or SEQ ID NO: 30.

4. The process of claim 1, wherein the mature polypeptide is amino acids 19 to 495 of SEQ ID NO: 2, amino acids 29 to 559 of SEQ ID NO: 4, amino acids 20 to 561 of SEQ ID NO: 6, amino acids 23 to 502 of SEQ ID NO: 10, amino acids 20 to 497 of SEQ ID NO: 12, amino acids 21 to 564 of SEQ ID NO: 14, amino acids 26 to 574 of SEQ ID NO: 16, amino acids 22 to 495 of SEQ ID NO: 18, amino acids 26 to 504 of SEQ ID NO: 22, amino acids 20 to 631 of SEQ ID NO: 24, amino acids 21 to 631 of SEQ ID NO: 26, amino acids 22 to 533 of SEQ ID NO: 28, or amino acids 25 to 627 of SEQ ID NO: 30.

5. The process of claim 1, further comprising recovering the ethanol.

6. The process of claim 1, wherein the saccharification step (ii) and the fermentation step (iii) are carried out as a simultaneous saccharification and fermentation process.

7. A process for producing ethanol from an ungelatinized starch, the process comprising:
(i) contacting an ungelatinized starch with a polypeptide having alpha-amylase activity to degrade the ungelatinized starch and obtain a mash;
(ii) saccharifying the mash using a glucoamylase; and
(iii) fermenting the material obtained in step (ii) in the presence of a yeast fermenting organism to produce ethanol, wherein the polypeptide having alpha-amylase activity is selected from the group consisting of:
(a) a polypeptide having at least 90% sequence identity to the mature polypeptide of SEQ ID NO: 2;
(b) a polypeptide having at least 90% sequence identity to the mature polypeptide of SEQ ID NO: 4;
(c) a polypeptide having at least 90% sequence identity to the mature polypeptide of SEQ ID NO: 6;
(d) a polypeptide having at least 90% sequence identity to the mature polypeptide of SEQ ID NO: 10;
(e) a polypeptide having at least 90% sequence identity to the mature polypeptide of SEQ ID NO: 12;
(f) a polypeptide having at least 90% sequence identity to the mature polypeptide of SEQ ID NO: 14;
(g) a polypeptide having at least 90% sequence identity to the mature polypeptide of SEQ ID NO: 16;
(h) a polypeptide having at least 90% sequence identity to the mature polypeptide of SEQ ID NO: 18;
(i) a polypeptide having at least 90% sequence identity to the mature polypeptide of SEQ ID NO: 22;
(j) a polypeptide having at least 90% sequence identity to the mature polypeptide of SEQ ID NO: 24;
(k) a polypeptide having at least 90% sequence identity to the mature polypeptide of SEQ ID NO: 26;
(l) a polypeptide having at least 90% sequence identity to the mature polypeptide of SEQ ID NO: 28; and
(m) a polypeptide having at least 90% sequence identity to the mature polypeptide of SEQ ID NO: 30.

8. The process of claim 7, wherein the polypeptide having alpha-amylase activity is selected from the group consisting of:
(a) a polypeptide having at least 95% sequence identity to the mature polypeptide of SEQ ID NO: 2;
(b) a polypeptide having at least 95% sequence identity to the mature polypeptide of SEQ ID NO: 4;
(c) a polypeptide having at least 95% sequence identity to the mature polypeptide of SEQ ID NO: 6;
(d) a polypeptide having at least 95% sequence identity to the mature polypeptide of SEQ ID NO: 10;
(e) a polypeptide having at least 95% sequence identity to the mature polypeptide of SEQ ID NO: 12;
(f) a polypeptide having at least 95% sequence identity to the mature polypeptide of SEQ ID NO: 14;
(g) a polypeptide having at least 95% sequence identity to the mature polypeptide of SEQ ID NO: 16;
(h) a polypeptide having at least 95% sequence identity to the mature polypeptide of SEQ ID NO: 18;
(i) a polypeptide having at least 95% sequence identity to the mature polypeptide of SEQ ID NO: 22;
(j) a polypeptide having at least 95% sequence identity to the mature polypeptide of SEQ ID NO: 24;
(k) a polypeptide having at least 95% sequence identity to the mature polypeptide of SEQ ID NO: 26;
(l) a polypeptide having at least 95% sequence identity to the mature polypeptide of SEQ ID NO: 28; and
(m) a polypeptide having at least 95% sequence identity to the mature polypeptide of SEQ ID NO: 30.

9. The process of claim 7, wherein the polypeptide comprises or consists of SEQ ID NO: 2, SEQ ID NO: 4, SEQ ID NO: 6, SEQ ID NO: 10, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, and SEQ ID NO: 30, or the mature polypeptide of SEQ ID NO: 10, SEQ ID NO: 2, SEQ ID NO: 4, SEQ ID NO: 6, SEQ ID NO: 12, SEQ ID NO: 14, SEQ ID NO: 16, SEQ ID NO: 18, SEQ ID NO: 22, SEQ ID NO: 24, SEQ ID NO: 26, SEQ ID NO: 28, or SEQ ID NO: 30.

10. The process of claim 7, wherein the mature polypeptide is amino acids 19 to 495 of SEQ ID NO: 2, amino acids 29 to 559 of SEQ ID NO: 4, amino acids 20 to 561 of SEQ ID NO: 6, amino acids 23 to 502 of SEQ ID NO: 10, amino acids 20 to 497 of SEQ ID NO: 12, amino acids 21 to 564 of SEQ ID NO: 14, amino acids 26 to 574 of SEQ ID NO:

16, amino acids 22 to 495 of SEQ ID NO: 18, amino acids 26 to 504 of SEQ ID NO: 22, amino acids 20 to 631 of SEQ ID NO: 24, amino acids 21 to 631 of SEQ ID NO: 26, amino acids 22 to 533 of SEQ ID NO: 28, or amino acids 25 to 627 of SEQ ID NO: 30.

11. The process of claim 7, further comprising recovering the ethanol.

\* \* \* \* \*

SEQUENCE LISTING

```
<160> NUMBER OF SEQ ID NOS: 60

<210> SEQ ID NO 1
<211> LENGTH: 1702
<212> TYPE: DNA
<213> ORGANISM: Thermoascus aurantiacus
<220> FEATURE:
<221> NAME/KEY: sig_peptide
<222> LOCATION: (1)..(54)
<220> FEATURE:
<221> NAME/KEY: exon
<222> LOCATION: (1)..(231)
<220> FEATURE:
```

```
<221> NAME/KEY: exon
<222> LOCATION: (287)..(445)
<220> FEATURE:
<221> NAME/KEY: exon
<222> LOCATION: (500)..(761)
<220> FEATURE:
<221> NAME/KEY: exon
<222> LOCATION: (816)..(978)
<220> FEATURE:
<221> NAME/KEY: exon
<222> LOCATION: (1030)..(1699)

<400> SEQUENCE: 1 atg aag ttt tcc gta ctc ttt aca agt gct ctg tac gct cgt gca gtc         48
Met Lys Phe Ser Val Leu Phe Thr Ser Ala Leu Tyr Ala Arg Ala Val
1               5                   10                  15 ctg gca gcc agc cct ata gac tgg cgc tcg aga tcc ata tac cag gtc         96
Leu Ala Ala Ser Pro Ile Asp Trp Arg Ser Arg Ser Ile Tyr Gln Val
            20                  25                  30 ctc acg gat agg ttc gcg cgc act gac gga tca acg aca gca cct tgt        144
Leu Thr Asp Arg Phe Ala Arg Thr Asp Gly Ser Thr Thr Ala Pro Cys
        35                  40                  45 cgc ctc gaa gac cgc acg tat tgc ggc ggt acg tac cga ggc att ata        192
Arg Leu Glu Asp Arg Thr Tyr Cys Gly Gly Thr Tyr Arg Gly Ile Ile
50                  55                  60 aac cgc ctg gat tac att cag gga atg ggg ttt aat gcc gtatgttttt         241
Asn Arg Leu Asp Tyr Ile Gln Gly Met Gly Phe Asn Ala
65                  70                  75 ttgtccttgg accaagattg aacacatgct tactttggcc actag ata tgg atc tcc      298
                                                 Ile Trp Ile Ser
                                                             80 ccc att acc ctt cag att gaa ggg cag aca tcc tat gga gag gcg tat        346
Pro Ile Thr Leu Gln Ile Glu Gly Gln Thr Ser Tyr Gly Glu Ala Tyr
                85                  90                  95 cac ggc tac tgg cag cag aaa atc tac gag ctg aat ccg cat ttt gga        394
His Gly Tyr Trp Gln Gln Lys Ile Tyr Glu Leu Asn Pro His Phe Gly
            100                 105                 110 tct ggt gac gac ctg agg gct cta gcc acg gag ctc cac aat cgc ggc        442
Ser Gly Asp Asp Leu Arg Ala Leu Ala Thr Glu Leu His Asn Arg Gly
        115                 120                 125 atg gtatcttcct gatgaaagta ttccttgctg aataatttct gataaaaatg gcag        499
Met
130 tat cta atg ctg gac att att gtc aat cac aac gcc tgg aat gga gaa        547
Tyr Leu Met Leu Asp Ile Ile Val Asn His Asn Ala Trp Asn Gly Glu
                135                 140                 145 agc tcc act gtg gat tat tca agg ttc cat ccc ttc aac cgc cag gac        595
Ser Ser Thr Val Asp Tyr Ser Arg Phe His Pro Phe Asn Arg Gln Asp
            150                 155                 160 ttc tat cat ccg tat tgc ccc ata tcg aac tgg tca aat cag tgg cag        643
Phe Tyr His Pro Tyr Cys Pro Ile Ser Asn Trp Ser Asn Gln Trp Gln
        165                 170                 175 gtc gag aac tgt tgg atg gga gat gat agt gtt gct ctt gcg gat ctg        691
Val Glu Asn Cys Trp Met Gly Asp Asp Ser Val Ala Leu Ala Asp Leu
180                 185                 190 gat acg cag tct gct gtt gtt gcg aac gag tac aat gca tgg ata tcc        739
Asp Thr Gln Ser Ala Val Val Ala Asn Glu Tyr Asn Ala Trp Ile Ser
195                 200                 205                 210 gcc ctc gtt tcc aac tac tct g gtacgttgcc gccctgaaca taaataatt         791
Ala Leu Val Ser Asn Tyr Ser
            215 ggagcgtctc atcgttcgct gtag tg  gat ggt ctg cga ata gac agc gcg         841
```

```
                    Val Asp Gly Leu Arg Ile Asp Ser Ala
                        220                 225 aaa cat gtt caa aag gaa ttt tgg cct ggc ttc aag gca gca tct ggg          889
Lys His Val Gln Lys Glu Phe Trp Pro Gly Phe Lys Ala Ala Ser Gly
        230                 235                 240 gtt ttc act atg ggt gaa gtt ttc acc agc gac gct ggc tac acc tgt          937
Val Phe Thr Met Gly Glu Val Phe Thr Ser Asp Ala Gly Tyr Thr Cys
            245                 250                 255 ccg tat cag caa tat ctg gac agt gtc atg aac tat cct at                   978
Pro Tyr Gln Gln Tyr Leu Asp Ser Val Met Asn Tyr Pro Ile
    260                 265                 270 gtatatttct tcgtgtctg cttcagcaat acttctgctt acattcagca g c tat           1033
                                                          Tyr gac tct ctt att ggc gcg ttc aac tca aca tcg ggt agc atc agc ggc         1081
Asp Ser Leu Ile Gly Ala Phe Asn Ser Thr Ser Gly Ser Ile Ser Gly
    275                 280                 285 ctg gtc aac cag atc aat ata gta aaa tca gcc tgt gca gac tcg acc         1129
Leu Val Asn Gln Ile Asn Ile Val Lys Ser Ala Cys Ala Asp Ser Thr
290                 295                 300                 305 atc ttg ggc acc ttc tcc gag aac cat gac aac ccg cgt ttt ccc tgc         1177
Ile Leu Gly Thr Phe Ser Glu Asn His Asp Asn Pro Arg Phe Pro Cys
                310                 315                 320 cat act tct gac ctt tct ctc gcg aag aat gtc att gct ttt aca ata         1225
His Thr Ser Asp Leu Ser Leu Ala Lys Asn Val Ile Ala Phe Thr Ile
            325                 330                 335 ctt gct gac ggt atc ccc atc atc tac tcc ggg cag gag cag cat tat         1273
Leu Ala Asp Gly Ile Pro Ile Ile Tyr Ser Gly Gln Glu Gln His Tyr
        340                 345                 350 gct ggc tgt gct gat cct gca aac cgt gag gcg ctt tgg cct tca ggc         1321
Ala Gly Cys Ala Asp Pro Ala Asn Arg Glu Ala Leu Trp Pro Ser Gly
    355                 360                 365 tac gac act tca gcg cca ctc tac aca cac atc gcg cag tta aat cgg         1369
Tyr Asp Thr Ser Ala Pro Leu Tyr Thr His Ile Ala Gln Leu Asn Arg
370                 375                 380                 385 atc cgg aat cga gct atc tat atg gac ccc gcg tac ctc agc tat aag         1417
Ile Arg Asn Arg Ala Ile Tyr Met Asp Pro Ala Tyr Leu Ser Tyr Lys
                390                 395                 400 aac gaa cca atc tat agc gat tcg acg aca atc gct atg cgg aag ggt         1465
Asn Glu Pro Ile Tyr Ser Asp Ser Thr Thr Ile Ala Met Arg Lys Gly
            405                 410                 415 ttc aat gga aac caa gtt gtg aca gtg ctg agc aat cag ggg tca agc         1513
Phe Asn Gly Asn Gln Val Val Thr Val Leu Ser Asn Gln Gly Ser Ser
        420                 425                 430 ggt ccg agc tac aca ttc ttg ctc gga aat act ggc cat acg agc ggg         1561
Gly Pro Ser Tyr Thr Phe Leu Leu Gly Asn Thr Gly His Thr Ser Gly
    435                 440                 445 cag cag ctg gtc gaa gtg cta aca tgc tcc tct gtg att gtg gat ggc         1609
Gln Gln Leu Val Glu Val Leu Thr Cys Ser Ser Val Ile Val Asp Gly
450                 455                 460                 465 aac ggg aat atc ccc gtc agt atg aac caa ggc atg cca agg gtg ttc         1657
Asn Gly Asn Ile Pro Val Ser Met Asn Gln Gly Met Pro Arg Val Phe
                470                 475                 480 tat ccg gca cac cag ctt tcg ggg tcg ggt ata tgt ggt cgt tga             1702
Tyr Pro Ala His Gln Leu Ser Gly Ser Gly Ile Cys Gly Arg
            485                 490                 495

<210> SEQ ID NO 2
<211> LENGTH: 495
<212> TYPE: PRT
<213> ORGANISM: Thermoascus aurantiacus
```

<400> SEQUENCE: 2

```
Met Lys Phe Ser Val Leu Phe Thr Ser Ala Leu Tyr Ala Arg Ala Val
1               5                   10                  15

Leu Ala Ala Ser Pro Ile Asp Trp Arg Ser Arg Ser Ile Tyr Gln Val
            20                  25                  30

Leu Thr Asp Arg Phe Ala Arg Thr Asp Gly Ser Thr Thr Ala Pro Cys
        35                  40                  45

Arg Leu Glu Asp Arg Thr Tyr Cys Gly Gly Thr Tyr Arg Gly Ile Ile
    50                  55                  60

Asn Arg Leu Asp Tyr Ile Gln Gly Met Gly Phe Asn Ala Ile Trp Ile
65                  70                  75                  80

Ser Pro Ile Thr Leu Gln Ile Glu Gly Gln Thr Ser Tyr Gly Glu Ala
                85                  90                  95

Tyr His Gly Tyr Trp Gln Gln Lys Ile Tyr Glu Leu Asn Pro His Phe
            100                 105                 110

Gly Ser Gly Asp Asp Leu Arg Ala Leu Ala Thr Glu Leu His Asn Arg
        115                 120                 125

Gly Met Tyr Leu Met Leu Asp Ile Ile Val Asn His Asn Ala Trp Asn
130                 135                 140

Gly Glu Ser Ser Thr Val Asp Tyr Ser Arg Phe His Pro Phe Asn Arg
145                 150                 155                 160

Gln Asp Phe Tyr His Pro Tyr Cys Pro Ile Ser Asn Trp Ser Asn Gln
                165                 170                 175

Trp Gln Val Glu Asn Cys Trp Met Gly Asp Asp Ser Val Ala Leu Ala
            180                 185                 190

Asp Leu Asp Thr Gln Ser Ala Val Val Ala Asn Glu Tyr Asn Ala Trp
        195                 200                 205

Ile Ser Ala Leu Val Ser Asn Tyr Ser Val Asp Gly Leu Arg Ile Asp
    210                 215                 220

Ser Ala Lys His Val Gln Lys Glu Phe Trp Pro Gly Phe Lys Ala Ala
225                 230                 235                 240

Ser Gly Val Phe Thr Met Gly Glu Val Phe Thr Ser Asp Ala Gly Tyr
                245                 250                 255

Thr Cys Pro Tyr Gln Gln Tyr Leu Asp Ser Val Met Asn Tyr Pro Ile
            260                 265                 270

Tyr Asp Ser Leu Ile Gly Ala Phe Asn Ser Thr Ser Gly Ser Ile Ser
        275                 280                 285

Gly Leu Val Asn Gln Ile Asn Ile Val Lys Ser Ala Cys Ala Asp Ser
    290                 295                 300

Thr Ile Leu Gly Thr Phe Ser Glu Asn His Asp Asn Pro Arg Phe Pro
305                 310                 315                 320

Cys His Thr Ser Asp Leu Ser Leu Ala Lys Asn Val Ile Ala Phe Thr
                325                 330                 335

Ile Leu Ala Asp Gly Ile Pro Ile Ile Tyr Ser Gly Gln Glu Gln His
            340                 345                 350

Tyr Ala Gly Cys Ala Asp Pro Ala Asn Arg Glu Ala Leu Trp Pro Ser
        355                 360                 365

Gly Tyr Asp Thr Ser Ala Pro Leu Tyr Thr His Ile Ala Gln Leu Asn
    370                 375                 380

Arg Ile Arg Asn Arg Ala Ile Tyr Met Asp Pro Ala Tyr Leu Ser Tyr
385                 390                 395                 400

Lys Asn Glu Pro Ile Tyr Ser Asp Ser Thr Thr Ile Ala Met Arg Lys
```

```
                            405                 410                 415
Gly Phe Asn Gly Asn Gln Val Val Thr Val Leu Ser Asn Gln Gly Ser
                420                 425                 430

Ser Gly Pro Ser Tyr Thr Phe Leu Leu Gly Asn Thr Gly His Thr Ser
            435                 440                 445

Gly Gln Gln Leu Val Glu Val Leu Thr Cys Ser Ser Val Ile Val Asp
        450                 455                 460

Gly Asn Gly Asn Ile Pro Val Ser Met Asn Gln Gly Met Pro Arg Val
465                 470                 475                 480

Phe Tyr Pro Ala His Gln Leu Ser Gly Ser Gly Ile Cys Gly Arg
                485                 490                 495

<210> SEQ ID NO 3
<211> LENGTH: 1746
<212> TYPE: DNA
<213> ORGANISM: Thermoascus aurantiacus
<220> FEATURE:
<221> NAME/KEY: sig_peptide
<222> LOCATION: (1)..(84)
<220> FEATURE:
<221> NAME/KEY: exon
<222> LOCATION: (1)..(1020)
<220> FEATURE:
<221> NAME/KEY: exon
<222> LOCATION: (1087)..(1743)

<400> SEQUENCE: 3 atg gtc aag atg ttt ggg tca cga cgt tat tca cat tcg ctt tcc ctc        48
Met Val Lys Met Phe Gly Ser Arg Arg Tyr Ser His Ser Leu Ser Leu
1               5                   10                  15 ttt tcg gta ttc ggc ctt gta aca tca gca ttt gcg gca gat ctt gct        96
Phe Ser Val Phe Gly Leu Val Thr Ser Ala Phe Ala Ala Asp Leu Ala
                20                  25                  30 gct tgg aag tca agg tcg gta tat cag gtc atg acg gac agg ttt gca       144
Ala Trp Lys Ser Arg Ser Val Tyr Gln Val Met Thr Asp Arg Phe Ala
            35                  40                  45 cgg aca gat gga tcc acg gat gca cct tgc aac acc aca gca gga ttg       192
Arg Thr Asp Gly Ser Thr Asp Ala Pro Cys Asn Thr Thr Ala Gly Leu
        50                  55                  60 tac tgt ggc ggt acg tgg aga gga cta atc aat cac ctg gac tac atc       240
Tyr Cys Gly Gly Thr Trp Arg Gly Leu Ile Asn His Leu Asp Tyr Ile
65                  70                  75                  80 cag ggc atg gga ttc gat gct atc atg atc tct cct gtc atc aag aat       288
Gln Gly Met Gly Phe Asp Ala Ile Met Ile Ser Pro Val Ile Lys Asn
                85                  90                  95 gtc gag ggg agg gtt tca tac ggc gaa gcc tac cat ggt tac tgg cag       336
Val Glu Gly Arg Val Ser Tyr Gly Glu Ala Tyr His Gly Tyr Trp Gln
            100                 105                 110 gaa gat atg tac gca ttg aac gaa cat ttt ggc acc cat cag gac ctg       384
Glu Asp Met Tyr Ala Leu Asn Glu His Phe Gly Thr His Gln Asp Leu
        115                 120                 125 ctt gat ctc agc gct gct ctc cac aag cgg gat atg ttt ttg atg gtc       432
Leu Asp Leu Ser Ala Ala Leu His Lys Arg Asp Met Phe Leu Met Val
    130                 135                 140 gat tct gtt atc aac aac atg gcc tac atc acc aat gga agc gat cca       480
Asp Ser Val Ile Asn Asn Met Ala Tyr Ile Thr Asn Gly Ser Asp Pro
145                 150                 155                 160 gcc acc tca gtc gac tac tcg gtt ttc acg ccc ttc aat agc aag gac       528
Ala Thr Ser Val Asp Tyr Ser Val Phe Thr Pro Phe Asn Ser Lys Asp
                165                 170                 175 tac ttc cac cct tac tgt gag att acg gat tat aac aat tac cct ctc       576
```

-continued

```
                    Tyr Phe His Pro Tyr Cys Glu Ile Thr Asp Tyr Asn Asn Tyr Pro Leu
                                180             185                 190 gcg caa agg tgc tgg acg ggt gat gat atc gtt ccg ctc ccc gat ctc         624
Ala Gln Arg Cys Trp Thr Gly Asp Asp Ile Val Pro Leu Pro Asp Leu
            195                 200                 205 aaa acg gag gat agc acg gtt caa aaa ctt ttg gag gac tgg gcc aaa         672
Lys Thr Glu Asp Ser Thr Val Gln Lys Leu Leu Glu Asp Trp Ala Lys
210                 215                 220 gat ctg att gcc aac tat tct gtc gat ggc tta cgt atc gac gcc gcg         720
Asp Leu Ile Ala Asn Tyr Ser Val Asp Gly Leu Arg Ile Asp Ala Ala
225                 230                 235                 240 aaa cat gtt acc ccg agt ttc ctt ccg aaa ttc tac gat gca gct ggc         768
Lys His Val Thr Pro Ser Phe Leu Pro Lys Phe Tyr Asp Ala Ala Gly
                245                 250                 255 gta tac atg acg gga gaa gtt tac gag tac aac gcc gac att ata tgc         816
Val Tyr Met Thr Gly Glu Val Tyr Glu Tyr Asn Ala Asp Ile Ile Cys
                260                 265                 270 aag tac caa aaa gac tac ctt cct agc gtt cct aac tac ccg gtc tat         864
Lys Tyr Gln Lys Asp Tyr Leu Pro Ser Val Pro Asn Tyr Pro Val Tyr
            275                 280                 285 aat gcg ata atg caa act ttt aca acc ggg aac acg aca gca ttg acg         912
Asn Ala Ile Met Gln Thr Phe Thr Thr Gly Asn Thr Thr Ala Leu Thr
290                 295                 300 aac gaa att act gtc atg aag gag aca tgc cag gat gtt act gca tta         960
Asn Glu Ile Thr Val Met Lys Glu Thr Cys Gln Asp Val Thr Ala Leu
305                 310                 315                 320 gct tca ttc tcc gaa aac cat gac gtc cct cgg ttc gcc tct att caa        1008
Ala Ser Phe Ser Glu Asn His Asp Val Pro Arg Phe Ala Ser Ile Gln
                325                 330                 335 aag gat ctg gcg gtaagtacct gttcttcaat gaaatgaatg tctcccgaaa            1060
Lys Asp Leu Ala
            340 agcactaacg acttgactct ttacag ctc gcc aag aat gtc att act ttc acc       1113
                              Leu Ala Lys Asn Val Ile Thr Phe Thr
                                              345 att ctc gcc gat gga ata cct atg atc tat caa ggt caa gag caa cac        1161
Ile Leu Ala Asp Gly Ile Pro Met Ile Tyr Gln Gly Gln Glu Gln His
350                 355                 360                 365 ttt ggc gtt gaa acg ccc ccc aat aaa gct gga aca ccc gcc aat aga        1209
Phe Gly Val Glu Thr Pro Pro Asn Lys Ala Gly Thr Pro Ala Asn Arg
                370                 375                 380 gaa gcc ctg tgg ctc tct aaa tac gac acc agc gct ccg ttg tac aaa        1257
Glu Ala Leu Trp Leu Ser Lys Tyr Asp Thr Ser Ala Pro Leu Tyr Lys
            385                 390                 395 ttg acc gca acc ctg aac aaa atc cgc aaa cag gct atc cgg gtt gat        1305
Leu Thr Ala Thr Leu Asn Lys Ile Arg Lys Gln Ala Ile Arg Val Asp
400                 405                 410 ccg aca tat gtt gac tac aaa tcc tat ccc ata tgg acc ggt cca agt        1353
Pro Thr Tyr Val Asp Tyr Lys Ser Tyr Pro Ile Trp Thr Gly Pro Ser
            415                 420                 425 gaa ctc gct atc cgc aag ggt cag gaa ggg cag cac gtc atc atg gtt        1401
Glu Leu Ala Ile Arg Lys Gly Gln Glu Gly Gln His Val Ile Met Val
430                 435                 440                 445 ctc tcg acc gga gga tcg aag agc ggg gac tat acc cta acc ctg cct        1449
Leu Ser Thr Gly Gly Ser Lys Ser Gly Asp Tyr Thr Leu Thr Leu Pro
                450                 455                 460 gtc acc tat gaa caa ggc att gag att atg gag gtg ctg aac tgt gtc        1497
Val Thr Tyr Glu Gln Gly Ile Glu Ile Met Glu Val Leu Asn Cys Val
            465                 470                 475
```

```
aag tac aac ttg act gag aat gga gag ctc gtg gtg cca atg agc aag       1545
Lys Tyr Asn Leu Thr Glu Asn Gly Glu Leu Val Val Pro Met Ser Lys
            480                 485                 490 ggc gag ccc agg gtg ttc ttc cct gcc gac aag cta gat gga agc ggg       1593
Gly Glu Pro Arg Val Phe Phe Pro Ala Asp Lys Leu Asp Gly Ser Gly
    495                 500                 505 ctg tgc ggc tac gcc aac tcg tcc gca gtc aat ggc acc aac ggt gct       1641
Leu Cys Gly Tyr Ala Asn Ser Ser Ala Val Asn Gly Thr Asn Gly Ala
510                 515                 520                 525 ttc gca tct gcc gcc agt gac ggc atc tac tcg aga tct ctg agc acg       1689
Phe Ala Ser Ala Ala Ser Asp Gly Ile Tyr Ser Arg Ser Leu Ser Thr
                530                 535                 540 ctg tgg ctg gcc ctg ttc aca tcg ttc atg gcc ggc gcc gct gtt ttt       1737
Leu Trp Leu Ala Leu Phe Thr Ser Phe Met Ala Gly Ala Ala Val Phe
            545                 550                 555 atg gta tag                                                            1746
Met Val <210> SEQ ID NO 4
<211> LENGTH: 559
<212> TYPE: PRT
<213> ORGANISM: Thermoascus aurantiacus

<400> SEQUENCE: 4

Met Val Lys Met Phe Gly Ser Arg Arg Tyr Ser His Ser Leu Ser Leu
1               5                   10                  15

Phe Ser Val Phe Gly Leu Val Thr Ser Ala Phe Ala Ala Asp Leu Ala
            20                  25                  30

Ala Trp Lys Ser Arg Ser Val Tyr Gln Val Met Thr Asp Arg Phe Ala
        35                  40                  45

Arg Thr Asp Gly Ser Thr Asp Ala Pro Cys Asn Thr Thr Ala Gly Leu
    50                  55                  60

Tyr Cys Gly Gly Thr Trp Arg Gly Leu Ile Asn His Leu Asp Tyr Ile
65                  70                  75                  80

Gln Gly Met Gly Phe Asp Ala Ile Met Ile Ser Pro Val Ile Lys Asn
                85                  90                  95

Val Glu Gly Arg Val Ser Tyr Gly Glu Ala Tyr His Gly Tyr Trp Gln
            100                 105                 110

Glu Asp Met Tyr Ala Leu Asn Glu His Phe Gly Thr His Gln Asp Leu
        115                 120                 125

Leu Asp Leu Ser Ala Ala Leu His Lys Arg Asp Met Phe Leu Met Val
    130                 135                 140

Asp Ser Val Ile Asn Asn Met Ala Tyr Ile Thr Asn Gly Ser Asp Pro
145                 150                 155                 160

Ala Thr Ser Val Asp Tyr Ser Val Phe Thr Pro Phe Asn Ser Lys Asp
                165                 170                 175

Tyr Phe His Pro Tyr Cys Glu Ile Thr Asp Tyr Asn Asn Tyr Pro Leu
            180                 185                 190

Ala Gln Arg Cys Trp Thr Gly Asp Asp Ile Val Pro Leu Pro Asp Leu
        195                 200                 205

Lys Thr Glu Asp Ser Thr Val Gln Lys Leu Leu Glu Asp Trp Ala Lys
    210                 215                 220

Asp Leu Ile Ala Asn Tyr Ser Val Asp Gly Leu Arg Ile Asp Ala Ala
225                 230                 235                 240

Lys His Val Thr Pro Ser Phe Leu Pro Lys Phe Tyr Asp Ala Ala Gly
                245                 250                 255
```

```
Val Tyr Met Thr Gly Glu Val Tyr Tyr Asn Ala Asp Ile Ile Cys
            260                 265                 270

Lys Tyr Gln Lys Asp Tyr Leu Pro Ser Val Pro Asn Tyr Pro Val Tyr
        275                 280                 285

Asn Ala Ile Met Gln Thr Phe Thr Thr Gly Asn Thr Thr Ala Leu Thr
    290                 295                 300

Asn Glu Ile Thr Val Met Lys Glu Thr Cys Gln Asp Val Thr Ala Leu
305                 310                 315                 320

Ala Ser Phe Ser Glu Asn His Asp Val Pro Arg Phe Ala Ser Ile Gln
                325                 330                 335

Lys Asp Leu Ala Leu Ala Lys Asn Val Ile Thr Phe Thr Ile Leu Ala
            340                 345                 350

Asp Gly Ile Pro Met Ile Tyr Gln Gly Gln Glu Gln His Phe Gly Val
        355                 360                 365

Glu Thr Pro Pro Asn Lys Ala Gly Thr Pro Ala Asn Arg Glu Ala Leu
    370                 375                 380

Trp Leu Ser Lys Tyr Asp Thr Ser Ala Pro Leu Tyr Lys Leu Thr Ala
385                 390                 395                 400

Thr Leu Asn Lys Ile Arg Lys Gln Ala Ile Arg Val Asp Pro Thr Tyr
                405                 410                 415

Val Asp Tyr Lys Ser Tyr Pro Ile Trp Thr Gly Pro Ser Glu Leu Ala
            420                 425                 430

Ile Arg Lys Gly Gln Glu Gly Gln His Val Ile Met Val Leu Ser Thr
        435                 440                 445

Gly Gly Ser Lys Ser Gly Asp Tyr Thr Leu Thr Leu Pro Val Thr Tyr
    450                 455                 460

Glu Gln Gly Ile Glu Ile Met Glu Val Leu Asn Cys Val Lys Tyr Asn
465                 470                 475                 480

Leu Thr Glu Asn Gly Glu Leu Val Pro Met Ser Lys Gly Glu Pro
                485                 490                 495

Arg Val Phe Phe Pro Ala Asp Lys Leu Asp Gly Ser Gly Leu Cys Gly
            500                 505                 510

Tyr Ala Asn Ser Ser Ala Val Asn Gly Thr Asn Gly Ala Phe Ala Ser
        515                 520                 525

Ala Ala Ser Asp Gly Ile Tyr Ser Arg Ser Leu Ser Thr Leu Trp Leu
    530                 535                 540

Ala Leu Phe Thr Ser Phe Met Ala Gly Ala Ala Val Phe Met Val
545                 550                 555

<210> SEQ ID NO 5
<211> LENGTH: 2287
<212> TYPE: DNA
<213> ORGANISM: Thermoascus aurantiacus
<220> FEATURE:
<221> NAME/KEY: sig_peptide
<222> LOCATION: (1)..(57)
<220> FEATURE:
<221> NAME/KEY: exon
<222> LOCATION: (1)..(234)
<220> FEATURE:
<221> NAME/KEY: exon
<222> LOCATION: (342)..(396)
<220> FEATURE:
<221> NAME/KEY: exon
<222> LOCATION: (447)..(550)
<220> FEATURE:
<221> NAME/KEY: exon
<222> LOCATION: (614)..(769)
<220> FEATURE:
<221> NAME/KEY: exon
```

```
<222> LOCATION: (833)..(941)
<220> FEATURE:
<221> NAME/KEY: exon
<222> LOCATION: (995)..(1157)
<220> FEATURE:
<221> NAME/KEY: exon
<222> LOCATION: (1214)..(1304)
<220> FEATURE:
<221> NAME/KEY: exon
<222> LOCATION: (1372)..(1446)
<220> FEATURE:
<221> NAME/KEY: exon
<222> LOCATION: (1511)..(1562)
<220> FEATURE:
<221> NAME/KEY: exon
<222> LOCATION: (1641)..(2284)

<400> SEQUENCE: 5
```

| | | | | | | | | | | | | | | | | |
|---|---|---|---|---|---|---|---|---|---|---|---|---|---|---|---|---|
| atg | gaa | gtg | tgg | aag | ata | gtg | ctg | gtc | ttt | atg | acc | tgg | ata | ccc | tct | 48 |
| Met | Glu | Val | Trp | Lys | Ile | Val | Leu | Val | Phe | Met | Thr | Trp | Ile | Pro | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| att | cag | gcg | gca | tcc | aaa | gac | gaa | tgg | aaa | tca | agg | tcc | ata | tac | cag | 96 |
| Ile | Gln | Ala | Ala | Ser | Lys | Asp | Glu | Trp | Lys | Ser | Arg | Ser | Ile | Tyr | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | gtg | acg | gac | cgc | ttc | gct | cgg | tcg | gat | ggc | tcg | acc | tcc | gct | tca | 144 |
| Val | Val | Thr | Asp | Arg | Phe | Ala | Arg | Ser | Asp | Gly | Ser | Thr | Ser | Ala | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| tgc | gac | cct | gga | aag | gga | cta | tac | tgc | gga | ggc | act | ttc | cac | ggt | att | 192 |
| Cys | Asp | Pro | Gly | Lys | Gly | Leu | Tyr | Cys | Gly | Gly | Thr | Phe | His | Gly | Ile | |
| 50 | | | | | 55 | | | | | 60 | | | | | | |

| | | | | | | | | | | | | |
|---|---|---|---|---|---|---|---|---|---|---|---|---|
| att | gaa | aag | ctg | gat | tat | att | caa | aac | ctc | ggg | ttt | tca | gcc | 234 |
| Ile | Glu | Lys | Leu | Asp | Tyr | Ile | Gln | Asn | Leu | Gly | Phe | Ser | Ala | |
| 65 | | | | 70 | | | | | 75 | | | | | |

```
gtgagcatct ccttctgccc ttatttctgg acgtcgctca gtaagattgt gcttcagtgc        294
acggtttgtc atcacaacta acacattaac gcttgcgcaa tttgcag atc tgg ata          350
                                                    Ile Trp Ile
                                                         80
```

| | | | | | | | | | | | |
|---|---|---|---|---|---|---|---|---|---|---|---|
| tca | cct | gtc | aca | tat | cct | att | caa | gag | gtc | act | gca | gat | tta | tca | g | 396 |
| Ser | Pro | Val | Thr | Tyr | Pro | Ile | Gln | Glu | Val | Thr | Ala | Asp | Leu | Ser | | |
| | | 85 | | | | | 90 | | | | | 95 | | | | |

```
gtgcttccac tttcacaccg ttgaggacaa taattctgac ccttgctcag ca tat            451
                                                           Ala Tyr
```

| | | | | | | | | | | | | | | | |
|---|---|---|---|---|---|---|---|---|---|---|---|---|---|---|---|
| cat | gga | tac | tgg | caa | cag | gat | ctt | tac | tcg | atc | aac | ccg | aag | ttc | ggc | 499 |
| His | Gly | Tyr | Trp | Gln | Gln | Asp | Leu | Tyr | Ser | Ile | Asn | Pro | Lys | Phe | Gly | |
| | | | 100 | | | | | 105 | | | | | 110 | | | |

| | | | | | | | | | | | | | | | |
|---|---|---|---|---|---|---|---|---|---|---|---|---|---|---|---|
| acg | cct | aat | gat | ctc | aag | gcg | ctc | tcc | cat | gag | ctt | cat | tca | cgt | gga | 547 |
| Thr | Pro | Asn | Asp | Leu | Lys | Ala | Leu | Ser | His | Glu | Leu | His | Ser | Arg | Gly | |
| 115 | | | | | 120 | | | | | 125 | | | | | 130 | |

```
atg gtccgcataa actcctgcat atatctgcgc ctatttcctg aaaatgcacg              600
Met
```

| | | | | | | | | | | | |
|---|---|---|---|---|---|---|---|---|---|---|---|
| ctaacagata | cag | tac | ctg | atg | gtc | gac | gtg | gtc | gcc | aac | aac | atg | gca | 649 |
| | Tyr | Leu | Met | Val | Asp | Val | Val | Ala | Asn | Asn | Met | Ala | | |
| | | 135 | | | | | | 140 | | | | | | |

| | | | | | | | | | | | | | | | |
|---|---|---|---|---|---|---|---|---|---|---|---|---|---|---|---|
| tgg | gct | ggt | aac | gga | aat | act | gtc | aat | tat | agc | aag | ttg | aag | cct | ttt | 697 |
| Trp | Ala | Gly | Asn | Gly | Asn | Thr | Val | Asn | Tyr | Ser | Lys | Leu | Lys | Pro | Phe | |
| | 145 | | | | | 150 | | | | | 155 | | | | | |

| | | | | | | | | | | | | | | | |
|---|---|---|---|---|---|---|---|---|---|---|---|---|---|---|---|
| gat | aac | gag | ggt | tac | tac | cat | cca | ctc | cgg | ttg | ctc | tca | gat | gat | cca | 745 |
| Asp | Asn | Glu | Gly | Tyr | Tyr | His | Pro | Leu | Arg | Leu | Leu | Ser | Asp | Asp | Pro | |
| | 160 | | | | | 165 | | | | | 170 | | | | | 175 |

| | | | | | | | | |
|---|---|---|---|---|---|---|---|---|
| ctg | aat | gag | acg | tgc | gtg | gaa | aag | gtggatacaa tcctgtaaaa gattctggat | 799 |
| Leu | Asn | Glu | Thr | Cys | Val | Glu | Lys | | |
| | | | 180 | | | | | | |

| | | |
|---|---|---|
| ctaatggctt cttcgctaac gtcgatccta cag tgc tgg cta ggc gac aca gtc<br>                Cys Trp Leu Gly Asp Thr Val<br>                 185         190 | | 853 |
| gtt tcg ctt ccg gac ctg aga aca gaa gac gac aaa gtg tcg tcg atg<br>Val Ser Leu Pro Asp Leu Arg Thr Glu Asp Asp Lys Val Ser Ser Met<br>       195        200        205 | | 901 |
| cta tac tcc tgg ata aga gag atg gtg tct aat tat tca a gtaggtggtg<br>Leu Tyr Ser Trp Ile Arg Glu Met Val Ser Asn Tyr Ser<br>      210        215 | | 951 |
| cagttaacag ccgctttcgc atgcaattct aacctccgca cag tt gat ggc ttg<br>                                  Ile Asp Gly Leu | | 1005 |
| cgt ctc gac agt ata ttc aat gtc aac aag gat ttc tgg tct gga ttc<br>Arg Leu Asp Ser Ile Phe Asn Val Asn Lys Asp Phe Trp Ser Gly Phe<br>    225         230        235 | | 1053 |
| aac cat gcc gct ggc gtt ttc tgt ctc ggg gaa ggt att acc aac aat<br>Asn His Ala Ala Gly Val Phe Cys Leu Gly Glu Gly Ile Thr Asn Asn<br>240         245        250        255 | | 1101 |
| gcg atg acc ctg tgc cct ctt caa aat aat gtg gat ggg gtc ttg gat<br>Ala Met Thr Leu Cys Pro Leu Gln Asn Asn Val Asp Gly Val Leu Asp<br>         260        265        270 | | 1149 |
| tat ccc at gttcgtgtaa actcgaccat agaaatatgc ataccgtgtc<br>Tyr Pro Met | | 1197 |
| tgattgttgt taccag g tat tat cac ctc aca gac gcc ttc aac agc acg<br>               Tyr Tyr His Leu Thr Asp Ala Phe Asn Ser Thr<br>                 275        280        285 | | 1247 |
| aat ggc aac ctc cat tat gtg gtg gaa gga atg aac ttc gtg aag aac<br>Asn Gly Asn Leu His Tyr Val Val Glu Gly Met Asn Phe Val Lys Asn<br>            290        295        300 | | 1295 |
| acg tgc aag gtaacttggc gatggctgta tctcagcgcg cagttcaacc<br>Thr Cys Lys | | 1344 |
| actggccaag tctgacatgt acaacag gat att ttc acg ttg gga acg ttt acc<br>                      Asp Ile Phe Thr Leu Gly Thr Phe Thr<br>                           305        310 | | 1398 |
| gag aac caa gac gtc cct cgc ttt gct tcc tat acg caa gat tta tct<br>Glu Asn Gln Asp Val Pro Arg Phe Ala Ser Tyr Thr Gln Asp Leu Ser<br>315         320        325 | | 1446 |
| gtccgtcccg ctccctgttt tgaatcattc agccttactg tatatctaac cctgtcttct | | 1506 |
| ccag ttg gct cgg aac atc atc acc tac aat ctc ctt gga gac ggt ata<br>   Leu Ala Arg Asn Ile Ile Thr Tyr Asn Leu Leu Gly Asp Gly Ile<br>         330        335        340 | | 1555 |
| cca gtt c gtaagtctcc tcttcccata atatctgtcg aatggtgacg aaatgataaa<br>Pro Val<br>345 | | 1612 |
| aataaattaa ccaacttgag aaatatag tc tat tac ggc caa gaa caa cat<br>                          Leu Tyr Tyr Gly Gln Glu Gln His<br>                               350 | | 1663 |
| cta tca ggc gcc tcc aac ccc ctc aac cgt gaa gcg ctc tgg ctc acc<br>Leu Ser Gly Ala Ser Asn Pro Leu Asn Arg Glu Ala Leu Trp Leu Thr<br>355         360        365        370 | | 1711 |
| gga tac aga aac caa agc acc tcc ctt ccc tcc ctc atc caa tcc ctc<br>Gly Tyr Arg Asn Gln Ser Thr Ser Leu Pro Ser Leu Ile Gln Ser Leu<br>       375        380        385 | | 1759 |
| aat cgc ctc cgc tcc cac gcc gca ggc aac gga agc cgg ttc acg gac<br>Asn Arg Leu Arg Ser His Ala Ala Gly Asn Gly Ser Arg Phe Thr Asp<br>      390        395        400 | | 1807 |
| ccc tca gaa cca cac cgc gac tac ctc acc tac atc acg ctc ccg atc<br>Pro Ser Glu Pro His Arg Asp Tyr Leu Thr Tyr Ile Thr Leu Pro Ile<br>405         410        415 | | 1855 |

-continued

| | | |
|---|---|---|
| cac gac agc gac cac gtc ctc gcg ctg cgg aag ggc ttc gcg ggg aac<br>His Asp Ser Asp His Val Leu Ala Leu Arg Lys Gly Phe Ala Gly Asn<br>420                        425                      430 | 1903 |
| cag gtg gtg agc gtg ctg tcg aac ctc gga tcc cac ccc agc ggg gac<br>Gln Val Val Ser Val Leu Ser Asn Leu Gly Ser His Pro Ser Gly Asp<br>435                        440                    445                  450 | 1951 |
| gcc gag acg agc gtg ctg ctc ccc gcg gag ggc acg ggg ttc cgg cct<br>Ala Glu Thr Ser Val Leu Leu Pro Ala Glu Gly Thr Gly Phe Arg Pro<br>                                455                    460                    465 | 1999 |
| gag cag aat gtg acc gag atc ctg tcc tgc agg acc ctc gtc acc gac<br>Glu Gln Asn Val Thr Glu Ile Leu Ser Cys Arg Thr Leu Val Thr Asp<br>                    470                    475                    480 | 2047 |
| cgg tcg ggc aat ctc cgc gcg agc ctg gag gac ggg ccg cgg gtt<br>Arg Ser Gly Asn Leu Arg Ala Ser Leu Glu Asp Gly Gly Pro Arg Val<br>485                        490                    495 | 2095 |
| tac tat ccg act gag agc ctg aac atg tcc ggg ctc tgt ggc cac cat<br>Tyr Tyr Pro Thr Glu Ser Leu Asn Met Ser Gly Leu Cys Gly His His<br>500                        505                    510 | 2143 |
| gtg cgc gtg ggc cgc gtg gcg tcg agt gaa agt aaa tta tcg cta gcg<br>Val Arg Val Gly Arg Val Ala Ser Ser Glu Ser Lys Leu Ser Leu Ala<br>515                        520                    525                    530 | 2191 |
| gcg acg acg acg atg acc gcg gcg gtt att agg agt tcg ggg tgg tta<br>Ala Thr Thr Thr Met Thr Ala Ala Val Ile Arg Ser Ser Gly Trp Leu<br>                    535                    540                    545 | 2239 |
| atc agc ctg gga ctg gct gtg ctg ttc gct gtg gag gtg ttg ttc tga<br>Ile Ser Leu Gly Leu Ala Val Leu Phe Ala Val Glu Val Leu Phe<br>550                        555                    560 | 2287 |

<210> SEQ ID NO 6
<211> LENGTH: 561
<212> TYPE: PRT
<213> ORGANISM: Thermoascus aurantiacus

<400> SEQUENCE: 6

Met Glu Val Trp Lys Ile Val Leu Val Phe Met Thr Trp Ile Pro Ser
1               5                   10                  15

Ile Gln Ala Ala Ser Lys Asp Glu Trp Lys Ser Arg Ser Ile Tyr Gln
            20                  25                  30

Val Val Thr Asp Arg Phe Ala Arg Ser Asp Gly Ser Thr Ser Ala Ser
        35                  40                  45

Cys Asp Pro Gly Lys Gly Leu Tyr Cys Gly Gly Thr Phe His Gly Ile
    50                  55                  60

Ile Glu Lys Leu Asp Tyr Ile Gln Asn Leu Gly Phe Ser Ala Ile Trp
65                  70                  75                  80

Ile Ser Pro Val Thr Tyr Pro Ile Gln Glu Val Thr Ala Asp Leu Ser
                85                  90                  95

Ala Tyr His Gly Tyr Trp Gln Gln Asp Leu Tyr Ser Ile Asn Pro Lys
            100                 105                 110

Phe Gly Thr Pro Asn Asp Leu Lys Ala Leu Ser His Glu Leu His Ser
        115                 120                 125

Arg Gly Met Tyr Leu Met Val Asp Val Val Ala Asn Met Ala Trp
    130                 135                 140

Ala Gly Asn Gly Asn Thr Val Asn Tyr Ser Lys Leu Lys Pro Phe Asp
145                 150                 155                 160

Asn Glu Gly Tyr Tyr His Pro Leu Arg Leu Leu Ser Asp Pro Leu
                165                 170                 175

Asn Glu Thr Cys Val Glu Lys Cys Trp Leu Gly Asp Thr Val Val Ser
            180                 185                 190

```
Leu Pro Asp Leu Arg Thr Glu Asp Asp Lys Val Ser Ser Met Leu Tyr
            195                 200                 205

Ser Trp Ile Arg Glu Met Val Ser Asn Tyr Ser Ile Asp Gly Leu Arg
    210                 215                 220

Leu Asp Ser Ile Phe Asn Val Asn Lys Asp Phe Trp Ser Gly Phe Asn
225                 230                 235                 240

His Ala Ala Gly Val Phe Cys Leu Gly Glu Gly Ile Thr Asn Asn Ala
                245                 250                 255

Met Thr Leu Cys Pro Leu Gln Asn Asn Val Asp Gly Val Leu Asp Tyr
            260                 265                 270

Pro Met Tyr Tyr His Leu Thr Asp Ala Phe Asn Ser Thr Asn Gly Asn
            275                 280                 285

Leu His Tyr Val Val Glu Gly Met Asn Phe Val Lys Asn Thr Cys Lys
    290                 295                 300

Asp Ile Phe Thr Leu Gly Thr Phe Thr Glu Asn Gln Asp Val Pro Arg
305                 310                 315                 320

Phe Ala Ser Tyr Thr Gln Asp Leu Ser Leu Ala Arg Asn Ile Ile Thr
                325                 330                 335

Tyr Asn Leu Leu Gly Asp Gly Ile Pro Val Leu Tyr Tyr Gly Gln Glu
            340                 345                 350

Gln His Leu Ser Gly Ala Ser Asn Pro Leu Asn Arg Glu Ala Leu Trp
            355                 360                 365

Leu Thr Gly Tyr Arg Asn Gln Ser Thr Ser Leu Pro Ser Leu Ile Gln
    370                 375                 380

Ser Leu Asn Arg Leu Arg Ser His Ala Ala Gly Asn Gly Ser Arg Phe
385                 390                 395                 400

Thr Asp Pro Ser Glu Pro His Arg Asp Tyr Leu Thr Tyr Ile Thr Leu
                405                 410                 415

Pro Ile His Asp Ser Asp His Val Leu Ala Leu Arg Lys Gly Phe Ala
            420                 425                 430

Gly Asn Gln Val Val Ser Val Leu Ser Asn Leu Gly Ser His Pro Ser
            435                 440                 445

Gly Asp Ala Glu Thr Ser Val Leu Leu Pro Ala Glu Gly Thr Gly Phe
    450                 455                 460

Arg Pro Glu Gln Asn Val Thr Glu Ile Leu Ser Cys Arg Thr Leu Val
465                 470                 475                 480

Thr Asp Arg Ser Gly Asn Leu Arg Ala Ser Leu Glu Asp Gly Gly Pro
                485                 490                 495

Arg Val Tyr Tyr Pro Thr Glu Ser Leu Asn Met Ser Gly Leu Cys Gly
            500                 505                 510

His His Val Arg Val Gly Arg Val Ala Ser Ser Glu Ser Lys Leu Ser
            515                 520                 525

Leu Ala Ala Thr Thr Thr Met Thr Ala Ala Val Ile Arg Ser Ser Gly
    530                 535                 540

Trp Leu Ile Ser Leu Gly Leu Ala Val Leu Phe Ala Val Glu Val Leu
545                 550                 555                 560

Phe
```

<210> SEQ ID NO 7
<211> LENGTH: 1695
<212> TYPE: DNA
<213> ORGANISM: Talaromyces emersonii
<220> FEATURE:
<221> NAME/KEY: sig_peptide

```
<222> LOCATION: (1)..(60)
<220> FEATURE:
<221> NAME/KEY: exon
<222> LOCATION: (1)..(990)
<220> FEATURE:
<221> NAME/KEY: exon
<222> LOCATION: (1048)..(1692)

<400> SEQUENCE: 7 atg aaa ttc cca acg tcc atc gcg ttg gtc ctc gcc ggt ctg gca gga      48
Met Lys Phe Pro Thr Ser Ile Ala Leu Val Leu Ala Gly Leu Ala Gly
1               5                  10                  15 tgc tcc cag gcc gcc acg ccc gat gag tgg gcg cgg cgg tcc atc tac      96
Cys Ser Gln Ala Ala Thr Pro Asp Glu Trp Ala Arg Arg Ser Ile Tyr
            20                  25                  30 cag gtc atc acc gac cgg ttt gca cgg tca acc gat cag aat gct ccc     144
Gln Val Ile Thr Asp Arg Phe Ala Arg Ser Thr Asp Gln Asn Ala Pro
        35                  40                  45 tgc aac atc acc aaa tac tgc ggt ggt aac tgg gca ggt ttg gtg gac     192
Cys Asn Ile Thr Lys Tyr Cys Gly Gly Asn Trp Ala Gly Leu Val Asp
50                  55                  60 cag ctc gac tac atc caa gac atg ggc ttc acc gcc gtc cag atc tcg     240
Gln Leu Asp Tyr Ile Gln Asp Met Gly Phe Thr Ala Val Gln Ile Ser
65                  70                  75                  80 cct atc aac gcg aat ctg cct cag gat acc atc tac ggc gag gcc tac     288
Pro Ile Asn Ala Asn Leu Pro Gln Asp Thr Ile Tyr Gly Glu Ala Tyr
                85                  90                  95 cac gga tac tgg ccg cag aat ttc tac gag cta aat ccg cac ttt ggg     336
His Gly Tyr Trp Pro Gln Asn Phe Tyr Glu Leu Asn Pro His Phe Gly
            100                 105                 110 tcg cca gat gat ctc aag aac ctc gcc tcg gaa ctg cac aag cgc ggc     384
Ser Pro Asp Asp Leu Lys Asn Leu Ala Ser Glu Leu His Lys Arg Gly
        115                 120                 125 atg tac ctc ttg gtg gac atc gtc gca aat gag atg gcc tac gat att     432
Met Tyr Leu Leu Val Asp Ile Val Ala Asn Glu Met Ala Tyr Asp Ile
130                 135                 140 gga aac gcc aac atg agc tcg acg act ccg att gac tac tcg gtc ttc     480
Gly Asn Ala Asn Met Ser Ser Thr Thr Pro Ile Asp Tyr Ser Val Phe
145                 150                 155                 160 gtg ccc ttc aac agc tcg cat gac ttc act ccg tat tgc cca atc gtt     528
Val Pro Phe Asn Ser Ser His Asp Phe Thr Pro Tyr Cys Pro Ile Val
                165                 170                 175 gac tgg aac aac cag acc gag ttc caa aac tgc tgg ctg ggt ttc gag     576
Asp Trp Asn Asn Gln Thr Glu Phe Gln Asn Cys Trp Leu Gly Phe Glu
            180                 185                 190 ggc gtg gcc acg ccg cgg ctg aag acc aca gac tcc aac atc gcc aac     624
Gly Val Ala Thr Pro Arg Leu Lys Thr Thr Asp Ser Asn Ile Ala Asn
        195                 200                 205 aca ctc aac cag tgg atc aag gat ctg gtc ggc acc tac aac atc gac     672
Thr Leu Asn Gln Trp Ile Lys Asp Leu Val Gly Thr Tyr Asn Ile Asp
210                 215                 220 ggc att cgt gtg gac ggt gcc aag cag atc gag tat agc ttc ttc cag     720
Gly Ile Arg Val Asp Gly Ala Lys Gln Ile Glu Tyr Ser Phe Phe Gln
225                 230                 235                 240 ccc ttc ctc aag agc gcg ggt gtc tac gcc atg gct gaa gtg gac gac     768
Pro Phe Leu Lys Ser Ala Gly Val Tyr Ala Met Ala Glu Val Asp Asp
                245                 250                 255 ggc gat gcg cag ttc acc tgc aat tac cag aat ttg acg ggg gga ctg     816
Gly Asp Ala Gln Phe Thr Cys Asn Tyr Gln Asn Leu Thr Gly Gly Leu
            260                 265                 270 gag aac tac ccg ctc tac tac acc atc aaa gaa gca ttc acg gcc gga     864
```

```
                Glu Asn Tyr Pro Leu Tyr Tyr Thr Ile Lys Glu Ala Phe Thr Ala Gly
                             275                 280                 285 aag atg gcg gat ctc gtg tcg atg gtg ggt tcg atg cga cag gcc tgt        912
Lys Met Ala Asp Leu Val Ser Met Val Gly Ser Met Arg Gln Ala Cys
290                 295                 300 tcc aag ccg cag tac ttg gcg acc ttt att gaa aac caa gac aac ccg        960
Ser Lys Pro Gln Tyr Leu Ala Thr Phe Ile Glu Asn Gln Asp Asn Pro
305                 310                 315                 320 cgg ttt gcc tcg ttt acg gag gac ttg gcg gtcagtccct ccccttcct          1010
Arg Phe Ala Ser Phe Thr Glu Asp Leu Ala
                    325                 330 tttgtcctga tttcgtgcaa ctgacttgtt tttctag ctg gct aag aat gca ctg      1065
                                        Leu Ala Lys Asn Ala Leu
                                                            335 gct ttc act atc ttg gcc gat gga atc ccc aaa gtc tac tac gga caa       1113
Ala Phe Thr Ile Leu Ala Asp Gly Ile Pro Lys Val Tyr Tyr Gly Gln
                340                 345                 350 gag cag cac ctg gct ggc aac tac tcg ccg tac aac cgc cag gcg ttg       1161
Glu Gln His Leu Ala Gly Asn Tyr Ser Pro Tyr Asn Arg Gln Ala Leu
355                 360                 365 tgg ccg acc aac tac gac aag tcg gcg ccg ctg tac acc ctg acg gcg       1209
Trp Pro Thr Asn Tyr Asp Lys Ser Ala Pro Leu Tyr Thr Leu Thr Ala
370                 375                 380 tcg ctg aac aag ttg cgg aac cac gcc atc tcg atc gac agc aac tac       1257
Ser Leu Asn Lys Leu Arg Asn His Ala Ile Ser Ile Asp Ser Asn Tyr
385                 390                 395                 400 gtc acc aac ttg agc cag atc ctc tac acg gat gga tcg acg tac gcg       1305
Val Thr Asn Leu Ser Gln Ile Leu Tyr Thr Asp Gly Ser Thr Tyr Ala
                405                 410                 415 acg cgt aag ggc ccg aac ggc gtg cag atc atc gcg gtg ttg tcg aac       1353
Thr Arg Lys Gly Pro Asn Gly Val Gln Ile Ile Ala Val Leu Ser Asn
                420                 425                 430 cag ggt agc aat ggc gga gca tac cag ctg agt gtg cct ggc gcg gcc       1401
Gln Gly Ser Asn Gly Gly Ala Tyr Gln Leu Ser Val Pro Gly Ala Ala
                435                 440                 445 gat ccg ggc acg aac ctg act gag gtg acg gag tgc aag acg act gtc       1449
Asp Pro Gly Thr Asn Leu Thr Glu Val Thr Glu Cys Lys Thr Thr Val
450                 455                 460 gtg gcc ggg gaa aac ggc acc atc gtc gtc ccg atg gac aag ggc cag       1497
Val Ala Gly Glu Asn Gly Thr Ile Val Val Pro Met Asp Lys Gly Gln
465                 470                 475                 480 ccg cgc gtc ttc ttc ccg acc ttc aac ctg aac gga tcc ggc ctg tgc       1545
Pro Arg Val Phe Phe Pro Thr Phe Asn Leu Asn Gly Ser Gly Leu Cys
                485                 490                 495 ggg cag ccg ttg gcc aag tcg agc aac ccg tct acc acc ggt agc gcg       1593
Gly Gln Pro Leu Ala Lys Ser Ser Asn Pro Ser Thr Thr Gly Ser Ala
            500                 505                 510 gca tcg gcc acg acc agc tcg aag agc atg gcc gag cat ctc cag acc       1641
Ala Ser Ala Thr Thr Ser Ser Lys Ser Met Ala Glu His Leu Gln Thr
            515                 520                 525 ccg att tgg ctg acg ctg gcg gtg ctc gcc ata tct gcc gtg att gtg       1689
Pro Ile Trp Leu Thr Leu Ala Val Leu Ala Ile Ser Ala Val Ile Val
            530                 535                 540 ctg taa                                                                1695
Leu
545

<210> SEQ ID NO 8
<211> LENGTH: 545
<212> TYPE: PRT
```

<213> ORGANISM: Talaromyces emersonii

<400> SEQUENCE: 8

Met Lys Phe Pro Thr Ser Ile Ala Leu Val Leu Ala Gly Leu Ala Gly
1               5                   10                  15

Cys Ser Gln Ala Ala Thr Pro Asp Glu Trp Ala Arg Arg Ser Ile Tyr
            20                  25                  30

Gln Val Ile Thr Asp Arg Phe Ala Arg Ser Thr Asp Gln Asn Ala Pro
        35                  40                  45

Cys Asn Ile Thr Lys Tyr Cys Gly Gly Asn Trp Ala Gly Leu Val Asp
50                  55                  60

Gln Leu Asp Tyr Ile Gln Asp Met Gly Phe Thr Ala Val Gln Ile Ser
65                  70                  75                  80

Pro Ile Asn Ala Asn Leu Pro Gln Asp Thr Ile Tyr Gly Glu Ala Tyr
                85                  90                  95

His Gly Tyr Trp Pro Gln Asn Phe Tyr Glu Leu Asn Pro His Phe Gly
            100                 105                 110

Ser Pro Asp Asp Leu Lys Asn Leu Ala Ser Glu Leu His Lys Arg Gly
        115                 120                 125

Met Tyr Leu Leu Val Asp Ile Val Ala Asn Glu Met Ala Tyr Asp Ile
    130                 135                 140

Gly Asn Ala Asn Met Ser Ser Thr Thr Pro Ile Asp Tyr Ser Val Phe
145                 150                 155                 160

Val Pro Phe Asn Ser Ser His Asp Phe Thr Pro Tyr Cys Pro Ile Val
                165                 170                 175

Asp Trp Asn Asn Gln Thr Glu Phe Gln Asn Cys Trp Leu Gly Phe Glu
            180                 185                 190

Gly Val Ala Thr Pro Arg Leu Lys Thr Thr Asp Ser Asn Ile Ala Asn
        195                 200                 205

Thr Leu Asn Gln Trp Ile Lys Asp Leu Val Gly Thr Tyr Asn Ile Asp
    210                 215                 220

Gly Ile Arg Val Asp Gly Ala Lys Gln Ile Glu Tyr Ser Phe Phe Gln
225                 230                 235                 240

Pro Phe Leu Lys Ser Ala Gly Val Tyr Ala Met Ala Glu Val Asp Asp
                245                 250                 255

Gly Asp Ala Gln Phe Thr Cys Asn Tyr Gln Asn Leu Thr Gly Gly Leu
            260                 265                 270

Glu Asn Tyr Pro Leu Tyr Tyr Thr Ile Lys Glu Ala Phe Thr Ala Gly
        275                 280                 285

Lys Met Ala Asp Leu Val Ser Met Val Gly Ser Met Arg Gln Ala Cys
    290                 295                 300

Ser Lys Pro Gln Tyr Leu Ala Thr Phe Ile Glu Asn Gln Asp Asn Pro
305                 310                 315                 320

Arg Phe Ala Ser Phe Thr Glu Asp Leu Ala Leu Ala Lys Asn Ala Leu
                325                 330                 335

Ala Phe Thr Ile Leu Ala Asp Gly Ile Pro Lys Val Tyr Tyr Gly Gln
            340                 345                 350

Glu Gln His Leu Ala Gly Asn Tyr Ser Pro Tyr Asn Arg Gln Ala Leu
        355                 360                 365

Trp Pro Thr Asn Tyr Asp Lys Ser Ala Pro Leu Tyr Thr Leu Thr Ala
    370                 375                 380

Ser Leu Asn Lys Leu Arg Asn His Ala Ile Ser Ile Asp Ser Asn Tyr
385                 390                 395                 400

| | | | | | | | | | | | | |
|---|---|---|---|---|---|---|---|---|---|---|---|---|
|Val|Thr|Asn|Leu|Ser|Gln|Ile|Leu|Tyr|Thr|Asp|Gly|Ser|Thr|Tyr|Ala|
| | | | |405| | | |410| | | |415| | |

Val Thr Asn Leu Ser Gln Ile Leu Tyr Thr Asp Gly Ser Thr Tyr Ala
                405                 410                 415

Thr Arg Lys Gly Pro Asn Gly Val Gln Ile Ile Ala Val Leu Ser Asn
            420                 425                 430

Gln Gly Ser Asn Gly Gly Ala Tyr Gln Leu Ser Val Pro Gly Ala Ala
            435                 440                 445

Asp Pro Gly Thr Asn Leu Thr Glu Val Thr Glu Cys Lys Thr Thr Val
        450                 455                 460

Val Ala Gly Glu Asn Gly Thr Ile Val Val Pro Met Asp Lys Gly Gln
465                 470                 475                 480

Pro Arg Val Phe Phe Pro Thr Phe Asn Leu Asn Gly Ser Gly Leu Cys
                485                 490                 495

Gly Gln Pro Leu Ala Lys Ser Ser Asn Pro Ser Thr Thr Gly Ser Ala
            500                 505                 510

Ala Ser Ala Thr Thr Ser Ser Lys Ser Met Ala Glu His Leu Gln Thr
        515                 520                 525

Pro Ile Trp Leu Thr Leu Ala Val Leu Ala Ile Ser Ala Val Ile Val
        530                 535                 540

Leu
545

<210> SEQ ID NO 9
<211> LENGTH: 1509
<212> TYPE: DNA
<213> ORGANISM: Talaromyces emersonii
<220> FEATURE:
<221> NAME/KEY: sig_peptide
<222> LOCATION: (1)..(66)

<400> SEQUENCE: 9

```
atgaaggggc cgcggccgtc aatactgttg ttgtccctgc tgggactggt gccctccgca      60
tggggtgcag gcgtggaggc ttggaaatct cggagcgtct atcagctgat gaccgacaga     120
tttgctctta ccgacttgtc cacgaacgcg ccatgcgatc ccggggaagg actctactgc     180
gggggtacgt ggaggggcat catcaacaat ctggactata tccagggcat gggtttcgac     240
gccatttatg tctccccat catcaagaac ttggagggtc gcgtatccta tggcgaggcc     300
taccacggct attgggctca agatctctac gcgttaaatc cgcatttcgg tacagaacag     360
gacttccagg acttgattac ggctcttcac aaccggagca tgtatctcat ggtggatacc     420
accatcaaca catggcgta catgaccaat ggaagcgacc cggctacctc ggtcaactac     480
ggcattctga cgcccttcaa ccaggcgagc tactaccatc cttactgtcc catcaccaac     540
tacgaagact accctctggc ccaaagatgc tggaccggcg atgacatcgt tgcgctgccc     600
gacttggctc aggagaaaat cgaggtagcc tcgatgctga atgttggat caaatcgacg     660
ctagcaaatt attcaatcga tggtttacgt atcgacgccg ccaagcatgt atatccgaat     720
tatctgccgc aattctttct agctaccgat tcgatgttca tgacggggga ggtcttcgag     780
cagagcgcag aaatcatctg caattatcag aagaactacc tgcctagtgt gcccaactat     840
ccgatctact atgccgtgat cagtgccttt accgagggga acgtcagcgc tttgtcggac     900
gaaattcagc tcatgtcgga cttatgtccg gatgttactg cattgaccac cttcaccgaa     960
aaccatgata tcacccgttt tgcgtcatat accgatgatc tcgcgctggc caagaatgtt    1020
atggcattca ccatcctttt cgacggcgtg ccgatgatct atcagggcca ggagcaaccc    1080
tttaaaggca atgggacccc ttataaccgt caagccctat ggacctcagg ctataacacc    1140
```

```
aacgcccctc tgtatcagct cgctgccacg ttgaacaagg ttcgcaagca agctggccgt    1200
gtcgacccgc agtactttga cgtcgtatct tatccgatct acaccggctc tagcgagatt    1260
gcaatccgca agggcaacga gggacggcag actattctgg ttctctcgtc gaatggggcc    1320
aatggtggcg catacacctt aacgttaccg gtcacatacg aaccgggcaa ggtggtcacc    1380
gaggtgataa cctgcaccaa ctacaccatc aaggatgatg ggtctcttga cctagcgatg    1440
gacaaaggag aacccgagt gctgtggccg ccgaccaga tgggtggaag cggcctctgc    1500
ggtgtagct                                                            1509
```

```
<210> SEQ ID NO 10
<211> LENGTH: 502
<212> TYPE: PRT
<213> ORGANISM: Talaromyces emersonii

<400> SEQUENCE: 10

Met Lys Gly Pro Arg Pro Ser Ile Leu Leu Ser Leu Leu Gly Leu
1               5                   10                  15

Val Pro Ser Ala Trp Gly Ala Gly Val Glu Ala Trp Lys Ser Arg Ser
                20                  25                  30

Val Tyr Gln Leu Met Thr Asp Arg Phe Ala Leu Thr Asp Leu Ser Thr
            35                  40                  45

Asn Ala Pro Cys Asp Pro Gly Glu Gly Leu Tyr Cys Gly Gly Thr Trp
        50                  55                  60

Arg Gly Ile Ile Asn Asn Leu Asp Tyr Ile Gln Gly Met Gly Phe Asp
65                  70                  75                  80

Ala Ile Tyr Val Ser Pro Ile Ile Lys Asn Leu Glu Gly Arg Val Ser
                85                  90                  95

Tyr Gly Glu Ala Tyr His Gly Tyr Trp Ala Gln Asp Leu Tyr Ala Leu
            100                 105                 110

Asn Pro His Phe Gly Thr Glu Gln Asp Phe Gln Asp Leu Ile Thr Ala
        115                 120                 125

Leu His Asn Arg Ser Met Tyr Leu Met Val Asp Thr Thr Ile Asn Asn
    130                 135                 140

Met Ala Tyr Met Thr Asn Gly Ser Asp Pro Ala Thr Ser Val Asn Tyr
145                 150                 155                 160

Gly Ile Leu Thr Pro Phe Asn Gln Ala Ser Tyr Tyr His Pro Tyr Cys
                165                 170                 175

Pro Ile Thr Asn Tyr Glu Asp Tyr Pro Leu Ala Gln Arg Cys Trp Thr
            180                 185                 190

Gly Asp Asp Ile Val Ala Leu Pro Asp Leu Ala Gln Glu Lys Ile Glu
        195                 200                 205

Val Ala Ser Met Leu Asn Ser Trp Ile Lys Ser Thr Leu Ala Asn Tyr
    210                 215                 220

Ser Ile Asp Gly Leu Arg Ile Asp Ala Ala Lys His Val Tyr Pro Asn
225                 230                 235                 240

Tyr Leu Pro Gln Phe Phe Leu Ala Thr Asp Ser Met Phe Met Thr Gly
                245                 250                 255

Glu Val Phe Glu Gln Ser Ala Glu Ile Ile Cys Asn Tyr Gln Lys Asn
            260                 265                 270

Tyr Leu Pro Ser Val Pro Asn Tyr Pro Ile Tyr Tyr Ala Val Ile Ser
        275                 280                 285

Ala Phe Thr Glu Gly Asn Val Ser Ala Leu Ser Asp Glu Ile Gln Leu
    290                 295                 300
```

```
Met Ser Asp Leu Cys Pro Asp Val Thr Ala Leu Thr Thr Phe Thr Glu
305                 310                 315                 320

Asn His Asp Ile Thr Arg Phe Ala Ser Tyr Thr Asp Asp Leu Ala Leu
            325                 330                 335

Ala Lys Asn Val Met Ala Phe Thr Ile Leu Phe Asp Gly Val Pro Met
        340                 345                 350

Ile Tyr Gln Gly Gln Glu Gln His Phe Lys Gly Asn Gly Thr Pro Tyr
            355                 360                 365

Asn Arg Gln Ala Leu Trp Thr Ser Gly Tyr Asn Thr Asn Ala Pro Leu
        370                 375                 380

Tyr Gln Leu Ala Ala Thr Leu Asn Lys Val Arg Lys Gln Ala Gly Arg
385                 390                 395                 400

Val Asp Pro Gln Tyr Phe Asp Val Val Ser Tyr Pro Ile Tyr Thr Gly
            405                 410                 415

Ser Ser Glu Ile Ala Ile Arg Lys Gly Asn Glu Gly Arg Gln Thr Ile
        420                 425                 430

Leu Val Leu Ser Ser Asn Gly Ala Asn Gly Gly Ala Tyr Thr Leu Thr
            435                 440                 445

Leu Pro Val Thr Tyr Glu Pro Gly Lys Val Val Thr Glu Val Ile Thr
450                 455                 460

Cys Thr Asn Tyr Thr Ile Lys Asp Asp Gly Ser Leu Asp Leu Ala Met
465                 470                 475                 480

Asp Lys Gly Glu Pro Arg Val Leu Trp Pro Ala Asp Gln Met Gly Gly
            485                 490                 495

Ser Gly Leu Cys Gly Val
            500

<210> SEQ ID NO 11
<211> LENGTH: 1967
<212> TYPE: DNA
<213> ORGANISM: Talaromyces emersonii
<220> FEATURE:
<221> NAME/KEY: sig_peptide
<222> LOCATION: (1)..(57)
<220> FEATURE:
<221> NAME/KEY: exon
<222> LOCATION: (1)..(162)
<220> FEATURE:
<221> NAME/KEY: exon
<222> LOCATION: (309)..(424)
<220> FEATURE:
<221> NAME/KEY: exon
<222> LOCATION: (512)..(620)
<220> FEATURE:
<221> NAME/KEY: exon
<222> LOCATION: (674)..(902)
<220> FEATURE:
<221> NAME/KEY: exon
<222> LOCATION: (950)..(1112)
<220> FEATURE:
<221> NAME/KEY: exon
<222> LOCATION: (1179)..(1325)
<220> FEATURE:
<221> NAME/KEY: exon
<222> LOCATION: (1374)..(1618)
<220> FEATURE:
<221> NAME/KEY: exon
<222> LOCATION: (1684)..(1964)

<400> SEQUENCE: 11 atg ctg tcg ttt atc ctt gca gtt ttc acc ggg ctg ctg gct gcg tcg    48
Met Leu Ser Phe Ile Leu Ala Val Phe Thr Gly Leu Leu Ala Ala Val
1               5                   10                  15 gtc aat gca gca aca cca gca gac tgg cgc tcg cgg tcc atc tac ttc    96
```

```
                Val Asn Ala Ala Thr Pro Ala Asp Trp Arg Ser Arg Ser Ile Tyr Phe
                                20                  25                  30 ctg ctg act gac cgg ttc gga cga aca gac aat tcc atc acc gca cca         144
Leu Leu Thr Asp Arg Phe Gly Arg Thr Asp Asn Ser Ile Thr Ala Pro
            35                  40                  45 tgc gat acc tac gcc cga gtccgttctt tcttgactgt tctcgttgag                192
Cys Asp Thr Tyr Ala Arg
50 acaacggggc ggctgacttg cgaatagaaa tactgcggcg gttcctggca agggattatc       252 aaccacgtga gcaggacgct tttgactgaa acccattttc ttacattgag gtctag ctg       311
                                                               Leu
                                                               55 gat tac att caa gga atg gga ttc acg gcc atc tgg att acc ccc gtg         359
Asp Tyr Ile Gln Gly Met Gly Phe Thr Ala Ile Trp Ile Thr Pro Val
                60                  65                  70 acg aag cag ctg tcg cag ggc acc gga gac gga aca ggc tat cac ggt         407
Thr Lys Gln Leu Ser Gln Gly Thr Gly Asp Gly Thr Gly Tyr His Gly
            75                  80                  85 tac tgg cag caa gat at  gtgagtgtct cgctgatgag ctcgggctcg                454
Tyr Trp Gln Gln Asp Ile
            90 tacctgcttc tttccccaaa tccctacttc tcatatactg actcctgata tctacag c        512 tac tct ctc aat cca aat ttt ggc acc tct cag gac ctg aag aac ctt         560
Tyr Ser Leu Asn Pro Asn Phe Gly Thr Ser Gln Asp Leu Lys Asn Leu
        95                  100                 105 gcg tct gcc ctt cat agc cgc ggg atg tat ctc atg gtt gat gtc gta         608
Ala Ser Ala Leu His Ser Arg Gly Met Tyr Leu Met Val Asp Val Val
110                 115                 120                 125 gcg aat cat ctg gtgacagtag ccattcacac tgctaggact atctgctgat             660
Ala Asn His Leu gatctatctt cag ggg tac gcc ggc tca ggg acc aac atg gat tgc agc         709
            Gly Tyr Ala Gly Ser Gly Thr Asn Met Asp Cys Ser
                130                 135                 140 ctg ttc aac ccg ttc aac aac aag gag tac ttc cac ccg tac tgt gct         757
Leu Phe Asn Pro Phe Asn Asn Lys Glu Tyr Phe His Pro Tyr Cys Ala
                145                 150                 155 atc acc aac tac agc aat cag acc aac gtg gag gat tgc tgg ctg ggc         805
Ile Thr Asn Tyr Ser Asn Gln Thr Asn Val Glu Asp Cys Trp Leu Gly
            160                 165                 170 gac aac ata gtg gcg gca gca gat ttg aac acc tca cga aca gat gtg         853
Asp Asn Ile Val Ala Ala Ala Asp Leu Asn Thr Ser Arg Thr Asp Val
        175                 180                 185 cag aat gtc tgg tac agt tgg gtg gga agc ttg gtg tcc aat tac tca a       902
Gln Asn Val Trp Tyr Ser Trp Val Gly Ser Leu Val Ser Asn Tyr Ser
190                 195                 200                 205 gtgagtcaat cacctacaag aacggtgctg tatctgatcc gctttag tc  gac gga         957
                                                       Ile Asp Gly ttg aga atc gac acc gta aaa cat gtc cag aag gac ttc tgg cca gga        1005
Leu Arg Ile Asp Thr Val Lys His Val Gln Lys Asp Phe Trp Pro Gly
            210                 215                 220 tat aat aaa gct gct ggc gtg tac tgt gtg ggt gaa gtc ctg cat ggt        1053
Tyr Asn Lys Ala Ala Gly Val Tyr Cys Val Gly Glu Val Leu His Gly
225                 230                 235                 240 gac cca acg tac acc tgt ccg tat cag aac tat ctc gat gga gta ttg        1101
Asp Pro Thr Tyr Thr Cys Pro Tyr Gln Asn Tyr Leu Asp Gly Val Leu
                245                 250                 255 aac tac ccg ac  gtgagtggaa acacacatac attaggggta tgggtggaac            1152
Asn Tyr Pro Thr
```

```
tgacggaatc actttgatct ccccag a tac tat caa ata cta tcc gca ttc    1203
                               Tyr Tyr Gln Ile Leu Ser Ala Phe
                                                       265 cag tcg aca agc ggg agc atc agc aat ctg tat aac atg ata aac cag   1251
Gln Ser Thr Ser Gly Ser Ile Ser Asn Leu Tyr Asn Met Ile Asn Gln
    270                 275                 280 gtg aaa tcg agc tgc aag gac tcc acc ctg ctg ggg act ttt gtc gaa   1299
Val Lys Ser Ser Cys Lys Asp Ser Thr Leu Leu Gly Thr Phe Val Glu
285                 290                 295                 300 aac cac gac aac ccg cga ttt gcc ag  gtcagtatca gccatcctgg         1345
Asn His Asp Asn Pro Arg Phe Ala Ser
                305 aaatttctcc tgttctaact ttctacag c cac acg agc gac tac tcc ctt gcc  1398
                                 His Thr Ser Asp Tyr Ser Leu Ala
                                     310                 315 aag aac gcc atc gcc ttc gtc ttt tta tca gat gga atc ccc atc atc   1446
Lys Asn Ala Ile Ala Phe Val Phe Leu Ser Asp Gly Ile Pro Ile Ile
            320                 325                 330 tac gcc ggt caa gag cag cac tac tcc ggt ggg aac gat cct ggc aat   1494
Tyr Ala Gly Gln Glu Gln His Tyr Ser Gly Gly Asn Asp Pro Gly Asn
        335                 340                 345 cga gaa gcg aca tgg cta tcg gga tac gac acc tcc gcc gaa ctg tac   1542
Arg Glu Ala Thr Trp Leu Ser Gly Tyr Asp Thr Ser Ala Glu Leu Tyr
350                 355                 360                 365 aag ttt att gcg tct gta aat gcg atg cgc tcc cac gcg att agc aaa   1590
Lys Phe Ile Ala Ser Val Asn Ala Met Arg Ser His Ala Ile Ser Lys
                370                 375                 380 gac ggt gga tac ctg acc tgc aag gcg a gtcagcatcc aatcttcctt       1638
Asp Gly Gly Tyr Leu Thr Cys Lys Ala
            385                 390 ttgaaagaag accagagttg agtccaatgg ctaactgaca tcaga ac  tac cct atc 1694
                                                     Tyr Pro Ile tat caa gac acc agc aca att gcc atg cgc aag ggc acc gat ggc agt   1742
Tyr Gln Asp Thr Ser Thr Ile Ala Met Arg Lys Gly Thr Asp Gly Ser
395                 400                 405                 410 cag gta atc act gtg ctg tca aac ctt ggt gca tcc ggc agc tcc tac   1790
Gln Val Ile Thr Val Leu Ser Asn Leu Gly Ala Ser Gly Ser Ser Tyr
                415                 420                 425 acc ctg tcg ctg ggg ggc acg ggc tac tcg gcc ggc gag cag ctg aca   1838
Thr Leu Ser Leu Gly Gly Thr Gly Tyr Ser Ala Gly Glu Gln Leu Thr
            430                 435                 440 gag ctg ttt tca tgc act cat gtg acc gtt gac tcg agt ggg aat gtc   1886
Glu Leu Phe Ser Cys Thr His Val Thr Val Asp Ser Ser Gly Asn Val
        445                 450                 455 cct gtg ccg atg gcg agc gga ctg ccg agg gtg tta tac ccg acg agg   1934
Pro Val Pro Met Ala Ser Gly Leu Pro Arg Val Leu Tyr Pro Thr Arg
    460                 465                 470 ctg ctg gcg ggg ggc aag ctg tgt cag tcg taa                       1967
Leu Leu Ala Gly Gly Lys Leu Cys Gln Ser
475                 480

<210> SEQ ID NO 12
<211> LENGTH: 497
<212> TYPE: PRT
<213> ORGANISM: Talaromyces emersonii

<400> SEQUENCE: 12

Met Leu Ser Phe Ile Leu Ala Val Phe Thr Gly Leu Leu Ala Ala Val
1               5                   10                  15
```

```
Val Asn Ala Ala Thr Pro Ala Asp Trp Arg Ser Arg Ser Ile Tyr Phe
            20                  25                  30

Leu Leu Thr Asp Arg Phe Gly Arg Thr Asp Asn Ser Ile Thr Ala Pro
            35                  40                  45

Cys Asp Thr Tyr Ala Arg Lys Tyr Cys Gly Ser Trp Gln Gly Ile
50                  55                  60

Ile Asn His Leu Asp Tyr Ile Gln Gly Met Gly Phe Thr Ala Ile Trp
65                  70                  75                  80

Ile Thr Pro Val Thr Lys Gln Leu Ser Gln Gly Thr Gly Asp Gly Thr
                85                  90                  95

Gly Tyr His Gly Tyr Trp Gln Gln Asp Ile Tyr Ser Leu Asn Pro Asn
                100                 105                 110

Phe Gly Thr Ser Gln Asp Leu Lys Asn Leu Ala Ser Ala Leu His Ser
            115                 120                 125

Arg Gly Met Tyr Leu Met Val Asp Val Val Ala Asn His Leu Gly Tyr
            130                 135                 140

Ala Gly Ser Gly Thr Asn Met Asp Cys Ser Leu Phe Asn Pro Phe Asn
145                 150                 155                 160

Asn Lys Glu Tyr Phe His Pro Tyr Cys Ala Ile Thr Asn Tyr Ser Asn
                165                 170                 175

Gln Thr Asn Val Glu Asp Cys Trp Leu Gly Asp Asn Ile Val Ala Ala
            180                 185                 190

Ala Asp Leu Asn Thr Ser Arg Thr Asp Val Gln Asn Val Trp Tyr Ser
            195                 200                 205

Trp Val Gly Ser Leu Val Ser Asn Tyr Ser Ile Asp Gly Leu Arg Ile
210                 215                 220

Asp Thr Val Lys His Val Gln Lys Asp Phe Trp Pro Gly Tyr Asn Lys
225                 230                 235                 240

Ala Ala Gly Val Tyr Cys Val Gly Glu Val Leu His Gly Asp Pro Thr
                245                 250                 255

Tyr Thr Cys Pro Tyr Gln Asn Tyr Leu Asp Gly Val Leu Asn Tyr Pro
            260                 265                 270

Thr Tyr Tyr Gln Ile Leu Ser Ala Phe Gln Ser Thr Ser Gly Ser Ile
            275                 280                 285

Ser Asn Leu Tyr Asn Met Ile Asn Gln Val Lys Ser Ser Cys Lys Asp
290                 295                 300

Ser Thr Leu Leu Gly Thr Phe Val Glu Asn His Asp Asn Pro Arg Phe
305                 310                 315                 320

Ala Ser His Thr Ser Asp Tyr Ser Leu Ala Lys Asn Ala Ile Ala Phe
                325                 330                 335

Val Phe Leu Ser Asp Gly Ile Pro Ile Ile Tyr Ala Gly Gln Glu Gln
            340                 345                 350

His Tyr Ser Gly Gly Asn Asp Pro Gly Asn Arg Glu Ala Thr Trp Leu
            355                 360                 365

Ser Gly Tyr Asp Thr Ser Ala Glu Leu Tyr Lys Phe Ile Ala Ser Val
370                 375                 380

Asn Ala Met Arg Ser His Ala Ile Ser Lys Asp Gly Tyr Leu Thr
385                 390                 395                 400

Cys Lys Ala Asn Tyr Pro Ile Tyr Gln Asp Thr Ser Thr Ile Ala Met
                405                 410                 415

Arg Lys Gly Thr Asp Gly Ser Gln Val Ile Thr Val Leu Ser Asn Leu
            420                 425                 430

Gly Ala Ser Gly Ser Ser Tyr Thr Leu Ser Leu Gly Gly Thr Gly Tyr
```

```
                 435                 440                 445
Ser Ala Gly Glu Gln Leu Thr Glu Leu Phe Ser Cys Thr His Val Thr
        450                 455                 460

Val Asp Ser Ser Gly Asn Val Pro Val Pro Met Ala Ser Gly Leu Pro
465                 470                 475                 480

Arg Val Leu Tyr Pro Thr Arg Leu Leu Ala Gly Gly Lys Leu Cys Gln
                485                 490                 495

Ser

<210> SEQ ID NO 13
<211> LENGTH: 2326
<212> TYPE: DNA
<213> ORGANISM: Talaromyces emersonii
<220> FEATURE:
<221> NAME/KEY: sig_peptide
<222> LOCATION: (1)..(60)
<220> FEATURE:
<221> NAME/KEY: exon
<222> LOCATION: (1)..(237)
<220> FEATURE:
<221> NAME/KEY: exon
<222> LOCATION: (348)..(402)
<220> FEATURE:
<221> NAME/KEY: exon
<222> LOCATION: (484)..(587)
<220> FEATURE:
<221> NAME/KEY: exon
<222> LOCATION: (679)..(834)
<220> FEATURE:
<221> NAME/KEY: exon
<222> LOCATION: (906)..(1014)
<220> FEATURE:
<221> NAME/KEY: exon
<222> LOCATION: (1072)..(1234)
<220> FEATURE:
<221> NAME/KEY: exon
<222> LOCATION: (1288)..(1378)
<220> FEATURE:
<221> NAME/KEY: exon
<222> LOCATION: (1434)..(1508)
<220> FEATURE:
<221> NAME/KEY: exon
<222> LOCATION: (1567)..(1618)
<220> FEATURE:
<221> NAME/KEY: exon
<222> LOCATION: (1674)..(2323)

<400> SEQUENCE: 13 atg gcc ttg aga aag gta gca ttg gct gcg ttc gca acc tgg acg tct      48
Met Ala Leu Arg Lys Val Ala Leu Ala Ala Phe Ala Thr Trp Thr Ser
1               5                   10                  15 cta gtc cag gcg gca tcc aga gac caa tgg ata tcc aga tcc atc tat      96
Leu Val Gln Ala Ala Ser Arg Asp Gln Trp Ile Ser Arg Ser Ile Tyr
            20                  25                  30 caa att gtg acc gat cgc ttt gcc cgt tcg gat aac tcg acg act gct     144
Gln Ile Val Thr Asp Arg Phe Ala Arg Ser Asp Asn Ser Thr Thr Ala
        35                  40                  45 ccg tgt gat gcc cag aag ggt tac tac tgc gga gga gac ttc caa ggc     192
Pro Cys Asp Ala Gln Lys Gly Tyr Tyr Cys Gly Gly Asp Phe Gln Gly
    50                  55                  60 atc atc aac aag ttg gat tac atc cag gat ttg ggg ttt tca gca         237
Ile Ile Asn Lys Leu Asp Tyr Ile Gln Asp Leu Gly Phe Ser Ala
65                  70                  75 gtaagataat actcctacac atgacccatc gctctcaggt tcaccggaat ttcgaatccg   297
taggctcgag attcctacaa ctggaaactg agaatagtcg caattcacag att tgg      353
                                                         Ile Trp
                                                         80
```

-continued

| | |
|---|---|
| ata tca ccc gtg cag tcc caa ata aca gag agg acg gca gat ctt tca g<br>Ile Ser Pro Val Gln Ser Gln Ile Thr Glu Arg Thr Ala Asp Leu Ser<br>      85                    90                    95 | 402 |
| gtactcgcaa accttgtctt tgacacatga ttcttacgtc gcgttcaata atatgctaaa | 462 |
| cttagcaatt caaactgcta g ca tac cat gga tat tgg ccg aga gat ctc<br>                                    Ala Tyr His Gly Tyr Trp Pro Arg Asp Leu<br>                                            100                       105 | 512 |
| tat agc atc aac tct cat ttc ggt tct cct gaa gac ctc aag gcg ctc<br>Tyr Ser Ile Asn Ser His Phe Gly Ser Pro Glu Asp Leu Lys Ala Leu<br>      110                   115                    120 | 560 |
| tcc gat gcg ctc cat gct cgt ggc atg gtaagtggcg acattgcgtt<br>Ser Asp Ala Leu His Ala Arg Gly Met<br>      125                   130 | 607 |
| aagatcaatc tctacgcttt cccttttat cttattttgt cgcagactga caagtaataa | 667 |
| catctgctca g tac ttg atg ctc gat gtc gtt gtc aat gat atg gcc tgg<br>              Tyr Leu Met Leu Asp Val Val Val Asn Asp Met Ala Trp<br>                             135                    140                    145 | 717 |
| gct gga aat gca tcg acg gtc gat tac agc cag ttc aac ccc ttc aac<br>Ala Gly Asn Ala Ser Thr Val Asp Tyr Ser Gln Phe Asn Pro Phe Asn<br>             150                    155                    160 | 765 |
| agc gag gag tac ttc cac cca tat cga ctc cta tcg gat gat cca tcg<br>Ser Glu Glu Tyr Phe His Pro Tyr Arg Leu Leu Ser Asp Asp Pro Ser<br>             165                    170                    175 | 813 |
| aat gaa acc tgc gtc att gat gtaagtactt acacaaactc gccctacagt<br>Asn Glu Thr Cys Val Ile Asp<br>             180 | 864 |
| tataatgcaa gatggatgaa ttgctaatat tacctaaaca g tgc tgg ctt ggg gat<br>                                                              Cys Trp Leu Gly Asp<br>                                                                185 | 920 |
| acg gta gtg tcg ctt cca gac gta cga acg gaa gac gac aaa gtc gca<br>Thr Val Val Ser Leu Pro Asp Val Arg Thr Glu Asp Asp Lys Val Ala<br>190                    195                    200                    205 | 968 |
| gcc atg ctc cac tcc tgg atc acg gag ctg gta tct aat tat tca g<br>Ala Met Leu His Ser Trp Ile Thr Glu Leu Val Ser Asn Tyr Ser<br>             210                    215                    220 | 1014 |
| gtaagcgtgt cttcatttac ttctgtaatg gcatagaaga tctaattgcc atctcag | 1071 |
| tc gac ggc ttg cgt atc gac agt gta ttc aat gtt gac ccc ggt ttc<br>Val Asp Gly Leu Arg Ile Asp Ser Val Phe Asn Val Asp Pro Gly Phe<br>             225                    230                    235 | 1118 |
| tgg cct ggt ttc aac agt tca gcc ggt gtc ttc tgc att ggg gaa ggt<br>Trp Pro Gly Phe Asn Ser Ser Ala Gly Val Phe Cys Ile Gly Glu Gly<br>             240                    245                    250 | 1166 |
| agc acg cgc aac gca act gag ttg tgc ccc ctg caa gac agt ctc aat<br>Ser Thr Arg Asn Ala Thr Glu Leu Cys Pro Leu Gln Asp Ser Leu Asn<br>             255                    260                    265 | 1214 |
| ggc ctc ttg aat tat cct ct gtttgtgcat catgatctct ggatttccag<br>Gly Leu Leu Asn Tyr Pro Leu<br>      270                   275 | 1264 |
| ttcgcctact tattttggca cag g tat tat atc ctg acg gag tct ttc aat<br>                              Tyr Tyr Ile Leu Thr Glu Ser Phe Asn<br>                                              280 | 1315 |
| gac act gct agc gac ctc aac act gtc gtt cgc gcc atg gag ttt atg<br>Asp Thr Ala Ser Asp Leu Asn Thr Val Val Arg Ala Met Glu Phe Met<br>285                    290                    295                    300 | 1363 |
| ctg act caa tgc agg gtatgttcct aatgcaatag cataggctac agcaatatgg<br>Leu Thr Gln Cys Arg<br>             305 | 1418 |

```
actgaatatc aatag gat ata att gct ttg ggg acc ttt acg gag aac caa         1469
              Asp Ile Ile Ala Leu Gly Thr Phe Thr Glu Asn Gln
                  310                 315 gac gtt cct cgc ttt gcg tcc tat acc caa gac ctg tct gtacgtctcg          1518
Asp Val Pro Arg Phe Ala Ser Tyr Thr Gln Asp Leu Ser
320             325                 330 cctttgccaa gatgcctctc atttctgtgt tctaattgtt cattctag ctt gct cga        1575
                                                    Leu Ala Arg aac ata ata acc ttc aat ctc ctg gga gac gga ata ccc gtc t              1618
Asn Ile Ile Thr Phe Asn Leu Leu Gly Asp Gly Ile Pro Val
335             340             345 gtaagtcaac gagtactccg catgtaacat tctctctgga ggctaattgg gatag tt         1675
                                                              Phe tac tac ggc gaa gaa caa cat ttg tca ggc gca tac aat ccc gtc aat        1723
Tyr Tyr Gly Glu Glu Gln His Leu Ser Gly Ala Tyr Asn Pro Val Asn
350                 355                 360 cga gaa gcg ctc tgg ctc acc cat tac tcc tgg aac aca acg tct ctt        1771
Arg Glu Ala Leu Trp Leu Thr His Tyr Ser Trp Asn Thr Thr Ser Leu
365                 370                 375                 380 ccc tcc ctg gtc aag tcc ctg aat cgc ctc cga tca tat gct gca ttc        1819
Pro Ser Leu Val Lys Ser Leu Asn Arg Leu Arg Ser Tyr Ala Ala Phe
                385                 390                 395 aat ggg acg cag ttc acg gca gcc agt gaa cca ggc aac gac tat ctc        1867
Asn Gly Thr Gln Phe Thr Ala Ala Ser Glu Pro Gly Asn Asp Tyr Leu
            400                 405                 410 tcc ttc atc acg tat ccg atc tat aac agc acc cat atc ctt gcc ctg        1915
Ser Phe Ile Thr Tyr Pro Ile Tyr Asn Ser Thr His Ile Leu Ala Leu
        415                 420                 425 cgc aaa ggc ttc gtc ggg aat cag gtc atc agc gtc ttg tcg aat ttg        1963
Arg Lys Gly Phe Val Gly Asn Gln Val Ile Ser Val Leu Ser Asn Leu
    430                 435                 440 ggc aca tac ccc gac ggc aac gag gag acc aaa atc gtc ctg aat gcg        2011
Gly Thr Tyr Pro Asp Gly Asn Glu Glu Thr Lys Ile Val Leu Asn Ala
445                 450                 455                 460 acc ggc aca gga ttc caa ccg gga cag aat gtc acc gag atc ctt tcc        2059
Thr Gly Thr Gly Phe Gln Pro Gly Gln Asn Val Thr Glu Ile Leu Ser
                465                 470                 475 tgc cag acg gtc ctg aca gac gaa aat ggc aat ctg gag gtg gac ctc        2107
Cys Gln Thr Val Leu Thr Asp Glu Asn Gly Asn Leu Glu Val Asp Leu
            480                 485                 490 cac gac ggc gga ccg agg gtt tac tat cct act gac agc ctc aat att        2155
His Asp Gly Gly Pro Arg Val Tyr Tyr Pro Thr Asp Ser Leu Asn Ile
        495                 500                 505 tac tcc gac atc tgc gga cac tgt gag gag cag acc gcg aca cct ggg        2203
Tyr Ser Asp Ile Cys Gly His Cys Glu Glu Gln Thr Ala Thr Pro Gly
    510                 515                 520 aat tcc agt ggg ggt aca tcg ccg aaa aag tct ggt gct tcc ttg tca        2251
Asn Ser Ser Gly Gly Thr Ser Pro Lys Lys Ser Gly Ala Ser Leu Ser
525                 530                 535                 540 aca tca tct gag ttg ttg aac atc ctg tcc tcg gta tct atc aca ctg        2299
Thr Ser Ser Glu Leu Leu Asn Ile Leu Ser Ser Val Ser Ile Thr Leu
                545                 550                 555 ttc ctt gtc atg ggc ttt ccc ttc taa                                     2326
Phe Leu Val Met Gly Phe Pro Phe
            560

<210> SEQ ID NO 14
<211> LENGTH: 564
<212> TYPE: PRT
<213> ORGANISM: Talaromyces emersonii
```

<400> SEQUENCE: 14

Met Ala Leu Arg Lys Val Ala Leu Ala Ala Phe Ala Thr Trp Thr Ser
1               5                   10                  15

Leu Val Gln Ala Ala Ser Arg Asp Gln Trp Ile Ser Arg Ser Ile Tyr
                20                  25                  30

Gln Ile Val Thr Asp Arg Phe Ala Arg Ser Asp Asn Ser Thr Thr Ala
            35                  40                  45

Pro Cys Asp Ala Gln Lys Gly Tyr Tyr Cys Gly Gly Asp Phe Gln Gly
50                  55                  60

Ile Ile Asn Lys Leu Asp Tyr Ile Gln Asp Leu Gly Phe Ser Ala Ile
65                  70                  75                  80

Trp Ile Ser Pro Val Gln Ser Gln Ile Thr Glu Arg Thr Ala Asp Leu
                85                  90                  95

Ser Ala Tyr His Gly Tyr Trp Pro Arg Asp Leu Tyr Ser Ile Asn Ser
                100                 105                 110

His Phe Gly Ser Pro Glu Asp Leu Lys Ala Leu Ser Asp Ala Leu His
            115                 120                 125

Ala Arg Gly Met Tyr Leu Met Leu Asp Val Val Asn Asp Met Ala
130                 135                 140

Trp Ala Gly Asn Ala Ser Thr Val Asp Tyr Ser Gln Phe Asn Pro Phe
145                 150                 155                 160

Asn Ser Glu Glu Tyr Phe His Pro Tyr Arg Leu Leu Ser Asp Asp Pro
                165                 170                 175

Ser Asn Glu Thr Cys Val Ile Asp Cys Trp Leu Gly Asp Thr Val Val
            180                 185                 190

Ser Leu Pro Asp Val Arg Thr Glu Asp Asp Lys Val Ala Ala Met Leu
            195                 200                 205

His Ser Trp Ile Thr Glu Leu Val Ser Asn Tyr Ser Val Asp Gly Leu
210                 215                 220

Arg Ile Asp Ser Val Phe Asn Val Asp Pro Gly Phe Trp Pro Gly Phe
225                 230                 235                 240

Asn Ser Ser Ala Gly Val Phe Cys Ile Gly Glu Gly Ser Thr Arg Asn
                245                 250                 255

Ala Thr Glu Leu Cys Pro Leu Gln Asp Ser Leu Asn Gly Leu Leu Asn
            260                 265                 270

Tyr Pro Leu Tyr Tyr Ile Leu Thr Glu Ser Phe Asn Asp Thr Ala Ser
            275                 280                 285

Asp Leu Asn Thr Val Val Arg Ala Met Glu Phe Met Leu Thr Gln Cys
290                 295                 300

Arg Asp Ile Ile Ala Leu Gly Thr Phe Thr Glu Asn Gln Asp Val Pro
305                 310                 315                 320

Arg Phe Ala Ser Tyr Thr Gln Asp Leu Ser Leu Ala Arg Asn Ile Ile
                325                 330                 335

Thr Phe Asn Leu Leu Gly Asp Gly Ile Pro Val Phe Tyr Tyr Gly Glu
            340                 345                 350

Glu Gln His Leu Ser Gly Ala Tyr Asn Pro Val Asn Arg Glu Ala Leu
            355                 360                 365

Trp Leu Thr His Tyr Ser Trp Asn Thr Thr Ser Leu Pro Ser Leu Val
            370                 375                 380

Lys Ser Leu Asn Arg Leu Arg Ser Tyr Ala Ala Phe Asn Gly Thr Gln
385                 390                 395                 400

Phe Thr Ala Ala Ser Glu Pro Gly Asn Asp Tyr Leu Ser Phe Ile Thr

```
                     405                 410                 415
Tyr Pro Ile Tyr Asn Ser Thr His Ile Leu Ala Leu Arg Lys Gly Phe
            420                 425                 430

Val Gly Asn Gln Val Ile Ser Val Leu Ser Asn Leu Gly Thr Tyr Pro
            435                 440                 445

Asp Gly Asn Glu Glu Thr Lys Ile Val Leu Asn Ala Thr Gly Thr Gly
            450                 455                 460

Phe Gln Pro Gly Gln Asn Val Thr Glu Ile Leu Ser Cys Gln Thr Val
465                 470                 475                 480

Leu Thr Asp Glu Asn Gly Asn Leu Glu Val Asp Leu His Asp Gly Gly
            485                 490                 495

Pro Arg Val Tyr Tyr Pro Thr Asp Ser Leu Asn Ile Tyr Ser Asp Ile
            500                 505                 510

Cys Gly His Cys Glu Glu Gln Thr Ala Thr Pro Gly Asn Ser Ser Gly
            515                 520                 525

Gly Thr Ser Pro Lys Lys Ser Gly Ala Ser Leu Ser Thr Ser Ser Glu
            530                 535                 540

Leu Leu Asn Ile Leu Ser Ser Val Ser Ile Thr Leu Phe Leu Val Met
545                 550                 555                 560

Gly Phe Pro Phe

<210> SEQ ID NO 15
<211> LENGTH: 2435
<212> TYPE: DNA
<213> ORGANISM: Talaromyces emersonii
<220> FEATURE:
<221> NAME/KEY: sig_peptide
<222> LOCATION: (1)..(75)
<220> FEATURE:
<221> NAME/KEY: exon
<222> LOCATION: (1)..(252)
<220> FEATURE:
<221> NAME/KEY: exon
<222> LOCATION: (373)..(427)
<220> FEATURE:
<221> NAME/KEY: exon
<222> LOCATION: (511)..(614)
<220> FEATURE:
<221> NAME/KEY: exon
<222> LOCATION: (724)..(879)
<220> FEATURE:
<221> NAME/KEY: exon
<222> LOCATION: (972)..(1080)
<220> FEATURE:
<221> NAME/KEY: exon
<222> LOCATION: (1137)..(1314)
<220> FEATURE:
<221> NAME/KEY: exon
<222> LOCATION: (1376)..(1466)
<220> FEATURE:
<221> NAME/KEY: exon
<222> LOCATION: (1517)..(1618)
<220> FEATURE:
<221> NAME/KEY: exon
<222> LOCATION: (1680)..(1731)
<220> FEATURE:
<221> NAME/KEY: exon
<222> LOCATION: (1810)..(2432)

<400> SEQUENCE: 15 atg gcg ccc cct tgg acg aca gta ctt ctg gca gtc ttc ttc gta ttc    48
Met Ala Pro Pro Trp Thr Thr Val Leu Leu Ala Val Phe Phe Val Phe
1               5                   10                  15 tgc acg tta cct cgc ctc gcg cag gcc gcg aca agc gat gaa tgg aag    96
Cys Thr Leu Pro Arg Leu Ala Gln Ala Ala Thr Ser Asp Glu Trp Lys
            20                  25                  30
```

```
tcg cga tcc att tac caa atc gtg aca gac cgc ttc gcc cgg tcc gac      144
Ser Arg Ser Ile Tyr Gln Ile Val Thr Asp Arg Phe Ala Arg Ser Asp
         35                  40                  45 aat tca act gtt gcg cca tgc aat gcc gca gca ggt gag tac tgc ggc      192
Asn Ser Thr Val Ala Pro Cys Asn Ala Ala Ala Gly Glu Tyr Cys Gly
 50                  55                  60 ggc gac ttt cga ggc atc atc aac aag ctg gat tac att cag gat ctc      240
Gly Asp Phe Arg Gly Ile Ile Asn Lys Leu Asp Tyr Ile Gln Asp Leu
 65                  70                  75                  80 ggg ttc tca gcg gtaagttctc tgctttccct tcttctctcc tggaaatggt         292
Gly Phe Ser Ala gacaaacaag ccacaccgcc tcgtgttcac aatgcgccac gatggagcgc cacgatgcct    352
cgtgacacta acaggtgcag ata tgg ata tcg cct gtg acc tat cca gtc cag    405
                     Ile Trp Ile Ser Pro Val Thr Tyr Pro Val Gln
                          85                  90                  95 caa gac acc cca gat ctg tcc t gtaagtttca ctcacacgtt ctctctcacc      457
Gln Asp Thr Pro Asp Leu Ser
                100 tccactcttc gcgtgccacc caggctccta atgcatccaa atccttgccc cag ca       512
                                                                Ser tac cat gga tat tgg cag caa gac atc tac cgg atc aat ccc cga ttc      560
Tyr His Gly Tyr Trp Gln Gln Asp Ile Tyr Arg Ile Asn Pro Arg Phe
    105                 110                 115 ggc acg cct gac gat ctc aag gag ctc tct gat gag ctc cat gca cgc      608
Gly Thr Pro Asp Asp Leu Lys Glu Leu Ser Asp Glu Leu His Ala Arg
120                 125                 130                 135 gga atg gtcagtctct acccttcttt accatcgaca ccgttaaccg tatctgatcg      664
Gly Met ttgctgtcga tctctgtccc gttcctctct ccaattcttg cccatgctca caagcgcag    723 tat ctg atg ctc gac gtg gtg acc aat cat ttc gcg tgg gcc gga aat      771
Tyr Leu Met Leu Asp Val Val Thr Asn His Phe Ala Trp Ala Gly Asn
        140                 145                 150 tat acc acg atc gat tat ggc caa ttc cac ccg ttc aac cgc cag gat      819
Tyr Thr Thr Ile Asp Tyr Gly Gln Phe His Pro Phe Asn Arg Gln Asp
    155                 160                 165 tat ttc cat cct ttc cgg ctt ctc aag gac gat ccg gat aat gag aca      867
Tyr Phe His Pro Phe Arg Leu Leu Lys Asp Asp Pro Asp Asn Glu Thr
170                 175                 180                 185 tgc gtg gtg gat gtaagtccat ccaagagaaa gacccatgac atgaagggta         919
Cys Val Val Asp aatttattgc tgcagagagg aattgcctcc taacgctatt gaattgtacc ag tgt tgg    977
                                                          Cys Trp
                                                           190 ctt gga gat gaa att gtg acg ctt ccc gat ctc aga acg gaa gac agc     1025
Leu Gly Asp Glu Ile Val Thr Leu Pro Asp Leu Arg Thr Glu Asp Ser
            195                 200                 205 aat gta gca tcg aca ctc tat tcc tgg atc agc gaa ctg gtc tcc aat     1073
Asn Val Ala Ser Thr Leu Tyr Ser Trp Ile Ser Glu Leu Val Ser Asn
        210                 215                 220 tat tca g gtcagtatcc ctccctacgt tgaacaagat tcatgaacta ggaccaattc   1130
Tyr Ser
    225 taacag ct cgt ctt att ata gtc gac ggc ctg cgt ctt gac agc gta      1177
       Ala Arg Leu Ile Ile Val Asp Gly Leu Arg Leu Asp Ser Val
                   230                 235 ttc aat gtc aat caa gat ttc tgg caa ggg ttc aat aag gct tca ggg     1225
Phe Asn Val Asn Gln Asp Phe Trp Gln Gly Phe Asn Lys Ala Ser Gly
```

```
                240                 245                 250                 255
gtg ttt tgc atc ggc gaa ggg aat aca aac gat gca tca tcc ata tgt           1273
Val Phe Cys Ile Gly Glu Gly Asn Thr Asn Asp Ala Ser Ser Ile Cys
                260                 265                 270 cct ctc cag tgg aaa atg gat ggt gtt ttg aac tac ccc at                    1314
Pro Leu Gln Trp Lys Met Asp Gly Val Leu Asn Tyr Pro Met
            275                 280                 285 gttcgtcttt gcgattcgct acccaacacc aaagcccaaa aagtgctgac aaacagctca         1374 g g tac tat cgc ctt acc agc aca ttc aac aac acg gat acg aat atg          1421
    Tyr Tyr Arg Leu Thr Ser Thr Phe Asn Asn Thr Asp Thr Asn Met
                    290                 295                 300 aat ggt cta ctc gaa ggc ctg gaa gag gtg aag cac gcg tgc agg              1466
Asn Gly Leu Leu Glu Gly Leu Glu Glu Val Lys His Ala Cys Arg
                305                 310                 315 gtatttaata tctatgattt catatgtcac atataaatta tataaattag tat gtt           1522
                                                        Tyr Val gct aat ttc aga gga aca cag gat atc ttc acg ctg gga acc ttc act         1570
Ala Asn Phe Arg Gly Thr Gln Asp Ile Phe Thr Leu Gly Thr Phe Thr
            320                 325                 330 gaa aat caa gat gtt cca cga ttc gct tct cag acc caa gac ata tcc         1618
Glu Asn Gln Asp Val Pro Arg Phe Ala Ser Gln Thr Gln Asp Ile Ser
        335                 340                 345 gttcgtgttc cctcgagcca atccctcaac cagttcaatt ctaacctatc ttttcctcta       1678 g cta gcc cgg aat att atc act ttc aat ctt ctt gga gac ggg ata cct       1727
  Leu Ala Arg Asn Ile Ile Thr Phe Asn Leu Leu Gly Asp Gly Ile Pro
            350                 355                 360                 365 atc c gtgcgtgttc cttttcttaa attttgtttc aaaagcatag tacttgcgat            1781
Ile attcaattaa cccgggttct ttctacag tc  tac tat ggc gaa gag cta cac          1832
                                   Leu Tyr Tyr Gly Glu Glu Leu His
                                                        370 ctg aca gga cca tat aac ccg gtc aac cgg gga gcg ctc tgg ctg acc         1880
Leu Thr Gly Pro Tyr Asn Pro Val Asn Arg Gly Ala Leu Trp Leu Thr
375                 380                 385                 390 gat tac gcg aat gac acc act tcc ctt ccc tcc ctc gtc cag tcc ctg         1928
Asp Tyr Ala Asn Asp Thr Thr Ser Leu Pro Ser Leu Val Gln Ser Leu
                395                 400                 405 aat aga ctg cgc gcc cac gcc gcc agc aac ggc act cga ttc acc gaa         1976
Asn Arg Leu Arg Ala His Ala Ala Ser Asn Gly Thr Arg Phe Thr Glu
            410                 415                 420 tct gct ccc tct tcc tcc cag caa aac gac tat ctc acc ttc gta tcg         2024
Ser Ala Pro Ser Ser Ser Gln Gln Asn Asp Tyr Leu Thr Phe Val Ser
        425                 430                 435 tac gcg atc cac aac agc tcc cac acc gtt tcc ctg cga aag ggg ttc         2072
Tyr Ala Ile His Asn Ser Ser His Thr Val Ser Leu Arg Lys Gly Phe
    440                 445                 450 gca gga aac caa gtc ata acc gtg ctg tcg aac ctc ggt tcc cag ccg         2120
Ala Gly Asn Gln Val Ile Thr Val Leu Ser Asn Leu Gly Ser Gln Pro
455                 460                 465                 470 agc cgc gac gac cca gag acc tcg ttc acg ctc tcc tcc gcg ggg acg         2168
Ser Arg Asp Asp Pro Glu Thr Ser Phe Thr Leu Ser Ser Ala Gly Thr
                475                 480                 485 ggc ttt cac ccg aac cag aac gtg acc gag atc ctc tcc tgc cgg acc         2216
Gly Phe His Pro Asn Gln Asn Val Thr Glu Ile Leu Ser Cys Arg Thr
            490                 495                 500 gtc ctg acg gac ggc gca ggc aat ctc aac gtg gac ctc gca gct gat         2264
Val Leu Thr Asp Gly Ala Gly Asn Leu Asn Val Asp Leu Ala Ala Asp
        505                 510                 515
```

```
ggc ggg ccc cga gtc tat tac ccg acc aac agc ctt aac ggc tct ggt   2312
Gly Gly Pro Arg Val Tyr Tyr Pro Thr Asn Ser Leu Asn Gly Ser Gly
        520             525                 530 ctc tgc gac gac gag ttg aaa tcg aca tcg gcg gcc gcc cca tta gtc   2360
Leu Cys Asp Asp Glu Leu Lys Ser Thr Ser Ala Ala Ala Pro Leu Val
535                 540                 545                 550 atg ttg cag cag ctt aca tgg ctg acc gtc ttc acg atg ttg gta ttc   2408
Met Leu Gln Gln Leu Thr Trp Leu Thr Val Phe Thr Met Leu Val Phe
                555                 560                 565 atg atg atg gag atg act ctg ttg tga                               2435
Met Met Met Glu Met Thr Leu Leu
                570
```

<210> SEQ ID NO 16
<211> LENGTH: 574
<212> TYPE: PRT
<213> ORGANISM: Talaromyces emersonii

<400> SEQUENCE: 16

```
Met Ala Pro Pro Trp Thr Thr Val Leu Leu Ala Val Phe Phe Val Phe
1               5                   10                  15

Cys Thr Leu Pro Arg Leu Ala Gln Ala Ala Thr Ser Asp Glu Trp Lys
            20                  25                  30

Ser Arg Ser Ile Tyr Gln Ile Val Thr Asp Arg Phe Ala Arg Ser Asp
        35                  40                  45

Asn Ser Thr Val Ala Pro Cys Asn Ala Ala Gly Glu Tyr Cys Gly
    50                  55                  60

Gly Asp Phe Arg Gly Ile Ile Asn Lys Leu Asp Tyr Ile Gln Asp Leu
65                  70                  75                  80

Gly Phe Ser Ala Ile Trp Ile Ser Pro Val Thr Tyr Pro Val Gln Gln
                85                  90                  95

Asp Thr Pro Asp Leu Ser Ser Tyr His Gly Tyr Trp Gln Gln Asp Ile
            100                 105                 110

Tyr Arg Ile Asn Pro Arg Phe Gly Thr Pro Asp Asp Leu Lys Glu Leu
        115                 120                 125

Ser Asp Glu Leu His Ala Arg Gly Met Tyr Leu Met Leu Asp Val Val
    130                 135                 140

Thr Asn His Phe Ala Trp Ala Gly Asn Tyr Thr Thr Ile Asp Tyr Gly
145                 150                 155                 160

Gln Phe His Pro Phe Asn Arg Gln Asp Tyr Phe His Pro Phe Arg Leu
                165                 170                 175

Leu Lys Asp Asp Pro Asp Asn Glu Thr Cys Val Val Asp Cys Trp Leu
            180                 185                 190

Gly Asp Glu Ile Val Thr Leu Pro Asp Leu Arg Thr Glu Asp Ser Asn
        195                 200                 205

Val Ala Ser Thr Leu Tyr Ser Trp Ile Ser Glu Leu Val Ser Asn Tyr
    210                 215                 220

Ser Ala Arg Leu Ile Ile Val Asp Gly Leu Arg Leu Asp Ser Val Phe
225                 230                 235                 240

Asn Val Asn Gln Asp Phe Trp Gln Gly Phe Asn Lys Ala Ser Gly Val
                245                 250                 255

Phe Cys Ile Gly Glu Gly Asn Thr Asn Asp Ala Ser Ser Ile Cys Pro
            260                 265                 270

Leu Gln Trp Lys Met Asp Gly Val Leu Asn Tyr Pro Met Tyr Tyr Arg
        275                 280                 285
```

```
Leu Thr Ser Thr Phe Asn Asn Thr Asp Thr Asn Met Asn Gly Leu Leu
    290                 295                 300

Glu Gly Leu Glu Glu Val Lys His Ala Cys Arg Tyr Val Ala Asn Phe
305                 310                 315                 320

Arg Gly Thr Gln Asp Ile Phe Thr Leu Gly Thr Phe Thr Glu Asn Gln
                325                 330                 335

Asp Val Pro Arg Phe Ala Ser Gln Thr Gln Asp Ile Ser Leu Ala Arg
            340                 345                 350

Asn Ile Ile Thr Phe Asn Leu Leu Gly Asp Gly Ile Pro Ile Leu Tyr
        355                 360                 365

Tyr Gly Glu Glu Leu His Leu Thr Gly Pro Tyr Asn Pro Val Asn Arg
370                 375                 380

Gly Ala Leu Trp Leu Thr Asp Tyr Ala Asn Asp Thr Thr Ser Leu Pro
385                 390                 395                 400

Ser Leu Val Gln Ser Leu Asn Arg Leu Arg Ala His Ala Ala Ser Asn
                405                 410                 415

Gly Thr Arg Phe Thr Glu Ser Ala Pro Ser Ser Gln Gln Asn Asp
            420                 425                 430

Tyr Leu Thr Phe Val Ser Tyr Ala Ile His Asn Ser Ser His Thr Val
        435                 440                 445

Ser Leu Arg Lys Gly Phe Ala Gly Asn Gln Val Ile Thr Val Leu Ser
450                 455                 460

Asn Leu Gly Ser Gln Pro Ser Arg Asp Asp Pro Glu Thr Ser Phe Thr
465                 470                 475                 480

Leu Ser Ser Ala Gly Thr Gly Phe His Pro Asn Gln Asn Val Thr Glu
                485                 490                 495

Ile Leu Ser Cys Arg Thr Val Leu Thr Asp Gly Ala Gly Asn Leu Asn
            500                 505                 510

Val Asp Leu Ala Ala Asp Gly Gly Pro Arg Val Tyr Tyr Pro Thr Asn
        515                 520                 525

Ser Leu Asn Gly Ser Gly Leu Cys Asp Asp Glu Leu Lys Ser Thr Ser
530                 535                 540

Ala Ala Ala Pro Leu Val Met Leu Gln Gln Leu Thr Trp Leu Thr Val
545                 550                 555                 560

Phe Thr Met Leu Val Phe Met Met Met Glu Met Thr Leu Leu
                565                 570

<210> SEQ ID NO 17
<211> LENGTH: 1715
<212> TYPE: DNA
<213> ORGANISM: Talaromyces emersonii
<220> FEATURE:
<221> NAME/KEY: sig_peptide
<222> LOCATION: (1)..(63)
<220> FEATURE:
<221> NAME/KEY: exon
<222> LOCATION: (1)..(231)
<220> FEATURE:
<221> NAME/KEY: exon
<222> LOCATION: (288)..(446)
<220> FEATURE:
<221> NAME/KEY: exon
<222> LOCATION: (502)..(763)
<220> FEATURE:
<221> NAME/KEY: exon
<222> LOCATION: (828)..(990)
<220> FEATURE:
<221> NAME/KEY: exon
<222> LOCATION: (1043)..(1712)

<400> SEQUENCE: 17
```

```
atg aag ttg ccc ctg ttt att gca agt aca gcc ttg acg aat gct gtt         48
Met Lys Leu Pro Leu Phe Ile Ala Ser Thr Ala Leu Thr Asn Ala Val
 1               5                  10                  15 ctg gct gct gat gcg gcc gat tgg cgc tcg agg tca ata tac caa cta         96
Leu Ala Ala Asp Ala Ala Asp Trp Arg Ser Arg Ser Ile Tyr Gln Leu
             20                  25                  30 ttg aca gat cga ttc gcc cgc cct gat gga tcg acg gcg gcg gcc tgt        144
Leu Thr Asp Arg Phe Ala Arg Pro Asp Gly Ser Thr Ala Ala Ala Cys
         35                  40                  45 gtt acc gaa gac cgt cga tac tgt ggc ggc acc ttc cag ggt atc ata        192
Val Thr Glu Asp Arg Arg Tyr Cys Gly Gly Thr Phe Gln Gly Ile Ile
     50                  55                  60 aac cag ctg gac tat att cag ggg atg ggc ttc acg gcg gttagtctgt        241
Asn Gln Leu Asp Tyr Ile Gln Gly Met Gly Phe Thr Ala
 65                  70                  75 cacacccaag atctcaaaca aggaacatg ctgatggccg ggacag att tgg ata          296
                                                    Ile Trp Ile
                                                            80 tcc ccc gtt act cat caa tta gaa ggg ata acg cct tat ggg gaa gcc        344
Ser Pro Val Thr His Gln Leu Glu Gly Ile Thr Pro Tyr Gly Glu Ala
                 85                  90                  95 tac cat ggc tac tgg cag caa gat ctc tac aag ctg aac tcc cac ttt        392
Tyr His Gly Tyr Trp Gln Gln Asp Leu Tyr Lys Leu Asn Ser His Phe
            100                 105                 110 ggg tcg ccg gac gac ttg cga gag tta gca gaa gaa ctg cat cga cgt        440
Gly Ser Pro Asp Asp Leu Arg Glu Leu Ala Glu Glu Leu His Arg Arg
        115                 120                 125 gac atg gtgtgtagta cgtttgaaac attcacctag gatgagctta ctgatgcagt        496
Asp Met
   130 attag tat ctc atg ctc gat gtc gtc gtc aat cac aac ggc tgg aac gga     546
      Tyr Leu Met Leu Asp Val Val Val Asn His Asn Gly Trp Asn Gly
                135                 140                 145 tcc gca tct gcc gtc gac tac agg gta ttc cat cct ttc gac aag aag        594
Ser Ala Ser Ala Val Asp Tyr Arg Val Phe His Pro Phe Asp Lys Lys
                150                 155                 160 gag tac tac cac aac tac tgc ccc ata gtc gac tgg tcc aac cag acg        642
Glu Tyr Tyr His Asn Tyr Cys Pro Ile Val Asp Trp Ser Asn Gln Thr
                165                 170                 175 cag gtt gag gat tgt tgg atc ggt gac aat ctt gtc tcc tgt cca gac        690
Gln Val Glu Asp Cys Trp Ile Gly Asp Asn Leu Val Ser Cys Pro Asp
            180                 185                 190 ctc tat acg caa cat ccg cac gtc agg caa gaa tac cag tcg tgg atc        738
Leu Tyr Thr Gln His Pro His Val Arg Gln Glu Tyr Gln Ser Trp Ile
        195                 200                 205 tct gat ctc gtc cgc aac tat tca g gtatggcact tgtctgcaat                783
Ser Asp Leu Val Arg Asn Tyr Ser
210                 215 tgcaatcaag accagggttc ggtatctcac atgttcttat ccag tg  gat ggg ttg       838
                                                    Val Asp Gly Leu
                                                                220 cgg atc gac acc gca agg gaa gtc gaa aat gac ttt ctc ttt ggt ttc        886
Arg Ile Asp Thr Ala Arg Glu Val Glu Asn Asp Phe Leu Phe Gly Phe
            225                 230                 235 gtt tca gca tct gga gtc ttc gct acc gga gag gtt atg gtc aac aac        934
Val Ser Ala Ser Gly Val Phe Ala Thr Gly Glu Val Met Val Asn Asn
        240                 245                 250 gcc aat gag gcc tgc cct tac cag ccg tac cta ggc agt ttc cta aat        982
Ala Asn Glu Ala Cys Pro Tyr Gln Pro Tyr Leu Gly Ser Phe Leu Asn
```

```
                  255                 260                 265
tac cct gc  gtaagttctc tgggtggtac gtccgtgatc ctgactgaca              1030
Tyr Pro Ala
270 aagcttctac ag t tac tac tca ttg ata gat gcg ttc aag agt ccg tcg     1079
                Tyr Tyr Ser Leu Ile Asp Ala Phe Lys Ser Pro Ser
                    275                 280 ggc aac atc tcc agc ttg gtc aat cag atc aac cag gtg aaa tcg act     1127
Gly Asn Ile Ser Ser Leu Val Asn Gln Ile Asn Gln Val Lys Ser Thr
285                 290                 295                 300 tgc atg gac tcc acc gtc ctg ggc agc ttt tcc gaa aat cac gac aac     1175
Cys Met Asp Ser Thr Val Leu Gly Ser Phe Ser Glu Asn His Asp Asn
                305                 310                 315 ccc cgt ttc gcc aac tac acc gcg gac atg tcc ctg gca aag aat atc     1223
Pro Arg Phe Ala Asn Tyr Thr Ala Asp Met Ser Leu Ala Lys Asn Ile
            320                 325                 330 atc gca ttc aca atg ctc gca gac ggg att ccc atc ata tac gct ggt     1271
Ile Ala Phe Thr Met Leu Ala Asp Gly Ile Pro Ile Ile Tyr Ala Gly
            335                 340                 345 caa gag cag cat tac tct ggc ggc aat gac ccc aac aac cgc gaa gcg     1319
Gln Glu Gln His Tyr Ser Gly Gly Asn Asp Pro Asn Asn Arg Glu Ala
350                 355                 360 ctt tgg ctt tct ggc tac gac act tcg gca ccg ctt tac cag cac gtc     1367
Leu Trp Leu Ser Gly Tyr Asp Thr Ser Ala Pro Leu Tyr Gln His Val
365                 370                 375                 380 gca cag ctg aat cgg ctt cgt agt cat gcc gca cgc cag agt ccg acg     1415
Ala Gln Leu Asn Arg Leu Arg Ser His Ala Ala Arg Gln Ser Pro Thr
                385                 390                 395 tac ctc acc tac aaa aac cag ccc att tac agc gat tcg acg acc ttg     1463
Tyr Leu Thr Tyr Lys Asn Gln Pro Ile Tyr Ser Asp Ser Thr Thr Leu
            400                 405                 410 gcc atg cgg aaa ggg gtc aac ggg caa cag gtc atc acc gtg ctc agc     1511
Ala Met Arg Lys Gly Val Asn Gly Gln Gln Val Ile Thr Val Leu Ser
            415                 420                 425 aac cgt ggc acc agc ggg ccg aag tat gtc tta tcc ctt ggg aac acg     1559
Asn Arg Gly Thr Ser Gly Pro Lys Tyr Val Leu Ser Leu Gly Asn Thr
430                 435                 440 gga tat cag cgt ggg cag aaa ctg gtc gag gtc ctg act tgt act ccc     1607
Gly Tyr Gln Arg Gly Gln Lys Leu Val Glu Val Leu Thr Cys Thr Pro
445                 450                 455                 460 gtc acg gtg gac gac aac gga aat gtt cca gtt cag atg gag cag gga     1655
Val Thr Val Asp Asp Asn Gly Asn Val Pro Val Gln Met Glu Gln Gly
                465                 470                 475 ctg ccg cga gtt ttc tac cca aga cat cag ctt cga ggc tca ggg ttg     1703
Leu Pro Arg Val Phe Tyr Pro Arg His Gln Leu Arg Gly Ser Gly Leu
            480                 485                 490 tgt gat ctg taa                                                     1715
Cys Asp Leu
        495

<210> SEQ ID NO 18
<211> LENGTH: 495
<212> TYPE: PRT
<213> ORGANISM: Talaromyces emersonii

<400> SEQUENCE: 18

Met Lys Leu Pro Leu Phe Ile Ala Ser Thr Ala Leu Thr Asn Ala Val
1               5                   10                  15

Leu Ala Ala Asp Ala Ala Asp Trp Arg Ser Arg Ser Ile Tyr Gln Leu
            20                  25                  30
```

-continued

Leu Thr Asp Arg Phe Ala Arg Pro Asp Gly Ser Thr Ala Ala Cys
    35                  40                  45

Val Thr Glu Asp Arg Arg Tyr Cys Gly Gly Thr Phe Gln Gly Ile Ile
    50                  55                  60

Asn Gln Leu Asp Tyr Ile Gln Gly Met Gly Phe Thr Ala Ile Trp Ile
65                  70                  75                  80

Ser Pro Val Thr His Gln Leu Glu Gly Ile Thr Pro Tyr Gly Glu Ala
                85                  90                  95

Tyr His Gly Tyr Trp Gln Gln Asp Leu Tyr Lys Leu Asn Ser His Phe
                100                 105                 110

Gly Ser Pro Asp Asp Leu Arg Glu Leu Ala Glu Glu Leu His Arg Arg
            115                 120                 125

Asp Met Tyr Leu Met Leu Asp Val Val Asn His Asn Gly Trp Asn
        130                 135                 140

Gly Ser Ala Ser Ala Val Asp Tyr Arg Val Phe His Pro Phe Asp Lys
145                 150                 155                 160

Lys Glu Tyr Tyr His Asn Tyr Cys Pro Ile Val Asp Trp Ser Asn Gln
                165                 170                 175

Thr Gln Val Glu Asp Cys Trp Ile Gly Asp Asn Leu Val Ser Cys Pro
            180                 185                 190

Asp Leu Tyr Thr Gln His Pro His Val Arg Gln Glu Tyr Gln Ser Trp
        195                 200                 205

Ile Ser Asp Leu Val Arg Asn Tyr Ser Val Asp Gly Leu Arg Ile Asp
210                 215                 220

Thr Ala Arg Glu Val Glu Asn Asp Phe Leu Phe Gly Phe Val Ser Ala
225                 230                 235                 240

Ser Gly Val Phe Ala Thr Gly Glu Val Met Val Asn Asn Ala Asn Glu
                245                 250                 255

Ala Cys Pro Tyr Gln Pro Tyr Leu Gly Ser Phe Leu Asn Tyr Pro Ala
            260                 265                 270

Tyr Tyr Ser Leu Ile Asp Ala Phe Lys Ser Pro Ser Gly Asn Ile Ser
        275                 280                 285

Ser Leu Val Asn Gln Ile Asn Gln Val Lys Ser Thr Cys Met Asp Ser
290                 295                 300

Thr Val Leu Gly Ser Phe Ser Glu Asn His Asp Asn Pro Arg Phe Ala
305                 310                 315                 320

Asn Tyr Thr Ala Asp Met Ser Leu Ala Lys Asn Ile Ile Ala Phe Thr
                325                 330                 335

Met Leu Ala Asp Gly Ile Pro Ile Ile Tyr Ala Gly Gln Glu Gln His
            340                 345                 350

Tyr Ser Gly Gly Asn Asp Pro Asn Asn Arg Glu Ala Leu Trp Leu Ser
        355                 360                 365

Gly Tyr Asp Thr Ser Ala Pro Leu Tyr Gln His Val Ala Gln Leu Asn
370                 375                 380

Arg Leu Arg Ser His Ala Ala Arg Gln Ser Pro Thr Tyr Leu Thr Tyr
385                 390                 395                 400

Lys Asn Gln Pro Ile Tyr Ser Asp Ser Thr Thr Leu Ala Met Arg Lys
                405                 410                 415

Gly Val Asn Gly Gln Gln Val Ile Thr Val Leu Ser Asn Arg Gly Thr
            420                 425                 430

Ser Gly Pro Lys Tyr Val Leu Ser Leu Gly Asn Thr Gly Tyr Gln Arg
        435                 440                 445

```
Gly Gln Lys Leu Val Glu Val Leu Thr Cys Thr Pro Val Thr Val Asp
    450                 455                 460
Asp Asn Gly Asn Val Pro Val Gln Met Glu Gln Gly Leu Pro Arg Val
465                 470                 475                 480
Phe Tyr Pro Arg His Gln Leu Arg Gly Ser Gly Leu Cys Asp Leu
                485                 490                 495

<210> SEQ ID NO 19
<211> LENGTH: 2409
<212> TYPE: DNA
<213> ORGANISM: Talaromyces emersonii
<220> FEATURE:
<221> NAME/KEY: sig_peptide
<222> LOCATION: (1)..(48)
<220> FEATURE:
<221> NAME/KEY: exon
<222> LOCATION: (1)..(153)
<220> FEATURE:
<221> NAME/KEY: exon
<222> LOCATION: (218)..(256)
<220> FEATURE:
<221> NAME/KEY: exon
<222> LOCATION: (332)..(447)
<220> FEATURE:
<221> NAME/KEY: exon
<222> LOCATION: (566)..(674)
<220> FEATURE:
<221> NAME/KEY: exon
<222> LOCATION: (734)..(962)
<220> FEATURE:
<221> NAME/KEY: exon
<222> LOCATION: (1027)..(1189)
<220> FEATURE:
<221> NAME/KEY: exon
<222> LOCATION: (1238)..(1384)
<220> FEATURE:
<221> NAME/KEY: exon
<222> LOCATION: (1434)..(1674)
<220> FEATURE:
<221> NAME/KEY: exon
<222> LOCATION: (1723)..(2406)

<400> SEQUENCE: 19 atg acg cct ttc gtc ctg ctg ccc ttg ctg ggc agt gcc gtg ttg gcc      48
Met Thr Pro Phe Val Leu Leu Pro Leu Leu Gly Ser Ala Val Leu Ala
1               5                   10                  15 ttg acc ccg gcc gaa tgg cgc aaa caa tcc atc tac ttt ctc ctc acg      96
Leu Thr Pro Ala Glu Trp Arg Lys Gln Ser Ile Tyr Phe Leu Leu Thr
            20                  25                  30 gac cgc ttt ggc aga gaa gat aac tcg acc acg gct gcc tgc gat gtc     144
Asp Arg Phe Gly Arg Glu Asp Asn Ser Thr Thr Ala Ala Cys Asp Val
        35                  40                  45 act gag cgg gtaagtaaaa aaagagttta tcggctggtc gatcatcgtc             193
Thr Glu Arg
    50 tctgagtgat aatggctgga acag att tac tgt ggc ggg agt tgg cga gga      244
                           Ile Tyr Cys Gly Gly Ser Trp Arg Gly
                                    55                  60 atc atc aac cat gtacgccaag ttgcctgctt tcccttgtca attcacggac         296
Ile Ile Asn His ggaatgtcta aattgttctt tctttctctc cccag ctc gac tac atc caa ggc      349
                                      Leu Asp Tyr Ile Gln Gly
                                                65          70 atg ggg ttc acg gcc atc tgg att tca ccg gtg acc gag caa ctg ccg     397
Met Gly Phe Thr Ala Ile Trp Ile Ser Pro Val Thr Glu Gln Leu Pro
                75                  80                  85 cag gat acg ggg gaa gga gaa gcc tat cat ggg tat tgg cag cag gaa     445
```

```
Gln Asp Thr Gly Glu Gly Glu Ala Tyr His Gly Tyr Trp Gln Glu
         90                  95                 100 at  gtgagttatc agttgaactg tcattctttg tgtgatctag atgatgcata        497
Ile attattaccc agtggataaa acgtattctt ccgggaattt actatgatc tctgcttacg   557 caaagcag a tac act ttc aac tcc cac ttc ggg aca tca gac gat ctc    605
           Tyr Thr Phe Asn Ser His Phe Gly Thr Ser Asp Asp Leu
               105                 110                 115 gca gcc ctg tcg acg gcg ctc cat gat cgt ggc atg tac ctc atg gtc  653
Ala Ala Leu Ser Thr Ala Leu His Asp Arg Gly Met Tyr Leu Met Val
            120                 125                 130 gat gtg gtt gcg aat cac atg gtcagtgacc tggttttctt ccttcttgac     704
Asp Val Val Ala Asn His Met
            135 aagaacgaac gtctctaaac tcaactcag gga tac gat gga gct ggc gac tcc  757
                                Gly Tyr Asp Gly Ala Gly Asp Ser
                                        140                 145 gtt gat tac agc gtc ttc aat cca ttc aat tcc tcg agc tat ttc cat  805
Val Asp Tyr Ser Val Phe Asn Pro Phe Asn Ser Ser Ser Tyr Phe His
            150                 155                 160 ccc tac tgc ctg att aca gac tac aac aat caa act gat gtg gaa gac  853
Pro Tyr Cys Leu Ile Thr Asp Tyr Asn Asn Gln Thr Asp Val Glu Asp
165                 170                 175 tgt tgg ctg ggt gat acg act gtc tcg ttg ccc gat ctc aac acc acg  901
Cys Trp Leu Gly Asp Thr Thr Val Ser Leu Pro Asp Leu Asn Thr Thr
180                 185                 190                 195 gag act gct gtg cgg act ata tgg tat gac tgg gtg aag gat ctc gtc  949
Glu Thr Ala Val Arg Thr Ile Trp Tyr Asp Trp Val Lys Asp Leu Val
                200                 205                 210 tcc aat tac tcc a gtatgtttga ttctttctct actttttttt gtctttgaag    1002
Ser Asn Tyr Ser
        215 catacagcta acactatcca atag tt  gat ggc ctt cgc att gac acg gtg    1052
                              Ile Asp Gly Leu Arg Ile Asp Thr Val
                                              220 aaa cac gtc gag aag tca ttc tgg cct ggt tac aac agc gcc gct ggt  1100
Lys His Val Glu Lys Ser Phe Trp Pro Gly Tyr Asn Ser Ala Ala Gly
225                 230                 235                 240 gtc tac tgt gtt ggc gag gtc ctc gat ggt gat ccg tct tac acc tgt  1148
Val Tyr Cys Val Gly Glu Val Leu Asp Gly Asp Pro Ser Tyr Thr Cys
                245                 250                 255 ccc tac cag gat tat ttg gat gga gta tta aac tat cca at           1189
Pro Tyr Gln Asp Tyr Leu Asp Gly Val Leu Asn Tyr Pro Ile
        260                 265                 270 gtgaggacct ctttcctgtt aaaaaagccg tttcctgaca acgtccag a tac tat    1244
                                                      Tyr Tyr caa ttg ctg tat gcg ttt gaa gcc tct aac ggt agc atc agc aat ctt  1292
Gln Leu Leu Tyr Ala Phe Glu Ala Ser Asn Gly Ser Ile Ser Asn Leu
        275                 280                 285 tac aac atg atc aac tct gtc gcc tct gct tgc tcc gat ccc act ctg  1340
Tyr Asn Met Ile Asn Ser Val Ala Ser Ala Cys Ser Asp Pro Thr Leu
        290                 295                 300 ttg ggc aac ttt atc gag aac cat gac aac ccc aga ttt gcc tc       1384
Leu Gly Asn Phe Ile Glu Asn His Asp Asn Pro Arg Phe Ala Ser
305                 310                 315 gtaagtagtc ttatctgggg taacccgagt caagactgac ttttttag c tat aca   1440
                                                       Tyr Thr
                                                            320
```

```
                                      -continued agc gat tat tct ctt gct aaa aat gtg att tct ttc atc ttc ttc tct         1488
Ser Asp Tyr Ser Leu Ala Lys Asn Val Ile Ser Phe Ile Phe Phe Ser
            325                 330                 335 gac ggc atc cct att gtc tat gcc ggt cag gag cag cat tac aac ggg         1536
Asp Gly Ile Pro Ile Val Tyr Ala Gly Gln Glu Gln His Tyr Asn Gly
        340                 345                 350 gga aat gac ccc tac aac cgt gag gcc acc tgg ctg tca gga tac tcg         1584
Gly Asn Asp Pro Tyr Asn Arg Glu Ala Thr Trp Leu Ser Gly Tyr Ser
    355                 360                 365 acg acc gcc gaa ctg tac acg ttc ata gcg acc acc aac gcg atc cgt         1632
Thr Thr Ala Glu Leu Tyr Thr Phe Ile Ala Thr Thr Asn Ala Ile Arg
370                 375                 380                 385 aag ttc gcg atc tcc gtc gac tcg gag tat ttg acg tcc aag                 1674
Lys Phe Ala Ile Ser Val Asp Ser Glu Tyr Leu Thr Ser Lys
                390                 395 gtatgtttgc gtatggatcg tgatggaaac tgaactcacc atctccag aat gac ccg         1731
                                                     Asn Asp Pro
                                                         400 ttc tac tac gat agc aat aac ctc gct atg cgc aag ggt tca gat ggc         1779
Phe Tyr Tyr Asp Ser Asn Asn Leu Ala Met Arg Lys Gly Ser Asp Gly
                405                 410                 415 ttg cag gtc atc acg gtt ctg tcc aat ctg ggc gcc gat ggc agc tcg         1827
Leu Gln Val Ile Thr Val Leu Ser Asn Leu Gly Ala Asp Gly Ser Ser
    420                 425                 430 tac acg ttg aca ctg agt ggc agt ggc tat tcg tct ggc acg gag ctg         1875
Tyr Thr Leu Thr Leu Ser Gly Ser Gly Tyr Ser Ser Gly Thr Glu Leu
435                 440                 445                 450 gtg gaa gct tac acc tgc aca acg gtc act gtc gac tcc aat ggc gat         1923
Val Glu Ala Tyr Thr Cys Thr Thr Val Thr Val Asp Ser Asn Gly Asp
                455                 460                 465 att ccg gtg ccc atg gag tcc ggc ctg ccg cgc gtt ttc cta cca tca         1971
Ile Pro Val Pro Met Glu Ser Gly Leu Pro Arg Val Phe Leu Pro Ser
            470                 475                 480 tcc tcg ctt ggt aat agc agt ctc tgc agt tct tcc ccg agc cct act         2019
Ser Ser Leu Gly Asn Ser Ser Leu Cys Ser Ser Ser Pro Ser Pro Thr
        485                 490                 495 act aca aca tcg aca tcg aca tcg aca tcg acc tcg acc tcg acg acg         2067
Thr Thr Thr Ser Thr Ser Thr Ser Thr Ser Thr Ser Thr Ser Thr Thr
    500                 505                 510 gca acg acg aca gcc tgt acc acc gcc acc gct ctg ccg gtc ctc ttc         2115
Ala Thr Thr Thr Ala Cys Thr Thr Ala Thr Ala Leu Pro Val Leu Phe
515                 520                 525                 530 gaa gag ttg gtg acg acc act tac ggt gaa aat gtc tac ctc agc gga         2163
Glu Glu Leu Val Thr Thr Thr Tyr Gly Glu Asn Val Tyr Leu Ser Gly
                535                 540                 545 tcg atc agc cag ctc ggc aac tgg aac acg gac gac gcc gtg gcc ctg         2211
Ser Ile Ser Gln Leu Gly Asn Trp Asn Thr Asp Asp Ala Val Ala Leu
            550                 555                 560 tca gca gct aat tac act tca tcg aat ccc ctg tgg tat gtg aca gtc         2259
Ser Ala Ala Asn Tyr Thr Ser Ser Asn Pro Leu Trp Tyr Val Thr Val
        565                 570                 575 aca ttg ccg gtc ggg acg tcc ttt gag tac aag ttc atc aag aag gaa         2307
Thr Leu Pro Val Gly Thr Ser Phe Glu Tyr Lys Phe Ile Lys Lys Glu
    580                 585                 590 gag gac ggc act gtc gag tgg gag agt gat ccc aat cgg acg tat act         2355
Glu Asp Gly Thr Val Glu Trp Glu Ser Asp Pro Asn Arg Thr Tyr Thr
595                 600                 605                 610 gtg ccg aca gcc tgc acg ggt gcg aca gag acg att gtc gac aca tgg         2403
Val Pro Thr Ala Cys Thr Gly Ala Thr Glu Thr Ile Val Asp Thr Trp
                615                 620                 625
```

```
aga tag                                                          2409
Arg

<210> SEQ ID NO 20
<211> LENGTH: 627
<212> TYPE: PRT
<213> ORGANISM: Talaromyces emersonii

<400> SEQUENCE: 20

Met Thr Pro Phe Val Leu Leu Pro Leu Leu Gly Ser Ala Val Leu Ala
1               5                   10                  15

Leu Thr Pro Ala Glu Trp Arg Lys Gln Ser Ile Tyr Phe Leu Leu Thr
            20                  25                  30

Asp Arg Phe Gly Arg Glu Asp Asn Ser Thr Thr Ala Ala Cys Asp Val
        35                  40                  45

Thr Glu Arg Ile Tyr Cys Gly Gly Ser Trp Arg Gly Ile Ile Asn His
    50                  55                  60

Leu Asp Tyr Ile Gln Gly Met Gly Phe Thr Ala Ile Trp Ile Ser Pro
65                  70                  75                  80

Val Thr Glu Gln Leu Pro Gln Asp Thr Gly Glu Gly Glu Ala Tyr His
                85                  90                  95

Gly Tyr Trp Gln Gln Glu Ile Tyr Thr Phe Asn Ser His Phe Gly Thr
            100                 105                 110

Ser Asp Asp Leu Ala Ala Leu Ser Thr Ala Leu His Asp Arg Gly Met
        115                 120                 125

Tyr Leu Met Val Asp Val Val Ala Asn His Met Gly Tyr Asp Gly Ala
    130                 135                 140

Gly Asp Ser Val Asp Tyr Ser Val Phe Asn Pro Phe Asn Ser Ser Ser
145                 150                 155                 160

Tyr Phe His Pro Tyr Cys Leu Ile Thr Asp Tyr Asn Asn Gln Thr Asp
                165                 170                 175

Val Glu Asp Cys Trp Leu Gly Asp Thr Thr Val Ser Leu Pro Asp Leu
            180                 185                 190

Asn Thr Thr Glu Thr Ala Val Arg Thr Ile Trp Tyr Asp Trp Val Lys
        195                 200                 205

Asp Leu Val Ser Asn Tyr Ser Ile Asp Gly Leu Arg Ile Asp Thr Val
    210                 215                 220

Lys His Val Glu Lys Ser Phe Trp Pro Gly Tyr Asn Ser Ala Ala Gly
225                 230                 235                 240

Val Tyr Cys Val Gly Glu Val Leu Asp Gly Asp Pro Ser Tyr Thr Cys
                245                 250                 255

Pro Tyr Gln Asp Tyr Leu Asp Gly Val Leu Asn Tyr Pro Ile Tyr Tyr
            260                 265                 270

Gln Leu Leu Tyr Ala Phe Glu Ala Ser Asn Gly Ser Ile Ser Asn Leu
        275                 280                 285

Tyr Asn Met Ile Asn Ser Val Ala Ser Ala Cys Ser Asp Pro Thr Leu
    290                 295                 300

Leu Gly Asn Phe Ile Glu Asn His Asp Asn Pro Arg Phe Ala Ser Tyr
305                 310                 315                 320

Thr Ser Asp Tyr Ser Leu Ala Lys Asn Val Ile Ser Phe Ile Phe Phe
                325                 330                 335

Ser Asp Gly Ile Pro Ile Val Tyr Ala Gly Gln Glu Gln His Tyr Asn
            340                 345                 350

Gly Gly Asn Asp Pro Tyr Asn Arg Glu Ala Thr Trp Leu Ser Gly Tyr
```

```
              355                 360                 365
Ser Thr Thr Ala Glu Leu Tyr Thr Phe Ile Ala Thr Thr Asn Ala Ile
        370                 375                 380

Arg Lys Phe Ala Ile Ser Val Asp Ser Glu Tyr Leu Thr Ser Lys Asn
385                 390                 395                 400

Asp Pro Phe Tyr Tyr Asp Ser Asn Asn Leu Ala Met Arg Lys Gly Ser
                405                 410                 415

Asp Gly Leu Gln Val Ile Thr Val Leu Ser Asn Leu Gly Ala Asp Gly
            420                 425                 430

Ser Ser Tyr Thr Leu Thr Leu Ser Gly Ser Gly Tyr Ser Ser Gly Thr
        435                 440                 445

Glu Leu Val Glu Ala Tyr Thr Cys Thr Thr Val Thr Val Asp Ser Asn
    450                 455                 460

Gly Asp Ile Pro Val Pro Met Glu Ser Gly Leu Pro Arg Val Phe Leu
465                 470                 475                 480

Pro Ser Ser Ser Leu Gly Asn Ser Ser Leu Cys Ser Ser Ser Pro Ser
                485                 490                 495

Pro Thr Thr Thr Thr Ser Thr Ser Thr Ser Thr Ser Thr Ser Thr Ser
            500                 505                 510

Thr Thr Ala Thr Thr Thr Ala Cys Thr Thr Ala Thr Ala Leu Pro Val
        515                 520                 525

Leu Phe Glu Glu Leu Val Thr Thr Thr Tyr Gly Glu Asn Val Tyr Leu
    530                 535                 540

Ser Gly Ser Ile Ser Gln Leu Gly Asn Trp Asn Thr Asp Asp Ala Val
545                 550                 555                 560

Ala Leu Ser Ala Ala Asn Tyr Thr Ser Ser Asn Pro Leu Trp Tyr Val
                565                 570                 575

Thr Val Thr Leu Pro Val Gly Thr Ser Phe Glu Tyr Lys Phe Ile Lys
            580                 585                 590

Lys Glu Glu Asp Gly Thr Val Glu Trp Glu Ser Asp Pro Asn Arg Thr
        595                 600                 605

Tyr Thr Val Pro Thr Ala Cys Thr Gly Ala Thr Glu Thr Ile Val Asp
    610                 615                 620

Thr Trp Arg
625

<210> SEQ ID NO 21
<211> LENGTH: 1512
<212> TYPE: DNA
<213> ORGANISM: Chaetomium thermophilum
<220> FEATURE:
<221> NAME/KEY: sig_peptide
<222> LOCATION: (1)..(75)

<400> SEQUENCE: 21
atgcgctcct cgctgtttgg agccgccgct gcggctgtcc tgtcgttcgt ggggctgact      60
gccgccgccg acgccgaaga atggaagaca cgctcggtct accaggtcat gattgaccgt     120
tttgcccgta ctgacggcag tacggaccat gagtgcgagt acttccgatt ctgcggcggc     180
acttggcgcg gtctaatcaa caagctggac tacatccagg acatgggctt cacggcgatc     240
cagatcagcc ctatcgtcaa gaacatcgac gaacacactg cggttggtga tgcctaccat     300
ggctattggt ctctcgacaa ctatgcgctc aaccccaagt tcggcacaga gaaggacttc     360
cgcgacctgg tcgacgaagt ccacaagcgc ggcatgttac tgatggtcga cgttgtcgtc     420
aacaacatgg ctcaagcctt cgacaacaag gtcccccccca agattgacta ctcgaagttt     480
```

```
aacccgttca acgaccagaa gtacttccac gactactgca acgtcaccag gtgggaggat    540
cccgagaact accagaactg ctggctctat ccctatggtg tcgccctggc cgacctcaag    600
accgagtcgg atgaggtcgt caaggagttc cagaactgga tcaagcagct ggtcgccaac    660
tactccatcg acggtctgcg catcgatgcc gccaagcacg ttaacgacga gttcctgccc    720
cagttcgtcg aggcttcggg tgtctttgcc tggggcgagg tcctgactgg tgtgacgaac    780
gatctctgcc gctaccagac caagggtctc ctgcctggca tgcccaacta cctcgagtac    840
taccctctgc tgcaggcttt caacggcggt tctatggaag aggttgccaa gtatcgcaac    900
gaggccgcct ctggctgcaa cgacacctct gttctcggca gcttcatcga gaaccacgat    960
atgcctcgct tcgccatgta caatgaggac atggccattg ctaagaacgc aatgacctac   1020
accttcttga cgacggcat cccgactgtt tatcaaggtc aagagcaaca ctttaagggc   1080
aacggcacgc cctacaaccg cgagcctctc tggatctcga atacgacaa gtctgcgccg   1140 ctctaccagc ttacctcgac cctcaacaag gtccgtaaca acgccatcaa gctttccaag   1200
gactatgtca acaccccagc cgagaccctc ttcaacgacg tcaaccacct ctgcctgcgc   1260
aagggcccct atggcagcca ggtcgtcttc tgcatcaaca accagagctc caagggcccc   1320
aagtacgagc tcaacatcag cggtggtttt cacccggcg ataaggtcgt cgaggtcacc   1380
cgctgcaggc acaccactgc tgacgcaacc ggcaccatta ccatgtacat gggcaatggt   1440
gagccccgtg tgtatgtaca tgctgatgcg attaagggta ccggcatttg ctcggacacc   1500
aaggaagatg gc                                                      1512

<210> SEQ ID NO 22
<211> LENGTH: 504
<212> TYPE: PRT
<213> ORGANISM: Chaetomium thermophilum

<400> SEQUENCE: 22

Met Arg Ser Ser Leu Phe Gly Ala Ala Ala Ala Val Leu Ser Phe
1               5                   10                  15

Val Gly Leu Thr Ala Ala Ala Asp Ala Glu Glu Trp Lys Thr Arg Ser
            20                  25                  30

Val Tyr Gln Val Met Ile Asp Arg Phe Ala Arg Thr Asp Gly Ser Thr
        35                  40                  45

Asp His Glu Cys Glu Tyr Phe Arg Phe Cys Gly Gly Thr Trp Arg Gly
    50                  55                  60

Leu Ile Asn Lys Leu Asp Tyr Ile Gln Asp Met Gly Phe Thr Ala Ile
65                  70                  75                  80

Gln Ile Ser Pro Ile Val Lys Asn Ile Asp Glu His Thr Ala Val Gly
                85                  90                  95

Asp Ala Tyr His Gly Tyr Trp Ser Leu Asp Asn Tyr Ala Leu Asn Pro
            100                 105                 110

Lys Phe Gly Thr Glu Lys Asp Phe Arg Asp Leu Val Asp Glu Val His
        115                 120                 125

Lys Arg Gly Met Leu Leu Met Val Asp Val Val Asn Asn Met Ala
    130                 135                 140

Gln Ala Phe Asp Asn Lys Val Pro Pro Lys Ile Asp Tyr Ser Lys Phe
145                 150                 155                 160

Asn Pro Phe Asn Asp Gln Lys Tyr Phe His Asp Tyr Cys Asn Val Thr
                165                 170                 175

Arg Trp Glu Asp Pro Glu Asn Tyr Gln Asn Cys Trp Leu Tyr Pro Tyr
```

```
               180                 185                 190
Gly Val Ala Leu Ala Asp Leu Lys Thr Glu Ser Asp Glu Val Val Lys
            195                 200                 205

Glu Phe Gln Asn Trp Ile Lys Gln Leu Val Ala Asn Tyr Ser Ile Asp
            210                 215                 220

Gly Leu Arg Ile Asp Ala Ala Lys His Val Asn Asp Glu Phe Leu Pro
225                 230                 235                 240

Gln Phe Val Glu Ala Ser Gly Val Phe Ala Trp Gly Glu Val Leu Thr
                245                 250                 255

Gly Val Thr Asn Asp Leu Cys Arg Tyr Gln Thr Lys Gly Leu Leu Pro
                260                 265                 270

Gly Met Pro Asn Tyr Leu Glu Tyr Tyr Pro Leu Leu Gln Ala Phe Asn
                275                 280                 285

Gly Gly Ser Met Glu Glu Val Ala Lys Tyr Arg Asn Glu Ala Ala Ser
                290                 295                 300

Gly Cys Asn Asp Thr Ser Val Leu Gly Ser Phe Ile Glu Asn His Asp
305                 310                 315                 320

Met Pro Arg Phe Ala Met Tyr Asn Glu Asp Met Ala Ile Ala Lys Asn
                325                 330                 335

Ala Met Thr Tyr Thr Phe Leu Asn Asp Gly Ile Pro Thr Val Tyr Gln
                340                 345                 350

Gly Gln Glu Gln His Phe Lys Gly Asn Gly Thr Pro Tyr Asn Arg Glu
                355                 360                 365

Pro Leu Trp Ile Ser Lys Tyr Asp Lys Ser Ala Pro Leu Tyr Gln Leu
            370                 375                 380

Thr Ser Thr Leu Asn Lys Val Arg Asn Asn Ala Ile Lys Leu Ser Lys
385                 390                 395                 400

Asp Tyr Val Asn Thr Pro Ala Glu Thr Leu Phe Asn Asp Val Asn His
                405                 410                 415

Leu Cys Leu Arg Lys Gly Pro Tyr Gly Ser Gln Val Val Phe Cys Ile
                420                 425                 430

Asn Asn Gln Ser Ser Lys Gly Pro Lys Tyr Glu Leu Asn Ile Ser Gly
                435                 440                 445

Gly Phe His Pro Gly Asp Lys Val Val Glu Val Thr Arg Cys Arg His
            450                 455                 460

Thr Thr Ala Asp Ala Thr Gly Thr Ile Thr Met Tyr Met Gly Asn Gly
465                 470                 475                 480

Glu Pro Arg Val Tyr Val His Ala Asp Ala Ile Lys Gly Thr Gly Ile
                485                 490                 495

Cys Ser Asp Thr Lys Glu Asp Gly
                500

<210> SEQ ID NO 23
<211> LENGTH: 2861
<212> TYPE: DNA
<213> ORGANISM: Chaetomium thermophilum
<220> FEATURE:
<221> NAME/KEY: sig_peptide
<222> LOCATION: (1)..(57)
<220> FEATURE:
<221> NAME/KEY: exon
<222> LOCATION: (1)..(220)
<220> FEATURE:
<221> NAME/KEY: exon
<222> LOCATION: (341)..(416)
<220> FEATURE:
<221> NAME/KEY: exon
<222> LOCATION: (474)..(582)
```

```
<220> FEATURE:
<221> NAME/KEY: exon
<222> LOCATION: (650)..(739)
<220> FEATURE:
<221> NAME/KEY: exon
<222> LOCATION: (798)..(856)
<220> FEATURE:
<221> NAME/KEY: exon
<222> LOCATION: (916)..(942)
<220> FEATURE:
<221> NAME/KEY: exon
<222> LOCATION: (1007)..(1030)
<220> FEATURE:
<221> NAME/KEY: exon
<222> LOCATION: (1087)..(1146)
<220> FEATURE:
<221> NAME/KEY: exon
<222> LOCATION: (1207)..(1368)
<220> FEATURE:
<221> NAME/KEY: exon
<222> LOCATION: (1435)..(1597)
<220> FEATURE:
<221> NAME/KEY: exon
<222> LOCATION: (1675)..(1689)
<220> FEATURE:
<221> NAME/KEY: exon
<222> LOCATION: (1756)..(1783)
<220> FEATURE:
<221> NAME/KEY: exon
<222> LOCATION: (1846)..(2382)
<220> FEATURE:
<221> NAME/KEY: exon
<222> LOCATION: (2445)..(2526)
<220> FEATURE:
<221> NAME/KEY: exon
<222> LOCATION: (2618)..(2858)

<400> SEQUENCE: 23 atg ggc tca tta agc cga tca cta ctt ctt ttt cta ggt ata ctt cca      48
Met Gly Ser Leu Ser Arg Ser Leu Leu Leu Phe Leu Gly Ile Leu Pro
1               5                   10                  15 cac aag gcc aac ata ggt gcg ctg tcg gca gcc gag tgg cgg aag cag      96
His Lys Ala Asn Ile Gly Ala Leu Ser Ala Ala Glu Trp Arg Lys Gln
            20                  25                  30 tcc att tat caa gtt gta acg gat agg ttt gct cgg acc gat ctc tcg     144
Ser Ile Tyr Gln Val Val Thr Asp Arg Phe Ala Arg Thr Asp Leu Ser
        35                  40                  45 aca aca gct ccc tgc gac ccg gac caa cag gcg tac tgc gga gga acg     192
Thr Thr Ala Pro Cys Asp Pro Asp Gln Gln Ala Tyr Cys Gly Gly Thr
    50                  55                  60 tgg caa ggg ctt aga tca aag ctg gac t gtatgtgttg cccgattccc         240
Trp Gln Gly Leu Arg Ser Lys Leu Asp
65                  70 cgcaagtgtc cactcgtaca tggagctttc gaactataga atagtgatat acctacagct   300
ctcggcaaag agcaaggctg tgactgacac ctcggagaag at  atc cag ggg atg     354
                                              Tyr Ile Gln Gly Met
                                                          75 ggg ttc aca gct gtt tgg att tct ccc att gtc aag cag gtt gac ggt     402
Gly Phe Thr Ala Val Trp Ile Ser Pro Ile Val Lys Gln Val Asp Gly
        80                  85                  90 acc tct tct gat gg  gtaggaggtt tgctctcgtc catgcccgac aattgctgac     456
Thr Ser Ser Asp Gly
95 caattgtgct atattag a tct ggc tac cat ggc tat tgg gct gaa gat att    507
                    Ser Gly Tyr His Gly Tyr Trp Ala Glu Asp Ile
                                100             105             110 tgg aca ttg aac cca gca ttt ggg aca gaa gat gac ttg cgt gaa cta     555
Trp Thr Leu Asn Pro Ala Phe Gly Thr Glu Asp Asp Leu Arg Glu Leu
```

-continued

```
                    115                 120                 125
gcc gca gag ctt cat gcc cgt ggc atg gtatgcgtag tttcagtgac           602
Ala Ala Glu Leu His Ala Arg Gly Met
        130                 135 ttgaacatca tcagatgagt caaatgctga caagtcttct ttcttag tac ctc atg     658
                                                    Tyr Leu Met gtt gac gtt gtc aca aac cat atg ggc tac atg ggg tgc aga tct tgt     706
Val Asp Val Val Thr Asn His Met Gly Tyr Met Gly Cys Arg Ser Cys
        140                 145                 150 gtc gac tat tcg cgc tta aag ccc ttt tcg tcg gtacatagca tattatgctt   759
Val Asp Tyr Ser Arg Leu Lys Pro Phe Ser Ser
155                 160                 165 ttgaggccat tcttcgaga gactgaccaa gatcacag tca tcg tac tat cat gcg    815
                                         Ser Ser Tyr Tyr His Ala
                                                             170 cca tgt gcc att gat tac aat aac caa aca tct gtt gag gt              856
Pro Cys Ala Ile Asp Tyr Asn Asn Gln Thr Ser Val Glu Val
        175                 180                 185 gtaagcattt gactttactc tcgagctttc gacctggccg tttcgctgat gtgccacag    915 g tgt tgg caa gga agc cac gtc gtc ag  gtatggcaaa gcctttcgat         962
  Cys Trp Gln Gly Ser His Val Val Ser
                      190 tgtcgagatg actgagaggg ccgagtctga cttatggttt gtag c ttg cca gat      1016
                                                  Leu Pro Asp
                                                         195 ctt cgt acg gaa ga  gtaagtgatt ctcgatctct ggcgctctgc agccctgcta     1070
Leu Arg Thr Glu Asp
        200 acttcacaaa ttatag c gaa gga gtg cgc cgt atc tgg aat gat tgg att     1120
                    Glu Gly Val Arg Arg Ile Trp Asn Asp Trp Ile
                            205                 210 aaa atc att gtc tcc aac tat tcc at  gtaagaaacg tgatttttttc          1166
Lys Ile Ile Val Ser Asn Tyr Ser Ile
        215                 220 acagcactcg cgccagcgct taaccttggt cctcctcaag t gac ggt tta cgg atc   1222
                                             Asp Gly Leu Arg Ile
                                                             225 gat agt gcg aag cat gtc gaa aag tct ttt tgg ccg gag ttc tcg tct     1270
Asp Ser Ala Lys His Val Glu Lys Ser Phe Trp Pro Glu Phe Ser Ser
        230                 235                 240 gcg gct gga gta ttt ctg ctt ggc gaa gta tac cac ggt gac cct gca     1318
Ala Ala Gly Val Phe Leu Leu Gly Glu Val Tyr His Gly Asp Pro Ala
        245                 250                 255 tat gtt gcg cct tat cag caa tat ctc gat ggt gtt ttg gac tat cca     1366
Tyr Val Ala Pro Tyr Gln Gln Tyr Leu Asp Gly Val Leu Asp Tyr Pro
260                 265                 270                 275 ag  gtgagctctt ccgaagccga gaggctcctg ggttctcttc acattggttc          1418
Ser tagcattcag gcacag c tac tac tgg att tta cga gct ttc cag tcc tca     1468
                   Tyr Tyr Trp Ile Leu Arg Ala Phe Gln Ser Ser
                                   280                 285 aat gga cgt atc agc gag ctt gtt tct ggg ttg aac acc cta cgt agt     1516
Asn Gly Arg Ile Ser Glu Leu Val Ser Gly Leu Asn Thr Leu Arg Ser
        290                 295                 300 aag gca acc gac ctc agc ttg tac gga tca ttt tta gag aac cat gac     1564
Lys Ala Thr Asp Leu Ser Leu Tyr Gly Ser Phe Leu Glu Asn His Asp
        305                 310                 315 gtt gcc cgc ttc cca tcc ttc acc agt gac atg gtatgtccga ttccaactgc  1617
```

```
Val Ala Arg Phe Pro Ser Phe Thr Ser Asp Met
320                 325                 330 tttaagcttg ctgtcttcta gatcttcctt tgaccactaa ccggcatgtt ttcgcag     1674 gcg agg gta aag aat gtaaggagcc ccaacctaac gtacgcttct gacaccaaga   1729
Ala Arg Val Lys Asn
            335 ctcgcaagtt aacacttgtt ttctag gca att gcc ttc act atg ctc aag gat  1782
                             Ala Ile Ala Phe Thr Met Leu Lys Asp
                                                         340 g gttggtgact agtatttatg tccaagtatt cattttgtat ggtccactta          1833
ccggagtgat ag ga  atc cca atc ata tac cag gga caa gag cac cat tat 1883
                  Ile Pro Ile Ile Tyr Gln Gly Gln Glu His His Tyr
                              345                 350                 355 gct ggg gca gat acc ccc aga aac cgc gaa gcg ctc tgg tct tcc agt   1931
Ala Gly Ala Asp Thr Pro Arg Asn Arg Glu Ala Leu Trp Ser Ser Ser
            360                 365                 370 tat tca acc tca tct gag ctt tac cag tgg att gca aaa ctg aac cag   1979
Tyr Ser Thr Ser Ser Glu Leu Tyr Gln Trp Ile Ala Lys Leu Asn Gln
    375                 380                 385 atc agg act tgg gcc att gca cag agt tct gat ttc ttg aca tac aac   2027
Ile Arg Thr Trp Ala Ile Ala Gln Ser Ser Asp Phe Leu Thr Tyr Asn
390                 395                 400                 405 agc cac ccg att tac tat gac agt cac acc att gct atg cgc aag gga   2075
Ser His Pro Ile Tyr Tyr Asp Ser His Thr Ile Ala Met Arg Lys Gly
            410                 415                 420 tca tcc gga tct cag atc atc gga atc ttt aca aac ctt gga tca tca   2123
Ser Ser Gly Ser Gln Ile Ile Gly Ile Phe Thr Asn Leu Gly Ser Ser
            425                 430                 435 cca tca tcg gtc aat gtt act ctg aga tcg tca gct gct ggc ttt tca   2171
Pro Ser Ser Val Asn Val Thr Leu Arg Ser Ser Ala Ala Gly Phe Ser
            440                 445                 450 gcc ggg cag acg ttg gtg gat gta atg gtt tgt acc gcc cat aca gct   2219
Ala Gly Gln Thr Leu Val Asp Val Met Val Cys Thr Ala His Thr Ala
            455                 460                 465 gac tct acc gga aac ctt gcc gta acg att tgg aac ggc ctt ccc aaa   2267
Asp Ser Thr Gly Asn Leu Ala Val Thr Ile Trp Asn Gly Leu Pro Lys
470                 475                 480                 485 gtc ttg tat ccc ctg aat cgt ctt att gga agc ggc att tgc cct tct   2315
Val Leu Tyr Pro Leu Asn Arg Leu Ile Gly Ser Gly Ile Cys Pro Ser
            490                 495                 500 ttg atc gat ctt aga cca act gcc aca gac ata acg tcg aca gcc atc   2363
Leu Ile Asp Leu Arg Pro Thr Ala Thr Asp Ile Thr Ser Thr Ala Ile
            505                 510                 515 gaa aca tcc aca cca acc a gtgagcgctc accggacggt attacttttg        2412
Glu Thr Ser Thr Pro Thr
            520 gttgattgaa tttgctaaca cggtcctgaa ag gc  acc tcc ggc tgt tct ctg   2464
                                       Ser Thr Ser Gly Cys Ser Leu
                                           525                 530 ata tcg gtc tat atc aca ttc aat gtc tcg gta aca act gac tgg ggg   2512
Ile Ser Val Tyr Ile Thr Phe Asn Val Ser Val Thr Thr Asp Trp Gly
            535                 540                 545 gag aca gtc aag at  gtcagtaatg agagatgctc ccccattttg ttcagttacg   2566
Glu Thr Val Lys Ile
            550 gaaagggtgc tcccttgggt aacagctaac tgacgtgatt acaatcctta g c act    2621
                                                          Thr ggc aat gtt cct gct ctc ggt aac tgg aat acg gcc gac gca gtg gct   2669
```

```
Gly Asn Val Pro Ala Leu Gly Asn Trp Asn Thr Ala Asp Ala Val Ala
            555                 560                 565 ctt agc gca gaa ggg tat acg tca agt tac ccc att tgg tcg ggt act    2717
Leu Ser Ala Glu Gly Tyr Thr Ser Ser Tyr Pro Ile Trp Ser Gly Thr
    570                 575                 580 gtc agc ttg aca cct gga act gtg att gag tac aaa ttt atc aga gtg    2765
Val Ser Leu Thr Pro Gly Thr Val Ile Glu Tyr Lys Phe Ile Arg Val
585                 590                 595                 600 ggc agc tta ggg act ata agc tgg gaa cgt gac ccg aac cat atc tac    2813
Gly Ser Leu Gly Thr Ile Ser Trp Glu Arg Asp Pro Asn His Ile Tyr
                605                 610                 615 act gtg ccc tgt gca acg gca act gtc agc agc tcg tgg caa ggt tga    2861
Thr Val Pro Cys Ala Thr Ala Thr Val Ser Ser Ser Trp Gln Gly
            620                 625                 630

<210> SEQ ID NO 24
<211> LENGTH: 631
<212> TYPE: PRT
<213> ORGANISM: Chaetomium thermophilum

<400> SEQUENCE: 24

Met Gly Ser Leu Ser Arg Ser Leu Leu Leu Phe Leu Gly Ile Leu Pro
1               5                   10                  15

His Lys Ala Asn Ile Gly Ala Leu Ser Ala Ala Glu Trp Arg Lys Gln
            20                  25                  30

Ser Ile Tyr Gln Val Val Thr Asp Arg Phe Ala Arg Thr Asp Leu Ser
        35                  40                  45

Thr Thr Ala Pro Cys Asp Pro Asp Gln Gln Ala Tyr Cys Gly Gly Thr
    50                  55                  60

Trp Gln Gly Leu Arg Ser Lys Leu Asp Tyr Ile Gln Gly Met Gly Phe
65                  70                  75                  80

Thr Ala Val Trp Ile Ser Pro Ile Val Lys Gln Val Asp Gly Thr Ser
                85                  90                  95

Ser Asp Gly Ser Gly Tyr His Gly Tyr Trp Ala Glu Asp Ile Trp Thr
            100                 105                 110

Leu Asn Pro Ala Phe Gly Thr Glu Asp Asp Leu Arg Glu Leu Ala Ala
        115                 120                 125

Glu Leu His Ala Arg Gly Met Tyr Leu Met Val Asp Val Val Thr Asn
    130                 135                 140

His Met Gly Tyr Met Gly Cys Arg Ser Cys Val Asp Tyr Ser Arg Leu
145                 150                 155                 160

Lys Pro Phe Ser Ser Ser Tyr Tyr His Ala Pro Cys Ala Ile Asp
                165                 170                 175

Tyr Asn Asn Gln Thr Ser Val Glu Val Cys Trp Gln Gly Ser His Val
            180                 185                 190

Val Ser Leu Pro Asp Leu Arg Thr Glu Asp Glu Gly Val Arg Arg Ile
        195                 200                 205

Trp Asn Asp Trp Ile Lys Ile Val Ser Asn Tyr Ser Ile Asp Gly
    210                 215                 220

Leu Arg Ile Asp Ser Ala Lys His Val Glu Lys Ser Phe Trp Pro Glu
225                 230                 235                 240

Phe Ser Ser Ala Ala Gly Val Phe Leu Leu Gly Glu Val Tyr His Gly
                245                 250                 255

Asp Pro Ala Tyr Val Ala Pro Tyr Gln Gln Tyr Leu Asp Gly Val Leu
            260                 265                 270

Asp Tyr Pro Ser Tyr Tyr Trp Ile Leu Arg Ala Phe Gln Ser Ser Asn
```

```
                275                 280                 285
Gly Arg Ile Ser Glu Leu Val Ser Gly Leu Asn Thr Leu Arg Ser Lys
    290                 295                 300

Ala Thr Asp Leu Ser Leu Tyr Gly Ser Phe Leu Glu Asn His Asp Val
305                 310                 315                 320

Ala Arg Phe Pro Ser Phe Thr Ser Asp Met Ala Arg Val Lys Asn Ala
                325                 330                 335

Ile Ala Phe Thr Met Leu Lys Asp Gly Ile Pro Ile Tyr Gln Gly
                340                 345                 350

Gln Glu His His Tyr Ala Gly Ala Asp Thr Pro Arg Asn Arg Glu Ala
                355                 360                 365

Leu Trp Ser Ser Tyr Ser Thr Ser Glu Leu Tyr Gln Trp Ile
    370                 375                 380

Ala Lys Leu Asn Gln Ile Arg Thr Trp Ala Ile Ala Gln Ser Ser Asp
385                 390                 395                 400

Phe Leu Thr Tyr Asn Ser His Pro Ile Tyr Tyr Asp Ser His Thr Ile
                405                 410                 415

Ala Met Arg Lys Gly Ser Ser Gly Ser Gln Ile Ile Gly Ile Phe Thr
                420                 425                 430

Asn Leu Gly Ser Ser Pro Ser Ser Val Asn Val Thr Leu Arg Ser Ser
                435                 440                 445

Ala Ala Gly Phe Ser Ala Gly Gln Thr Leu Val Asp Val Met Val Cys
                450                 455                 460

Thr Ala His Thr Ala Asp Ser Thr Gly Asn Leu Ala Val Thr Ile Trp
465                 470                 475                 480

Asn Gly Leu Pro Lys Val Leu Tyr Pro Leu Asn Arg Leu Ile Gly Ser
                485                 490                 495

Gly Ile Cys Pro Ser Leu Ile Asp Leu Arg Pro Thr Ala Thr Asp Ile
                500                 505                 510

Thr Ser Thr Ala Ile Glu Thr Ser Thr Pro Thr Ser Thr Ser Gly Cys
                515                 520                 525

Ser Leu Ile Ser Val Tyr Ile Thr Phe Asn Val Ser Val Thr Thr Asp
                530                 535                 540

Trp Gly Glu Thr Val Lys Ile Thr Gly Asn Val Pro Ala Leu Gly Asn
545                 550                 555                 560

Trp Asn Thr Ala Asp Ala Val Ala Leu Ser Ala Glu Gly Tyr Thr Ser
                565                 570                 575

Ser Tyr Pro Ile Trp Ser Gly Thr Val Ser Leu Thr Pro Gly Thr Val
                580                 585                 590

Ile Glu Tyr Lys Phe Ile Arg Val Gly Ser Leu Gly Thr Ile Ser Trp
                595                 600                 605

Glu Arg Asp Pro Asn His Ile Tyr Thr Val Pro Cys Ala Thr Ala Thr
    610                 615                 620

Val Ser Ser Ser Trp Gln Gly
625                 630

<210> SEQ ID NO 25
<211> LENGTH: 2676
<212> TYPE: DNA
<213> ORGANISM: Humicola insolens
<220> FEATURE:
<221> NAME/KEY: sig_peptide
<222> LOCATION: (1)..(60)
<220> FEATURE:
<221> NAME/KEY: exon
<222> LOCATION: (1)..(290)
```

```
<220> FEATURE:
<221> NAME/KEY: exon
<222> LOCATION: (344)..(452)
<220> FEATURE:
<221> NAME/KEY: exon
<222> LOCATION: (519)..(608)
<220> FEATURE:
<221> NAME/KEY: exon
<222> LOCATION: (670)..(728)
<220> FEATURE:
<221> NAME/KEY: exon
<222> LOCATION: (809)..(838)
<220> FEATURE:
<221> NAME/KEY: exon
<222> LOCATION: (925)..(948)
<220> FEATURE:
<221> NAME/KEY: exon
<222> LOCATION: (1015)..(1074)
<220> FEATURE:
<221> NAME/KEY: exon
<222> LOCATION: (1140)..(1301)
<220> FEATURE:
<221> NAME/KEY: exon
<222> LOCATION: (1356)..(1533)
<220> FEATURE:
<221> NAME/KEY: exon
<222> LOCATION: (1610)..(1637)
<220> FEATURE:
<221> NAME/KEY: exon
<222> LOCATION: (1694)..(2236)
<220> FEATURE:
<221> NAME/KEY: exon
<222> LOCATION: (2296)..(2377)
<220> FEATURE:
<221> NAME/KEY: exon
<222> LOCATION: (2436)..(2673)

<400> SEQUENCE: 25 atg aga aac ctt cga cat atc ctg cac cac agc ctc ctc ctc ctt cca      48
Met Arg Asn Leu Arg His Ile Leu His His Ser Leu Leu Leu Leu Pro
1               5                   10                  15 ggg gct aca gct ctc tcg gcc gag gag tgg agg aag cag tct att tac      96
Gly Ala Thr Ala Leu Ser Ala Glu Glu Trp Arg Lys Gln Ser Ile Tyr
            20                  25                  30 caa gtt gtt act gat cgg ttc gct cgg act gat ctc tcg acg acg gca     144
Gln Val Val Thr Asp Arg Phe Ala Arg Thr Asp Leu Ser Thr Thr Ala
        35                  40                  45 gcc tgt cgg aca gct gac caa ata tac tgt ggt gga aca tgg cgc ggc     192
Ala Cys Arg Thr Ala Asp Gln Ile Tyr Cys Gly Gly Thr Trp Arg Gly
    50                  55                  60 ctg ata tcg aaa ctc gac tac att cag ggc atg ggc ttc acc agc gta     240
Leu Ile Ser Lys Leu Asp Tyr Ile Gln Gly Met Gly Phe Thr Ser Val
65                  70                  75                  80 tgg att tcc ccc gtc gtg aag cag atc gac ggg tac tct ccc agc cac     288
Trp Ile Ser Pro Val Val Lys Gln Ile Asp Gly Tyr Ser Pro Ser His
                85                  90                  95 gg gtaggtggag gtcacgatat caaatatctg taagcatcgt taaccagcct tag t     344
Gly gcc ggg tac cat gga tat tgg gcc caa gac atc tgg tct ctg aac ccg     392
Ala Gly Tyr His Gly Tyr Trp Ala Gln Asp Ile Trp Ser Leu Asn Pro
            100                 105                 110 gcg ttc ggg acg gaa cag gac tta ata gac ctc tct caa gca ctt cac     440
Ala Phe Gly Thr Glu Gln Asp Leu Ile Asp Leu Ser Gln Ala Leu His
        115                 120                 125 tct cgg gga atg gtgagaccat tggccttgct gatagatgag acttaggctt         492
Ser Arg Gly Met
130 gtctctaact ccagagttga tgttag ttc ctc atg ctc gat gtc gtc aca aac    545
```

```
                   Phe Leu Met Leu Asp Val Val Thr Asn
                               135                 140 cac atg ggc tat atg ggc tgc agc tct tgt gtt gat tac agc caa ttt         593
His Met Gly Tyr Met Gly Cys Ser Ser Cys Val Asp Tyr Ser Gln Phe
        145                 150                 155 aac ccc ttc tca tca gtgtgtcccc ccgtctcggt tgtatgattc aaaagagatc         648
Asn Pro Phe Ser Ser
            160 atcggctaag caaagcggca g tct tca tat ttc cac tcg ccc tgc act atc         699
                         Ser Ser Tyr Phe His Ser Pro Cys Thr Ile
                                     165                 170 gac tac aac aac cag act tca gtg gag at  gtaggtcgct atcacctgga           748
Asp Tyr Asn Asn Gln Thr Ser Val Glu Ile
        175                 180 aggactggac atggcttagt tgcagccatc tttgcaatga atgactaaca aaattccaag       808 a tgc tgg caa ggg agc acc acc att gtc ag  gtatggaaga gcatttggcc         858
  Cys Trp Gln Gly Ser Thr Thr Ile Val Ser
      185                 190 ccgtccctct cctctgtcca gcagggggt tatgtcaaag aaacgcgctg acgagcattt        918 gcacag c ctt cca gac cta cgg act gag ga  gtaagcaatg tcagttagtc          968
        Leu Pro Asp Leu Arg Thr Glu Asp
            195                 200 ttcagactct tggatccgtc tactgactcg aatcccatgc gatcag c tcg ttt gta       1024
                                                    Ser Phe Val agg aac acc tgg aac caa tgg ata tca cac atc gtc tca aaa tat tcg       1072
Arg Asn Thr Trp Asn Gln Trp Ile Ser His Ile Val Ser Lys Tyr Ser
205                 210                 215                 220 gt  gtaaggcagt cccaaatctc atcgataagc actgagtggt tgcctaactc             1124
Val ctgactttga gccag a gac ggg ttg aga gtg gac agc gcg aaa cac gtt        1173
                  Asp Gly Leu Arg Val Asp Ser Ala Lys His Val
                                  225                 230 gaa acg tcc ttc tgg ccc ggc ttc tca acc gcc gcg ggt gtc ttt ata       1221
Glu Thr Ser Phe Trp Pro Gly Phe Ser Thr Ala Ala Gly Val Phe Ile
        235                 240                 245 ctc ggt gag ata tat cac ggc gac ccg gca tac ctg gct cct tac cag       1269
Leu Gly Glu Ile Tyr His Gly Asp Pro Ala Tyr Leu Ala Pro Tyr Gln
250                 255                 260 cag cac atg gac ggc gtg cta gac tat gcc ac  gtaagtgtca ctcatatcca     1321
Gln His Met Asp Gly Val Leu Asp Tyr Ala Thr
265                 270                 275 tggacagatg gcctgtgtcc tgacaccgga acag t tat tat tgg gcc aag agg       1374
                                        Tyr Tyr Trp Ala Lys Arg
                                                            280 gct ttc cag tct ccg aac aac aca ctg ggc gag ctc gtc ggt ggc ctc       1422
Ala Phe Gln Ser Pro Asn Asn Thr Leu Gly Glu Leu Val Gly Gly Leu
        285                 290                 295 agt acc atg agg aac gtg gct cga gat ctc agt cta tat gga tca ttc       1470
Ser Thr Met Arg Asn Val Ala Arg Asp Leu Ser Leu Tyr Gly Ser Phe
        300                 305                 310 ctc gag aac cac gat gtt gag cgt ttt gcg tcc ttg act caa gac aaa       1518
Leu Glu Asn His Asp Val Glu Arg Phe Ala Ser Leu Thr Gln Asp Lys
315                 320                 325 gcg ctc atc aaa aac gtaagcctgg actccgatcc ttgttctttc gcacccagtt       1573
Ala Leu Ile Lys Asn
330 gtgagtctgg tgctcacgat atcattggcg tggcag gca att gcg ttt acc att       1627
                                        Ala Ile Ala Phe Thr Ile
```

```
                                            335                 340
ctc aaa gac g gtatgtgaat accaatactc cctgaaattg actgacgcag          1677
Leu Lys Asp ctcaccgttt gatcag ga  att cct att gtg tat caa ggt caa gaa cag ctc   1728
                      Gly Ile Pro Ile Val Tyr Gln Gly Gln Glu Gln Leu
                                  345                 350                 355 tat tct ggt aca gga att cca agc aat cga gaa gcc ctc tgg ctg tct    1776
Tyr Ser Gly Thr Gly Ile Pro Ser Asn Arg Glu Ala Leu Trp Leu Ser
                360                 365                 370 gga tac caa acg gac tct gaa ctc tat aca tgg ata tcg aag ctg aat    1824
Gly Tyr Gln Thr Asp Ser Glu Leu Tyr Thr Trp Ile Ser Lys Leu Asn
                375                 380                 385 aag atc cga tct cgg gcc att tct gag gac agc aga cac gtc act tat    1872
Lys Ile Arg Ser Arg Ala Ile Ser Glu Asp Ser Arg His Val Thr Tyr
                390                 395                 400 atc agc caa acg ata tac tcc gat gac cat acc atc gcc att cga aag    1920
Ile Ser Gln Thr Ile Tyr Ser Asp Asp His Thr Ile Ala Ile Arg Lys
        405                 410                 415 ggg cac tca gga tat cag ttg gtc agc atc ttc acc aac att gga tct    1968
Gly His Ser Gly Tyr Gln Leu Val Ser Ile Phe Thr Asn Ile Gly Ser
420                 425                 430                 435 tcg aaa tca acg acg att acg ctc act tct tca gct acg gga ttt ggg    2016
Ser Lys Ser Thr Thr Ile Thr Leu Thr Ser Ser Ala Thr Gly Phe Gly
                440                 445                 450 ccc aac gaa gtc ttg gtg gat gtc ata gga tgt gtc ttg ttc acc gca    2064
Pro Asn Glu Val Leu Val Asp Val Ile Gly Cys Val Leu Phe Thr Ala
                455                 460                 465 gat tca agg ggt ggg cta gtt gtt ggt ctc ttc aac ggg tta cca agg    2112
Asp Ser Arg Gly Gly Leu Val Val Gly Leu Phe Asn Gly Leu Pro Arg
                470                 475                 480 gta ttg tac cct aga agc cgt ctc ctc agg agt ggc atc tgc ccc gag    2160
Val Leu Tyr Pro Arg Ser Arg Leu Leu Arg Ser Gly Ile Cys Pro Glu
        485                 490                 495 tta acc gac aca gtt acc aca aag acc gaa gca cct gga aca acg atc    2208
Leu Thr Asp Thr Val Thr Thr Lys Thr Glu Ala Pro Gly Thr Thr Ile
500                 505                 510                 515 tcg aca gcg aca tcg agc tcg aca ata g gtgagcgcgc ttgtgtcaac        2256
Ser Thr Ala Thr Ser Ser Ser Thr Ile
                520 ttcggtacca acgctggtca tgactgatag atacttcag cc  aca gca acc tgc     2309
                                              Ala Thr Ala Thr Cys acg atg acg agt gtg gcc gtt act ttg aac gtc ctt gcc act act agt    2357
Thr Met Thr Ser Val Ala Val Thr Leu Asn Val Leu Ala Thr Thr Ser
530                 535                 540                 545 tgg ggc gag att atc aag gt  gtacgttctt ggagctcagg gctgaaggta       2407
Trp Gly Glu Ile Ile Lys Val
                550 ttattgatac tgacgaggag gcgaacag g gtt ggc aac act cca gaa ctt ggg   2460
                                 Val Gly Asn Thr Pro Glu Leu Gly
                                                 555                 560 agc tgg agt cca ggc agt gct gtt acc ctt ggt gca tcg cag tac ata    2508
Ser Trp Ser Pro Gly Ser Ala Val Thr Leu Gly Ala Ser Gln Tyr Ile
                565                 570                 575 cca agc aac ccg ctc tgg tct ggc aca atc aag ctt cct cca gga gtg    2556
Pro Ser Asn Pro Leu Trp Ser Gly Thr Ile Lys Leu Pro Pro Gly Val
                580                 585                 590 gtg gtt cag tac aag ttt att cgg gtt ggt tct tcg ggg aca gtt acc    2604
Val Val Gln Tyr Lys Phe Ile Arg Val Gly Ser Ser Gly Thr Val Thr
                595                 600                 605
```

```
                 tgg gag tcg gat cca aat cgt aca ctc aac gtc cct tgt gct gct aca         2652
                 Trp Glu Ser Asp Pro Asn Arg Thr Leu Asn Val Pro Cys Ala Ala Thr
                     610                 615                 620 aca atc agc cat acg tgg aga tag                                          2676
                 Thr Ile Ser His Thr Trp Arg
                 625                 630

<210> SEQ ID NO 26
<211> LENGTH: 631
<212> TYPE: PRT
<213> ORGANISM: Humicola insolens

<400> SEQUENCE: 26

Met Arg Asn Leu Arg His Ile Leu His His Ser Leu Leu Leu Pro
1               5                   10                  15

Gly Ala Thr Ala Leu Ser Ala Glu Glu Trp Arg Lys Gln Ser Ile Tyr
                20                  25                  30

Gln Val Val Thr Asp Arg Phe Ala Arg Thr Asp Leu Ser Thr Thr Ala
            35                  40                  45

Ala Cys Arg Thr Ala Asp Gln Ile Tyr Cys Gly Gly Thr Trp Arg Gly
50                  55                  60

Leu Ile Ser Lys Leu Asp Tyr Ile Gln Gly Met Gly Phe Thr Ser Val
65                  70                  75                  80

Trp Ile Ser Pro Val Val Lys Gln Ile Asp Gly Tyr Ser Pro Ser His
                85                  90                  95

Gly Ala Gly Tyr His Gly Tyr Trp Ala Gln Asp Ile Trp Ser Leu Asn
                100                 105                 110

Pro Ala Phe Gly Thr Glu Gln Asp Leu Ile Asp Leu Ser Gln Ala Leu
            115                 120                 125

His Ser Arg Gly Met Phe Leu Met Leu Asp Val Val Thr Asn His Met
                130                 135                 140

Gly Tyr Met Gly Cys Ser Ser Cys Val Asp Tyr Ser Gln Phe Asn Pro
145                 150                 155                 160

Phe Ser Ser Ser Tyr Phe His Ser Pro Cys Thr Ile Asp Tyr Asn
                165                 170                 175

Asn Gln Thr Ser Val Glu Ile Cys Trp Gln Gly Ser Thr Thr Ile Val
                180                 185                 190

Ser Leu Pro Asp Leu Arg Thr Glu Asp Ser Phe Val Arg Asn Thr Trp
                195                 200                 205

Asn Gln Trp Ile Ser His Ile Val Ser Lys Tyr Ser Val Asp Gly Leu
        210                 215                 220

Arg Val Asp Ser Ala Lys His Val Glu Thr Ser Phe Trp Pro Gly Phe
225                 230                 235                 240

Ser Thr Ala Ala Gly Val Phe Ile Leu Gly Glu Ile Tyr His Gly Asp
                245                 250                 255

Pro Ala Tyr Leu Ala Pro Tyr Gln Gln His Met Asp Gly Val Leu Asp
            260                 265                 270

Tyr Ala Thr Tyr Tyr Trp Ala Lys Arg Ala Phe Gln Ser Pro Asn Asn
            275                 280                 285

Thr Leu Gly Glu Leu Val Gly Gly Leu Ser Thr Met Arg Asn Val Ala
            290                 295                 300

Arg Asp Leu Ser Leu Tyr Gly Ser Phe Leu Glu Asn His Asp Val Glu
305                 310                 315                 320

Arg Phe Ala Ser Leu Thr Gln Asp Lys Ala Leu Ile Lys Asn Ala Ile
                325                 330                 335
```

Ala Phe Thr Ile Leu Lys Asp Gly Ile Pro Ile Val Tyr Gln Gly Gln
                340                 345                 350

Glu Gln Leu Tyr Ser Gly Thr Gly Ile Pro Ser Asn Arg Glu Ala Leu
                355                 360                 365

Trp Leu Ser Gly Tyr Gln Thr Asp Ser Glu Leu Tyr Thr Trp Ile Ser
370                 375                 380

Lys Leu Asn Lys Ile Arg Ser Arg Ala Ile Ser Glu Asp Ser Arg His
385                 390                 395                 400

Val Thr Tyr Ile Ser Gln Thr Ile Tyr Ser Asp Asp His Thr Ile Ala
                405                 410                 415

Ile Arg Lys Gly His Ser Gly Tyr Gln Leu Val Ser Ile Phe Thr Asn
                420                 425                 430

Ile Gly Ser Ser Lys Ser Thr Thr Ile Thr Leu Thr Ser Ser Ala Thr
                435                 440                 445

Gly Phe Gly Pro Asn Glu Val Leu Val Asp Val Ile Gly Cys Val Leu
                450                 455                 460

Phe Thr Ala Asp Ser Arg Gly Gly Leu Val Val Gly Leu Phe Asn Gly
465                 470                 475                 480

Leu Pro Arg Val Leu Tyr Pro Arg Ser Arg Leu Leu Arg Ser Gly Ile
                485                 490                 495

Cys Pro Glu Leu Thr Asp Thr Val Thr Thr Lys Thr Glu Ala Pro Gly
                500                 505                 510

Thr Thr Ile Ser Thr Ala Thr Ser Ser Ser Thr Ile Ala Thr Ala Thr
                515                 520                 525

Cys Thr Met Thr Ser Val Ala Val Thr Leu Asn Val Leu Ala Thr Thr
                530                 535                 540

Ser Trp Gly Glu Ile Ile Lys Val Val Gly Asn Thr Pro Glu Leu Gly
545                 550                 555                 560

Ser Trp Ser Pro Gly Ser Ala Val Thr Leu Gly Ala Ser Gln Tyr Ile
                565                 570                 575

Pro Ser Asn Pro Leu Trp Ser Gly Thr Ile Lys Leu Pro Pro Gly Val
                580                 585                 590

Val Val Gln Tyr Lys Phe Ile Arg Val Gly Ser Ser Gly Thr Val Thr
                595                 600                 605

Trp Glu Ser Asp Pro Asn Arg Thr Leu Asn Val Pro Cys Ala Ala Thr
610                 615                 620

Thr Ile Ser His Thr Trp Arg
625                 630

<210> SEQ ID NO 27
<211> LENGTH: 1730
<212> TYPE: DNA
<213> ORGANISM: Humicola insolens
<220> FEATURE:
<221> NAME/KEY: sig_peptide
<222> LOCATION: (1)..(63)
<220> FEATURE:
<221> NAME/KEY: exon
<222> LOCATION: (1)..(217)
<220> FEATURE:
<221> NAME/KEY: exon
<222> LOCATION: (277)..(1104)
<220> FEATURE:
<221> NAME/KEY: exon
<222> LOCATION: (1174)..(1727)

<400> SEQUENCE: 27 atg ctt gcc aca atc tcg aag atc gct gtt ggc gtt ctg gcc ctc acc    48

```
                Met Leu Ala Thr Ile Ser Lys Ile Ala Val Gly Val Leu Ala Leu Thr
                1               5                   10                  15 ggc cgg aca tct gcg gcg gat gcc caa gaa tgg agg aca cga tcc atc            96
Gly Arg Thr Ser Ala Ala Asp Ala Gln Glu Trp Arg Thr Arg Ser Ile
            20                  25                  30 tac cag gtc atg atc gac cgg ttt gcc ctc acg gac ggg tcg acc gac            144
Tyr Gln Val Met Ile Asp Arg Phe Ala Leu Thr Asp Gly Ser Thr Asp
                35                  40                  45 aag gaa tgt gat gtg tcc cgc ttc tgc ggc ggc acg tgg aag gga ctc            192
Lys Glu Cys Asp Val Ser Arg Phe Cys Gly Gly Thr Trp Lys Gly Leu
50                  55                  60 agg aac aag ctg gat tac atc caa g gtgcgctcac accgccccgg                    237
Arg Asn Lys Leu Asp Tyr Ile Gln
65                  70 gtcgttctcg acgggatcct gacatatgat acctcccag gc  atg ggc ttc aca             290
                                              Gly Met Gly Phe Thr
                                                      75 gcc atc cag atc agc ccc atc gtc aaa aac acc gac gac cac acg gcg            338
Ala Ile Gln Ile Ser Pro Ile Val Lys Asn Thr Asp Asp His Thr Ala
            80                  85                  90 gtg ggc gac gcg tac cac ggg tac tgg gtg acg gac aac tac gcg ctc            386
Val Gly Asp Ala Tyr His Gly Tyr Trp Val Thr Asp Asn Tyr Ala Leu
95                  100                 105 aac gac cgg ttc ggc acc gag caa gac ttc aag gat ctc gta gcc gaa            434
Asn Asp Arg Phe Gly Thr Glu Gln Asp Phe Lys Asp Leu Val Ala Glu
110                 115                 120                 125 gtg cac aag cgc gac atg ctg atc atc gtc gac gtg gtg gtc aac aac            482
Val His Lys Arg Asp Met Leu Ile Ile Val Asp Val Val Val Asn Asn
                130                 135                 140 atg gcg cag ggc ttc gac aac acc gtc ccg ccc aag atc gac tac tcc            530
Met Ala Gln Gly Phe Asp Asn Thr Val Pro Pro Lys Ile Asp Tyr Ser
            145                 150                 155 aag ttc cac ccg ttc aac gac gac aag tac ttc cac ccg tac tgc aac            578
Lys Phe His Pro Phe Asn Asp Asp Lys Tyr Phe His Pro Tyr Cys Asn
            160                 165                 170 gtg acc aag tgg gag gac ccg gag gac tac cag aag tgc tgg ctg tat            626
Val Thr Lys Trp Glu Asp Pro Glu Asp Tyr Gln Lys Cys Trp Leu Tyr
175                 180                 185 ccg tac ggg gtg gcg ctc gcg gac ctg gcc acc gac acc aag gag gtc            674
Pro Tyr Gly Val Ala Leu Ala Asp Leu Ala Thr Asp Thr Lys Glu Val
190                 195                 200                 205 tcg gac gag ctg aac cgc tgg gtg aag cag ctg gtg tcc aac tac tcc            722
Ser Asp Glu Leu Asn Arg Trp Val Lys Gln Leu Val Ser Asn Tyr Ser
                210                 215                 220 att gac ggg ctg cgc atc gac gcg gcc aag cac gtc aac gac gag ttc            770
Ile Asp Gly Leu Arg Ile Asp Ala Ala Lys His Val Asn Asp Glu Phe
            225                 230                 235 ctg gcg ccc ttt gtg gcg tcg tcc ggg gtg ttt gcc ttt ggc gag gtg            818
Leu Ala Pro Phe Val Ala Ser Ser Gly Val Phe Ala Phe Gly Glu Val
            240                 245                 250 ctc tcg gga gtg ccg cag gac atg tgc cgg tac cag atg ctc ggc ctg            866
Leu Ser Gly Val Pro Gln Asp Met Cys Arg Tyr Gln Met Leu Gly Leu
        255                 260                 265 ctg ccc ggc atg ccc aac tac ctc gag tac tac gcg ctg gtg cgg gcc            914
Leu Pro Gly Met Pro Asn Tyr Leu Glu Tyr Tyr Ala Leu Val Arg Ala
270                 275                 280                 285 ttc aac ggc gag tcc ctc gag aag ctc gcc gac atg cgc aac cag gcg            962
Phe Asn Gly Glu Ser Leu Glu Lys Leu Ala Asp Met Arg Asn Gln Ala
            290                 295                 300
```

```
gcc tcg gct tgc aac gag acc acc ctc ctg ggc act ttc gcc gag aac      1010
Ala Ser Ala Cys Asn Glu Thr Thr Leu Leu Gly Thr Phe Ala Glu Asn
            305                 310                 315 cac gac atg gcg cgc ttc gct gcg cgc aac gac gat atg gcg ctg gcc      1058
His Asp Met Ala Arg Phe Ala Ala Arg Asn Asp Asp Met Ala Leu Ala
            320                 325                 330 aag aac gcc atg act tat gtg atc ctg aac gac ggt atc ccc act g        1104
Lys Asn Ala Met Thr Tyr Val Ile Leu Asn Asp Gly Ile Pro Thr
            335                 340                 345 gtatgtacag ttcccgtttg acaacctagt gtaggtagtg gcgaacgtcg gtggctaacg    1164 cgccgcaag tg  tat caa ggg cag gag cag cac ttc aac ggc ggt gac acc   1214
              Val Tyr Gln Gly Gln Glu Gln His Phe Asn Gly Gly Asp Thr
                          350                 355                 360 ccc gcc aac cgc gag gcg ctg tgg acg tcc aag tac gac acg gag gct      1262
Pro Ala Asn Arg Glu Ala Leu Trp Thr Ser Lys Tyr Asp Thr Glu Ala
            365                 370                 375 ccg ctc tat gtc ctg acg tcc aag ctc aac aag gtg cgc aac aac gcc      1310
Pro Leu Tyr Val Leu Thr Ser Lys Leu Asn Lys Val Arg Asn Asn Ala
            380                 385                 390 atc aag ctg tcc gag tcc tac gtc acg gaa ccg gcc aag acg ctg ctc      1358
Ile Lys Leu Ser Glu Ser Tyr Val Thr Glu Pro Ala Lys Thr Leu Leu
395                 400                 405                 410 gcc gac gtc aac cgc ctg tgc ctc aaa cag ggc ggg gac aac gca acc      1406
Ala Asp Val Asn Arg Leu Cys Leu Lys Gln Gly Gly Asp Asn Ala Thr
            415                 420                 425 gtc gtg ttc tgc atc acc aac gag agc agc gcg ggg tcc agc tac tcg      1454
Val Val Phe Cys Ile Thr Asn Glu Ser Ser Ala Gly Ser Ser Tyr Ser
            430                 435                 440 acc agc gtg ggc ggg ttc aag cct aac cag aag gtg gtg gag gtt gtg      1502
Thr Ser Val Gly Gly Phe Lys Pro Asn Gln Lys Val Val Glu Val Val
            445                 450                 455 cgc tgt cgg cac acc aag gcg gac ggt gtt ggg aat gtt gtt gtg tat      1550
Arg Cys Arg His Thr Lys Ala Asp Gly Val Gly Asn Val Val Val Tyr
460                 465                 470 atg gac cag ggc gaa ccg cgc gtg tat gtt gcc gaa gag gtg ctt gag      1598
Met Asp Gln Gly Glu Pro Arg Val Tyr Val Ala Glu Glu Val Leu Glu
475                 480                 485                 490 ggc atc gat gtg tgc gag gag acg acg aag gac ggg ccg gct gag aat      1646
Gly Ile Asp Val Cys Glu Glu Thr Thr Lys Asp Gly Pro Ala Glu Asn
            495                 500                 505 ggt gtt ggg cgg gtg atg gtt cag gga atg tcg ggg acc gtc atg ttg      1694
Gly Val Gly Arg Val Met Val Gln Gly Met Ser Gly Thr Val Met Leu
            510                 515                 520 gta ggt gtg ttg tca gct gtc ttc gtt gcg atg tag                      1730
Val Gly Val Leu Ser Ala Val Phe Val Ala Met
            525                 530

<210> SEQ ID NO 28
<211> LENGTH: 533
<212> TYPE: PRT
<213> ORGANISM: Humicola insolens

<400> SEQUENCE: 28

Met Leu Ala Thr Ile Ser Lys Ile Ala Val Gly Val Leu Ala Leu Thr
1               5                   10                  15

Gly Arg Thr Ser Ala Ala Asp Ala Gln Glu Trp Arg Thr Arg Ser Ile
            20                  25                  30

Tyr Gln Val Met Ile Asp Arg Phe Ala Leu Thr Asp Gly Ser Thr Asp
        35                  40                  45
```

```
Lys Glu Cys Asp Val Ser Arg Phe Cys Gly Gly Thr Trp Lys Gly Leu
 50                  55                  60

Arg Asn Lys Leu Asp Tyr Ile Gln Gly Met Gly Phe Thr Ala Ile Gln
 65                  70                  75                  80

Ile Ser Pro Ile Val Lys Asn Thr Asp His Thr Ala Val Gly Asp
                 85                  90                  95

Ala Tyr His Gly Tyr Trp Val Thr Asp Asn Tyr Ala Leu Asn Asp Arg
                100                 105                 110

Phe Gly Thr Glu Gln Asp Phe Lys Asp Leu Val Ala Glu Val His Lys
                115                 120                 125

Arg Asp Met Leu Ile Ile Val Asp Val Val Asn Asn Met Ala Gln
130                 135                 140

Gly Phe Asp Asn Thr Val Pro Pro Lys Ile Asp Tyr Ser Lys Phe His
145                 150                 155                 160

Pro Phe Asn Asp Asp Lys Tyr Phe His Pro Tyr Cys Asn Val Thr Lys
                165                 170                 175

Trp Glu Asp Pro Glu Asp Tyr Gln Lys Cys Trp Leu Tyr Pro Tyr Gly
                180                 185                 190

Val Ala Leu Ala Asp Leu Ala Thr Asp Thr Lys Glu Val Ser Asp Glu
                195                 200                 205

Leu Asn Arg Trp Val Lys Gln Leu Val Ser Asn Tyr Ser Ile Asp Gly
210                 215                 220

Leu Arg Ile Asp Ala Ala Lys His Val Asn Asp Glu Phe Leu Ala Pro
225                 230                 235                 240

Phe Val Ala Ser Ser Gly Val Phe Ala Phe Gly Glu Val Leu Ser Gly
                245                 250                 255

Val Pro Gln Asp Met Cys Arg Tyr Gln Met Leu Gly Leu Leu Pro Gly
                260                 265                 270

Met Pro Asn Tyr Leu Glu Tyr Tyr Ala Leu Val Arg Ala Phe Asn Gly
                275                 280                 285

Glu Ser Leu Glu Lys Leu Ala Asp Met Arg Asn Gln Ala Ala Ser Ala
                290                 295                 300

Cys Asn Glu Thr Thr Leu Leu Gly Thr Phe Ala Glu Asn His Asp Met
305                 310                 315                 320

Ala Arg Phe Ala Ala Arg Asn Asp Asp Met Ala Leu Ala Lys Asn Ala
                325                 330                 335

Met Thr Tyr Val Ile Leu Asn Asp Gly Ile Pro Thr Val Tyr Gln Gly
                340                 345                 350

Gln Glu Gln His Phe Asn Gly Gly Asp Thr Pro Ala Asn Arg Glu Ala
                355                 360                 365

Leu Trp Thr Ser Lys Tyr Asp Thr Glu Ala Pro Leu Tyr Val Leu Thr
370                 375                 380

Ser Lys Leu Asn Lys Val Arg Asn Asn Ala Ile Lys Leu Ser Glu Ser
385                 390                 395                 400

Tyr Val Thr Glu Pro Ala Lys Thr Leu Leu Ala Asp Val Asn Arg Leu
                405                 410                 415

Cys Leu Lys Gln Gly Gly Asp Asn Ala Thr Val Val Phe Cys Ile Thr
                420                 425                 430

Asn Glu Ser Ser Ala Gly Ser Ser Tyr Ser Thr Ser Val Gly Gly Phe
                435                 440                 445

Lys Pro Asn Gln Lys Val Val Glu Val Arg Cys Arg His Thr Lys
                450                 455                 460

Ala Asp Gly Val Gly Asn Val Val Val Tyr Met Asp Gln Gly Glu Pro
```

```
                  465                 470                 475                 480
Arg Val Tyr Val Ala Glu Glu Val Leu Glu Gly Ile Asp Val Cys Glu
                485                 490                 495

Glu Thr Thr Lys Asp Gly Pro Ala Glu Asn Gly Val Gly Arg Val Met
                500                 505                 510

Val Gln Gly Met Ser Gly Thr Val Met Leu Val Gly Val Leu Ser Ala
                515                 520                 525

Val Phe Val Ala Met
                530

<210> SEQ ID NO 29
<211> LENGTH: 2920
<212> TYPE: DNA
<213> ORGANISM: Myceliophthora fergusii
<220> FEATURE:
<221> NAME/KEY: sig_peptide
<222> LOCATION: (1)..(72)
<220> FEATURE:
<221> NAME/KEY: exon
<222> LOCATION: (1)..(299)
<220> FEATURE:
<221> NAME/KEY: exon
<222> LOCATION: (359)..(467)
<220> FEATURE:
<221> NAME/KEY: exon
<222> LOCATION: (539)..(628)
<220> FEATURE:
<221> NAME/KEY: exon
<222> LOCATION: (724)..(782)
<220> FEATURE:
<221> NAME/KEY: exon
<222> LOCATION: (861)..(887)
<220> FEATURE:
<221> NAME/KEY: exon
<222> LOCATION: (953)..(976)
<220> FEATURE:
<221> NAME/KEY: exon
<222> LOCATION: (1049)..(1108)
<220> FEATURE:
<221> NAME/KEY: exon
<222> LOCATION: (1181)..(1342)
<220> FEATURE:
<221> NAME/KEY: exon
<222> LOCATION: (1406)..(1580)
<220> FEATURE:
<221> NAME/KEY: exon
<222> LOCATION: (1755)..(1782)
<220> FEATURE:
<221> NAME/KEY: exon
<222> LOCATION: (1895)..(2419)
<220> FEATURE:
<221> NAME/KEY: exon
<222> LOCATION: (2491)..(2565)
<220> FEATURE:
<221> NAME/KEY: exon
<222> LOCATION: (2670)..(2917)

<400> SEQUENCE: 29 atg ttt cgc ctc gga cat gcc ctc ttc tgc ctc cta acg ggg tct ctc      48
Met Phe Arg Leu Gly His Ala Leu Phe Cys Leu Leu Thr Gly Ser Leu
1               5                   10                  15 ttg ggg agc ccc ggg att tct gcg ctt tcc gcg gcc gag tgg cgg aag      96
Leu Gly Ser Pro Gly Ile Ser Ala Leu Ser Ala Ala Glu Trp Arg Lys
            20                  25                  30 cag tcc atc tac caa gtc gtc acc gac aga ttc gcc cgg agc gac ctc     144
Gln Ser Ile Tyr Gln Val Val Thr Asp Arg Phe Ala Arg Ser Asp Leu
        35                  40                  45 tcg acc acc gcg ccc tgc aac acg gcc gac cag gcc tac tgc ggg ggc     192
Ser Thr Thr Ala Pro Cys Asn Thr Ala Asp Gln Ala Tyr Cys Gly Gly
    50                  55                  60
```

```
acg tgg aga gga ctg ata tcc aag ctc gac tac atc caa ggg atg ggg        240
Thr Trp Arg Gly Leu Ile Ser Lys Leu Asp Tyr Ile Gln Gly Met Gly
65                  70                  75                  80 ttc acg gcc gtg tgg atc tcc ccg gtc gtg aag cag atc gac ggc aac        288
Phe Thr Ala Val Trp Ile Ser Pro Val Val Lys Gln Ile Asp Gly Asn
            85                  90                  95 tcc agg gac gg  gtgagctcac gagtaccgtc acgattcacc gatgctcctg            339
Ser Arg Asp Gly ctcaccctac gagacacag g tcg tcc tac cac ggg tac tgg aca cag gac         389
                     Ser Ser Tyr His Gly Tyr Trp Thr Gln Asp
                                 105                 110 att tgg gcg gtc aat ccg gct ttt gga act gcc gcc gat cta gca gag        437
Ile Trp Ala Val Asn Pro Ala Phe Gly Thr Ala Ala Asp Leu Ala Glu
                115                 120                 125 ctg tct caa gag ctg cac tcc agg ggc atg gtgagcgcgg aagtgtgatg          487
Leu Ser Gln Glu Leu His Ser Arg Gly Met
130                 135 ctgcccggct ctccggtgat ttgctgaccc gcgttttact ttgttatcca g tat ctc       544
                                                        Tyr Leu atg gtc gac atc gtc acg aac cac atg gcg tac atg ggt tgc ggt aca        592
Met Val Asp Ile Val Thr Asn His Met Ala Tyr Met Gly Cys Gly Thr
    140                 145                 150 tgt gtc gac tat cgc cag ttt aac ccc ttc tgc tcg gtaagtgtct             638
Cys Val Asp Tyr Arg Gln Phe Asn Pro Phe Cys Ser
155                 160                 165 ctctccgccc tcggtctcg cctgatgcaa cgcgagtaaa cggggagag gaaaggcagt        698 cggctgattc gcggcatctc catag cca tcg tat ttt cac ccg tat tgc ccc        750
                            Pro Ser Tyr Phe His Pro Tyr Cys Pro
                                        170                 175 atc aac tac gat aat cag acc tct gtc gaa gt  gtgcgtatac ccgcccggac     802
Ile Asn Tyr Asp Asn Gln Thr Ser Val Glu Val
                180                 185 tcctcccctc tccccagccc tacaaaaact gggtggctgc tgagactcac ggccctag g      861 tgt tgg caa ggc agc aac att gtc ag  gtatgctgag ccgggcttgg              907
Cys Trp Gln Gly Ser Asn Ile Val Ser
190                 195 tgtgattaca ccaccctcat ggacctcgaa gcttacgtgt ctcag c cta cct gat        962
                                                   Leu Pro Asp ctg cgt acc gag ga  gtgagtgctt cgccaagcct tccccaagca tgaccacgga       1016
Leu Arg Thr Glu Asp
200 gcaatgcttc ctctgacagg tcgtgacgat ag c gag aac gta cga cgc atc tgg     1070
                                   Glu Asn Val Arg Arg Ile Trp
                                                205                 210 aac gac tgg gtg acc cag ctg gtc tct aac tac tcc gt  gtaagtgaac        1118
Asn Asp Trp Val Thr Gln Leu Val Ser Asn Tyr Ser Val
                215                 220 actttgccgg cttccggtct ggatctctcc caagcttagc tcacactccc cggcggtcgc     1178 ag t gac ggc ctt cga gtc gat agc gca aaa cac gtc gag acg tcc ttc      1226
    Asp Gly Leu Arg Val Asp Ser Ala Lys His Val Glu Thr Ser Phe
        225                 230                 235 tgg acc gga ttc tca aat gca gcg ggt gtc tac ctc ctg ggc gag gtt       1274
Trp Thr Gly Phe Ser Asn Ala Ala Gly Val Tyr Leu Leu Gly Glu Val
    240                 245                 250 ttc cac gga gac ccc gcg tac gtg gct ccc tac cag gac tat ctc gac       1322
Phe His Gly Asp Pro Ala Tyr Val Ala Pro Tyr Gln Asp Tyr Leu Asp
255                 260                 265                 270
```

-continued

| | |
|---|---|
| ggg gtg tta gac tat cct ag   gtgagaaaga gcagctcctc catggcccgc<br>Gly Val Leu Asp Tyr Pro Ser<br>                275 | 1372 |
| ctccatccag ttctctgact tgcgtggcg cag t tat tac tgg gta ctc agg<br>                                              Tyr Tyr Trp Val Leu Arg<br>                                                      280 | 1424 |
| gca ttc cag tct aca agc ggc agc atc agc gag ctc gtc gct ggt ctc<br>Ala Phe Gln Ser Thr Ser Gly Ser Ile Ser Glu Leu Val Ala Gly Leu<br>    285                 290                 295 | 1472 |
| acc aat ctg cag gat act gca cga gac att agt ctc tat ggt gct ttt<br>Thr Asn Leu Gln Asp Thr Ala Arg Asp Ile Ser Leu Tyr Gly Ala Phe<br>300                 305                 310                 315 | 1520 |
| ctg gag aat cat gac gtg gag aga ttc ccg tcc ttg acc aag gac aag<br>Leu Glu Asn His Asp Val Glu Arg Phe Pro Ser Leu Thr Lys Asp Lys<br>            320                 325                 330 | 1568 |
| gtt ggt agt cag gtccctcccc cttgcttgaa cggcgccttt tccgccttgt<br>Val Gly Ser Gln<br>            335 | 1620 |
| gctgacgatc ctcccttggc taggcactcg ctaaaaatgt gagcactcgt tatagggttt | 1680 |
| aacgtaatcg cttgtttgtt ctcatctcgg aaatagaggt tgactaacat gagctgggcc | 1740 |
| tttttgacgc gtag gcg atc gcc ttt acg atg ctc aaa gac g gtaagtaaac<br>              Ala Ile Ala Phe Thr Met Leu Lys Asp<br>                                  340 | 1792 |
| ggccgcgtca tgctggggtc tttccattgg acccataacg ccggcagagg ggagagagga | 1852 |
| gggaaaaggg gggaaaaggg agaagctgac ggatggtgtt ag gc   att ccg att<br>                                                    Gly Ile Pro Ile | 1905 |
| ctt tac caa ggg cag gag cag tac tac gac ggc tcc aga acc cct tcc<br>Leu Tyr Gln Gly Gln Glu Gln Tyr Tyr Asp Gly Ser Arg Thr Pro Ser<br>    350                 355                 360 | 1953 |
| aac cgc gag gcg ctc tgg acc tcc ggc tat tcg gcg agc tcg gag ttt<br>Asn Arg Glu Ala Leu Trp Thr Ser Gly Tyr Ser Ala Ser Ser Glu Phe<br>365                 370                 375                 380 | 2001 |
| tac caa tgg atc acg aaa ctc aac cgg atc cga gcc ctg gcc ata gcc<br>Tyr Gln Trp Ile Thr Lys Leu Asn Arg Ile Arg Ala Leu Ala Ile Ala<br>            385                 390                 395 | 2049 |
| cag gac gag gac tac gtt acc tcc aag atc aca ttc gtc tat tcg gat<br>Gln Asp Glu Asp Tyr Val Thr Ser Lys Ile Thr Phe Val Tyr Ser Asp<br>400                 405                 410 | 2097 |
| agc cat acc gtc gcc acg cgc aag ggc aac gcc ggg cac cag att gtg<br>Ser His Thr Val Ala Thr Arg Lys Gly Asn Ala Gly His Gln Ile Val<br>    415                 420                 425 | 2145 |
| agc ata ttc acg aac atg ggg gca tcg tcc tcg gca tcc gtc act ctc<br>Ser Ile Phe Thr Asn Met Gly Ala Ser Ser Ser Ala Ser Val Thr Leu<br>430                 435                 440 | 2193 |
| cct tcg tct gcc acg ggc ttc gat gcc aac cag cag ctc ctc gac gtc<br>Pro Ser Ser Ala Thr Gly Phe Asp Ala Asn Gln Gln Leu Leu Asp Val<br>445                 450                 455                 460 | 2241 |
| ctg agc tgc acc cta ttt acc aca gac tcg agc ggc ggc ctc aca gtg<br>Leu Ser Cys Thr Leu Phe Thr Thr Asp Ser Ser Gly Gly Leu Thr Val<br>            465                 470                 475 | 2289 |
| acc ctg gtc gac gga ctg ccg cgc gtt ctg tat ccc acg tct cgt ctg<br>Thr Leu Val Asp Gly Leu Pro Arg Val Leu Tyr Pro Thr Ser Arg Leu<br>        480                 485                 490 | 2337 |
| gcc ggc agc agc ctc tgc ccg gac tcg gac acc ggg gcc acc gcg acc<br>Ala Gly Ser Ser Leu Cys Pro Asp Ser Asp Thr Gly Ala Thr Ala Thr<br>    495                 500                 505 | 2385 |
| gct tca cca acg cgg gca ccg aca aca tcc gca g gtaggagcgc<br> Ala Ser Pro Thr Arg Ala Pro Thr Thr Ser Ala | 2429 |

```
Ala Ser Pro Thr Arg Ala Pro Thr Thr Ser Ala
    510                 515
```

```
cgcggcgacg ttggaggcga ggagcaggag gcagagtcta acaatacacg cgatgttata    2489
```

```
g gc  gac ccc gct tgc gcc ctg tcc gcc gtc gat atc acc ttc aac gaa    2537
  Gly Asp Pro Ala Cys Ala Leu Ser Ala Val Asp Ile Thr Phe Asn Glu
  520             525                 530                 535
```

```
cta gcg acc acg gta tgg ggg gga gac g gtcaagatgt aagtcgatcg          2585
Leu Ala Thr Thr Val Trp Gly Gly Asp
            540
```

```
atgtgcttta catgcacttg ccccgctccg ttttgcttcc atttcttagg ggttacaaag    2645
```

```
cctaataatt tagggccgtg gtag cg  ttg gga acg ttc ccg aac tcg gca       2695
                               Ala Leu Gly Thr Phe Pro Asn Ser Ala
                                   545                 550
```

```
act gga acc ctg cca gtg caa tca gtt acc ctt gac gca tcg cga tac      2743
Thr Gly Thr Leu Pro Val Gln Ser Val Thr Leu Asp Ala Ser Arg Tyr
    555                 560                 565
```

```
gca tcg agc aac ccg ctg tgg ttt gtc gtc gtc cga ctt ccc ccc cag      2791
Ala Ser Ser Asn Pro Leu Trp Phe Val Val Val Arg Leu Pro Pro Gln
570                 575                 580                 585
```

```
atc ccg gcc cag tac aag tac atc aag gtg agc cag tcc ggg acg gtg      2839
Ile Pro Ala Gln Tyr Lys Tyr Ile Lys Val Ser Gln Ser Gly Thr Val
                590                 595                 600
```

```
act tgg gaa gcg ggt ccg aat cgc acc tac aat gtc aat gtc ccc tgc      2887
Thr Trp Glu Ala Gly Pro Asn Arg Thr Tyr Asn Val Asn Val Pro Cys
            605                 610                 615
```

```
gtg acc gca acg gtg agc agc acc tgg agg tga                         2920
Val Thr Ala Thr Val Ser Ser Thr Trp Arg
        620                 625
```

<210> SEQ ID NO 30
<211> LENGTH: 627
<212> TYPE: PRT
<213> ORGANISM: Myceliophthora fergusii

<400> SEQUENCE: 30

```
Met Phe Arg Leu Gly His Ala Leu Phe Cys Leu Leu Thr Gly Ser Leu
1               5                   10                  15

Leu Gly Ser Pro Gly Ile Ser Ala Leu Ser Ala Ala Glu Trp Arg Lys
                20                  25                  30

Gln Ser Ile Tyr Gln Val Val Thr Asp Arg Phe Ala Arg Ser Asp Leu
            35                  40                  45

Ser Thr Thr Ala Pro Cys Asn Thr Ala Asp Gln Ala Tyr Cys Gly Gly
        50                  55                  60

Thr Trp Arg Gly Leu Ile Ser Lys Leu Asp Tyr Ile Gln Gly Met Gly
65              70                  75                  80

Phe Thr Ala Val Trp Ile Ser Pro Val Val Lys Gln Ile Asp Gly Asn
                85                  90                  95

Ser Arg Asp Gly Ser Ser Tyr His Gly Tyr Trp Thr Gln Asp Ile Trp
            100                 105                 110

Ala Val Asn Pro Ala Phe Gly Thr Ala Ala Asp Leu Ala Glu Leu Ser
        115                 120                 125

Gln Glu Leu His Ser Arg Gly Met Tyr Leu Met Val Asp Ile Val Thr
    130                 135                 140

Asn His Met Ala Tyr Met Gly Cys Gly Thr Cys Val Asp Tyr Arg Gln
145                 150                 155                 160

Phe Asn Pro Phe Cys Ser Pro Ser Tyr Phe His Pro Tyr Cys Pro Ile
                165                 170                 175
```

```
Asn Tyr Asp Asn Gln Thr Ser Val Glu Val Cys Trp Gln Gly Ser Asn
            180                 185                 190

Ile Val Ser Leu Pro Asp Leu Arg Thr Glu Asp Glu Asn Val Arg Arg
        195                 200                 205

Ile Trp Asn Asp Trp Val Thr Gln Leu Val Ser Asn Tyr Ser Val Asp
210                 215                 220

Gly Leu Arg Val Asp Ser Ala Lys His Val Glu Thr Ser Phe Trp Thr
225                 230                 235                 240

Gly Phe Ser Asn Ala Ala Gly Val Tyr Leu Leu Gly Glu Val Phe His
                245                 250                 255

Gly Asp Pro Ala Tyr Val Ala Pro Tyr Gln Asp Tyr Leu Asp Gly Val
            260                 265                 270

Leu Asp Tyr Pro Ser Tyr Tyr Trp Val Leu Arg Ala Phe Gln Ser Thr
        275                 280                 285

Ser Gly Ser Ile Ser Glu Leu Val Ala Gly Leu Thr Asn Leu Gln Asp
    290                 295                 300

Thr Ala Arg Asp Ile Ser Leu Tyr Gly Ala Phe Leu Glu Asn His Asp
305                 310                 315                 320

Val Glu Arg Phe Pro Ser Leu Thr Lys Asp Lys Val Gly Ser Gln Ala
                325                 330                 335

Ile Ala Phe Thr Met Leu Lys Asp Gly Ile Pro Ile Leu Tyr Gln Gly
            340                 345                 350

Gln Glu Gln Tyr Tyr Asp Gly Ser Arg Thr Pro Ser Asn Arg Glu Ala
        355                 360                 365

Leu Trp Thr Ser Gly Tyr Ser Ala Ser Ser Glu Phe Tyr Gln Trp Ile
370                 375                 380

Thr Lys Leu Asn Arg Ile Arg Ala Leu Ala Ile Ala Gln Asp Glu Asp
385                 390                 395                 400

Tyr Val Thr Ser Lys Ile Thr Phe Val Tyr Ser Asp Ser His Thr Val
                405                 410                 415

Ala Thr Arg Lys Gly Asn Ala Gly His Gln Ile Val Ser Ile Phe Thr
            420                 425                 430

Asn Met Gly Ala Ser Ser Ser Ala Ser Val Thr Leu Pro Ser Ser Ala
        435                 440                 445

Thr Gly Phe Asp Ala Asn Gln Gln Leu Leu Asp Val Leu Ser Cys Thr
450                 455                 460

Leu Phe Thr Thr Asp Ser Ser Gly Gly Leu Thr Val Thr Leu Val Asp
465                 470                 475                 480

Gly Leu Pro Arg Val Leu Tyr Pro Thr Ser Arg Leu Ala Gly Ser Ser
                485                 490                 495

Leu Cys Pro Asp Ser Asp Thr Gly Ala Thr Ala Thr Ser Pro Thr
            500                 505                 510

Arg Ala Pro Thr Thr Ser Ala Gly Asp Pro Ala Cys Ala Leu Ser Ala
        515                 520                 525

Val Asp Ile Thr Phe Asn Glu Leu Ala Thr Thr Val Trp Gly Gly Asp
530                 535                 540

Ala Leu Gly Thr Phe Pro Asn Ser Ala Thr Gly Thr Leu Pro Val Gln
545                 550                 555                 560

Ser Val Thr Leu Asp Ala Ser Arg Tyr Ala Ser Ser Asn Pro Leu Trp
                565                 570                 575

Phe Val Val Arg Leu Pro Pro Gln Ile Pro Ala Gln Tyr Lys Tyr
            580                 585                 590
```

```
                Ile Lys Val Ser Gln Ser Gly Thr Val Thr Trp Glu Ala Gly Pro Asn
                            595                 600                 605

Arg Thr Tyr Asn Val Asn Val Pro Cys Val Thr Ala Thr Val Ser Ser
                            610                 615                 620

Thr Trp Arg
                625

<210> SEQ ID NO 31
<211> LENGTH: 1680
<212> TYPE: DNA
<213> ORGANISM: Myceliophthora fergusii
<220> FEATURE:
<221> NAME/KEY: sig_peptide
<222> LOCATION: (1)..(60)
<220> FEATURE:
<221> NAME/KEY: exon
<222> LOCATION: (1)..(220)
<220> FEATURE:
<221> NAME/KEY: exon
<222> LOCATION: (306)..(1133)
<220> FEATURE:
<221> NAME/KEY: exon
<222> LOCATION: (1199)..(1677)

<400> SEQUENCE: 31 atg agg acc tcc atc atc agg gcc gcg gtg gcc atc gcc tta gcc acc        48
Met Arg Thr Ser Ile Ile Arg Ala Ala Val Ala Ile Ala Leu Ala Thr
1               5                   10                  15 gcc agc ttg ggg tca gga gcg aac atc gcc gaa tgg aag tcc cgt tcc        96
Ala Ser Leu Gly Ser Gly Ala Asn Ile Ala Glu Trp Lys Ser Arg Ser
                20                  25                  30 atc tac cag gtc atg att gac cgg ttt gcc cgc act gac ggt tcc acg       144
Ile Tyr Gln Val Met Ile Asp Arg Phe Ala Arg Thr Asp Gly Ser Thr
            35                  40                  45 gat gcg ccg tgc gat gtc tca cgg ttt tgc gga ggc acc tgg aag ggc       192
Asp Ala Pro Cys Asp Val Ser Arg Phe Cys Gly Gly Thr Trp Lys Gly
50                  55                  60 ctc ctg aac aat ctg gac tat att cag g gtgagcatgt cgtgaatgac           240
Leu Leu Asn Asn Leu Asp Tyr Ile Gln
65                  70 ttacctcccg tcgttatcta tccgaggagc ttggcggcca gcctaaccgg gttcgtggga     300 ggcag ac  atg ggc ttt acc gcc atc cag atc agc ccc atc gtg aag aac     349
          Asp Met Gly Phe Thr Ala Ile Gln Ile Ser Pro Ile Val Lys Asn
               75                  80                  85 atc gat gag cat acc gca gtc ggc gac gcg tac cat ggc tat tgg tcg       397
Ile Asp Glu His Thr Ala Val Gly Asp Ala Tyr His Gly Tyr Trp Ser
            90                  95                  100 gtc gac aac tac gcg ctg aac gac cgc ttc ggc acg aag cag gat ttc       445
Val Asp Asn Tyr Ala Leu Asn Asp Arg Phe Gly Thr Lys Gln Asp Phe
105                 110                 115                 120 gag gac ctg gtg gcc gag ctc cac aag cgt gac atg ttc ctc atg gtc       493
Glu Asp Leu Val Ala Glu Leu His Lys Arg Asp Met Phe Leu Met Val
                125                 130                 135 gac gtc gtg gtc aac aac atg gcc cag gca ttc gac aac gtc atc ccg       541
Asp Val Val Val Asn Asn Met Ala Gln Ala Phe Asp Asn Val Ile Pro
            140                 145                 150 ccc aag gtc gac tac tcc aag ttc aat ccg ttc gac gac aag aaa tac       589
Pro Lys Val Asp Tyr Ser Lys Phe Asn Pro Phe Asp Asp Lys Lys Tyr
        155                 160                 165 ttc cac ccc tac tgc aac gtg acc aac tgg ggc gat acg acc gag tct       637
Phe His Pro Tyr Cys Asn Val Thr Asn Trp Gly Asp Thr Thr Glu Ser
    170                 175                 180
```

|     |     |
| --- | --- |
| cag aac tgc tgg ctg tac ccg tac ggc gtt gcc ctg gcc gat ctg gct<br>Gln Asn Cys Trp Leu Tyr Pro Tyr Gly Val Ala Leu Ala Asp Leu Ala<br>185                       190                       195                   200 | 685 |
| acc gag acc ggg ccg gtg gcg gat gag ctg ggc cgg tgg gtt aag gag<br>Thr Glu Thr Gly Pro Val Ala Asp Glu Leu Gly Arg Trp Val Lys Glu<br>                     205                       210                     215 | 733 |
| ctt gtc gcc aac tac tcg atc gac ggc atc cgc atc gac gct gcg aag<br>Leu Val Ala Asn Tyr Ser Ile Asp Gly Ile Arg Ile Asp Ala Ala Lys<br>220                       225                       230 | 781 |
| cat gtc aac gac gac ttc ctc ccc ggc ttt gtc gag gca tct ggc gtc<br>His Val Asn Asp Asp Phe Leu Pro Gly Phe Val Glu Ala Ser Gly Val<br>             235                     240                     245 | 829 |
| ttc gcc ctc ggc gag gtc ttc agc ggg ggg gct gag gac atg tgc cgc<br>Phe Ala Leu Gly Glu Val Phe Ser Gly Gly Ala Glu Asp Met Cys Arg<br>250                       255                       260 | 877 |
| tat cag aac cgc ggc ttc ctc ccg ggc atg ccc aac tat ccc gag ttc<br>Tyr Gln Asn Arg Gly Phe Leu Pro Gly Met Pro Asn Tyr Pro Glu Phe<br>265                       270                       275                     280 | 925 |
| tac gag ctc acc aag gct ttc aat ggc gga tcc atg gcc gat ttt gcc<br>Tyr Glu Leu Thr Lys Ala Phe Asn Gly Gly Ser Met Ala Asp Phe Ala<br>             285                     290                     295 | 973 |
| gag atg cgc aac agc gtg gct tcc agc tgc aac gac acg gcc gcg ctg<br>Glu Met Arg Asn Ser Val Ala Ser Ser Cys Asn Asp Thr Ala Ala Leu<br>300                       305                       310 | 1021 |
| gga agt ttc ctc gag aac cac gac cag ccc cgg ttc gcg aac tcc aac<br>Gly Ser Phe Leu Glu Asn His Asp Gln Pro Arg Phe Ala Asn Ser Asn<br>             315                     320                     325 | 1069 |
| gac gac atc gca ctc gcg aag aac ggc atg acg tac att ctg ctc aac<br>Asp Asp Ile Ala Leu Ala Lys Asn Gly Met Thr Tyr Ile Leu Leu Asn<br>330                       335                       340 | 1117 |
| gac ggc att ccc aca g gtaactatcc ccccttttgg aaggcgcctc gtctccctgc<br>Asp Gly Ile Pro Thr<br>345 | 1173 |
| gggcagtgcg gctgattgct cgcag tc tac cag ggc cag gaa cag cac ttc<br>                                                  Val Tyr Gln Gly Gln Glu Gln His Phe<br>                                                    350                       355 | 1224 |
| atg ggc aac gac acc ccc ttc aac cgt gag gcc ctt tgg aca tcc ggg<br>Met Gly Asn Asp Thr Pro Phe Asn Arg Glu Ala Leu Trp Thr Ser Gly<br>360                       365                       370 | 1272 |
| tac gac agg aaa tcg cct ctg tac gtc ctc acg gcg acg ctg aac aag<br>Tyr Asp Arg Lys Ser Pro Leu Tyr Val Leu Thr Ala Thr Leu Asn Lys<br>375                       380                       385                     390 | 1320 |
| gtg cgc aac aac gcc atc aag ctg tcg tcg gac tac gtc tcg acg ccg<br>Val Arg Asn Asn Ala Ile Lys Leu Ser Ser Asp Tyr Val Ser Thr Pro<br>                     395                       400                     405 | 1368 |
| gcg gag acg ctc aag gcc gat gtg aac cac ctc tgt ctc cgg aag ggc<br>Ala Glu Thr Leu Lys Ala Asp Val Asn His Leu Cys Leu Arg Lys Gly<br>             410                     415                     420 | 1416 |
| ccg gat ggc agc cag gtg gtg ttt tgc atc agc aac cag agc agc aat<br>Pro Asp Gly Ser Gln Val Val Phe Cys Ile Ser Asn Gln Ser Ser Asn<br>425                       430                       435 | 1464 |
| ggc ggc caa tac gat cta gac gtc gct ggc ggt ttc gag aag gac gag<br>Gly Gly Gln Tyr Asp Leu Asp Val Ala Gly Gly Phe Glu Lys Asp Glu<br>440                       445                       450 | 1512 |
| gag gtc gtc gag gtc ttg act tgc agg acc aac aag gcg gac ttc tcg<br>Glu Val Val Glu Val Leu Thr Cys Arg Thr Asn Lys Ala Asp Phe Ser<br>455                       460                       465                     470 | 1560 |
| ggc agc atc acc atg tat atg aac aag ggc gag ccc aag gtg tac gtc<br>Gly Ser Ile Thr Met Tyr Met Asn Lys Gly Glu Pro Lys Val Tyr Val<br>             475                     480                     485 | 1608 |

```
cct cgg aag gca ctc cgc ggc acc ggc ctt tgc gag aag aca gag gaa    1656
Pro Arg Lys Ala Leu Arg Gly Thr Gly Leu Cys Glu Lys Thr Glu Glu
            490                 495                 500 gat aaa ccg gat agc agc gcg tga                                    1680
Asp Lys Pro Asp Ser Ser Ala
        505
```

<210> SEQ ID NO 32
<211> LENGTH: 509
<212> TYPE: PRT
<213> ORGANISM: Myceliophthora fergusii

<400> SEQUENCE: 32

```
Met Arg Thr Ser Ile Ile Arg Ala Ala Val Ala Ile Ala Leu Ala Thr
1               5                   10                  15

Ala Ser Leu Gly Ser Gly Ala Asn Ile Ala Glu Trp Lys Ser Arg Ser
            20                  25                  30

Ile Tyr Gln Val Met Ile Asp Arg Phe Ala Arg Thr Asp Gly Ser Thr
        35                  40                  45

Asp Ala Pro Cys Asp Val Ser Arg Phe Cys Gly Gly Thr Trp Lys Gly
    50                  55                  60

Leu Leu Asn Asn Leu Asp Tyr Ile Gln Asp Met Gly Phe Thr Ala Ile
65                  70                  75                  80

Gln Ile Ser Pro Ile Val Lys Asn Ile Asp Glu His Thr Ala Val Gly
                85                  90                  95

Asp Ala Tyr His Gly Tyr Trp Ser Val Asp Asn Tyr Ala Leu Asn Asp
            100                 105                 110

Arg Phe Gly Thr Lys Gln Asp Phe Glu Asp Leu Val Ala Glu Leu His
        115                 120                 125

Lys Arg Asp Met Phe Leu Met Val Asp Val Val Asn Asn Met Ala
    130                 135                 140

Gln Ala Phe Asp Asn Val Ile Pro Pro Lys Val Asp Tyr Ser Lys Phe
145                 150                 155                 160

Asn Pro Phe Asp Asp Lys Lys Tyr Phe His Pro Tyr Cys Asn Val Thr
                165                 170                 175

Asn Trp Gly Asp Thr Thr Glu Ser Gln Asn Cys Trp Leu Tyr Pro Tyr
            180                 185                 190

Gly Val Ala Leu Ala Asp Leu Ala Thr Glu Thr Gly Pro Val Ala Asp
        195                 200                 205

Glu Leu Gly Arg Trp Val Lys Glu Leu Val Ala Asn Tyr Ser Ile Asp
    210                 215                 220

Gly Ile Arg Ile Asp Ala Ala Lys His Val Asn Asp Phe Leu Pro
225                 230                 235                 240

Gly Phe Val Glu Ala Ser Gly Val Phe Ala Leu Gly Glu Val Phe Ser
                245                 250                 255

Gly Gly Ala Glu Asp Met Cys Arg Tyr Gln Asn Arg Gly Phe Leu Pro
            260                 265                 270

Gly Met Pro Asn Tyr Pro Glu Phe Tyr Glu Leu Thr Lys Ala Phe Asn
        275                 280                 285

Gly Gly Ser Met Ala Asp Phe Ala Glu Met Arg Asn Ser Val Ala Ser
    290                 295                 300

Ser Cys Asn Asp Thr Ala Leu Gly Ser Phe Leu Glu Asn His Asp
305                 310                 315                 320

Gln Pro Arg Phe Ala Asn Ser Asn Asp Asp Ile Ala Leu Ala Lys Asn
                325                 330                 335
```

Gly Met Thr Tyr Ile Leu Leu Asn Asp Gly Ile Pro Thr Val Tyr Gln
                340                 345                 350

Gly Gln Glu Gln His Phe Met Gly Asn Asp Thr Pro Phe Asn Arg Glu
            355                 360                 365

Ala Leu Trp Thr Ser Gly Tyr Asp Arg Lys Ser Pro Leu Tyr Val Leu
    370                 375                 380

Thr Ala Thr Leu Asn Lys Val Arg Asn Ala Ile Lys Leu Ser Ser
385                 390                 395                 400

Asp Tyr Val Ser Thr Pro Ala Glu Thr Leu Lys Ala Asp Val Asn His
                405                 410                 415

Leu Cys Leu Arg Lys Gly Pro Asp Gly Ser Gln Val Val Phe Cys Ile
            420                 425                 430

Ser Asn Gln Ser Ser Asn Gly Gly Gln Tyr Asp Leu Asp Val Ala Gly
        435                 440                 445

Gly Phe Glu Lys Asp Glu Glu Val Glu Val Leu Thr Cys Arg Thr
    450                 455                 460

Asn Lys Ala Asp Phe Ser Gly Ser Ile Thr Met Tyr Met Asn Lys Gly
465                 470                 475                 480

Glu Pro Lys Val Tyr Val Pro Arg Lys Ala Leu Arg Gly Thr Gly Leu
                485                 490                 495

Cys Glu Lys Thr Glu Glu Asp Lys Pro Asp Ser Ser Ala
            500                 505

<210> SEQ ID NO 33
<211> LENGTH: 48
<212> TYPE: DNA
<213> ORGANISM: Artificial Sequence
<220> FEATURE:
<223> OTHER INFORMATION: Synthetic construct

<400> SEQUENCE: 33
acacaactgg ggatccacca tgaagttttc cgtactcttt acaagtgc                48

<210> SEQ ID NO 34
<211> LENGTH: 40
<212> TYPE: DNA
<213> ORGANISM: Artificial Sequence
<220> FEATURE:
<223> OTHER INFORMATION: Synthetic construct

<400> SEQUENCE: 34
ccctctagat ctcgagaatt tcaacgacca catatacccg                         40

<210> SEQ ID NO 35
<211> LENGTH: 42
<212> TYPE: DNA
<213> ORGANISM: Artificial Sequence
<220> FEATURE:
<223> OTHER INFORMATION: Synthetic construct

<400> SEQUENCE: 35
acacaactgg ggatccacca tggtcaagat gtttgggtca cg                      42

<210> SEQ ID NO 36
<211> LENGTH: 44
<212> TYPE: DNA
<213> ORGANISM: Artificial Sequence
<220> FEATURE:
<223> OTHER INFORMATION: Synthetic construct

<400> SEQUENCE: 36

```
gtcaccctct agatctcgag cccagtgatc ctcccgatcc tata                44
```

<210> SEQ ID NO 37
<211> LENGTH: 42
<212> TYPE: DNA
<213> ORGANISM: Artificial Sequence
<220> FEATURE:
<223> OTHER INFORMATION: Synthetic construct

<400> SEQUENCE: 37

```
acacaactgg ggatccacca tggaagtgtg gaagatagtg ct                 42
```

<210> SEQ ID NO 38
<211> LENGTH: 35
<212> TYPE: DNA
<213> ORGANISM: Artificial Sequence
<220> FEATURE:
<223> OTHER INFORMATION: Synthetic construct

<400> SEQUENCE: 38

```
ccctctagat ctcgagtgct ttccccgtca gaaca                         35
```

<210> SEQ ID NO 39
<211> LENGTH: 41
<212> TYPE: DNA
<213> ORGANISM: Artificial Sequence
<220> FEATURE:
<223> OTHER INFORMATION: Synthetic construct

<400> SEQUENCE: 39

```
acacaactgg ggatccacca tgaaattccc aacgtccatc g                  41
```

<210> SEQ ID NO 40
<211> LENGTH: 43
<212> TYPE: DNA
<213> ORGANISM: Artificial Sequence
<220> FEATURE:
<223> OTHER INFORMATION: Synthetic construct

<400> SEQUENCE: 40

```
ccctctagat ctcgagattt acagcacaat cacggcagat atg                43
```

<210> SEQ ID NO 41
<211> LENGTH: 46
<212> TYPE: DNA
<213> ORGANISM: Artificial Sequence
<220> FEATURE:
<223> OTHER INFORMATION: Synthetic construct

<400> SEQUENCE: 41

```
acacaactgg ggatccacca tgctgtcgtt tatccttgca gttttc             46
```

<210> SEQ ID NO 42
<211> LENGTH: 44
<212> TYPE: DNA
<213> ORGANISM: Artificial Sequence
<220> FEATURE:
<223> OTHER INFORMATION: Synthetic construct

<400> SEQUENCE: 42

```
acacaactgg ggatccacca tgctgtcgtt tatccttgca gttt               44
```

<210> SEQ ID NO 43
<211> LENGTH: 38
<212> TYPE: DNA

```
<213> ORGANISM: Artificial Sequence
<220> FEATURE:
<223> OTHER INFORMATION: Synthetic construct

<400> SEQUENCE: 43
ccctctagat ctcgagttac gactgacaca gcttgccc                                38

<210> SEQ ID NO 44
<211> LENGTH: 40
<212> TYPE: DNA
<213> ORGANISM: Artificial Sequence
<220> FEATURE:
<223> OTHER INFORMATION: Synthetic construct

<400> SEQUENCE: 44
ccctctagat ctcgagacct tttagaaggg aaagcccatg                              40

<210> SEQ ID NO 45
<211> LENGTH: 35
<212> TYPE: DNA
<213> ORGANISM: Artificial Sequence
<220> FEATURE:
<223> OTHER INFORMATION: Synthetic construct

<400> SEQUENCE: 45
acacaactgg ggatccacca tggcgccccc ttgga                                   35

<210> SEQ ID NO 46
<211> LENGTH: 42
<212> TYPE: DNA
<213> ORGANISM: Artificial Sequence
<220> FEATURE:
<223> OTHER INFORMATION: Synthetic construct

<400> SEQUENCE: 46
ccctctagat ctcgagacca tcacaacaga gtcatctcca tc                           42

<210> SEQ ID NO 47
<211> LENGTH: 45
<212> TYPE: DNA
<213> ORGANISM: Artificial Sequence
<220> FEATURE:
<223> OTHER INFORMATION: Synthetic construct

<400> SEQUENCE: 47
acacaactgg ggatccacca tgaagttgcc cctgtttatt gcaag                        45

<210> SEQ ID NO 48
<211> LENGTH: 43
<212> TYPE: DNA
<213> ORGANISM: Artificial Sequence
<220> FEATURE:
<223> OTHER INFORMATION: Synthetic construct

<400> SEQUENCE: 48
ccctctagat ctcgagactg ttacagatca cacaaccctg agc                          43

<210> SEQ ID NO 49
<211> LENGTH: 39
<212> TYPE: DNA
<213> ORGANISM: Artificial Sequence
<220> FEATURE:
<223> OTHER INFORMATION: Synthetic construct

<400> SEQUENCE: 49
acacaactgg ggatccacca tgacgccttt cgtcctgct                               39
```

<210> SEQ ID NO 50
<211> LENGTH: 43
<212> TYPE: DNA
<213> ORGANISM: Artificial Sequence
<220> FEATURE:
<223> OTHER INFORMATION: Synthetic construct

<400> SEQUENCE: 50
ccctctagat ctcgagacta tctccatgtg tcgacaatcg tct            43

<210> SEQ ID NO 51
<211> LENGTH: 33
<212> TYPE: DNA
<213> ORGANISM: Artificial Sequence
<220> FEATURE:
<223> OTHER INFORMATION: Synthetic construct

<400> SEQUENCE: 51
attattcgaa ggatccaaaa tgaaggggcc gcg                       33

<210> SEQ ID NO 52
<211> LENGTH: 38
<212> TYPE: DNA
<213> ORGANISM: Artificial Sequence
<220> FEATURE:
<223> OTHER INFORMATION: Synthetic construct

<400> SEQUENCE: 52
ggtgctgatg gaattcagct acaccgcaga ggccgctt                  38

<210> SEQ ID NO 53
<211> LENGTH: 43
<212> TYPE: DNA
<213> ORGANISM: Artificial Sequence
<220> FEATURE:
<223> OTHER INFORMATION: Synthetic construct

<400> SEQUENCE: 53
acacaactgg ggatccacca tgcttgccac aatctcgaag atc            43

<210> SEQ ID NO 54
<211> LENGTH: 39
<212> TYPE: DNA
<213> ORGANISM: Artificial Sequence
<220> FEATURE:
<223> OTHER INFORMATION: Synthetic construct

<400> SEQUENCE: 54
ccctctagat ctcgagctac atcgcaacga agacagctg                 39

<210> SEQ ID NO 55
<211> LENGTH: 42
<212> TYPE: DNA
<213> ORGANISM: Artificial Sequence
<220> FEATURE:
<223> OTHER INFORMATION: Synthetic construct

<400> SEQUENCE: 55
attattcgaa ggatccacca tgagaaacct tcgacatatc ct             42

<210> SEQ ID NO 56
<211> LENGTH: 36
<212> TYPE: DNA
<213> ORGANISM: Artificial Sequence
<220> FEATURE:

<210> SEQ ID NO 57
<211> LENGTH: 39
<212> TYPE: DNA
<213> ORGANISM: Artificial Sequence
<220> FEATURE:
<223> OTHER INFORMATION: Synthetic construct

<400> SEQUENCE: 56
ggtgctgatg gaattctctc cacgtatggc tgattg        36

<210> SEQ ID NO 57
<211> LENGTH: 39
<212> TYPE: DNA
<213> ORGANISM: Artificial Sequence
<220> FEATURE:
<223> OTHER INFORMATION: Synthetic construct

<400> SEQUENCE: 57
acacaactgg ggatccacca tgtttcgcct cggacatgc        39

<210> SEQ ID NO 58
<211> LENGTH: 39
<212> TYPE: DNA
<213> ORGANISM: Artificial Sequence
<220> FEATURE:
<223> OTHER INFORMATION: Synthetic construct

<400> SEQUENCE: 58
gtcaccctct agatctcgag aaagccaccc cgtcacctc        39

<210> SEQ ID NO 59
<211> LENGTH: 40
<212> TYPE: DNA
<213> ORGANISM: Artificial Sequence
<220> FEATURE:
<223> OTHER INFORMATION: Synthetic construct

<400> SEQUENCE: 59
acacaactgg ggatccacca tgaggacctc catcatcagg        40

<210> SEQ ID NO 60
<211> LENGTH: 43
<212> TYPE: DNA
<213> ORGANISM: Artificial Sequence
<220> FEATURE:
<223> OTHER INFORMATION: Synthetic construct

<400> SEQUENCE: 60
gtcaccctct agatctcgag tcacgcgctg ctatccggtt tat        43